(12) United States Patent
Katana et al.

(10) Patent No.: US 11,987,577 B2
(45) Date of Patent: May 21, 2024

(54) THERAPEUTIC COMPOUNDS AND METHODS

(71) Applicant: Actio Biosciences, Inc., San Diego, CA (US)

(72) Inventors: Ashley Katana, Fairview Park, OH (US); John Otto Link, San Francisco, CA (US)

(73) Assignee: Actio Biosciences, Inc., San Diego, CA (US)

( * ) Notice: Subject to any disclaimer, the term of this patent is extended or adjusted under 35 U.S.C. 154(b) by 0 days.

(21) Appl. No.: 18/363,195

(22) Filed: Aug. 1, 2023

(65) Prior Publication Data

US 2024/0076294 A1    Mar. 7, 2024

Related U.S. Application Data

(63) Continuation of application No. PCT/US2023/069762, filed on Jul. 7, 2023.

(60) Provisional application No. 63/385,282, filed on Nov. 29, 2022, provisional application No. 63/359,715, filed on Jul. 8, 2022.

(51) Int. Cl.
    *C07D 413/14*    (2006.01)
    *C07D 413/08*    (2006.01)

(52) U.S. Cl.
    CPC ......... *C07D 413/14* (2013.01); *C07D 413/08* (2013.01)

(58) Field of Classification Search
    CPC ............................ C07D 413/14; C07D 413/08
    USPC ........................................................ 514/374
    See application file for complete search history.

(56) References Cited

U.S. PATENT DOCUMENTS 9,187,464 B2    11/2015  Brooks et al.
2014/0121206 A1   5/2014  Brooks et al.

FOREIGN PATENT DOCUMENTS

| WO | WO-2008129007 A1 | 10/2008 |
| WO | WO-2009095377 A1 | 8/2009 |
| WO | WO-2012024183 A1 | 2/2012 |
| WO | WO-2012174340 A1 | 12/2012 |
| WO | WO-2012174342 A1 | 12/2012 |
| WO | WO-2013012500 A1 | 1/2013 |
| WO | WO-2017199199 A1 | 11/2017 |

OTHER PUBLICATIONS

Grace, M.S., et al.; "Modulation of the TRPV4 ion channel as a therapeutic target for disease," Pharmacology & Therapeutics, (2017) 177: 9-22.

Lawhorn et al., "TRPV4 antagonists: a patent review (2015-2020)," Expert Opin Ther Pat., (Sep. 2021); 31(9):773-784.

Alessandri-Haber et al. "Transient receptor potential vanilloid 4 is essential in chemotherapy-induced neuropathic pain in the rat", Journal of Neuroscience, (2004); 24(18):4444-4452.

Birder et al. "Activation of urothelial transient receptor potential vanilloid 4 by 4α-phorbol 12, 13-didecanoate contributes to altered bladder reflexes in the rat", Journal of Pharmacology and Experimental Therapeutics, (2007); 323(1):227-235.

Everaerts et al. "The vanilloid transient receptor potential channel TRPV4: from structure to disease", Progress in Biophysics and Molecular Biology, (2010); 103(1):2-17.

Goyal et al. "Clinical pharmacokinetics, safety, and tolerability of a novel, first-in-class TRPV4 ion channel inhibitor, GSK2798745, in healthy and heart failure subjects", American Journal of Cardiovascular Drugs, (2019); 19:335-342.

Koivisto et al. "Advances in TRP channel drug discovery: from target validation to clinical studies", Nature Reviews Drug Discovery, (2022); 21(1):41-59.

Landoure et al. "Mutations in TRPV4 cause Charcot-Marie-Tooth disease type 2C", Nature Genetics, (2010); 42(2):170-174.

Nishimura et al. "TRPV4-associated skeletal dysplasias", In American Journal of Medical Genetics Part C: Seminars in Medical Genetics, (2012); 160(3):190-204.

Pero et al. "Identification, synthesis, and characterization of a major circulating human metabolite of TRPV4 antagonist GSK2798745", ACS Medicinal Chemistry Letters, (2021); 12(9):1498-1502.

Qu et al. "Effect of TRPV4-p38 MAPK pathway on neuropathic pain in rats with chronic compression of the dorsal root ganglion", BioMed Research International, (2016); 2016(Article 6978923):1-12.

Toft-Bertelsen et al. "TRPing to the point of clarity: understanding the function of the complex TRPV4 ion channel", Cells, (2021); 10(1):165.

Venkatachalam et al. "TRP channels", Annu. Rev. Biochem., (2007); 76:387-417.

*Primary Examiner* — Kahsay Habte
(74) *Attorney, Agent, or Firm* — COOLEY LLP; Heidi A. Erlacher; Christine E. Dunne

(57) ABSTRACT

The disclosure provides a compound of formula I:

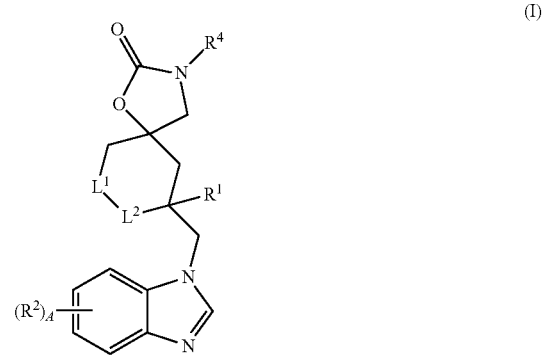

(I)

or a salt thereof, wherein $R^1$, $R^2$, $R^4$, $L^1$, $L^2$, and A have any of the values described in the specification, as well as compositions comprising a compound of formula (I). The compounds are useful as TRPV4 antagonists.

20 Claims, 1 Drawing Sheet

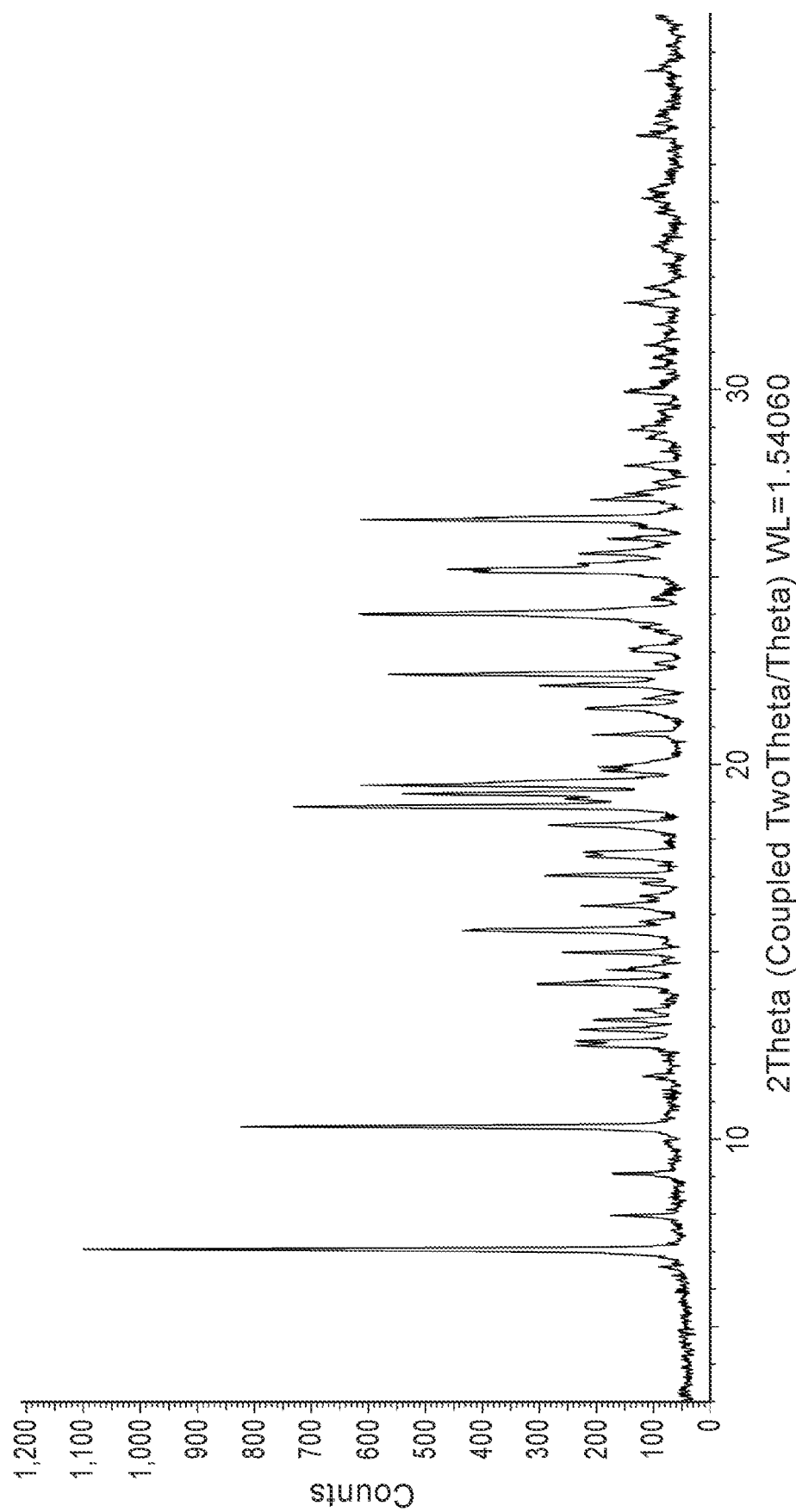

THERAPEUTIC COMPOUNDS AND METHODS

PRIORITY

This application is a continuation of International Patent Application No. PCT/US2023/069762, filed Jul. 7, 2023, which claims priority to U.S. Provisional Application No. 63/359,715, filed 8 Jul. 2022 and to U.S. Provisional Application No. 63/385,282, filed 29 Nov. 2022. The entire content of each of these United States Provisional Patent Applications is hereby incorporated herein by reference.

FIELD

This disclosure relates to pharmaceutical compositions that act as antagonists of both wildtype TRPV4 channels and of TRPV4 channels that carry disease-causing activating mutations.

BACKGROUND

The transient receptor potential vanilloid type 4, TRPV4, is a member of the Transient Receptor Potential (TRP) super family (Venkatachalam and Craig Montell 2007 Annual Reviews Biochemistry). The TRPV4 gene encodes a non-selective cation channel highly permeable to calcium. TRPV4 is activated by a variety of different stimuli including heat, mechanical stress, and chemicals including arachidonic acid metabolites. TRPV4 is expressed in a number of different tissues including the brain, bladder, skin, heart, lung and musculoskeletal tissues, among others.

The TRPV4 channel is widely expressed in diverse human cell types. In particular, TRPV4 is expressed in epithelial and endothelial cells, fibroblasts, chondrocytes, neurons, and various inflammatory cells (Koivisto et al 2021 NRDD). TRPV4 has been directly implicated in epithelial and endothelial barrier function with relevance to lung injury and has been further associated with respiratory diseases through TRPV4-induced ATP release (Koivisto). Genetic and pharmacologic studies have implicated TRPV4 as therapeutic target for chronic cough, pulmonary edema, chronic obstructive pulmonary disease, and pulmonary fibrosis (Grace et al 2017, Pharmacology and Therapeutics). Genetic knockout of TRPV4 results in decreased osteoclast function and calcium regulation and is critical for bone homeostasis, suggesting a role for TRPV4 in osteoporosis and other joint diseases. Inflammatory hyperalgesia and mechanical pain are reduced in TRPV4 knockout mice (J. Neurosci. 2004, 18, 4444-4452, Qu, et al., 2016 BioMed Research International) and a variety of functional studies have demonstrated TRPV4 signaling in neuropathic pain. TRPV4 is also expressed in urothelium and detrusor muscles of the bladder and activation causes muscle contraction (Birder et al 2007 J. Pharmacol. Exp. Ther.). Consistent with a role for TRPV4 in bladder related conditions, it has been shown that inhibition of TRPV4 improves bladder function in mice and rat models of cyclophosphamide-induced cystitis (Prog. Biophys. Mol. Biol. 2010, 1, 2-17). This provides evidence for TRPV4 as a therapeutic target in multiple diseases, including respiratory disease, joint diseases, pain, and bladder dysfunction.

Additionally, activating pathogenic mutations in TRPV4 have been shown to cause multiple severe Mendelian diseases including a set of skeletal dysplasias (Nishimura et al 2012 AJMG) and a peripheral neuropathy (Landoure et al. Nature Genetics 2009). All disease-causing mutations appear to contribute to risk of disease by increasing calcium influx into cells (Toft-Beterlsen and MacAulay 2021 Cells) suggesting therapeutic benefit of TRPV4 inhibitors. These observations suggest a benefit of inhibition of TRPV4 in genetic diseases due to activating mutations, in addition to a number of different common diseases resulting from activation of the wildtype receptor.

GSK2798745 advanced to Phase II clinical trials. Further exploration uncovered a circulating active metabolite (ACS Med. Chem. Lett. 2021, 12, 9, 1498-1502) and a lower safety margin established by a three month dog toxicity study resulted in a 4.8-fold decrease in the maximum clinically administered dose (Am. J. Cardiovasc. Drugs 2019, 19, 335-342). GSK2798745 failed to show efficacy across several human disease indications. Currently there is a need for agents that are useful for antagonizing TRPV4. In particular, there is a need for agents with lower toxicity, improved potency, improved metabolic stability (e.g., against CYP3A4), lower levels of active circulating metabolites, and/or a higher safety margin.

SUMMARY OF THE DISCLOSURE

In one aspect, the disclosure provides compounds that are useful for antagonizing TRPV4.

In some aspects, the disclosure provides a compound of formula I:

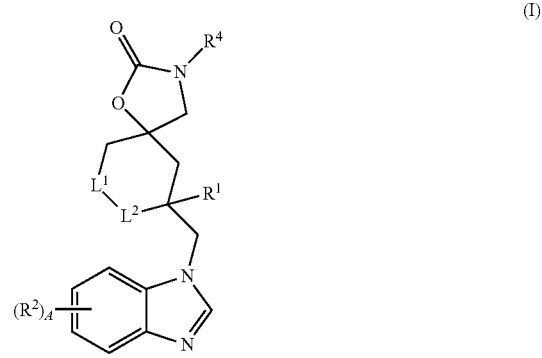

(I)

or a salt thereof, wherein:
  $L^1$ is $CR^aR^b$;
  $L^2$ is $CR^cR^d$;
  $R^a$ is H, halo, cyano, $(C_1-C_5)$alkyl, $(C_1-C_5)$alkoxy, $(C_3-C_5)$cycloalkyloxy, or $(C_3-C_5)$cycloalkyl, wherein any $(C_1-C_5)$alkyl, $(C_1-C_5)$alkoxy, $(C_3-C_5)$cycloalkyloxy, and $(C_3-C_5)$cycloalkyl is optionally substituted with one or more fluoro;
  $R^b$ is H, halo, cyano, $(C_1-C_5)$alkyl, $(C_1-C_5)$alkoxy, or $(C_3-C_5)$cycloalkyl, wherein any $(C_1-C_5)$alkyl, $(C_1-C_5)$alkoxy, and $(C_3-C_5)$cycloalkyl is optionally substituted with one or more fluoro; or $R^a$ and $R^b$ taken together are oxo (=O) methylene (=CH$_2$),
  or $R^a$ and $R^b$ taken together with the atom to which they are attached form a spiro$(C_3-C_5)$cycloalkyl;
  $R^c$ is H, halo, cyano, $(C_1-C_5)$alkyl, $(C_1-C_5)$alkoxy, $(C_3-C_5)$cycloalkyloxy, or $(C_3-C_5)$cycloalkyl, wherein any $(C_1-C_5)$alkyl, $(C_1-C_5)$alkoxy, $(C_3-C_5)$cycloalkyloxy, and $(C_3-C_5)$cycloalkyl is optionally substituted with one or more fluoro;
  $R^d$ is H, halo, cyano, $(C_1-C_5)$alkyl, $(C_1-C_5)$alkoxy, or $(C_3-C_5)$cycloalkyl, wherein any $(C_1-C_5)$alkyl, $(C_1-C_5)$alkoxy, and $(C_3-C_5)$cycloalkyl is optionally substituted with one or more fluoro;

or $R^c$ and $R^d$ taken together with the atoms to which they are attached form a fused cyclopropyl ring; or $R^c$ and $R^d$ taken together are oxo (=O) or methylene (=CH$_2$), or $R^c$ and $R^d$ taken together with the atom to which they are attached form a spiro(C$_3$-C$_5$)cycloalkyl;

wherein at least one of $R^a$, $R^b$, $R^c$, and $R^d$ is other than H;

$R^1$ is H, hydroxy, cyano, halo, methoxycarbonyl, cyclopropyl, (C$_1$-C$_3$)alkyl, or (C$_1$-C$_3$)alkoxy, wherein any cyclopropyl, (C$_1$-C$_3$)alkyl, and (C$_1$-C$_3$)alkoxy is optionally substituted with one or more groups independently selected from hydroxy, (C$_1$-C$_3$)alkoxy, benzyloxy, cyano, and fluoro, or $R^1$ and $R^c$ taken together with the atoms to which they are attached form a fused cyclopropyl ring;

each $R^2$ is independently selected from the group consisting of halo, cyano, hydroxy, ethynyl, (C$_1$-C$_3$)alkylsulfonyl, cyclopropyl, (C$_1$-C$_3$)alkyl, and (C$_1$-C$_3$)alkoxy, wherein any cyclopropyl, (C$_1$-C$_3$)alkyl, and (C$_1$-C$_3$)alkoxy is optionally substituted with one or more fluoro;

$R^4$ is (C$_1$-C$_7$)alkyl, (C$_3$-C$_7$)cycloalkyl, phenyl or a 6-membered heteroaryl, wherein any $R^4$ is optionally substituted with one or more $R^x$;

each $R^x$ is independently selected from the group consisting of hydroxy, halo, cyano, C$_1$-C$_5$)alkyl, (C$_1$-C$_5$)alkoxy, (C$_3$-C$_5$)cycloalkyloxy, and (C$_3$-C$_7$)cycloalkyl, wherein any (C$_1$-C$_5$)alkyl, (C$_1$-C$_5$)alkoxy, (C$_3$-C$_5$)cycloalkyloxy, and (C$_3$-C$_5$)cycloalkyl is optionally substituted with one or more groups independently selected from halo, cyano, C$_1$-C$_5$)alkyl, and hydroxy; and A is 0, 1, or 2;

In some aspects, the disclosure provides a compound of formula I:

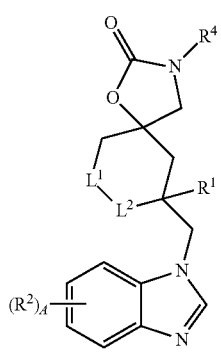

(I)

or a salt thereof, wherein:

$L^1$ is CR$^a$R$^b$;

$L^2$ is CR$^c$R$^d$;

$R^a$ is H, halo, cyano, (C$_1$-C$_5$)alkyl, (C$_1$-C$_5$)alkoxy, (C$_3$-C$_5$)cycloalkyloxy, or (C$_3$-C$_5$)cycloalkyl, wherein any (C$_1$-C$_5$)alkyl, (C$_1$-C$_5$)alkoxy, (C$_3$-C$_5$)cycloalkyloxy, and (C$_3$-C$_5$)cycloalkyl is optionally substituted with one or more fluoro;

$R^b$ is H, halo, cyano, (C$_1$-C$_5$)alkyl, (C$_1$-C$_5$)alkoxy, or (C$_3$-C$_5$)cycloalkyl, wherein any (C$_1$-C$_5$)alkyl, (C$_1$-C$_5$)alkoxy, and (C$_3$-C$_5$)cycloalkyl is optionally substituted with one or more fluoro; or $R^a$ and $R^b$ taken together are oxo (=O) methylene (=CH$_2$), or $R^a$ and $R^b$ taken together with the atom to which they are attached form a spiro(C$_3$-C$_5$)cycloalkyl;

$R^c$ is H, halo, cyano, (C$_1$-C$_5$)alkyl, (C$_1$-C$_5$)alkoxy, (C$_3$-C$_5$)cycloalkyloxy, or (C$_3$-C$_5$)cycloalkyl, wherein any (C$_1$-C$_5$)alkyl, (C$_1$-C$_5$)alkoxy, (C$_3$-C$_5$)cycloalkyloxy, and (C$_3$-C$_5$)cycloalkyl is optionally substituted with one or more fluoro;

$R^d$ is H, halo, cyano, (C$_1$-C$_5$)alkyl, (C$_1$-C$_5$)alkoxy, or (C$_3$-C$_5$)cycloalkyl, wherein any (C$_1$-C$_5$)alkyl, (C$_1$-C$_5$)alkoxy, and (C$_3$-C$_5$)cycloalkyl is optionally substituted with one or more fluoro; or $R^c$ and $R^d$ taken together with the atoms to which they are attached form a fused cyclopropyl ring; or $R^c$ and $R^d$ taken together are oxo (=O) or methylene (=CH$_2$), or $R^c$ and $R^d$ taken together with the atom to which they are attached form a spiro(C$_3$-C$_5$)cycloalkyl;

$R^1$ is (C$_1$-C$_3$)alkyl that is substituted with one or more fluoro;

each $R^2$ is independently selected from the group consisting of halo, cyano, hydroxy, ethynyl, (C$_1$-C$_3$)alkylsulfonyl, cyclopropyl, (C$_1$-C$_3$)alkyl, and (C$_1$-C$_3$)alkoxy, wherein any cyclopropyl, (C$_1$-C$_3$)alkyl, and (C$_1$-C$_3$)alkoxy is optionally substituted with one or more fluoro;

$R^4$ is (C$_1$-C$_7$)alkyl, (C$_3$-C$_7$)cycloalkyl, phenyl or a 6-membered heteroaryl, wherein any $R^4$ is optionally substituted with one or more $R^x$;

each $R^x$ is independently selected from the group consisting of hydroxy, halo, cyano, C$_1$-C$_5$)alkyl, (C$_1$-C$_5$)alkoxy, (C$_3$-C$_5$)cycloalkyloxy, and (C$_3$-C$_7$)cycloalkyl, wherein any (C$_1$-C$_5$)alkyl, (C$_1$-C$_5$)alkoxy, (C$_3$-C$_5$)cycloalkyloxy, and (C$_3$-C$_5$)cycloalkyl is optionally substituted with one or more groups independently selected from halo, cyano, and hydroxy; and A is 0, 1, or 2.

The disclosure also provides a pharmaceutical composition comprising a compound of formula I or a pharmaceutically acceptable salt thereof, and a pharmaceutically acceptable excipient.

The disclosure also provides a method for treating a condition associated with TRPV4 modulation in an animal comprising administering a compound of formula (I) or a pharmaceutically acceptable salt thereof to the animal.

The disclosure also provides a compound of formula (I) or a pharmaceutically acceptable salt thereof for use in medical therapy.

The disclosure also provides a compound of formula (I) or a pharmaceutically acceptable salt thereof for the prophylactic or therapeutic treatment a condition associated with TRPV4 modulation.

The disclosure also provides the use of a compound of formula (I) or a pharmaceutically acceptable salt thereof to prepare a medicament for treating a condition associated with TRPV4 modulation in an animal.

The disclosure also provides processes and intermediates disclosed herein that are useful for preparing a compound of formula I or a salt thereof.

Certain compounds of formula (I) demonstrate lower toxicity, improved potency, improved metabolic stability (e.g., against CYP3A4), lower levels of active circulating metabolites, and/or a higher safety margin.

BRIEF DESCRIPTION OF THE FIGURES

FIG. 1 shows X-Ray Powder Diffraction (XRPD) data from Example 21.

DETAILED DESCRIPTION OF THE DISCLOSURE

The following definitions are used, unless otherwise described: halo or halogen is fluoro, chloro, bromo, or iodo.

Alkyl, alkoxy, etc. denote both straight and branched groups; but reference to an individual radical such as propyl embraces only the straight chain radical, a branched chain isomer such as isopropyl being specifically referred to.

The term "alkyl," by itself or as part of another substituent, means, unless otherwise stated, a straight or branched chain hydrocarbon radical, having the number of carbon atoms designated (i.e., $C_{1-5}$ means one to five carbons). Examples include $(C_1-C_5)$alkyl, $(C_2-C_5)$alkyl, $C_1-C_3)$alkyl, $(C_2-C_3)$alkyl and $(C_3-C_5)$alkyl. Examples of alkyl groups include methyl, ethyl, n-propyl, iso-propyl, n-butyl, t-butyl, iso-butyl, sec-butyl, and n-pentyl.

The term "alkoxy" refers to an alkyl groups attached to the remainder of the molecule via an oxygen atom ("oxy").

The term "carbocycle" refers to a saturated or partially unsaturated (non-aromatic) all carbon ring having the number of carbons designated.

The term 6-membered heteroaryl includes the following rings:

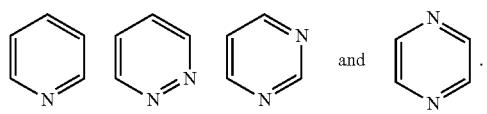

As used herein a wavy line " " that intersects a bond in a chemical structure indicates the point of attachment of the bond that the wavy bond intersects in the chemical structure to the remainder of a molecule.

The terms "treat," "treatment," or "treating" to the extent it relates to a disease or condition includes inhibiting the disease or condition, eliminating the disease or condition, and/or relieving one or more symptoms of the disease or condition. The terms "treat," "treatment," or "treating" also refer to both therapeutic treatment and/or prophylactic treatment or preventative measures, wherein the object is to prevent or slow down (lessen) an undesired physiological change or disorder, such as, for example, the development or spread of cancer.

For example, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treat," "treatment," or "treating" can also mean prolonging survival as compared to expected survival if not receiving treatment. Those in need of treatment include those already with the disease or disorder as well as those prone to have the disease or disorder or those in which the disease or disorder is to be prevented. In some embodiments, "treat", "treatment", or "treating" does not include preventing or prevention, The phrase "therapeutically effective amount" or "effective amount" includes but is not limited to an amount of a compound of the present disclosure that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

In one aspect, the compounds of the present disclosure modulate TRPV4. In some embodiments, modulation is antagonism. In one aspect, the TRPV4 antagonists of the disclosure are useful for treating conditions associated with TRPV4 overactivation. Such conditions include diseases caused by activating mutations in TRPV4 including for example, but not limited to, congenital distal spinal motor neuropathy, scapuloperoneal spinal muscular atrophy, Charcot-Marie-Tooth disease type 2C (CMT2C), metatropic dysplasia (MD), spondylometaphyseal dysplasia Kozlowski type (SMDK), spondyloepiphyseal dysplasia, Maroteaux type, pseudo-Morquio syndrome type 2, parastremmatic dysplasia, autosomal dominant brachyolmia, and familial digital arthropathy-brachydactyly.

In one aspect, the TRPV4 antagonists of the disclosure may be useful for treating related conditions associated with elevated wildtype TRPV4 and/or with symptomology overlapping with diseases caused by TRPV4 activating mutations. Such conditions include, but are not limited to, skeletal dysplasia, bone dysplasia, osteoarthritis, reduced bone density, osteoporosis, peripheral neuropathies, inherited neuropathies, spinal muscular atrophies, Charcot-Marie-Tooth diseases, diseases of the bladder including but not limited to overactive bladder, urinary incontinence, interstitial cystitis, painful bladder syndrome, bladder urgency and neurogenic bladder.

In one aspect, TRPV4 antagonists of the disclosure are useful to treat other bone disorders including bone infections, osteogenesis imperfecta, osteonecrosis, Paget's disease of bone, rickets, achondroplasia, dwarfism, short stature, hypochondroplasia, genetic diseases of the skeleton. In one aspect TRPV4 antagonists may be useful to treat other neuropathies including spinal muscle atrophies, neuropathic pain, pain, motor neuron disorders, chronic pain, intestinal pain and cramping. In one aspect, TRPV4 antagonists of the disclosure are useful to treat diseases with compromised barrier integrity and dysregulation of vascular permeability including but not limited to retinal edema, retinal leak, diabetic or other causes of macular edema, diabetic neuropathy, disorders related to intestinal edema, post-surgical abdominal edema, local and systemic edema, fluid retention, congestive heart failure, irritable bowel syndrome (IBS), Crohn's disease, diarrhea, intestinal irregularity (hyperreactivity/hyporeactivity), fecal incontinence, constipation, celiac disease, lactose intolerance, and flatulence, obesity and type-II diabetes (T2D), colitis/ulcerative colitis, hypertension, atherosclerosis, diseases with edema as a symptom, congestive heart failure, kidney disease or cirrhosis of the liver, kidney infections, urinary tract infections, and enlarged prostate. In one aspect, TRPV4 antagonists of the disclosure are useful to treat diseases of the lung including but not limited to pulmonary disorders, chronic obstructive pulmonary disorder, ventilator induced lung injury, ventilator-associated lung parenchymal overdistension, high altitude induced pulmonary edema, acute respiratory distress syndrome, acute lung injury, pulmonary fibrosis, sinusitis/rhinitis, asthma, cough, chronic cough, bronchiectasis, sarcoidosis, and pulmonary hypertension. In one aspect, TRPV4 antagonists of the disclosure are useful to treat diseases of inflammation, including but not limited to sepsis, diseases with macrophage activation, microglial activation, neuroinflammation, Alzheimer's disease, Parkinson's disease, multiple sclerosis, as well as cardiac diseases, glaucoma, and viral and bacterial infections, infection, chronic inflammatory diseases (rheumatoid arthritis), tissue repair, multiple organ dysfunction/multiple organ failure, microbial infection, acute brain/lung/hepatic/renal injuries, neurodegenerative disorders, tumorigenesis, cardiovascular and metabolic diseases, and autoimmune diseases.

The term "mammal" as used herein refers to humans, higher non-human primates, rodents, domestic, cows, horses, pigs, sheep, dogs, and cats. In some embodiments, the mammal is a human. The term "patient" as used herein refers to any animal including mammals. In one embodiment, the patient is a mammalian patient. In some embodiments, the patient is a human patient.

The compounds disclosed herein can exist as tautomeric isomers in certain cases. Although only one delocalized resonance structure may be depicted, all such forms are contemplated within the scope of the disclosure.

It is understood by one skilled in the art that this disclosure also includes any compound claimed that may be enriched at any or all atoms above naturally occurring isotopic ratios with one or more isotopes such as, but not limited to, deuterium ($^2$H or D). As a non-limiting example, a —CH$_3$ group may be substituted with -CD$_3$. In some embodiments, the compound is enriched with deuterium at one position above naturally occurring isotopic ratio for deuterium. In some embodiments, the compound is enriched with deuterium at two positions above naturally occurring isotopic ratio for deuterium. In some embodiments, the compound is enriched with deuterium at one position by at least about 75%. In some embodiments, the compound is enriched with deuterium at two positions by at least about 75%. In some embodiments, the compound is enriched with deuterium at one position by at least about 95%. In some embodiments, the compound is enriched with deuterium at two positions by at least about 95%. The pharmaceutical compositions of the disclosure can comprise one or more excipients. When used in combination with the pharmaceutical compositions of the disclosure the term "excipients" refers generally to an additional ingredient that is combined with the compound of formula (I) or the pharmaceutically acceptable salt thereof to provide a corresponding composition. For example, when used in combination with the pharmaceutical compositions of the disclosure the term "excipients" includes, but is not limited to: carriers, binders, disintegrating agents, lubricants, sweetening agents, flavoring agents, coatings, preservatives, and dyes.

As used herein, the term "about" refers to a recited amount, value, or duration±10% or less of said amount, value, or duration. In some embodiments, "about" refers to a recited amount, value, or duration±10%, ±8%, ±6%, ±5%, ±4%, ±2%, ±1%, or ±0.5%. In other embodiments, "about" refers to a recited amount, value, or duration±10%, ±8%, ±6%, ±5%, ±4%, or ±2%. In other embodiments, "about" refers to a recited amount, value, or duration±5%. In some embodiments, "about" refers to a listed amount, value, or duration±2% or ±1%. For example, in some embodiments, when the term "about" is used when reciting a temperature or temperature range, these terms refer to the recited temperature or temperature range±5° C., ±2° C., or ±1° C. In other embodiments, the term "about" refers to the recited temperature or temperature range±2° C.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the disclosure can contain asymmetric or chiral centers, and therefore exist in different stereoisomeric forms. It is intended that all stereoisomeric forms of the compounds of the disclosure, including but not limited to, diastereomers, enantiomers and atropisomers, as well as mixtures thereof such as racemic mixtures, form part of the present disclosure.

It will be appreciated by those skilled in the art that compounds of the disclosure having a chiral center may exist in and be isolated in optically active and racemic forms. Some compounds may exhibit polymorphism. It is to be understood that the present disclosure encompasses any racemic, optically-active, polymorphic, or stereoisomeric form, or mixtures thereof, of a compound of the disclosure, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities.

Bold-rectangles and dashed-rectangles (  ), designate relative stereochemistry. When a bond in a compound formula herein is drawn as a bold-wedge or a dashed-wedge (  ), it is to be understood that the atom to which the stereochemical bond is attached is enriched in the absolute stereoisomer depicted unless otherwise noted. In some embodiments, the compound may be at least 51% the absolute stereoisomer depicted. In some embodiments, the compound may be at least 60% the absolute stereoisomer depicted. In some embodiments, the compound may be at least 80% the absolute stereoisomer depicted. In some embodiments, the compound may be at least 90% the absolute stereoisomer depicted. In some embodiments, the compound may be at least 95 the absolute stereoisomer depicted. In some embodiments, the compound may be at least 99% the absolute stereoisomer depicted.

Specific values listed below for radicals, substituents, and ranges, are for illustration only; they do not exclude other defined values or other values within defined ranges for the radicals and substituents. It is to be understood that two or more values may be combined. It is also to be understood that the values listed herein below (or subsets thereof) can be excluded.

It is understood that, for a compound of the present disclosure, variables $L^1$, $L^2$, $R^a$, $R^b$, $R^c$, $R^d$, $R^1$, $R^2$, $R^4$, and $R^x$ can each be, where applicable, selected from the groups described herein, and any group described herein for any of variables $L^1$, $L^2$, $R^a$, $R^b$, $R^c$, $R^d$, $R^1$, $R^2$, $R^4$, and $R^x$ can be combined, where applicable, with any group described herein for one or more of the remainder of variables Lt, $L^2$, $R^a$, $R^b$, $R^c$, $R^d$, $R^1$, $R^2$, $R^4$, and $R^x$.

Specifically, $(C_1-C_5)$alkyl can be methyl, ethyl, propyl, isopropyl, butyl, iso-butyl, sec-butyl, pentyl, or 3-pentyl; $(C_3-C_6)$cycloalkyl can be cyclopropyl, cyclobutyl, cyclopentyl, or cyclohexyl; and $(C_1-C_5)$alkoxy can be methoxy, ethoxy, propoxy, isopropoxy, butoxy, iso-butoxy, sec-butoxy, pentoxy, or 3-pentoxy.

In some embodiments of the compounds of Formula I,
$L^1$ is $CR^aR^b$;
$L^2$ is $CR^cR^d$;
$R^a$ is H, halo, cyano, $(C_1-C_5)$alkyl, $(C_1-C_5)$alkoxy, $(C_3-C_5)$cycloalkyloxy, or $(C_3-C_5)$cycloalkyl, wherein any $(C_1-C_5)$alkyl, $(C_1-C_5)$alkoxy, $(C_3-C_5)$cycloalkyloxy, and $(C_3-C_5)$cycloalkyl is optionally substituted with one or more fluoro; $R^b$ is H, halo, cyano, $(C_1-C_5)$alkyl, $(C_1-C_5)$alkoxy, or $(C_3-C_5)$cycloalkyl, wherein any $(C_1-C_5)$alkyl, $(C_1-C_5)$alkoxy, and $(C_3-C_5)$cycloalkyl is optionally substituted with one or more fluoro; or $R^a$ and $R^b$ taken together are oxo (=O) methylene (=CH$_2$) or $R^a$ and $R^b$ taken together with the atom to which they are attached form a spiro($C_3-C_5$)cycloalkyl;

$R^c$ is H, halo, cyano, $(C_1-C_5)$alkyl, $(C_1-C_5)$alkoxy, $(C_3-C_5)$cycloalkyloxy, or $(C_3-C_5)$cycloalkyl, wherein any $(C_1-C_5)$alkyl, $(C_1-C_5)$alkoxy, $(C_3-C_5)$cycloalkyloxy, and $(C_3-C_5)$cycloalkyl is optionally substituted with one or more fluoro; $R^d$ is H, halo, cyano, $(C_1-C_5)$alkyl, $(C_1-C_5)$alkoxy, or $(C_3-C_5)$cycloalkyl, wherein any $(C_1-C_5)$alkyl, $(C_1-C_5)$alkoxy, and $(C_3-C_5)$cycloalkyl is optionally substituted with one or more fluoro; or $R^c$ and $R^d$ taken together with the atoms to which they are attached form a fused cyclopropyl ring; or $R^c$ and $R^d$ taken together are oxo (=O) or methylene (=CH$_2$) or $R^c$ and $R^d$ taken together with the atom to which they are attached form a spiro$(C_3-C_5)$cycloalkyl;

wherein at least one of $R^a$, $R^b$, $R^c$, and $R^d$ is other than H;

$R^1$ is H, hydroxy, cyano, halo, methoxycarbonyl, cyclopropyl, $(C_1-C_3)$alkyl, or $(C_1-C_3)$alkoxy, wherein any cyclopropyl, $(C_1-C_3)$alkyl, and $(C_1-C_3)$alkoxy is optionally substituted with one or more groups independently selected from hydroxy, $(C_1-C_3)$alkoxy, benzyloxy, cyano, and fluoro; or $R^1$ and $R^c$ taken together with the atoms to which they are attached form a fused cyclopropyl ring;

each $R^2$ is independently selected from the group consisting of halo, cyano, hydroxy, ethynyl, $(C_1-C_3)$alkylsulfonyl, cyclopropyl, $(C_1-C_3)$alkyl, and $(C_1-C_3)$alkoxy, wherein any cyclopropyl, $(C_1-C_3)$alkyl, and $(C_1-C_3)$alkoxy is optionally substituted with one or more fluoro;

$R^4$ is $(C_1-C_7)$alkyl, $(C_3-C_7)$cycloalkyl, phenyl or a 6-membered heteroaryl, wherein any $R^4$ is optionally substituted with one or more $R^x$;

each $R^x$ is independently selected from the group consisting of hydroxy, halo, cyano, $C_1-C_5$)alkyl, $(C_1-C_5)$alkoxy, and $(C_3-C_7)$cycloalkyl, wherein any $(C_1-C_5)$alkyl, $(C_1-C_5)$alkoxy, and $(C_3-C_5)$cycloalkyl is optionally substituted with one or more groups independently selected from halo, cyano, $C_1-C_5)$alkyl, and hydroxy; and A is 0, 1, or 2.

In some embodiments of the compounds of Formula I, $L^1$ is $CR^aR^b$;

$L^2$ is $CR^cR^d$;

$R^a$ is H, halo, cyano, $(C_1-C_5)$alkyl, $(C_1-C_5)$alkoxy, $(C_3-C_5)$cycloalkyloxy, or $(C_3-C_5)$cycloalkyl, wherein any $(C_1-C_5)$alkyl, $(C_1-C_5)$alkoxy, $(C_3-C_5)$cycloalkyloxy, and $(C_3-C_5)$cycloalkyl is optionally substituted with one or more fluoro; $R^b$ is H, halo, cyano, $(C_1-C_5)$alkyl, $(C_1-C_5)$alkoxy, or $(C_3-C_5)$cycloalkyl, wherein any $(C_1-C_5)$alkyl, $(C_1-C_5)$alkoxy, and $(C_3-C_5)$cycloalkyl is optionally substituted with one or more fluoro; or $R^a$ and $R^b$ taken together are oxo (=O) methylene (=CH$_2$) or $R^a$ and $R^b$ taken together with the atom to which they are attached form a spiro$(C_3-C_5)$cycloalkyl;

$R^c$ is H, halo, cyano, $(C_1-C_5)$alkyl, $(C_1-C_5)$alkoxy, $(C_3-C_5)$cycloalkyloxy, or $(C_3-C_5)$cycloalkyl, wherein any $(C_1-C_5)$alkyl, $(C_1-C_5)$alkoxy, $(C_3-C_5)$cycloalkyloxy, and $(C_3-C_5)$cycloalkyl is optionally substituted with one or more fluoro; $R^d$ is H, halo, cyano, $(C_1-C_5)$alkyl, $(C_1-C_5)$alkoxy, or $(C_3-C_5)$cycloalkyl, wherein any $(C_1-C_5)$alkyl, $(C_1-C_5)$alkoxy, and $(C_3-C_5)$cycloalkyl is optionally substituted with one or more fluoro; or $R^c$ and $R^d$ taken together with the atoms to which they are attached form a fused cyclopropyl ring; or $R^c$ and $R^d$ taken together are oxo (=O) or methylene (=CH$_2$) or $R^c$ and $R^d$ taken together with the atom to which they are attached form a spiro$(C_3-C_5)$cycloalkyl;

wherein at least one of $R^a$, $R^b$, $R^c$, and $R^d$ is other than H;

$R^1$ is $(C_1-C_3)$alkyl that is substituted with one or more fluoro;

each $R^2$ is independently selected from the group consisting of halo, cyano, hydroxy, ethynyl, $(C_1-C_3)$alkylsulfonyl, cyclopropyl, $(C_1-C_3)$alkyl, and $(C_1-C_3)$alkoxy, wherein any cyclopropyl, $(C_1-C_3)$alkyl, and $(C_1-C_3)$alkoxy is optionally substituted with one or more fluoro; $R^4$ is $(C_1-C_7)$alkyl, $(C_3-C_7)$cycloalkyl, phenyl or a 6-membered heteroaryl, wherein any $R^4$ is optionally substituted with one or more $R^x$;

each $R^x$ is independently selected from the group consisting of hydroxy, halo, cyano, $C_1-C_5)$alkyl, $(C_1-C_5)$alkoxy, and $(C_3-C_7)$cycloalkyl, wherein any $(C_1-C_5)$alkyl, $(C_1-C_5)$alkoxy, and $(C_3-C_5)$cycloalkyl is optionally substituted with one or more groups independently selected from halo, cyano, and hydroxy; and A is 0, 1, or 2.

In some embodiments of the compounds of Formula I, $L^1$ is $CR^aR^b$;

$L^2$ is $CR^cR^d$;

$R^a$ is H, halo, cyano, $(C_1-C_5)$alkyl, $(C_1-C_5)$alkoxy, or $(C_3-C_5)$cycloalkyl, wherein any $(C_1-C_5)$alkyl, $(C_1-C_5)$alkoxy, and $(C_3-C_5)$cycloalkyl is optionally substituted with one or more fluoro; $R^b$ is H, halo, cyano, $(C_1-C_5)$alkyl, $(C_1-C_5)$alkoxy, or $(C_3-C_5)$cycloalkyl, wherein any $(C_1-C_5)$alkyl, $(C_1-C_5)$alkoxy, and $(C_3-C_5)$cycloalkyl is optionally substituted with one or more fluoro; or $R^a$ and $R^b$ taken together are oxo (=O) methylene (=CH$_2$) or $R^a$ and $R^b$ taken together with the atom to which they are attached form a spiro$(C_3-C_5)$cycloalkyl;

$R^c$ is H, halo, cyano, $(C_1-C_5)$alkyl, $(C_1-C_5)$alkoxy, or $(C_3-C_5)$cycloalkyl, wherein any $(C_1-C_5)$alkyl, $(C_1-C_5)$alkoxy, and $(C_3-C_5)$cycloalkyl is optionally substituted with one or more fluoro; $R^d$ is H, halo, cyano, $(C_1-C_5)$alkyl, $(C_1-C_5)$alkoxy, or $(C_3-C_5)$cycloalkyl, wherein any $(C_1-C_5)$alkyl, $(C_1-C_5)$alkoxy, and $(C_3-C_5)$cycloalkyl is optionally substituted with one or more fluoro; or $R^c$ and $R^d$ taken together with the atoms to which they are attached form a fused cyclopropyl ring; or $R^c$ and $R^d$ taken together are oxo (=O) or methylene (=CH$_2$) or $R^c$ and $R^d$ taken together with the atom to which they are attached form a spiro$(C_3-C_5)$cycloalkyl;

wherein at least one of $R^a$, $R^b$, $R^c$, and $R^d$ is other than H;

$R^1$ is H, hydroxy, cyano, halo, methoxycarbonyl, cyclopropyl, $(C_1-C_3)$alkyl, or $(C_1-C_3)$alkoxy, wherein any cyclopropyl, $(C_1-C_3)$alkyl, and $(C_1-C_3)$alkoxy is optionally substituted with one or more groups independently selected from hydroxy, $(C_1-C_3)$alkoxy, benzyloxy, cyano, and fluoro; or $R^1$ and $R^c$ taken together with the atoms to which they are attached form a fused cyclopropyl ring;

each $R^2$ is independently selected from the group consisting of halo, cyano, hydroxy, ethynyl, $(C_1-C_3)$alkylsulfonyl, cyclopropyl, $(C_1-C_3)$alkyl, and $(C_1-C_3)$alkoxy, wherein any cyclopropyl, $(C_1-C_3)$alkyl, and $(C_1-C_3)$alkoxy is optionally substituted with one or more fluoro;

$R^4$ is $(C_1-C_7)$alkyl, $(C_3-C_7)$cycloalkyl, phenyl or a 6-membered heteroaryl, wherein any $R^4$ is optionally substituted with one or more (e.g., 1, 2, 3, or 4) $R^x$;

each $R^x$ is independently selected from the group consisting of hydroxy, halo, cyano, $C_1-C_5)$alkyl, $(C_1-C_5)$alkoxy, and $(C_3-C_7)$cycloalkyl, wherein any $(C_1-C_5)$alkyl, $(C_1-C_5)$alkoxy, and $(C_3-C_5)$cycloalkyl is optionally substituted with one or more groups independently selected from halo, cyano, $C_1-C_5)$alkyl, and hydroxy; and A is 0, 1, or 2; or $L^1$ is $CR^aR^b$;

$L^2$ is $CR^cR^d$;

$R^a$ is H, halo, cyano, $(C_1-C_5)$alkyl, $(C_1-C_5)$alkoxy, or $(C_3-C_5)$cycloalkyl, wherein any $(C_1-C_5)$alkyl, $(C_1-C_5)$alkoxy, and $(C_3-C_5)$cycloalkyl is optionally substituted with one or more fluoro; $R^b$ is H, halo, cyano, $(C_1-C_5)$alkyl, $(C_1-C_5)$alkoxy, or $(C_3-C_5)$cycloalkyl, wherein any $(C_1-C_5)$alkyl, $(C_1-C_5)$alkoxy, and $(C_3-C_5)$cycloalkyl is optionally substituted with one or more fluoro; or $R^a$ and $R^b$ taken together are oxo (=O) methylene (=$CH_2$) or $R^a$ and $R^b$ taken together with the atom to which they are attached form a spiro$(C_3-C_5)$cycloalkyl;

$R^c$ is H, halo, cyano, $(C_1-C_5)$alkyl, $(C_1-C_5)$alkoxy, or $(C_3-C_5)$cycloalkyl, wherein any $(C_1-C_5)$alkyl, $(C_1-C_5)$alkoxy, and $(C_3-C_5)$cycloalkyl is optionally substituted with one or more fluoro; $R^d$ is H, halo, cyano, $(C_1-C_5)$alkyl, $(C_1-C_5)$alkoxy, or $(C_3-C_5)$cycloalkyl, wherein any $(C_1-C_5)$alkyl, $(C_1-C_5)$alkoxy, and $(C_3-C_5)$cycloalkyl is optionally substituted with one or more fluoro; or $R^c$ and $R^d$ taken together with the atoms to which they are attached form a fused cyclopropyl ring; or $R^c$ and $R^d$ taken together are oxo (=O) or methylene (=$CH_2$) or $R^c$ and $R^d$ taken together with the atom to which they are attached form a spiro$(C_3-C_5)$cycloalkyl;

$R^1$ is $(C_1-C_3)$alkyl that is substituted with one or more fluoro;

each $R^2$ is independently selected from the group consisting of halo, cyano, hydroxy, ethynyl, $(C_1-C_3)$alkylsulfonyl, cyclopropyl, $(C_1-C_3)$alkyl, and $(C_1-C_3)$alkoxy, wherein any cyclopropyl, $(C_1-C_3)$alkyl, and $(C_1-C_3)$alkoxy is optionally substituted with one or more fluoro;

$R^4$ is $(C_1-C_7)$alkyl, $(C_3-C_7)$cycloalkyl, phenyl or a 6-membered heteroaryl, wherein any $R^4$ is optionally substituted with one or more (e.g., 1, 2, 3, or 4) $R^x$;

each $R^x$ is independently selected from the group consisting of hydroxy, halo, cyano, $C_1-C_5$)alkyl, $(C_1-C_5)$alkoxy, and $(C_3-C_7)$cycloalkyl, wherein any $(C_1-C_5)$alkyl, $(C_1-C_5)$alkoxy, and $(C_3-C_5)$cycloalkyl is optionally substituted with one or more groups independently selected from halo, cyano, and hydroxy; and A is 0, 1, or 2.

In some embodiments of the compounds of Formula I, $L^1$ is $CR^aR^b$;

$L^2$ is $CR^cR^d$;

$R^a$ is H, halo, cyano, $(C_1-C_5)$alkyl, $(C_1-C_5)$alkoxy, or $(C_3-C_5)$cycloalkyl, wherein any $(C_1-C_5)$alkyl, $(C_1-C_5)$alkoxy, and $(C_3-C_5)$cycloalkyl is optionally substituted with one or more fluoro; $R^b$ is H, halo, cyano, $(C_1-C_5)$alkyl, $(C_1-C_5)$alkoxy, or $(C_3-C_5)$cycloalkyl, wherein any $(C_1-C_5)$alkyl, $(C_1-C_5)$alkoxy, and $(C_3-C_5)$cycloalkyl is optionally substituted with one or more fluoro; or $R^a$ and $R^b$ taken together are oxo (=O) methylene (=$CH_2$) or $R^a$ and $R^b$ taken together with the atom to which they are attached form a spiro$(C_3-C_5)$cycloalkyl spiro$(C_3-C_5)$cycloalkyl;

$R^c$ is H, halo, cyano, $(C_1-C_5)$alkyl, $(C_1-C_5)$alkoxy, or $(C_3-C_5)$cycloalkyl, wherein any $(C_1-C_5)$alkyl, $(C_1-C_5)$alkoxy, and $(C_3-C_5)$cycloalkyl is optionally substituted with one or more fluoro; $R^d$ is H, halo, cyano, Rc$(C_1-C_5)$alkyl, $(C_1-C_5)$alkoxy, or $(C_3-C_5)$cycloalkyl, wherein any $(C_1-C_5)$alkyl, $(C_1-C_5)$alkoxy, and $(C_3-C_5)$cycloalkyl is optionally substituted with one or more fluoro; or $R^c$ and $R^d$ taken together with the atoms to which they are attached form a fused cyclopropyl ring; or $R^c$ and $R^d$ taken together are oxo (=O) or methylene (=$CH_2$) or $R^c$ and $R^d$ taken together with the atom to which they are attached form a spiro$(C_3-C_5)$cycloalkyl spiro$(C_3-C_5)$cycloalkyl;

wherein at least one of $R^a$, $R^b$, $R^c$, and $R^d$ is other than H;

$R^1$ is H, hydroxy, cyano, halo, methoxycarbonyl, cyclopropyl, $(C_1-C_3)$alkyl, or $(C_1-C_3)$alkoxy, wherein any cyclopropyl, $(C_1-C_3)$alkyl, and $(C_1-C_3)$alkoxy is optionally substituted with one or more groups independently selected from hydroxy, $(C_1-C_3)$alkoxy, benzyloxy, cyano, and fluoro; or $R^1$ and $R^c$ taken together with the atoms to which they are attached form a fused cyclopropyl ring;

each $R^2$ is independently selected from the group consisting of halo, cyano, hydroxy, ethynyl, $(C_1-C_3)$alkylsulfonyl, cyclopropyl, $(C_1-C_3)$alkyl, and $(C_1-C_3)$alkoxy, wherein any cyclopropyl, $(C_1-C_3)$alkyl, and $(C_1-C_3)$alkoxy is optionally substituted with one or more fluoro;

$R^4$ is $(C_1-C_7)$alkyl, $(C_3-C_7)$cycloalkyl, phenyl or a 6-membered heteroaryl, wherein any $R^4$ is optionally substituted with one or more (e.g., 1, 2, 3, or 4) $R^x$;

each $R^x$ is independently selected from the group consisting of hydroxy, halo, cyano, $C_1-C_5$)alkyl, $(C_1-C_5)$alkoxy, and $(C_3-C_7)$cycloalkyl, wherein any $(C_1-C_5)$alkyl, $(C_1-C_5)$alkoxy, and $(C_3-C_5)$cycloalkyl is optionally substituted with one or more groups independently selected from halo, cyano, $C_1-C_5$)alkyl, and hydroxy; and A is 0, 1, or 2.

In some embodiments of the compounds of Formula I, $L^1$ is $CR^aR^b$;

$L^2$ is $CR^cR^d$;

$R^a$ is H, halo, cyano, $(C_1-C_5)$alkyl, $(C_1-C_5)$alkoxy, or $(C_3-C_5)$cycloalkyl, wherein any $(C_1-C_5)$alkyl, $(C_1-C_5)$alkoxy, and $(C_3-C_5)$cycloalkyl is optionally substituted with one or more fluoro; $R^b$ is H, halo, cyano, $(C_1-C_5)$alkyl, $(C_1-C_5)$alkoxy, or $(C_3-C_5)$cycloalkyl, wherein any $(C_1-C_5)$alkyl, $(C_1-C_5)$alkoxy, and $(C_3-C_5)$cycloalkyl is optionally substituted with one or more fluoro; or $R^a$ and $R^b$ taken together are oxo (=O) methylene (=$CH_2$) or $R^a$ and $R^b$ taken together with the atom to which they are attached form a spiro$(C_3-C_5)$cycloalkyl spiro$(C_3-C_5)$cycloalkyl;

$R^c$ is H, halo, cyano, $(C_1-C_5)$alkyl, $(C_1-C_5)$alkoxy, or $(C_3-C_5)$cycloalkyl, wherein any $(C_1-C_5)$alkyl, $(C_1-C_5)$alkoxy, and $(C_3-C_5)$cycloalkyl is optionally substituted with one or more fluoro; $R^d$ is H, halo, cyano, Rc$(C_1-C_5)$alkyl, $(C_1-C_5)$alkoxy, or $(C_3-C_5)$cycloalkyl, wherein any $(C_1-C_5)$alkyl, $(C_1-C_5)$alkoxy, and $(C_3-C_5)$cycloalkyl is optionally substituted with one or more fluoro; or $R^c$ and $R^d$ taken together with the atoms to which they are attached form a fused cyclopropyl ring; or $R^c$ and $R^d$ taken together are oxo (=O) or methylene (=$CH_2$) or $R^c$ and $R^d$ taken together with the atom to which they are attached form a spiro$(C_3-C_5)$cycloalkyl spiro$(C_3-C_5)$cycloalkyl;

$R^1$ is $(C_1-C_3)$alkyl that is substituted with one or more fluoro;

each $R^2$ is independently selected from the group consisting of halo, cyano, hydroxy, ethynyl, $(C_1-C_3)$alkylsulfonyl, cyclopropyl, $(C_1-C_3)$alkyl, and $(C_1-C_3)$alkoxy, wherein any cyclopropyl, $(C_1-C_3)$alkyl, and $(C_1-C_3)$alkoxy is optionally substituted with one or more fluoro;

$R^4$ is $(C_1-C_7)$alkyl, $(C_3-C_7)$cycloalkyl, phenyl or a 6-membered heteroaryl, wherein any $R^4$ is optionally substituted with one or more (e.g., 1, 2, 3, or 4) $R^x$;

each $R^x$ is independently selected from the group consisting of hydroxy, halo, cyano, $(C_1-C_5)$alkyl, $(C_1-C_5)$alkoxy, and $(C_3-C_7)$cycloalkyl, wherein any $(C_1-C_5)$alkyl, $(C_1-C_5)$alkoxy, and $(C_3-C_5)$cycloalkyl is optionally substituted with one or more groups independently selected from halo, cyano, and hydroxy; and A is 0, 1, or 2.

In some embodiments, the compound of formula (I) or the salt thereof is a compound of formula (II):

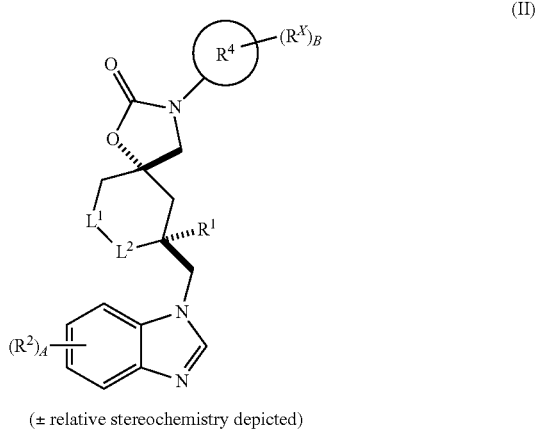

(II)

(± relative stereochemistry depicted)

or a salt thereof, wherein B is 0, 1, or 2.

In some embodiments of the compound of formula (II), $R^4$ is $(C_3-C_7)$cycloalkyl, phenyl or a 6-membered heteroaryl.

In some embodiments, the compound of formula (I) or the salt thereof is a compound of formula (III):

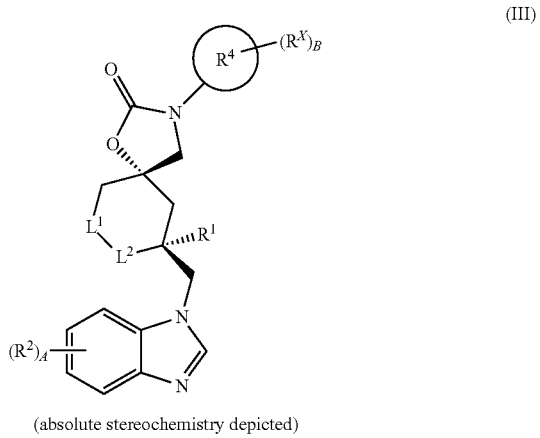

(III)

(absolute stereochemistry depicted)

or a salt thereof, wherein B is 0, 1, or 2.

In some embodiments of the compound of formula (III), $R^4$ is $(C_3-C_7)$cycloalkyl, phenyl or a 6-membered heteroaryl.

In some embodiments, $R^a$ is H.

In some embodiments, $R^a$ is selected from the group consisting of halo, cyano, $(C_1-C_5)$alkyl, $(C_1-C_5)$alkoxy, and $(C_3-C_5)$cycloalkyl, wherein any $(C_1-C_5)$alkyl, $(C_1-C_5)$alkoxy, and $(C_3-C_5)$cycloalkyl is optionally substituted with one or more fluoro.

In some embodiments, $R^a$ is H, halo, cyano, $CF_3$, $CF_2H$, $CFH_2$, $OCF_3$, $OCF_2H$, $OCH_2CF_3$, $OCH_2CF_2H$, $(C_1-C_5)$alkyl, or $(C_3-C_5)$cycloalkyl.

In some embodiments, $R^a$ is halo, cyano, $CF_3$, $CF_2H$, $CFH_2$, $OCF_3$, $OCF_2H$, $OCH_2CF_3$, $OCH_2CF_2H$, $(C_1-C_5)$alkyl, or $(C_3-C_5)$cycloalkyl.

In some embodiments, $R^b$ is H.

In some embodiments, $R^b$ is halo, cyano, $(C_1-C_5)$alkyl, $(C_1-C_5)$alkoxy, and $(C_3-C_5)$cycloalkyl, wherein any $(C_1-C_5)$alkyl, $(C_1-C_5)$alkoxy, and $(C_3-C_5)$cycloalkyl is optionally substituted with one or more fluoro.

In some embodiments, $R^b$ is H, halo, cyano, $CF_3$, $CF_2H$, $CFH_2$, $OCF_3$, $OCF_2H$, $OCH_2CF_3$, $OCH_2CF_2H$, $(C_1-C_5)$alkyl, or $(C_3-C_5)$cycloalkyl.

In some embodiments, $R^b$ is halo, cyano, $CF_3$, $CF_2H$, $CFH_2$, $OCF_3$, $OCF_2H$, $OCH_2CF_3$, $OCH_2CF_2H$, $(C_1-C_5)$alkyl, or $(C_3-C_5)$cycloalkyl.

In some embodiments, $R^c$ is H.

In some embodiments, $R^c$ is selected from the group consisting of halo, cyano, $(C_1-C_5)$alkyl, $(C_1-C_5)$alkoxy, and $(C_3-C_5)$cycloalkyl, wherein any $(C_1-C_5)$alkyl, $(C_1-C_5)$alkoxy, and $(C_3-C_5)$cycloalkyl is optionally substituted with one or more fluoro.

In some embodiments, $R^c$ is H, halo, cyano, $CF_3$, $CF_2H$, $CFH_2$, $OCF_3$, $OCF_2H$, $OCH_2CF_3$, $OCH_2CF_2H$, $(C_1-C_5)$alkyl, or $(C_3-C_5)$cycloalkyl.

In some embodiments, $R^c$ is halo, cyano, $CF_3$, $CF_2H$, $CFH_2$, $OCF_3$, $OCF_2H$, $OCH_2CF_3$, $OCH_2CF_2H$, $(C_1-C_5)$alkyl, or $(C_3-C_5)$cycloalkyl.

In some embodiments, $R^1$ and $R^c$ taken together with the atoms to which they are attached form a fused cyclopropyl ring.

In some embodiments, $R^d$ is H.

In some embodiments, $R^d$ is selected from the group consisting of halo, cyano, $(C_1-C_5)$alkyl, $(C_1-C_5)$alkoxy, and $(C_3-C_5)$cycloalkyl, wherein any $(C_1-C_5)$alkyl, $(C_1-C_5)$alkoxy, and $(C_3-C_5)$cycloalkyl is optionally substituted with one or more fluoro.

In some embodiments, $R^d$ is H, halo, cyano, $CF_3$, $CF_2H$, $CFH_2$, $OCF_3$, $OCF_2H$, $OCH_2CF_3$, $OCH_2CF_2H$, $(C_1-C_5)$alkyl, or $(C_3-C_5)$cycloalkyl.

In some embodiments, $R^d$ is halo, cyano, $CF_3$, $CF_2H$, $CFH_2$, $OCF_3$, $OCF_2H$, $OCH_2CF_3$, $OCH_2CF_2H$, $(C_1-C_5)$alkyl, or $(C_3-C_5)$cycloalkyl.

In some embodiments, $R^c$ and $R^d$ taken together with the atom to which they are attached form a spiro$(C_3-C_5)$cycloalkyl.

In some embodiments, $R^1$ is selected from the group consisting of cyano, halo, methoxycarbonyl, cyclopropyl, $(C_1-C_3)$alkyl, and $(C_1-C_3)$alkoxy, wherein any cyclopropyl, $(C_1-C_3)$alkyl, and $(C_1-C_3)$alkoxy is optionally substituted with one or more groups independently selected from hydroxy, $(C_1-C_3)$alkoxy, benzyloxy, and fluoro.

In some embodiments, $R^1$ is H, methyl, cyclopropyl, $CF_3$, $CF_2H$, $CFH_2$, $OCF_3$, or $OCF_2H$.

In some embodiments, $R^1$ is hydroxy, hydroxymethyl, or cyanomethyl.

In some embodiments, $R^1$ is methyl.

In some embodiments, $R^1$ is H.

In some embodiments, the group:

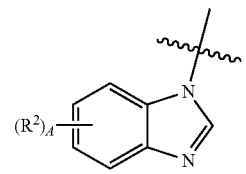

is selected from the group consisting of:

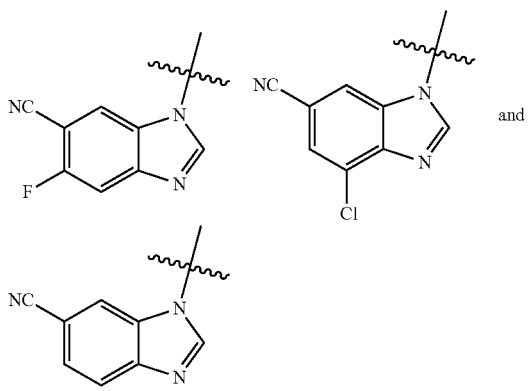

and

In some embodiments, A is 0.
In some embodiments, A is 1.
In some embodiments, $R^2$ is cyano.
In some embodiments, $R^2$ is 6-cyano.
In some embodiments, $R^4$ is phenyl that is optionally substituted with one or more $R^x$.
In some embodiments, $R^4$ is selected from the group consisting of:

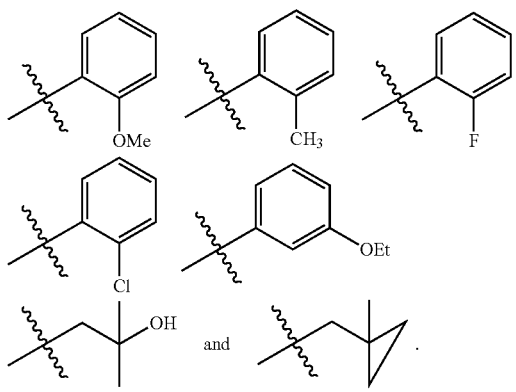

In some embodiments, $R^4$ is pyrimidin-2-yl. that is optionally substituted with one or more $R^x$.
In some embodiments, $R^4$ is selected from the group consisting of:

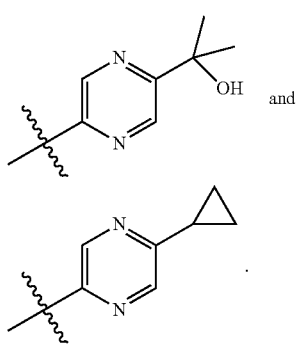

In some embodiments, $R^4$ is $(C_1-C_7)$alkyl that is optionally substituted with one $R^x$.

In some embodiments, $R^4$ is $(C_3-C_7)$cycloalkyl that is optionally substituted with one $R^x$.

In some embodiments, $R^4$ is a 6-membered heteroaryl that is optionally substituted with one $R^x$.

In some embodiments, $R^x$ is $C_1-C_5$alkyl that is optionally substituted with one or more groups independently selected from halo, cyano, and hydroxy.

In some embodiments, $R^x$ is $C_1-C_5$alkyl that is substituted with hydroxy.

In some embodiments, $R^x$ is 2-hydroxy-2-methylethyl.

In some embodiments, the compound of formula (I) or the salt thereof is a compound of formula IV or V:

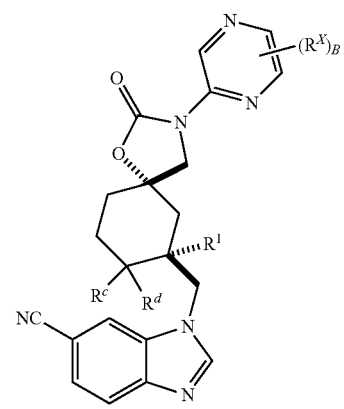

IV or

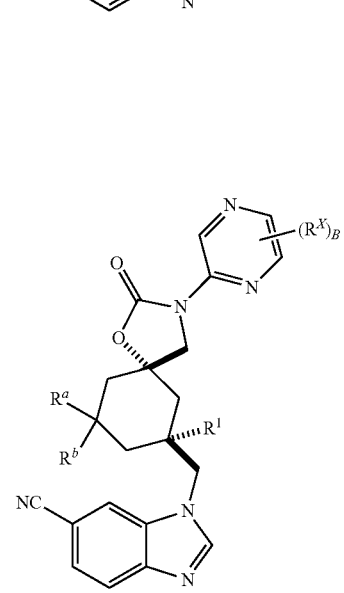

V ($\pm$ relative stereochemistry depicted)

or a salt thereof, wherein B is 0, 1, or 2.

In some embodiments, the compound of formula (I) or the salt thereof is a compound of formula IV or Va:

IVa

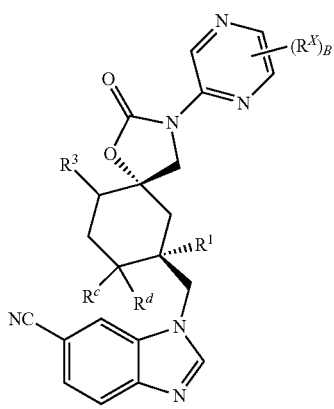

or

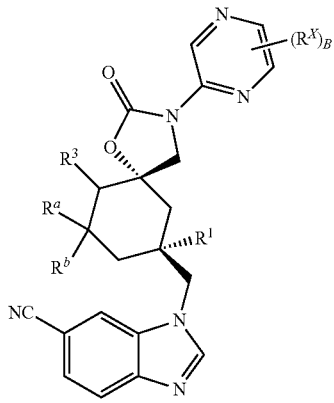

(absolute stereochemistry depicted)

Va or a salt thereof, wherein B is 0, 1, or 2.

In some embodiments, the compound of formula (I) or the salt thereof is a compound of formula VI or VII:

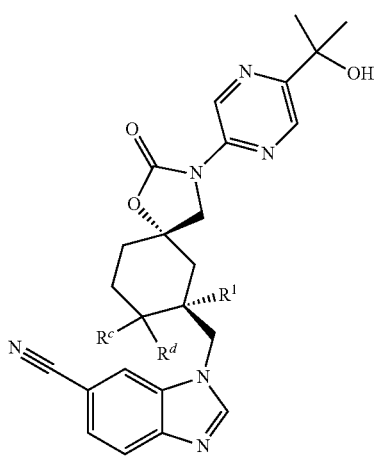

VI

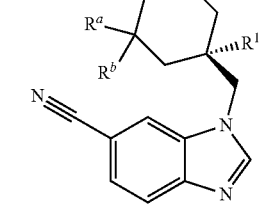

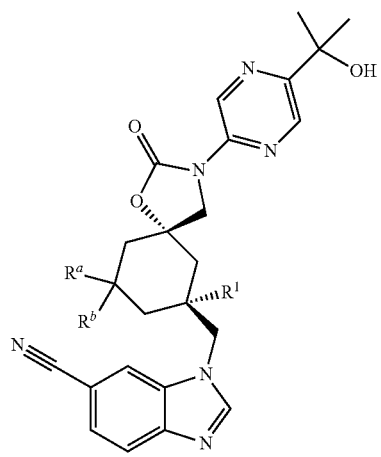

VII (absolute stereochemistry depicted for formula VI-VII)

or a salt thereof.

In some embodiments, $R^c$ is fluoro and $R^d$ is H or fluoro.

In some embodiments, the compound or salt is selected from the group consisting of:

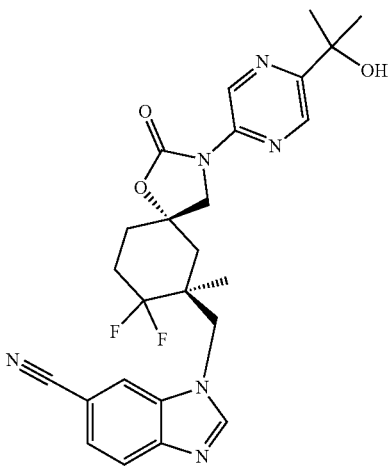

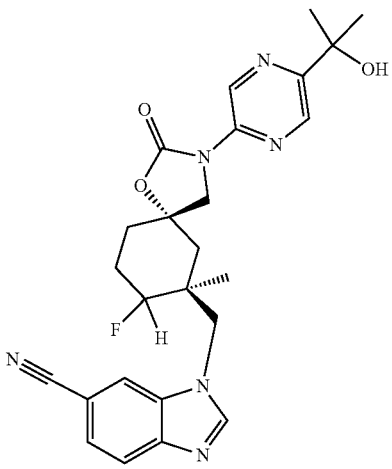

-continued
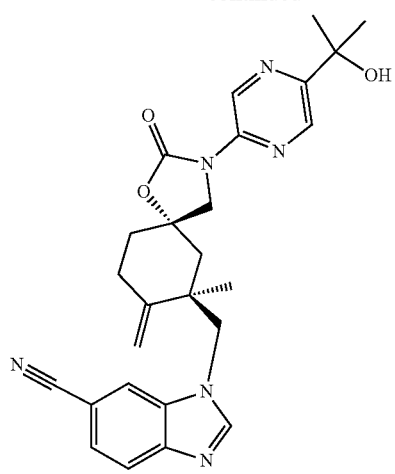
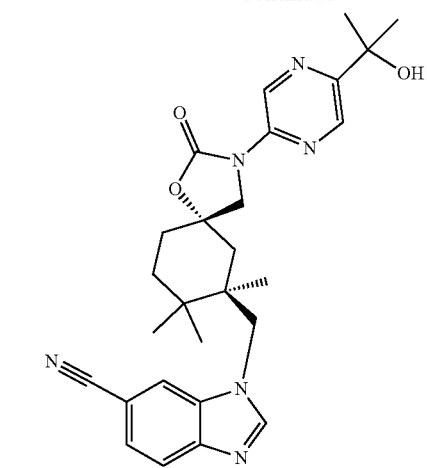
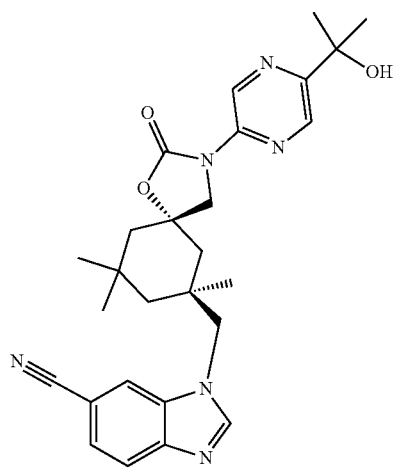
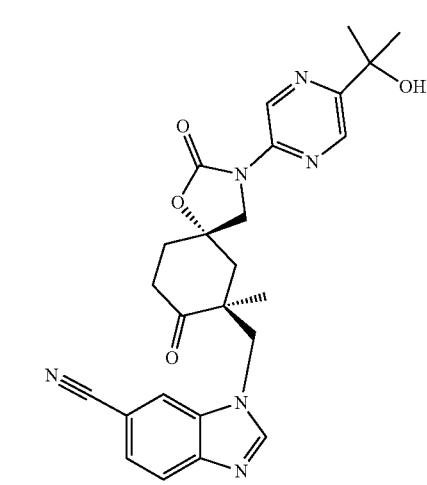
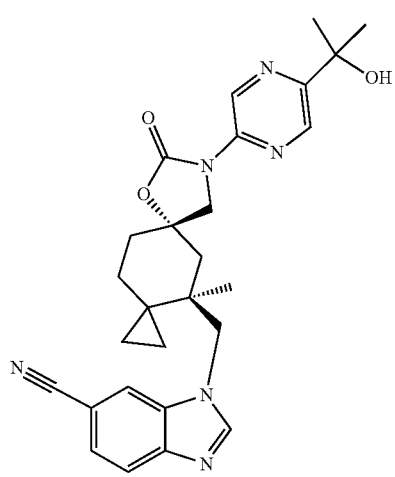
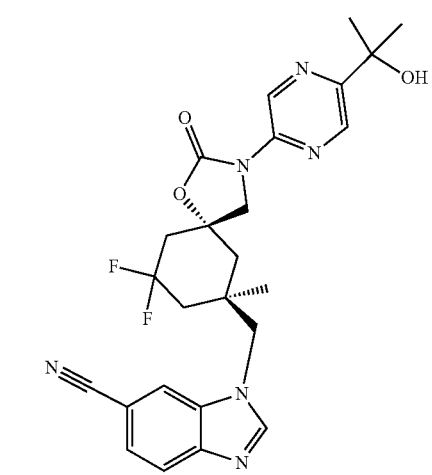

21
-continued
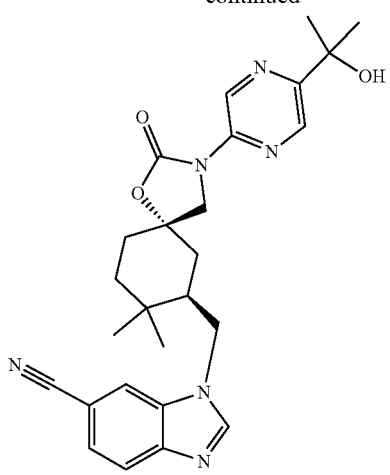
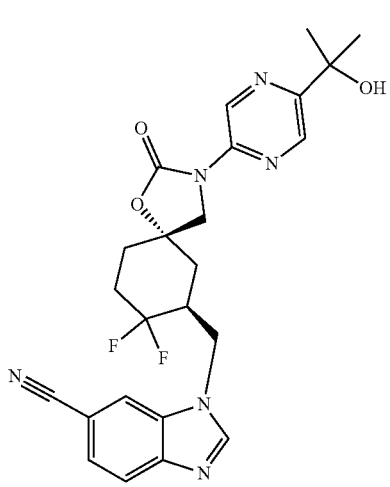
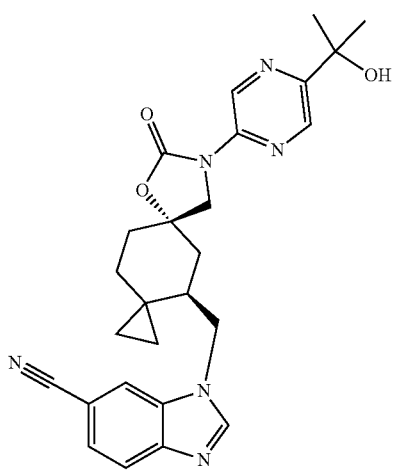
22
-continued
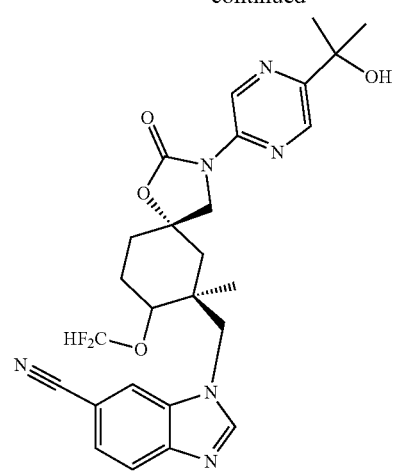
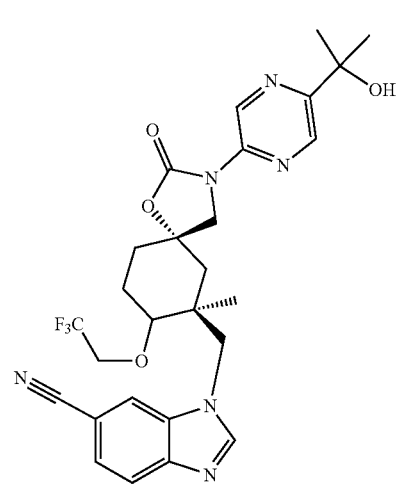
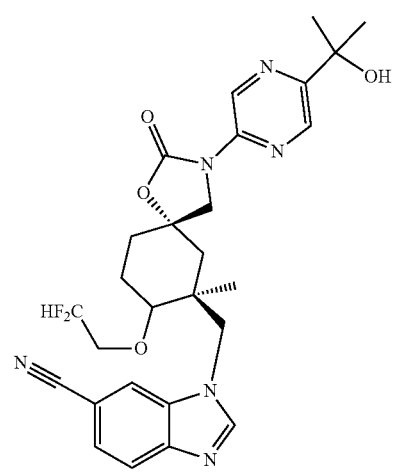
and -continued
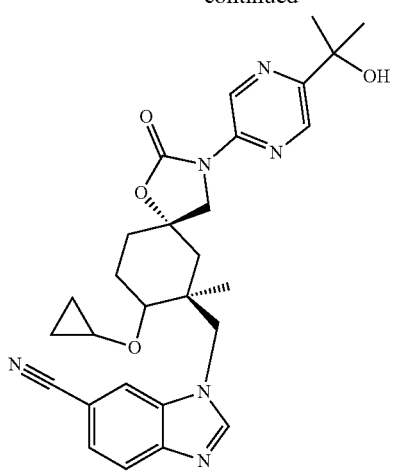
(absolute stereochemistry depicted)
and salts thereof.
In some embodiments, the compound or salt is selected from the group consisting of:
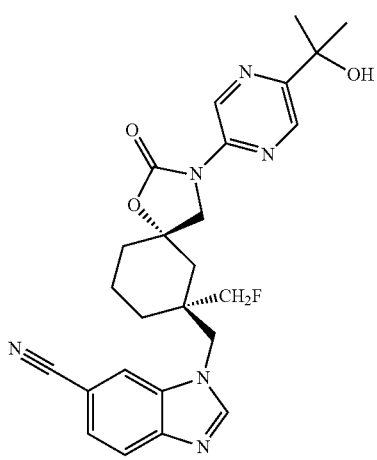
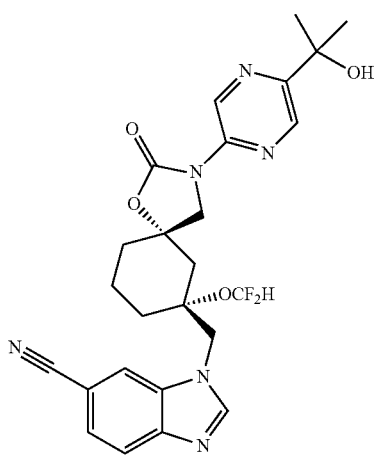
-continued
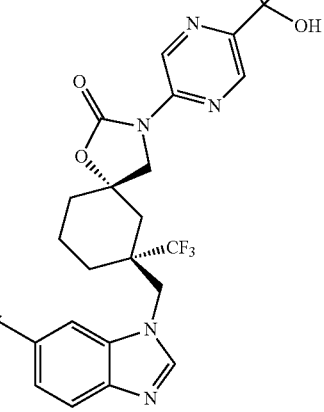
(absolute stereochemistry depicted)
and
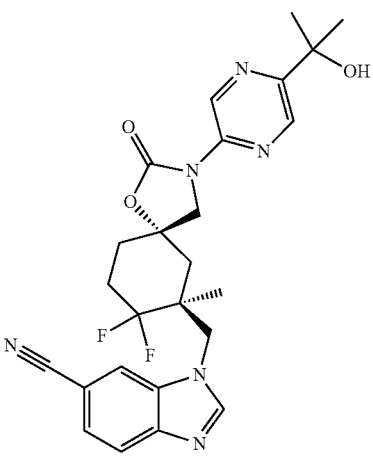
and salts thereof.
In some embodiments, the compound or salt is selected from the group consisting of:
and -continued
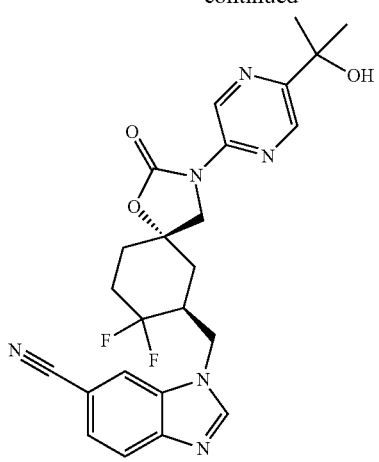
(absolute stereochemistry depicted)
and salts thereof.
In some embodiments, the compound or salt is selected from the group consisting of:
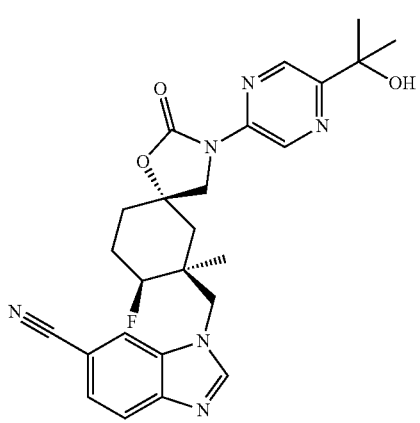
and
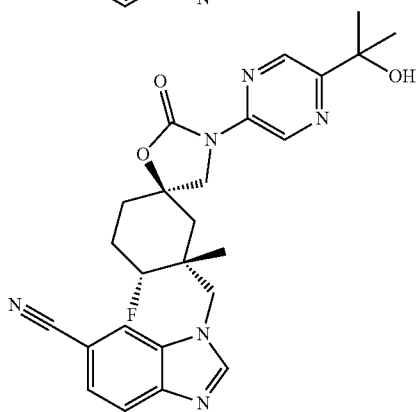
(absolute stereochemistry depicted)
and salts thereof.
In some embodiments, the compound or salt is selected from the group consisting of:
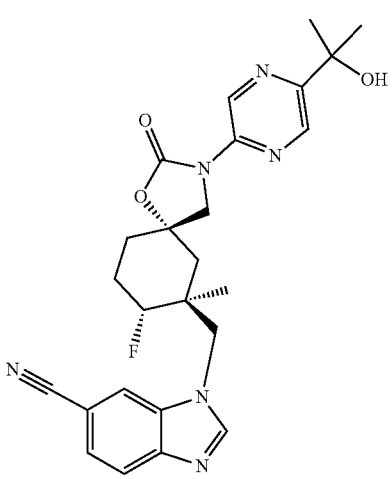
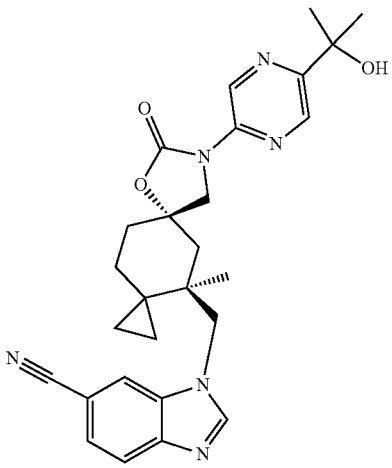
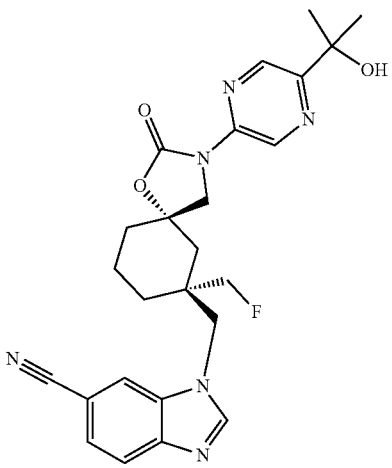

27
-continued
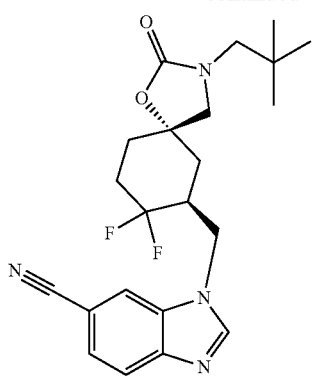
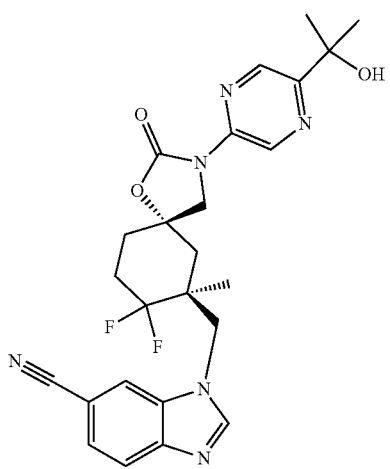
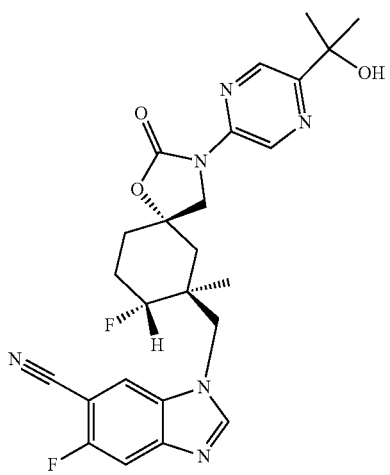
and
28
-continued
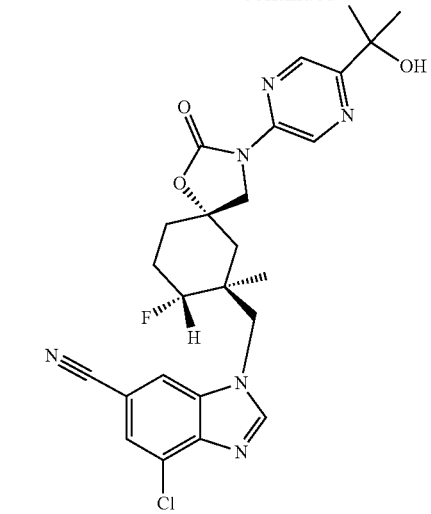 [SMILES: CC(C)(O)c1cnc(N2C[C@@]3(CC[C@@H](F)[C@](C)(Cn4cnc5c(Cl)cc(C#N)cc54)C3)OC2=O)cn1]
and salts thereof.
In some embodiments, the compound or salt is:
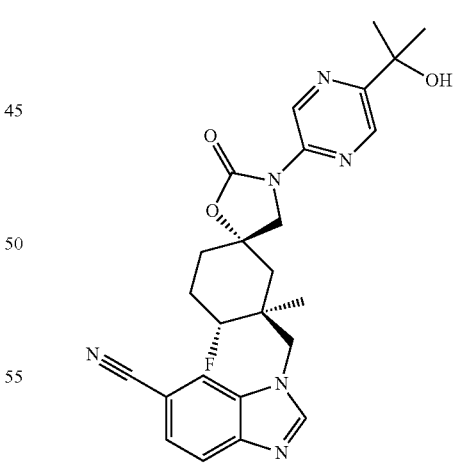
(absolute stereochemistry depicted)
or a salt thereof.

In some embodiments, the compound or salt is:

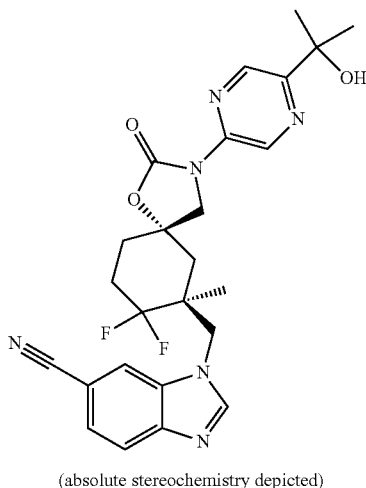 [SMILES: CC(C)(O)c1cnc(N2C[C@@]3(CCC(F)(F)[C@](C)(Cn4cnc5ccc(C#N)cc54)C3)OC2=O)cn1]

(absolute stereochemistry depicted)

or a salt thereof.

In some embodiments, the disclosure provides 1-(((5S,7S,8R)-8-fluoro-3-(5-(2-hydroxypropan-2-yl)pyrazin-2-yl)-7-methyl-2-oxo-1-oxa-3-azaspiro[4.5]decan-7-yl)methyl)-1H-benzo[d]imidazole-6-carbonitrile or a pharmaceutically acceptable salt thereof.

In some embodiments, the disclosure provides a compound of formula (I) or a salt thereof that has lower toxicity than GSK2798745.

In some embodiments, the disclosure provides a compound of formula (I) or a salt thereof that has improved potency compared to GSK2798745.

In some embodiments, the disclosure provides a compound of formula (I) or a salt thereof that has improved metabolic stability (e.g., against CYP3A4) compared to GSK2798745.

In some embodiments, the disclosure provides a compound of formula (I) or a salt thereof that has lower levels of active circulating metabolites than GSK2798745.

In some embodiments, the disclosure provides a compound of formula (I) or a salt thereof that has a higher safety maximum than GSK2798745.

In some embodiments, the disclosure provides a compound of formula (I) or a salt thereof that has improved metabolic stability (e.g., against CYP3A4) and similar or improved potency compared to GSK2798745.

In some embodiments, the disclosure provides a compound of formula (I) or a salt thereof that has improved metabolic stability (e.g., against CYP3A4) and similar or improved potency compared to GSK2798745.

In some embodiments, the disclosure provides a solid form of 1-(((5S,7S,8R)-8-fluoro-3-(5-(2-hydroxypropan-2-yl)pyrazin-2-yl)-7-methyl-2-oxo-1-oxa-3-azaspiro[4.5]decan-7-yl)methyl)-1H-benzo[d]imidazole-6-carbonitrile with one or more XRPD diffraction signals at about 7.04, about 7.07, about 7.09, about 10.33, about 10.35, about 18.87, or about 24.02 degree 2theta. In some embodiments, the disclosure provides a solid form of 1-(((5S,7S,8R)-8-fluoro-3-(5-(2-hydroxypropan-2-yl)pyrazin-2-yl)-7-methyl-2-oxo-1-oxa-3-azaspiro[4.5]decan-7-yl)methyl)-1H-benzo[d]imidazole-6-carbonitrile with XRPD diffraction signals at about 7.04, about 7.07, about 7.09, about 10.33, about 10.35, about 18.87, and about 24.02 degree 2theta. With respect to XRPD peaks, the term "about" means±0.01 degree 2theta.

In some embodiments, the disclosure provides a solid form of 1-(((5S,7S,8R)-8-fluoro-3-(5-(2-hydroxypropan-2-yl)pyrazin-2-yl)-7-methyl-2-oxo-1-oxa-3-azaspiro[4.5]decan-7-yl)methyl)-1H-benzo[d]imidazole-6-carbonitrile with an XRPD diffraction pattern substantially the same as that shown in FIG. 1. In some embodiments, "substantially the same" refers to an XRPD diffraction pattern that has at least three similar signals.

Processes for preparing compounds of formula I are provided as further embodiments of the disclosure and are illustrated by the following procedures in which the meanings of the generic radicals are as given above unless otherwise qualified.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts.

Salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Compounds of the disclosure can be administered alone or in conjunction with one or more other therapeutic agents, e.g., one or more agents selected from the group consisting of endothelin receptor antagonists, angiotensin converting enzyme (ACE) inhibitors, angiotension II receptor antagonists, vasopeptidase inhibitors, vasopressin receptor modulators, diuretics, digoxin, betablocker, aldosterone antagonists, ionotropes, NSAIDS, nitric oxide donors, calcium channel modulators, muscarinic antagonists, steroidal anti-inflammatory drugs, bronchodilators, anti-histamines, leukotriene antagonists, HMG-CoA reductase inhibitors, dual non-selective-adrenoceptor and al-adrenoceptor antagonists, type-5 phosphodiesterase inhibitors, and renin inhibitors.

Accordingly, in some embodiments the disclosure also provides a composition comprising a compound of formula I, or a pharmaceutically acceptable salt thereof, at least one other therapeutic agent, and a pharmaceutically acceptable diluent or carrier. The disclosure also provides a kit comprising a compound of formula I, or a pharmaceutically acceptable salt thereof, at least one other therapeutic agent, packaging material, and instructions for administering the compound of formula I or the pharmaceutically acceptable salt thereof and the other therapeutic agent or agents to an animal to treat a condition associated with TRPV4 modulation.

The biological activity of a compound can be determined using any suitable assay for evaluating TRPV4 antagonist activity, as well as using any suitable tissue or in vivo model. For example, the biological activity of a compound can be evaluated using the assays described in Example 23 herein, or using the assays and models described in International Patent Applications Publication Numbers WO2012/174340, WO2012/174342, WO2013/012500, and WO2017/199199.

Methods of Use

In some aspects, the present disclosure provides a method of modulating TRPV4 expression with a compound of the present disclosure or a salt thereof.

In some aspects, the present disclosure provides a method of modulating TRPV4 expression with a pharmaceutical compound comprising a compound of the present disclosure or a salt thereof.

In some aspects, the present disclosure provides a method of treating or preventing a disease or disorder disclosed herein in a subject in need thereof, comprising administering to the subject a therapeutically effective amount of a compound of the present disclosure or a salt thereof.

In some aspects, the present disclosure provides a method of treating a disease or disorder disclosed herein in a subject in need thereof, comprising administering to the subject a therapeutically effective amount of a compound of the present disclosure or a salt thereof, or a pharmaceutical composition of the present disclosure.

In some aspects, the present disclosure provides a method of treating or preventing a disease or disorder disclosed herein in a subject in need thereof, comprising administering to the subject a compound of the present disclosure or a salt thereof.

In some aspects, the present disclosure provides a method of treating a disease or disorder disclosed herein in a subject in need thereof, comprising administering to the subject a compound of the present disclosure or a salt thereof, or a pharmaceutical composition of the present disclosure.

In some aspects, the present disclosure provides a compound of the present disclosure or a pharmaceutically acceptable salt thereof, or a pharmaceutical composition of the present disclosure for use in modulating TRPV4 expression.

In some aspects, the present disclosure provides a compound of the present disclosure or a salt thereof, or a pharmaceutical composition of the present disclosure for use in treating or preventing a disease or disorder.

In some aspects, the present disclosure provides a compound of the present disclosure or a salt thereof for use in treating or preventing a disease or disorder disclosed herein.

In some aspects, the present disclosure provides a compound of the present disclosure or a salt thereof for use in treating a disease or disorder disclosed herein.

In some aspects, the present disclosure provides use of a compound of the present disclosure or a pharmaceutically acceptable salt thereof in the manufacture of a medicament for modulating TRPV4 expression.

In some aspects, the present disclosure provides use of a compound of the present disclosure or a salt thereof in the manufacture of a medicament for treating or preventing a disease or disorder disclosed herein.

In some aspects, the present disclosure provides use of a compound of the present disclosure or a salt thereof in the manufacture of a medicament for treating a disease or disorder disclosed herein.

In some embodiments, the disease or disorder is associated with an implicated TRPV4.

In some aspects, the present disclosure provides a method for treating a condition associated with TRPV4 modulation comprising administering a compound of the present disclosure, or a pharmaceutically acceptable salt thereof or a solid form thereof.

In some aspects, the present disclosure provides a compound of the present disclosure or a salt thereof or a solid form thereof for use in medical therapy.

In some aspects, the present disclosure provides a compound of the present disclosure or a salt thereof or a solid form thereof for the prophylactic or therapeutic treatment a condition associated with TRPV4 modulation.

In some aspects, the present disclosure provides the use of a compound of the present disclosure or a salt thereof or a solid form thereof to prepare a medicament for treating a condition associated with TRPV4 modulation in an animal.

In some embodiments, the salt thereof is a pharmaceutically acceptable salt thereof.

In some embodiments, the compound is administered to a subject.

In some embodiments, the compound is administered to an animal.

In some embodiments, the subject is an animal.

In some embodiments, the subject is a human.

In some embodiments, the disease or disorder is a respiratory disease or disorder.

In some embodiments, the disease or disorder is a chronic cough, pulmonary edema, chronic obstructive pulmonary disease or pulmonary fibrosis.

In some embodiments, the disease or disorder is inflammatory hyperalgesia.

In some embodiments, the disease or disorder is a mechanical pain.

In some embodiments, the disease or disorder is a neuropathic pain.

In some embodiments, the disease or disorder is a bladder related condition.

In some embodiments, the disease or disorder is a respiratory disease, joint disease, pain, or bladder dysfunction.

In some embodiments, the disease or disorder is a joint disease.

In some embodiments, the disease or disorder is a pain.

In some embodiments, the disease or disorder is bladder dysfunction.

In some embodiments, the disease or disorder is a Mendelian diseases.

In some embodiments, the disease or disorder is skeletal dysplasia.

In some embodiments, modulation is inhibition.

In some embodiments, modulation is antagonism.

Methods of Synthesis Compounds of formula (I) can be prepared using the synthetic methods and intermediates described in the Examples below. Compounds of formula (I) can also be prepared using known synthetic methods and intermediate compounds, including, for example, the synthetic methods and intermediate compounds described in International Patent Applications Publication Numbers WO2012/174340, WO2012/174342, WO2013/012500, and WO2017/199199. Schemes 1-6 illustrate intermediates and methods that can be used to prepare compounds of formula (I).

Scheme 1

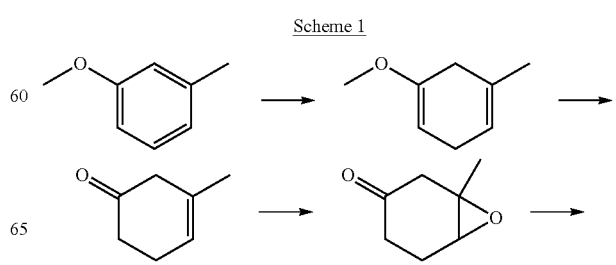

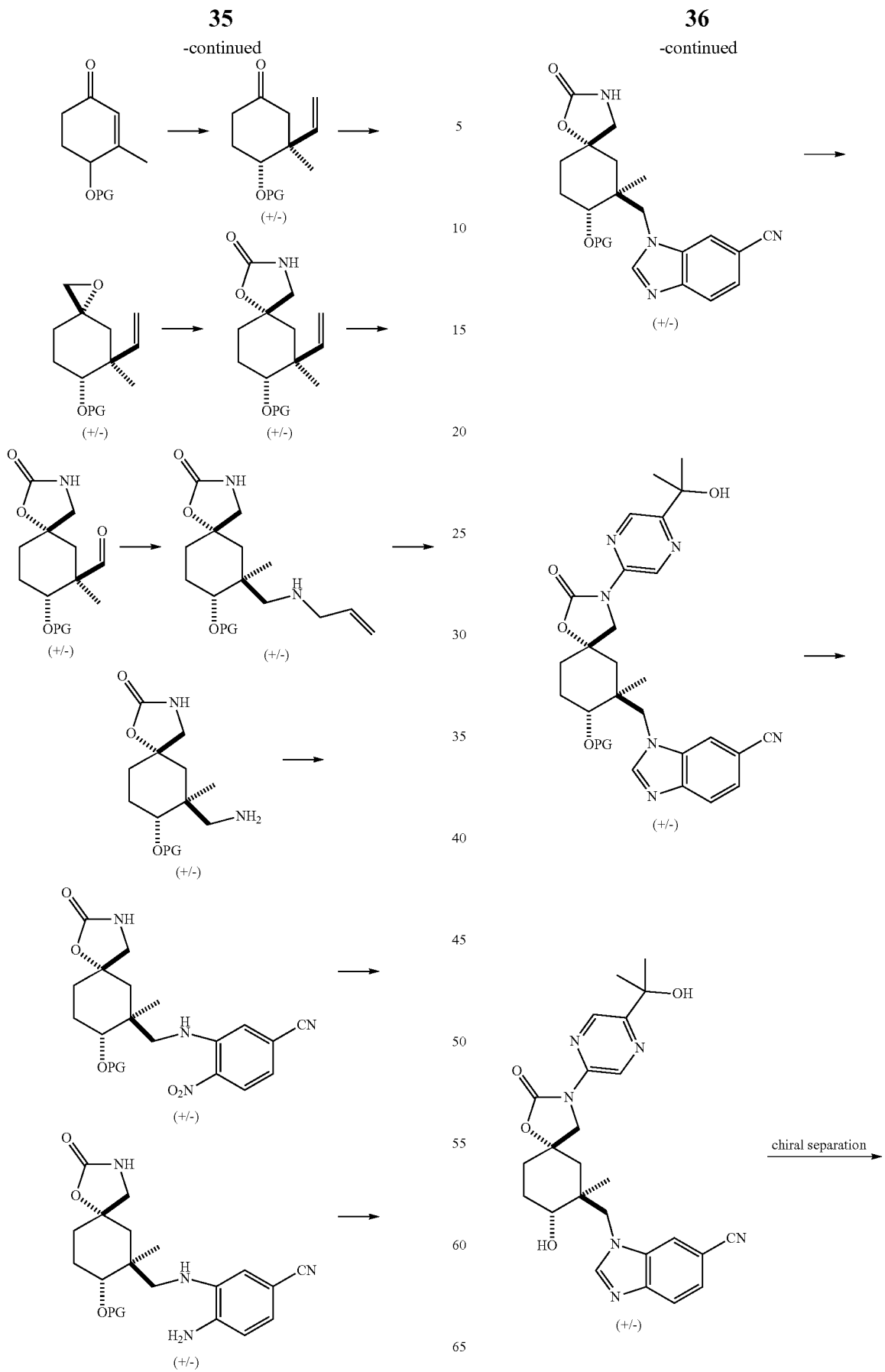

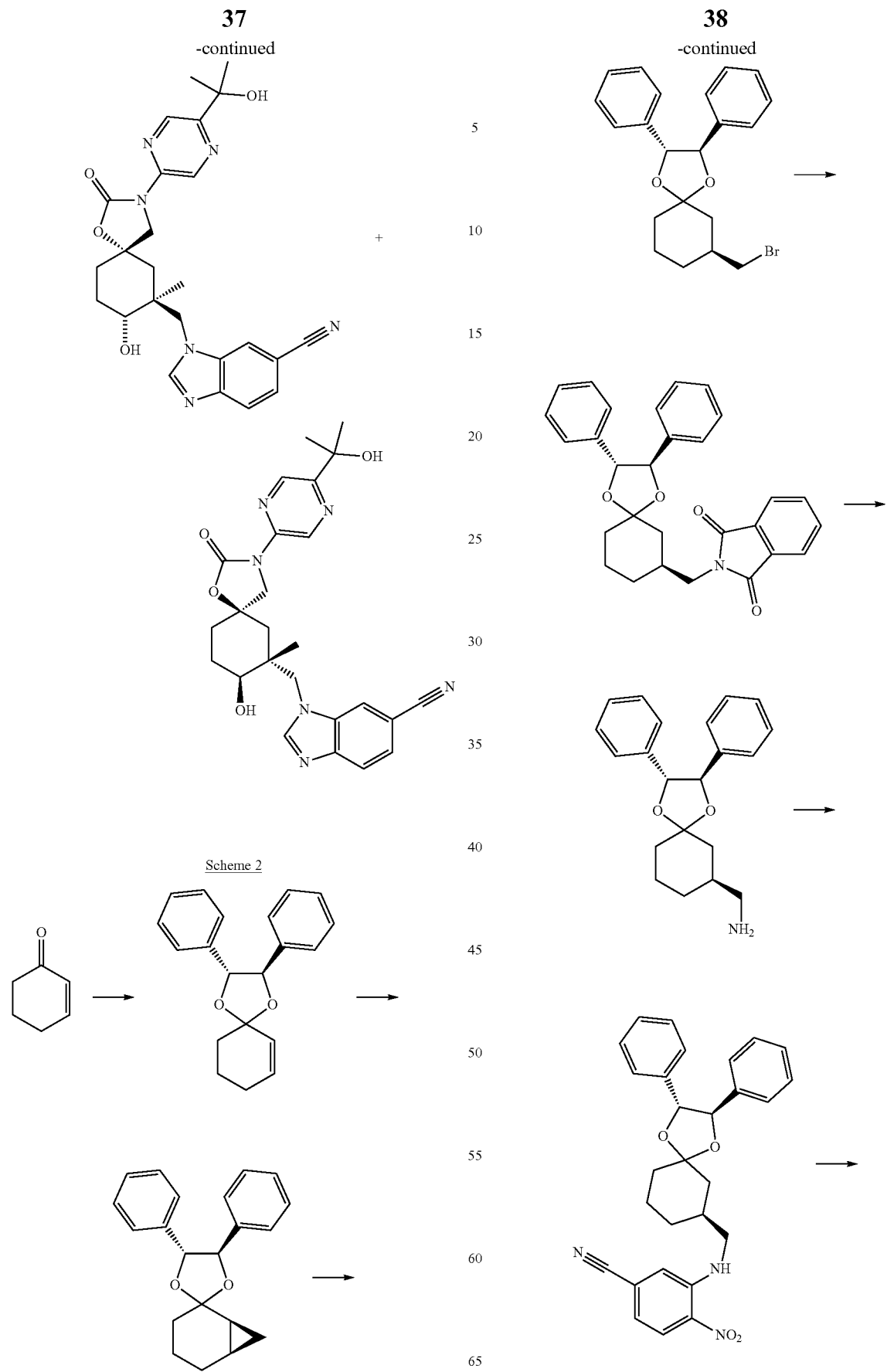

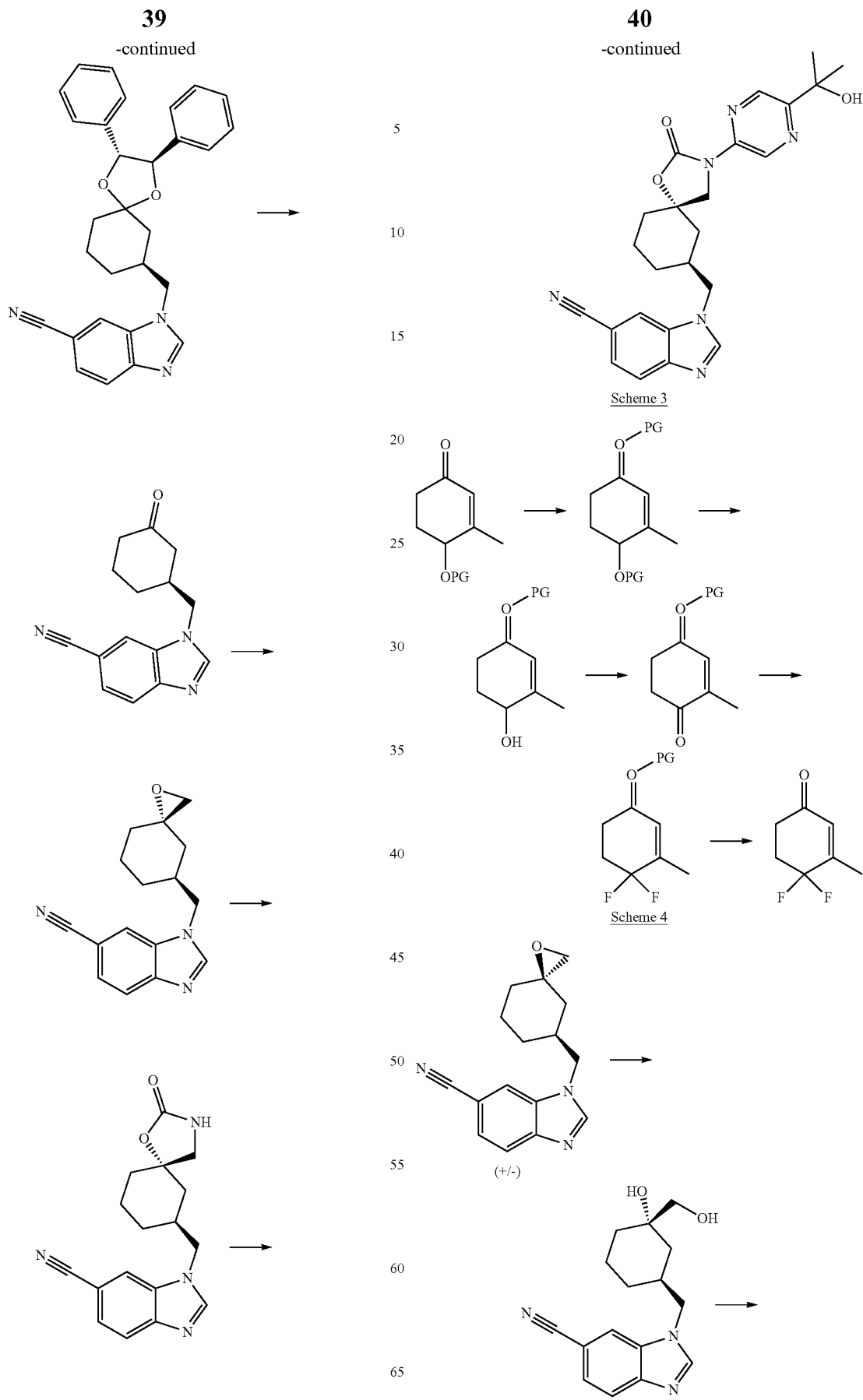

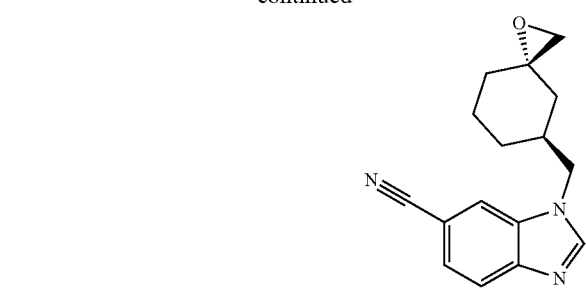
Scheme 5
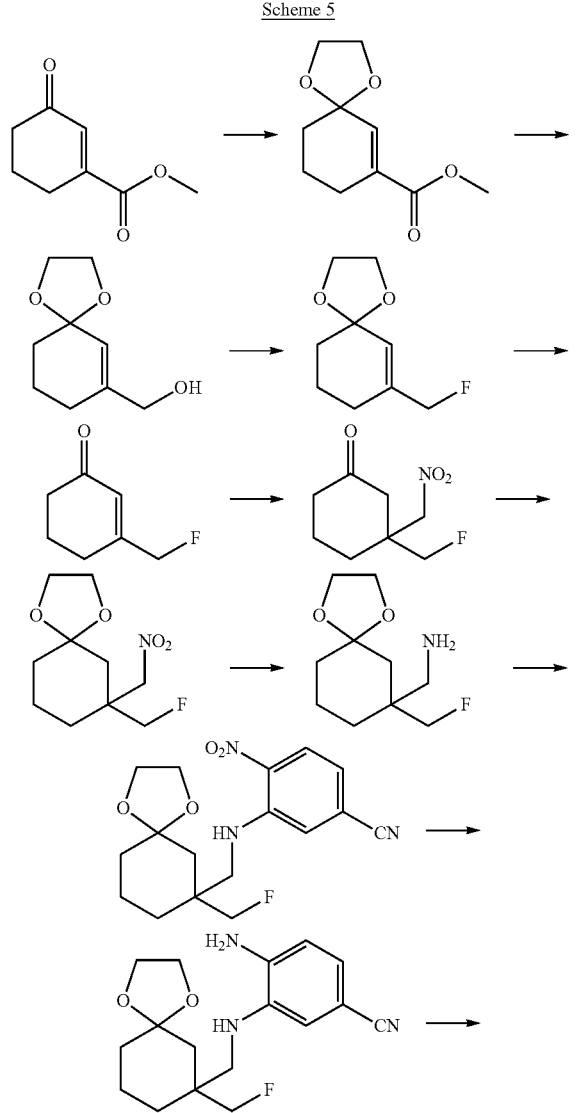
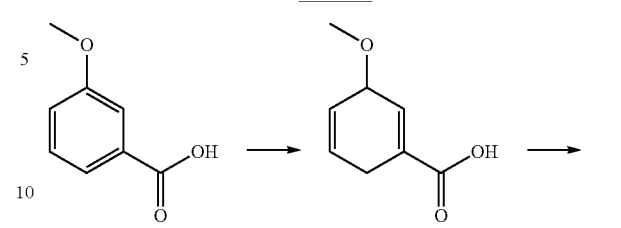
Scheme 6
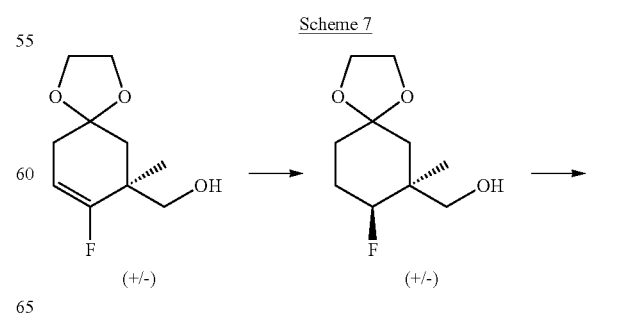
Scheme 7

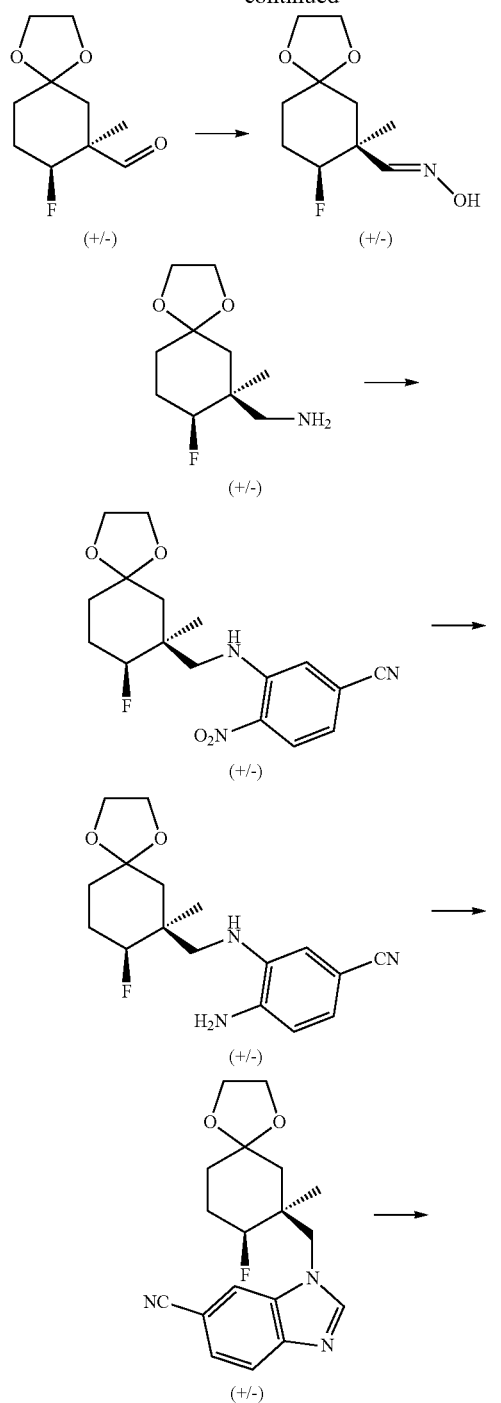

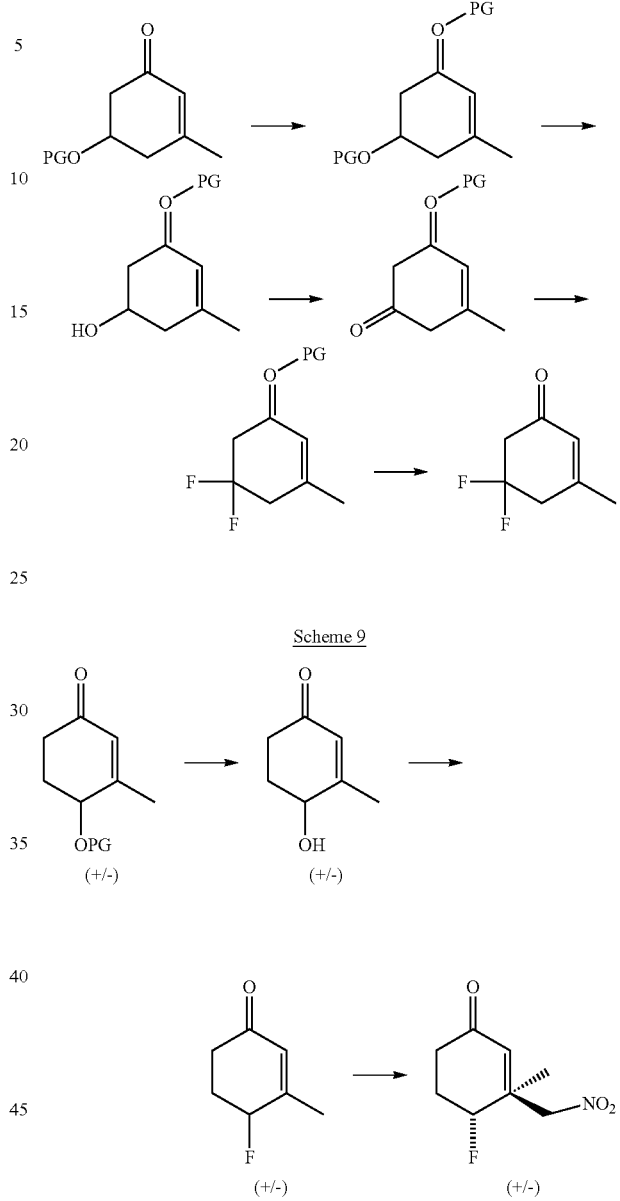

The disclosure will now be illustrated by the following non-limiting Examples.

EXAMPLES

For exemplary purpose, neutral compounds of Formula (I) are synthesized and tested in the examples. It is understood that the neutral compounds of Formula (I) may be converted to the corresponding salts of the compounds using routine techniques in the art (e.g., by saponification of an ester to the carboxylic acid salt, or by hydrolyzing an amide to form a corresponding carboxylic acid and then converting the carboxylic acid to a carboxylic acid salt).

Example 1. Preparation of: 1-(((5S,7R)-3-(5-(2-Hydroxypropan-2-yl)pyrazin-2-yl)-8,8-dimethyl-2-oxo-1-oxa-3-azaspiro[4.5]decan-7-yl)methyl)-1H-benzo[d]imidazole-6-carbonitrile
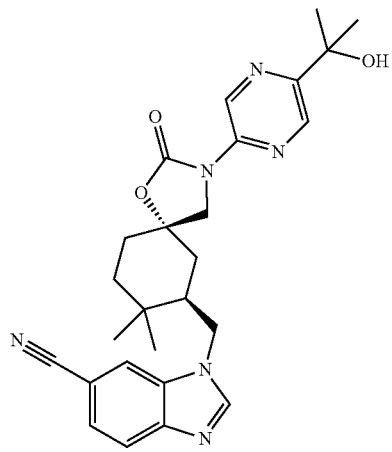 [SMILES: CC(C)(O)c1cnc(N2C[C@@]3(CCC(C)(C)[C@H](Cn4cnc5ccc(C#N)cc54)C3)OC2=O)cn1]
Reaction Scheme
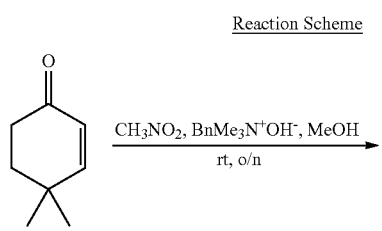
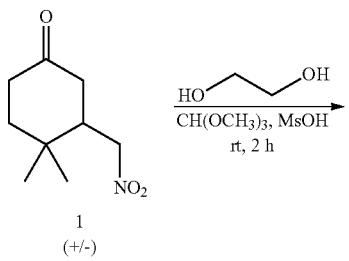
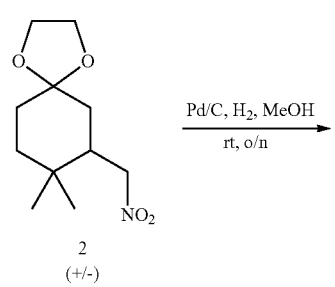
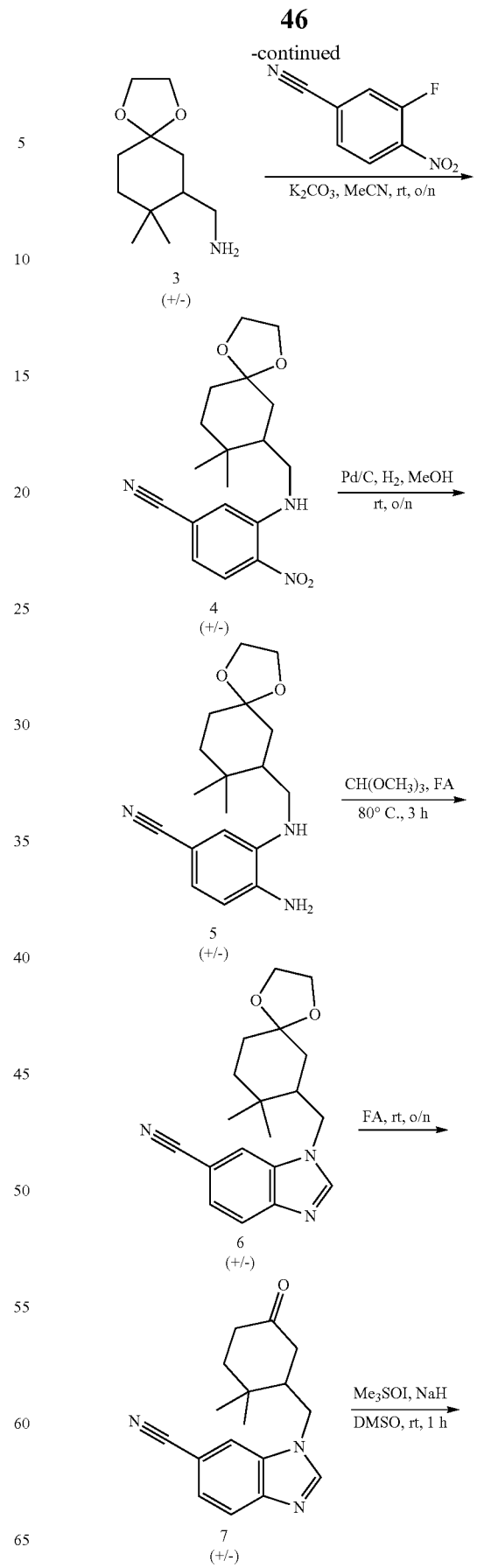

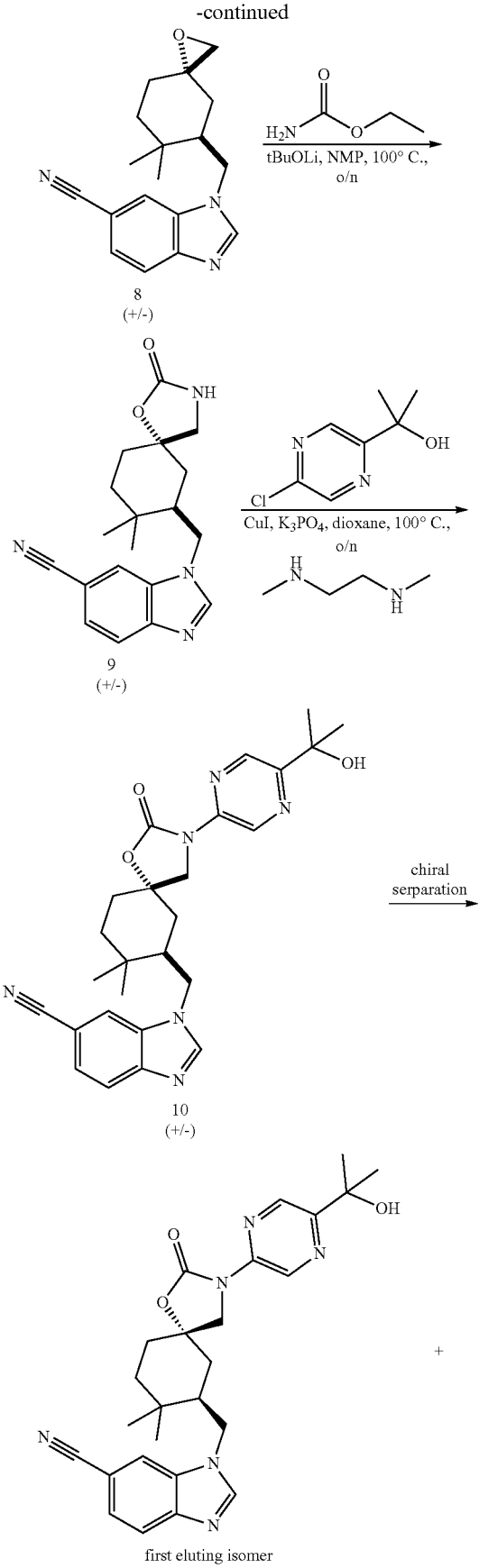

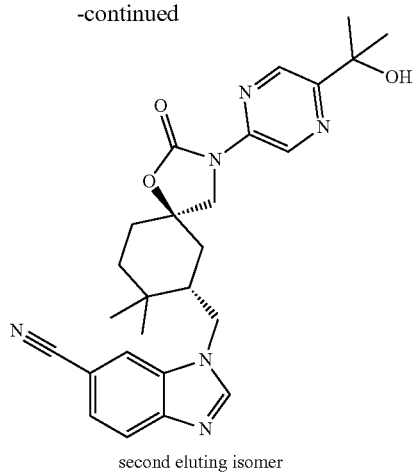

second eluting isomer

Detailed Procedure rac-4,4-Dimethyl-3-(nitromethyl)cyclohexan-1-one

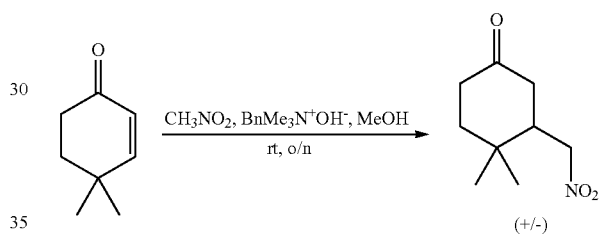

Nitromethane (3.83 g, 62.81 mmol, 1.2 eq.) was added to a solution of 4,4-dimethylcyclohex-2-en-1-one (6.50 g, 52.34 mmol, 1 eq.) and benzyltrimethylammonium hydroxide (13.13 g, 78.51 mmol, 1.5 eq.) in methanol (60 mL). The resulting mixture was stirred overnight at the room temperature and concentrated under vacuum to afford the crude product. The residue was purified by silica gel column chromatography, eluted with ethyl acetate in petroleum ether from 0% to 10%. The fractions were combined and concentrated under vacuum to afford the desired product 4,4-dimethyl-3-(nitromethyl)cyclohexan-1-one (6.70 g, 46% yield) as a light yellow oil.

rac-8,8-Dimethyl-7-(nitromethyl)-1,4-dioxaspiro[4.5]decane

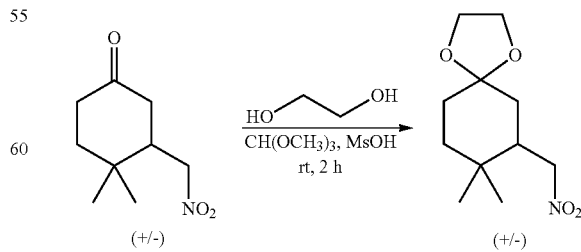

Ethylene glycol (3.37 g, 54.26 mmol, 1.5 eq.) was added to a solution of 4,4-dimethyl-3-(nitromethyl)-cyclohexan-1- one (6.70 g, 36.17 mmol, 1 eq.) and trimethoxymethane (5.76 g, 54.26 mmol, 1.5 eq.) in dichloromethane (100 mL). The resulting reaction mixture was stirred at room temperature for 5 minutes, then cooled to 0° C. in an ice bath. To this mixture was added methanesulfonic acid (0.52 g, 5.42 mmol, 0.15 eq.) dropwise. The resulting mixture was removed from the bath and allowed to warm to room temperature and stirred for 2 hours. The reaction mixture was concentrated under vacuum. The residue was purified by silica gel column chromatography, eluted with ethyl acetate in petroleum ether from 0% to 10%. The fractions were combined and concentrated under vacuum to afford the desired product rac-8,8-dimethyl-7-(nitromethyl)-1,4-dioxaspiro[4.5]decane (6 g, 72.3% yield) as a light yellow oil. $^1$H NMR (400 MHz, DMSO-$d_6$) δ 4.73 (dd, J=12.6, 3.9 Hz, 1H), 4.25 (dd, J=12.6, 10.1 Hz, 1H), 3.85-3.82 (m, 4H), 2.17 (dd, J=12.0, 10.1 Hz, 1H), 1.58-1.42 (m, 5H), 1.39-1.33 (m, 1H), 0.96 (s, 3H), 0.80 (s, 3H).

rac-(8,8-Dimethyl-1,4-dioxaspiro[4.5]decan-7-yl)methanamine

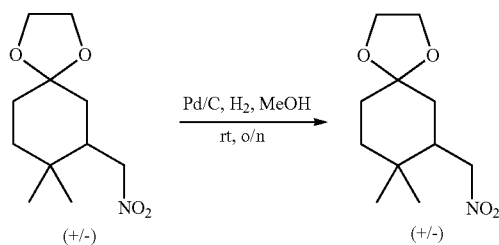 [SMILES: CC1(C)CCC2(CC1C[N+](=O)[O-])OCCO2 ; CC1(C)CCC2(CC1C[N+](=O)[O-])OCCO2]

Palladium on carbon (10%, 0.28 g, 2.62 mmol, 0.1 eq.) was added to a solution of rac-8,8-dimethyl-7-(nitromethyl)-1,4-dioxaspiro[4.5]decane (6.0 g, 26.17 mmol, 1 eq.) in methanol (60 mL). The resulting mixture was stirred overnight at the room temperature under a hydrogen atmosphere. The resulting mixture was filtered, the filter cake was washed with methanol (3×100 mL). The filtrate was concentrated under reduced pressure to afford the crude product rac-(8,8-dimethyl-1,4-dioxaspiro[4.5]decan-7-yl)methanamine (6 g crude) as a colorless oil.

LCMS (ESI-MS) m/z=200 [M+H]$^+$.

rac-3-(((8,8-Dimethyl-1,4-dioxaspiro[4.5]decan-7-yl)methyl)amino)-4-nitrobenzonitrile

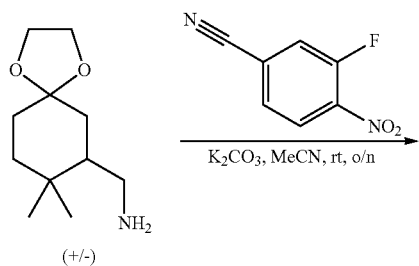

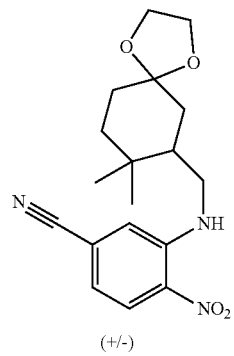

Potassium carbonate (8.32 g, 60.21 mmol, 2 eq.) was added to a solution of rac-(8,8-dimethyl-1,4-dioxaspiro[4.5]decan-7-yl)methanamine (6 g, 30.1 mmol, 1 eq.) and 3-fluoro-4-nitrobenzonitrile (5 g, 30.1 mmol, 1 eq.) in acetonitrile (60 mL). The resulting mixture was stirred overnight at room temperature. The reaction mixture was diluted with water (100 mL) and extracted with ethyl acetate (3×100 mL). The combined organic layers were dried over anhydrous sodium sulfate, filtered and the filtrate was concentrated under vacuum to afford the crude product. The residue was purified by silica gel column chromatography, eluted with ethyl acetate in petroleum ether from 0% to 10% and concentrated under vacuum to afford the desired product rac-3-(((8,8-dimethyl-1,4-dioxaspiro[4.5]decan-7-yl)methyl)amino)-4-nitrobenzonitrile (7 g, 67.3% yield) as an orange solid. $^1$H NMR (400 MHz, DMSO-$d_6$) δ 8.38-8.31 (m, 1H), 8.18 (dd, J=17.2, 8.6 Hz, 1H), 8.10-7.96 (m, 2H), 3.94-3.79 (m, 4H), 3.55-3.49 (m, 1H), 3.14-3.06 (m, 1H), 1.85-1.30 (m, 7H), 1.07-0.89 (m, 6H). LCMS (ESI-MS) m/z=346 [M+H]$^+$.

rac-4-Amino-3-(((8,8-dimethyl-1,4-dioxaspiro[4.5]decan-7-yl)methyl)amino)benzonitrile

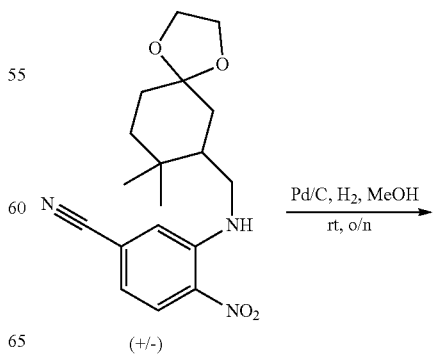

-continued

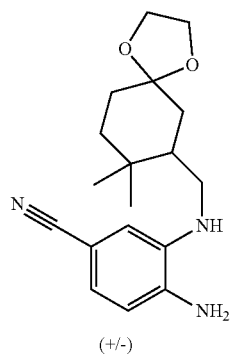
(+/-)

Palladium on carbon (10%, 0.22 g, 2.03 mmol, 0.1 eq.) was added to a solution of rac-3-(((8,8-dimethyl-1,4-dioxaspiro[4.5]decan-7-yl)methyl)amino)-4-nitrobenzonitrile (7 g, 20.27 mmol, 1 eq.) in methanol (70 mL). The resulting mixture was stirred overnight at room temperature under a hydrogen atmosphere. The resulting mixture was filtered, the filter cake was washed with methanol (3×100 mL). The filtrate was concentrated under reduced pressure to afford the crude product rac-4-amino-3-(((8,8-dimethyl-1,4-dioxaspiro[4.5]decan-7yl)methyl)amino)benzonitrile (6 g crude) as a colorless oil. LCMS (ESI-MS) m/z=316 [M+H]$^+$.

rac-1-((8,8-Dimethyl-1,4-dioxaspiro[4.5]decan-7-yl)methyl)-1H-benzo[d]imidazole-6-carbonitrile

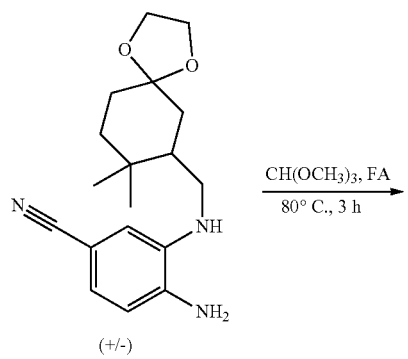

Formic acid (0.88 g, 19.02 mmol, 1 eq.) was added to a solution of rac-4-amino-3-(((8,8-dimethyl-1,4-dioxaspiro[4.5]decan-7-yl)methyl)amino)benzonitrile (6 g, 19.02 mmol, 1 eq.) in trimethoxymethane (58.54 g, 551.64 mmol, 29 eq.). The resulting mixture was heated to 80° C., stirred for 3 hours and concentrated under vacuum to afford the crude product. The residue was purified by silica gel column chromatography, eluted with ethyl acetate in petroleum ether from 0% to 100%. The fractions with desired mass signal were combined and concentrated under vacuum to afford the desired product rac-1-((8,8-dimethyl-1,4-dioxaspiro[4.5]decan-7-yl)methyl)-1H-benzo[d]imidazole-6-carbonitrile (4 g, 60.6% yield for 2 steps) as a white solid. LCMS (ESI-MS) m/z=326 [M+H]$^+$.

rac-1-((2,2-Dimethyl-5-oxocyclohexyl)methyl)-1H-benzo[d]imidazole-6-carbonitrile

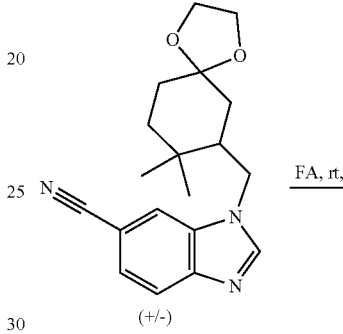
(+/-)

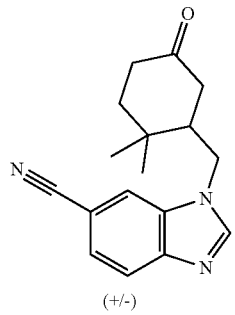
(+/-)

A solution of rac-1-((8,8-dimethyl-1,4-dioxaspiro[4.5]decan-7-yl)methyl)-1H-benzo[d]imidazole-6-carbonitrile (3.80 g, 11.68 mmol, 1 eq.) in formic acid (50 mL) was stirred overnight at the room temperature. The reaction mixture was diluted with saturated sodium bicarbonate aqueous solution (100 mL) and extracted with ethyl acetate (3×100 mL). The combined organic layers were washed with brine, dried over anhydrous sodium sulfate, filtered and concentrated under vacuum to afford the crude product rac-1-((2,2-dimethyl-5-oxocyclohexyl)methyl)-1H-benzo[d]imidazole-6-carbonitrile (3.50 g crude) as a white solid. LCMS (ESI-MS) m/z=282 [M+H]$^+$.

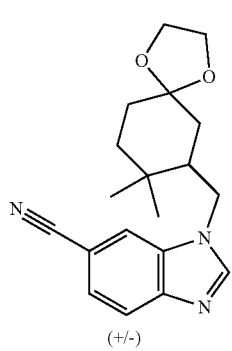
(+/-)

rac-1-(((3S,5R)-6,6-Dimethyl-1-oxaspiro[2.5]octan-5-yl)methyl)-1H-benzo[d]imidazole-6-carbonitrile

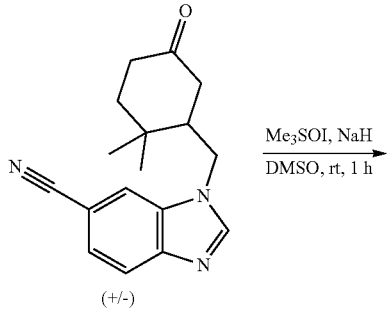

Sodium hydride (60% in oil, 1.19 g, 49.76 mmol, 4 eq.) was added to a solution of trimethylsulfoxonium iodide (10.95 g, 49.76 mmol, 4 eq.) in dimethyl sulfoxide (100 mL) and the resulting mixture was stirred at room temperature for 30 minutes. To this mixture was added a solution of rac-1-((2,2-dimethyl-5-oxocyclohexyl)methyl)-1H-benzo[d]imidazole-6-carbonitrile (3.50 g, 12.44 mmol, 1 eq.) in dimethyl sulfoxide (35 mL) dropwise. After 8 minutes, the reaction mixture was cooled to 0° C., quenched slowly with 200 mL water and extracted with ethyl acetate (3×200 mL). The combined organic layers were washed with brine, dried over anhydrous sodium sulfate, filtered and concentrated under vacuum to afford the crude product rac-1-(((3S,5R)-6,6-Dimethyl-1-oxaspiro[2.5]octan-5-yl)methyl)-1H-benzo[d]imidazole-6-carbonitrile (3 g crude) as a yellow oil. LCMS (ESI-MS) m/z=296 [M+H]+.

rac-1-(((5S,7R)-8,8-Dimethyl-2-oxo-1-oxa-3-azaspiro[4.5]decan-7-yl)methyl)-1H-benzo[d]imidazole-6-carbonitrile

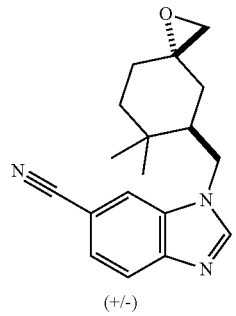
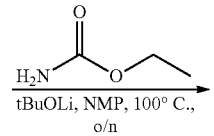

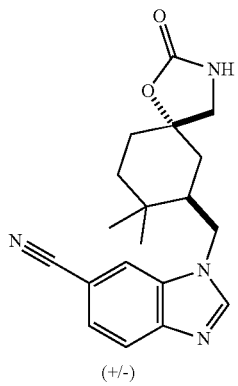

Lithium tert-butoxide (1.63 g, 20.31 mmol, 2 eq.) was added to a solution of ethyl carbamate (18.10 g, 203.12 mmol, 20 eq.) in N-methyl pyrrolidone (10 mL). After stirring for 5 minutes at room temperature, a solution of rac-1-(((3S,5R)-6,6-dimethyl-1-oxaspiro[2.5]octan-5-yl)methyl)-1H-benzo[d]imidazole-6-carbonitrile (3 g, 10.16 mmol, 1 eq.) in N-methyl pyrrolidone (10 mL) was added dropwise. The reaction mixture was subsequently heated to 100° C. and stirred overnight. After cooling to room temperature, the reaction mixture was diluted with water (100 mL) and extracted with ethyl acetate (3×100 mL). The combined organic layers were dried over anhydrous sodium sulfate, filtered and the filtrate was concentrated under vacuum to afford the crude product. The residue was purified by silica gel column chromatography, eluted with methanol in dichloromethane from 0% to 2% and concentrated under vacuum to afford the desired product rac-1-(((5S,7R)-8,8-dimethyl-2-oxo-1-oxa-3-azaspiro[4.5]decan-7-yl)methyl)-1H-benzo[d]imidazole-6-carbonitrile (3 g, 75.9% yield for 3 steps) as a white solid. LCMS (ESI-MS) m/z=339 [M+H]+.

rac-1-(((5S,7R)-3-(5-(2-Hydroxypropan-2-yl)pyrazin-2-yl)-8,8-dimethyl-2-oxo-1-oxa-3-azaspiro[4.5]decan-7-yl)methyl)-1H-benzo[d]imidazole-6-carbonitrile

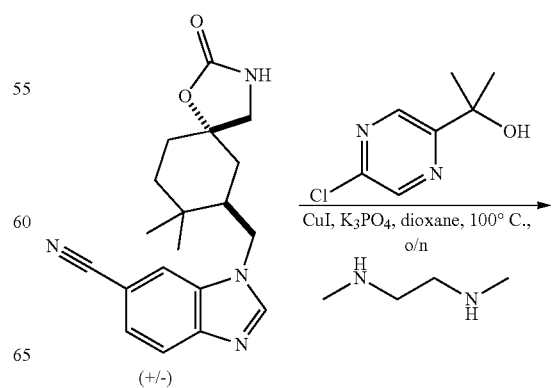

-continued

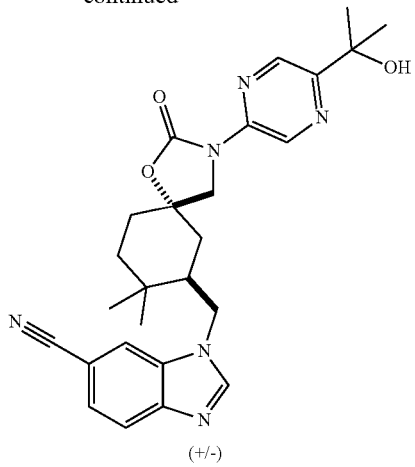
(+/-)

Copper (I) iodide (562.78 mg, 2.95 mmol, 1 eq.) was added to a solution of rac-1-(((5S,7R)-8,8-dimethyl-2-oxo-1-oxa-3-azaspiro[4.5]decan-7-yl)methyl)-1H-benzo[d]imidazole-6-carbonitrile (1 g, 2.95 mmol, 1 eq.), 2-(5-chloropyrazin-2-yl)propan-2-ol (0.51 g, 2.95 mmol, 1 eq.), $N^1,N^2$-dimethylethane-1,2-diamine (0.52 g, 5.91 mmol, 2 eq.) and tripotassium phosphate (1.25 g, 5.91 mmol, 2 eq.) in 1,4-dioxane (10 mL) under a nitrogen atmosphere. The resulting mixture was heated to 100° C. and stirred overnight. After cooling to room temperature, the resulting mixture was filtered and the filtrate was concentrated under vacuum. The residue was purified by silica gel column chromatography, eluted with methanol in dichloromethane from 0% to 4%. The fractions were combined and concentrated under vacuum to afford the desired product rac-1-(((5S,7R)-3-(5-(2-hydroxypropan-2-yl)pyrazin-2-yl)-8,8-dimethyl-2-oxo-1-oxa-3-azaspiro[4.5]decan-7-yl)methyl)-1H-benzo[d]imidazole-6-carbonitrile (800 mg, 57.1% yield) as a light yellow solid. $^1$H NMR (400 MHz, DMSO-d6) δ 9.10 (d, J=1.5 Hz, 1H), 8.56-8.54 (m, 2H), 8.22 (d, J=1.4 Hz, 1H), 7.81 (d, J=8.4 Hz, 1H), 7.59 (dd, J=8.4, 1.5 Hz, 1H), 5.38 (s, 1H), 4.52 (dd, J=14.2, 3.7 Hz, 1H), 4.07 (dd, J=14.3, 11.1 Hz, 1H), 3.86 (d, J=10.2 Hz, 1H), 3.75 (d, J=10.2 Hz, 1H), 2.11 (dd, J=15.1, 12.7 Hz, 1H), 1.87-1.64 (m, 4H), 1.42 (d, J=1.7 Hz, 8H), 1.20 (s, 3H), 1.01 (s, 3H). LCMS (ESI-MS) m/z=475 [M+H]$^+$.

1-(((5S,7R)-3-(5-(2-Hydroxypropan-2-yl)pyrazin-2-yl)-8,8-dimethyl-2-oxo-1-oxa-3-azaspiro[4.5] decan-7-yl)methyl)-1H-benzo[d]imidazole-6-carbonitrile and 1-(((5R,7S)-3-(5-(2-Hydroxypropan-2-yl)pyrazin-2-yl)-8,8-dimethyl-2-oxo-1-oxa-3-azaspiro[4.5]decan-7-yl)methyl)-1H-benzo[d]imidazole-6-carbonitrile

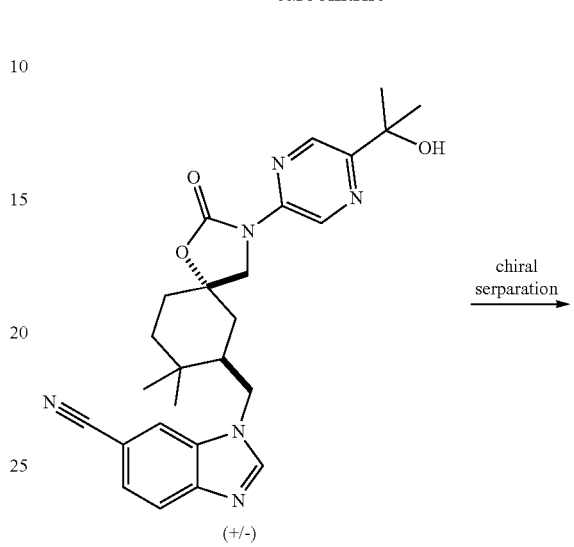
(+/-)

chiral serparation →

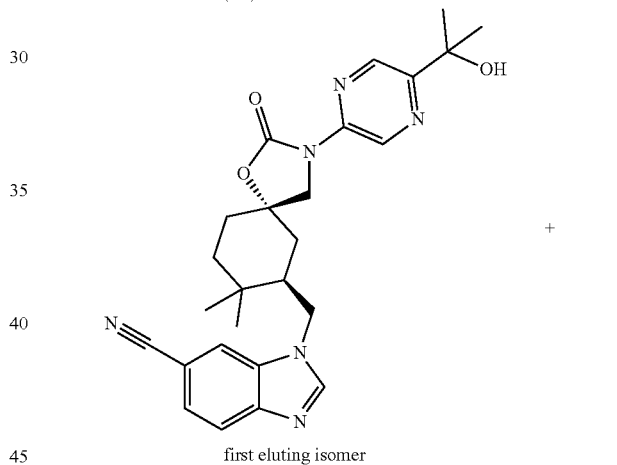
first eluting isomer

+

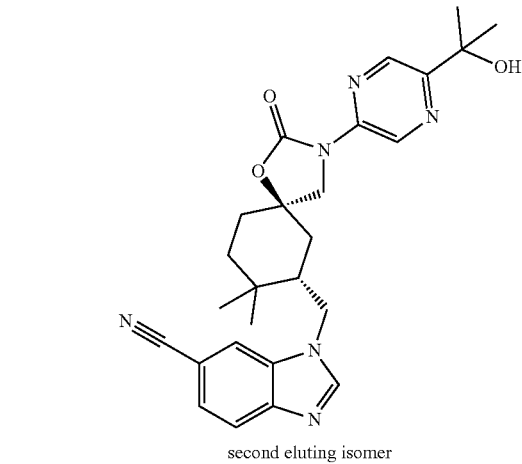
second eluting isomer rac-1-((((5S,7R)-3-(5-(2-Hydroxypropan-2-yl)pyrazin-2-yl)-8,8-dimethyl-2-oxo-1-oxa-3-azaspiro[4.5]decan-7-yl)methyl)-1H-benzo[d]imidazole-6-carbonitrile (800 mg, 1.68 mmol, 1 eq.) was separated by Prep-Chiral-HPLC with the condition: Column: CHIRALPAK IE, 2*25 cm, 5 μm; Mobile Phase A: MtBE (0.5% 2M NH$_3$-MeOH)-HPLC, Mobile Phase B: EtOH-HPLC; Flow rate: 15 mL/min; Gradient: 50% B to 50% B in 15 min; Wave Length: 220/254 nm; RT1(min): 7.11; RT2(min): 11.56; Sample Solvent: EtOH-HPLC; Injection Volume: 1 mL. The desired fractions were combined and lyophilized to afford the products:

First eluting isomer: 1-(((5S,7R)-3-(5-(2-Hydroxypropan-2-yl)pyrazin-2-yl)-8,8-dimethyl-2-oxo-1-oxa-3-azaspiro[4.5]decan-7-yl)methyl)-1H-benzo[d]imidazole-6-carbonitrile (228.7 mg, 96.6% purity, 100% ee, 28.5% yield) as a white solid. Confirmed by Xray crystal structure. $^1$H NMR (400 MHz, DMSO-d$_6$) δ 9.10 (d, J=1.5 Hz, 1H), 8.56-8.54 (m, 2H), 8.22 (d, J=1.4 Hz, 1H), 7.81 (d, J=8.4 Hz, 1H), 7.59 (dd, J=8.4, 1.5 Hz, 1H), 5.38 (s, 1H), 4.52 (dd, J=14.2, 3.7 Hz, 1H), 4.07 (dd, J=14.3, 11.1 Hz, 1H), 3.86 (d, J=10.2 Hz, 1H), 3.75 (d, J=10.2 Hz, 1H), 2.11 (dd, J=15.1, 12.7 Hz, 1H), 1.87-1.64 (m, 4H), 1.42 (d, J=1.7 Hz, 8H), 1.20 (s, 3H), 1.01 (s, 3H). LCMS (ESI-MS) m/z=475 [M+H]$^+$.

Second eluting isomer: 1-(((5R,7S)-3-(5-(2-Hydroxypropan-2-yl)pyrazin-2-yl)-8,8-dimethyl-2-oxo-1-oxa-3-azaspiro[4.5]decan-7-yl)methyl)-1H-benzo[d]imidazole-6-carbonitrile (213.1 mg, 99.9% purity, 100% ee, 26.6% yield) as a white solid. $^1$H NMR (400 MHz, DMSO-d$_6$) δ 9.10 (d, J=1.5 Hz, 1H), 8.56-8.54 (m, 2H), 8.22 (d, J=1.4 Hz, 1H), 7.81 (d, J=8.4 Hz, 1H), 7.59 (dd, J=8.4, 1.5 Hz, 1H), 5.38 (s, 1H), 4.52 (dd, J=14.2, 3.7 Hz, 1H), 4.07 (dd, J=14.3, 11.1 Hz, 1H), 3.86 (d, J=10.2 Hz, 1H), 3.75 (d, J=10.2 Hz, 1H), 2.11 (dd, J=15.1, 12.7 Hz, 1H), 1.87-1.64 (m, 4H), 1.42 (d, J=1.7 Hz, 8H), 1.20 (s, 3H), 1.01 (s, 3H). LCMS (ESI-MS) m/z=475 [M+H]$^+$.

Example 2. Preparation of: 1-(((5S,7S)-8,8-Difluoro-3-(5-(2-hydroxypropan-2-yl)pyrazin-2-yl)-2-oxo-1-oxa-3-azaspiro[4.5]decan-7-yl)methyl)-1H-benzo[d]imidazole-6-carbonitrile

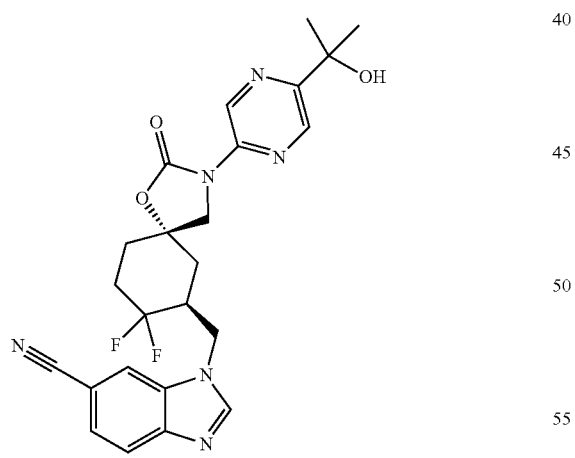

Reaction Scheme

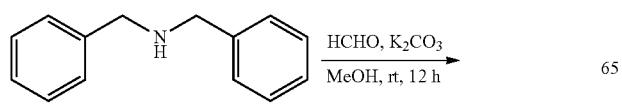

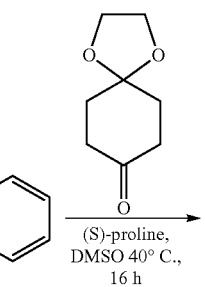

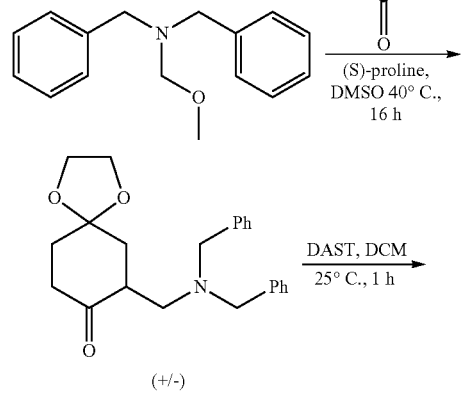

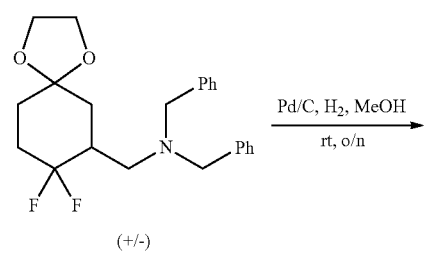

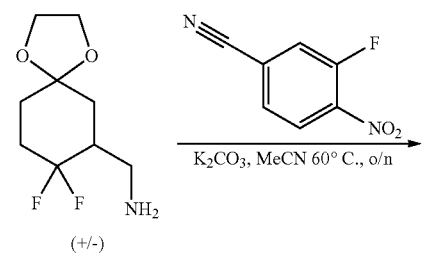

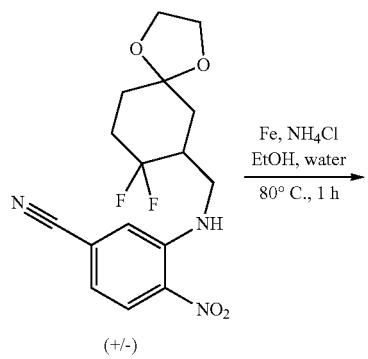

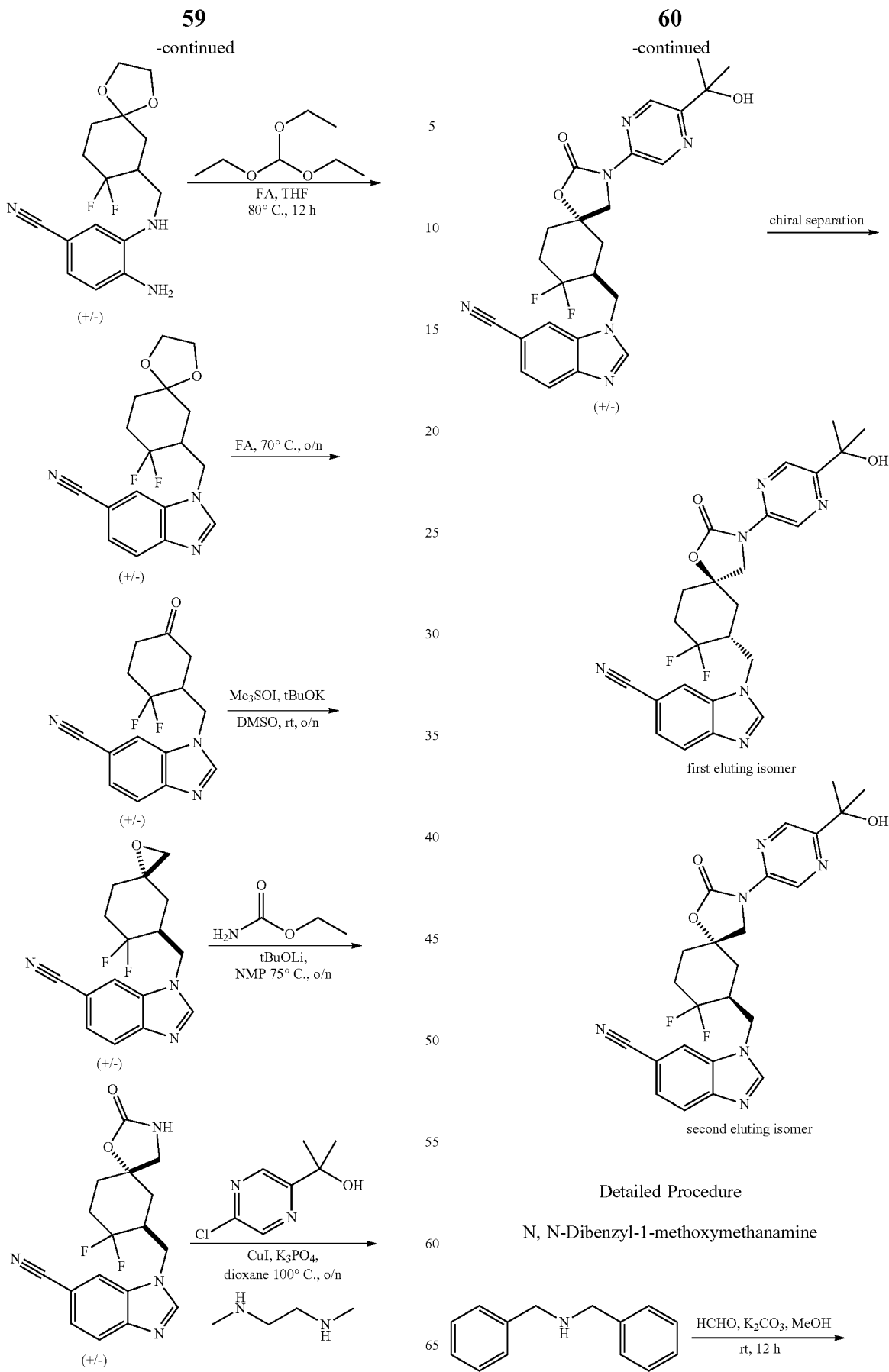
first eluting isomer
second eluting isomer
Detailed Procedure
N, N-Dibenzyl-1-methoxymethanamine -continued

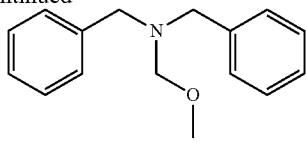

Potassium carbonate (47.29 g, 342.1 mmol, 1.5 eq.) and sodium sulfate (48.60 g, 342.1 mmol, 1.5 eq.) were added to a mixture of dibenzyl amine (45 g, 228.1 mmol, 1 eq.) and paraformaldehyde (6.78 g, 75.27 mmol, 0.3 eq.) in methanol (250 mL). The resulting mixture was stirred for 12 hours at room temperature. The resulting mixture was filtered through the celite and the filtrate was concentrated under vacuum to afford the crude product N,N-dibenzyl-1-methoxymethanamine (50 g crude) as yellow oil. $^1$H NMR (400 MHz, Chloroform-d) δ 7.44-7.33 (m, 9H), 7.31 (q, J=3.1, 2.3 Hz, 1H), 4.08 (s, 2H), 3.88 (s, 4H), 3.29 (s, 3H). LCMS (ESI-MS) m/z=242 [M+H]$^+$.

rac-7-((Dibenzylamino)methyl)-1,4-dioxaspiro[4.5]
decan-8-one

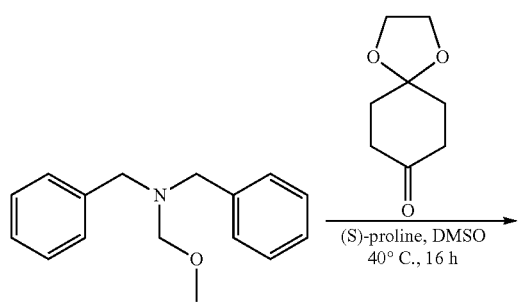

(S)-proline (4.77 g, 41.43 mmol, 0.2 eq.) was added to a stirred mixture of N,N-dibenzyl-1-methoxymethanamine (50 g, 207.18 mmol, 1 eq.) in dimethyl sulfoxide (500 mL), followed by addition of 1,4-dioxaspiro[4.5]decan-8-one (323.58 g, 2071.82 mmol, 10 eq.). The resulting mixture was stirred for 16 hours at 40° C., then diluted with water (2000 mL) and extracted with ether (3×500 mL). The combined organic layers were dried over anhydrous sodium sulfate, filtered and the filtrate was concentrated under vacuum to afford the crude product. The residue was purified by reverse phase (water with 0.1% ammonium bicarbonate) in acetonitrile from 0% to 50%) to afford the desired product rac-7-((dibenzylamino)methyl)-1,4-dioxaspiro[4.5]decan-8-one (30 g, 39.6% yield) as a light yellow solid. LCMS (ESI-MS) m/z=366 [M+H]$^+$.

rac-N,N-Dibenzyl-1-(8,8-difluoro-1,4-dioxaspiro
[4.5]decan-7-yl)methanamine

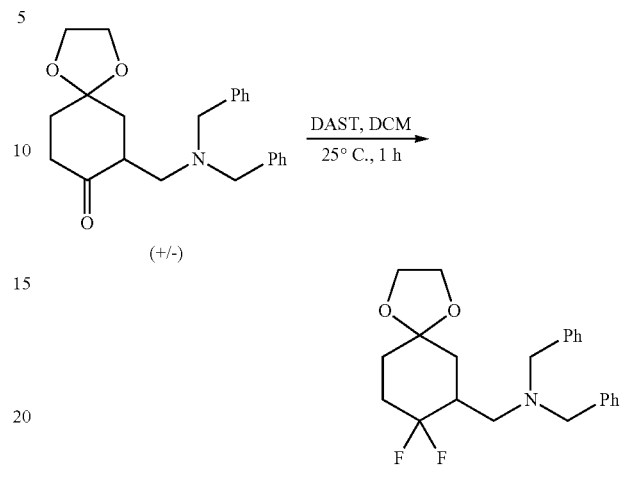

Diethylaminosulfur trifluoride (6.62 g, 41.04 mmol, 1.5 eq.) was added to a stirred mixture of rac-7-((dibenzylamino)methyl)-1,4-dioxaspiro[4.5]decan-8-one (10 g, 27.36 mmol, 1 eq.) in dichloromethane (100 mL) dropwise at 0° C. under nitrogen atmosphere. After addition complete, the reaction mixture was stirred at 25° C. for 1 hour. The reaction mixture was quenched by addition of saturated aqueous sodium bicarbonate (200 mL) and extracted with dichloromethane (3×150 mL). The combined organic layers were dried over sodium sulfate, concentrated under reduced pressure. The residue was purified by silica gel column chromatography, eluted with ethyl acetate in petroleum ether from 0% to 10%. The fractions were combined and concentrated under vacuum to afford rac-N,N-dibenzyl-1-(8,8-difluoro-1,4-dioxaspiro[4.5]decan-7-yl)methanamine (2.8 g, 26.4% yield) as colorless oil. LCMS (ESI-MS) m/z=388 [M+H]$^+$.

rac-(8,8-Difluoro-1,4-dioxaspiro[4.5]decan-7-yl)
methanamine

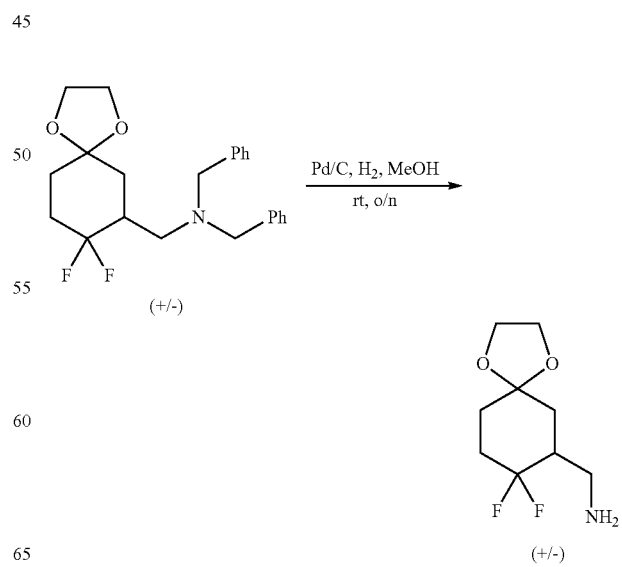

Palladium on carbon (10%, 1.0 g, 2.52 mmol, 0.35 eq.) was added to the solution of rac-N,N-dibenzyl-1-(8,8-difluoro-1,4-dioxaspiro[4.5]decan-7-yl)methanamine (2.8 g, 7.23 mmol, 1 eq.) in methanol (20 mL) under nitrogen atmosphere. The reaction mixture was stirred overnight under hydrogen atmosphere at room temperature. The reaction mixture was filtered, the filter cake was washed with methanol (20 mL). The filtrate was concentrated under reduced pressure to afford the crude product rac-(8,8-difluoro-1,4-dioxaspiro[4.5]decan-7-yl)methanamine (1.2 g crude) as colorless oil. LCMS (ESI-MS) m/z=208 [M+H]$^+$.

rac-3-(((8,8-Difluoro-1,4-dioxaspiro[4.5]decan-7-yl)methyl)amino)-4-nitrobenzonitrile

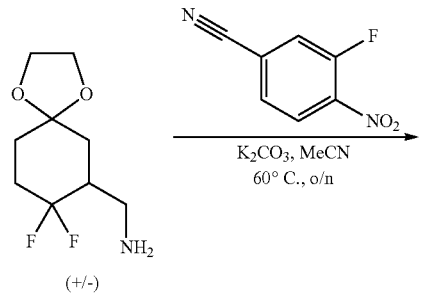

(+/-)

rac-4-Amino-3-(((8,8-difluoro-1,4-dioxaspiro[4.5]decan-7-yl)methyl)amino)benzonitrile

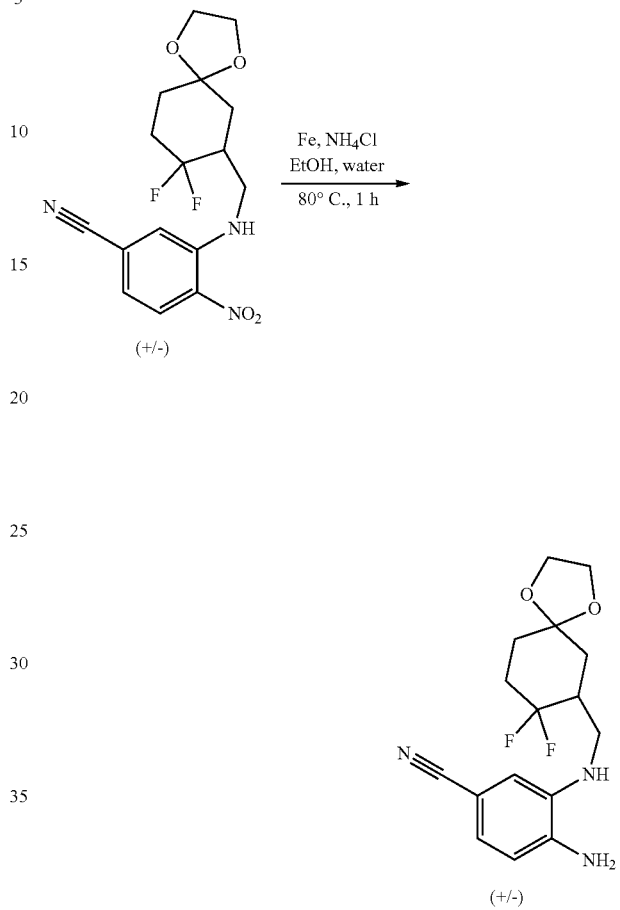

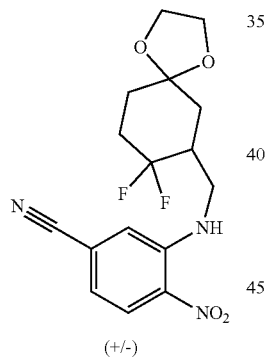

(+/-)

Potassium carbonate (2.4 g, 17.37 mmol, 3 eq.) was added to the mixture of rac-(8,8-difluoro-1,4-dioxaspiro[4.5]decan-7-yl)methanamine (1.2 g, 5.79 mmol, 1 eq.) and 3-fluoro-4-nitrobenzonitrile (0.96 g, 5.79 mmol, 1 eq.) in acetonitrile (15 mL). The resulting mixture was heated to 60° C., stirred overnight and quenched by addition of water (50 mL). The resulting mixture was extracted with ethyl acetate (3×50 mL). The combined organic layers were dried over anhydrous sodium sulfate, filtered and the filtrate was concentrated under vacuum to afford the crude product. The residue was purified by silica gel column chromatography, eluted with ethyl acetate in petroleum ether from 0% to 17%. The fractions were combined and concentrated under vacuum to afford rac-3-(((8,8-difluoro-1,4-dioxaspiro[4.5]decan-7-yl)methyl)amino)-4-nitrobenzonitrile (840 mg, 32.9% yield for 2 steps) as an orange oil. LCMS (ESI-MS) m/z=354 [M+H]$^+$.

Iron powder (1.58 g, 28.3 mmol, 10 eq.) was added to a mixture of rac-3-(((8,8-difluoro-1,4-dioxaspiro[4.5]decan-7-yl)methyl)amino)-4-nitrobenzonitrile (1 g, 2.83 mmol, 1 eq.) and ammonium chloride (0.61 g, 11.3 mmol, 4 eq.) in a mixed solvent of water (3 mL) and ethanol (6 mL). Then the resulting mixture was stirred at 80° C. for 1 hour. After cooling to room temperature, the reaction mixture was filtered, the filter cake was washed with ethanol (30 mL). The filtrate was concentrated under vacuum and the residue was diluted with dichloromethane (30 mL) and washed with water (3×30 mL). The organic layer was dried over anhydrous sodium sulfate, filtered and the filtrate was concentrated under vacuum to afford the crude product rac-4-amino-3-(((8,8-difluoro-1,4-dioxaspiro[4.5]decan-7-yl)methyl)amino)benzonitrile (700 mg crude) as a yellow solid. LCMS (ESI-MS) m/z=324 [M+H]$^+$.

rac-1-((8,8-Difluoro-1,4-dioxaspiro[4.5]decan-7-yl)methyl)-1H-benzo[d]imidazole-6-carbonitrile

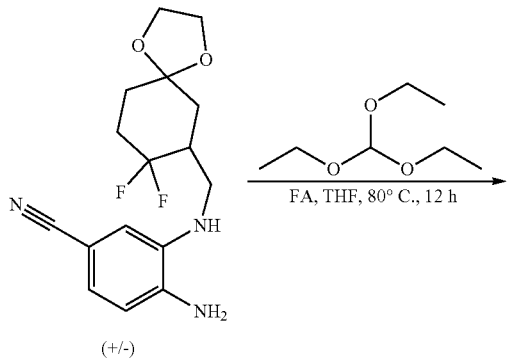

Formic acid (185 mg, 4.02 mmol, 2 eq.) was added to a mixture of rac-4-amino-3-(((8,8-difluoro-1,4-dioxaspiro[4.5]decan-7-yl)methyl)amino)benzonitrile (650 mg, 2.01 mmol, 1 eq.) and triethyl orthoformate (297.92 mg, 2.01 mmol, 1 eq.) in tetrahydrofuran (5 mL). The resulting mixture was heated to 80° C., stirred for 12 hours and then concentrated under vacuum to afford the crude product. The residue was purified by silica gel column chromatography, eluted with methanol in dichloromethane from 0% to 10%. The fractions were combined and concentrated under vacuum to afford rac-1-((8,8-difluoro-1,4-dioxaspiro[4.5]decan-7-yl)methyl)-1H-benzo[d]imidazole-6-carbonitrile (600 mg, 63.6% yield for 2 steps) as a yellow solid. LCMS (ESI-MS) m/z=334 [M+H]$^+$.

rac-1-((2,2-Difluoro-5-oxocyclohexyl)methyl)-1H-benzo[d]imidazole-6-carbonitrile

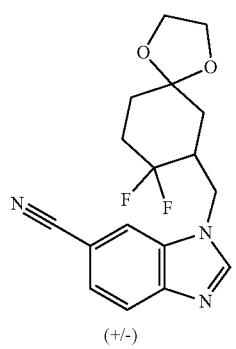

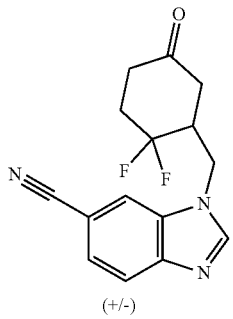

A solution of rac-1-((8,8-difluoro-1,4-dioxaspiro[4.5]decan-7-yl)methyl)-1H-benzo[d]imidazole-6-carbonitrile (600 mg, 1.8 mmol, 1 eq.) in formic acid (4 mL) was stirred at 70° C. overnight. The resulting mixture was concentrated under vacuum to afford the crude product rac-1-((2,2-difluoro-5-oxocyclohexyl)methyl)-1H-benzo[d]imidazole-6-carbonitrile (400 mg crude) as a yellow solid. LCMS (ESI-MS) m/z=290 [M+H]$^+$.

rac-1-(((3S,5S)-6,6-Difluoro-1-oxaspiro[2.5]octan-5-yl)methyl)-1H-benzo[d]imidazole-6-carbonitrile

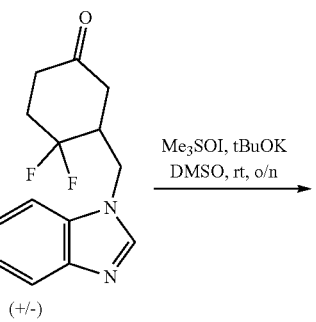

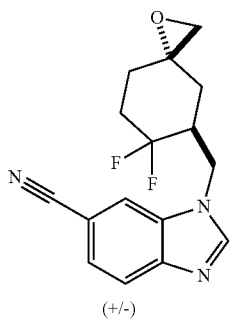

A stirred mixture of rac-1-((2,2-difluoro-5-oxocyclohexyl)methyl)-1H-benzo[d]imidazole-6-carbonitrile (400 mg, 1.38 mmol, 1 eq.) in dimethyl sulfoxide (5 mL) was heated to 35° C. to get all solids to go into solution. Trimethylsulfoxonium iodide (456.45 mg, 2.07 mmol, 1.5 eq.) was added to the solution above, followed by addition of potassium tert-butoxide (232.74 mg, 2.07 mmol, 1.5 eq.). The resulting mixture was stirred at room temperature for 1 hour. The reaction mixture was diluted with water (200 mL) and extracted with ethyl acetate (3×150 mL). The combined organic layers were dried over anhydrous sodium sulfate, filtered and the filtrate was concentrated under vacuum to afford the crude product. The residue was purified by silica

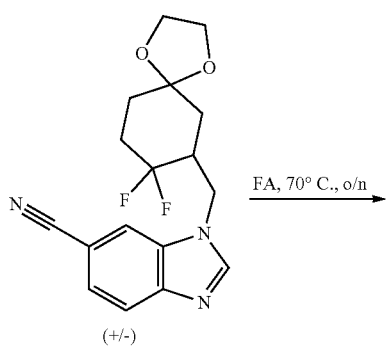

rac-1-(((5S,7S)-8,8-Difluoro-2-oxo-1-oxa-3-azaspiro[4.5]decan-7-yl)methyl)-1H-benzo[d]imidazole-6-carbonitrile

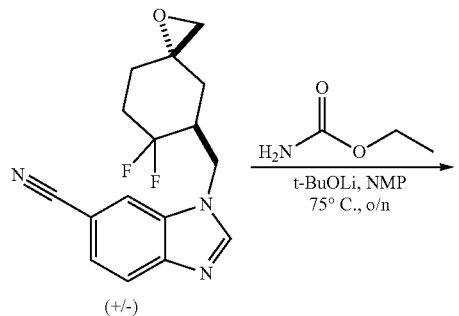

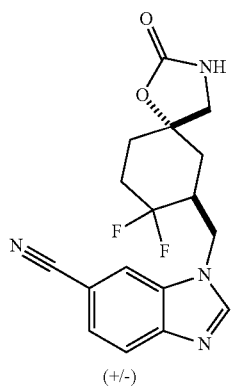

Lithium tert-butoxide (158.36 mg, 1.98 mmol, 2 eq.) was added to a mixture of rac-1-(((3S,5S)-6,6-difluoro-1-oxaspiro[2.5]octan-5-yl)methyl)-1H-benzo[d]imidazole-6-carbonitrile (300 mg, 0.99 mmol, 1 eq.) and ethyl carbamate (132.18 mg, 1.48 mmol, 1.5 eq.) in N-methyl-2-pyrrolidinone (5 mL). Then the reaction mixture was heated to 75° C. and stirred overnight. After cooling to room temperature, the reaction mixture was diluted with water (100 mL) and extracted with ethyl acetate (3×100 mL). The combined organic layers were dried over anhydrous sodium sulfate, filtered and the filtrate was concentrated under vacuum to afford the crude product. The residue was purified by silica gel column chromatography, eluted with methanol in dichloromethane from 0% to 10%. The fractions were combined and concentrated under vacuum to afford rac-1-(((5S,7S)-8,8-difluoro-2-oxo-1-oxa-3-azaspiro[4.5]decan-7-yl)methyl)-1H-benzo[d]imidazole-6-carbonitrile (300 mg, 87.4% yield) as a yellow solid. LCMS (ESI-MS) m/z=347 [M+H]⁺.

rac-1-(((5S,7S)-8,8-Difluoro-3-(5-(2-hydroxypropan-2-yl)pyrazin-2-yl)-2-oxo-1-oxa-3-azaspiro[4.5]decan-7-yl)methyl)-1H-benzo[d]imidazole-6-carbonitrile

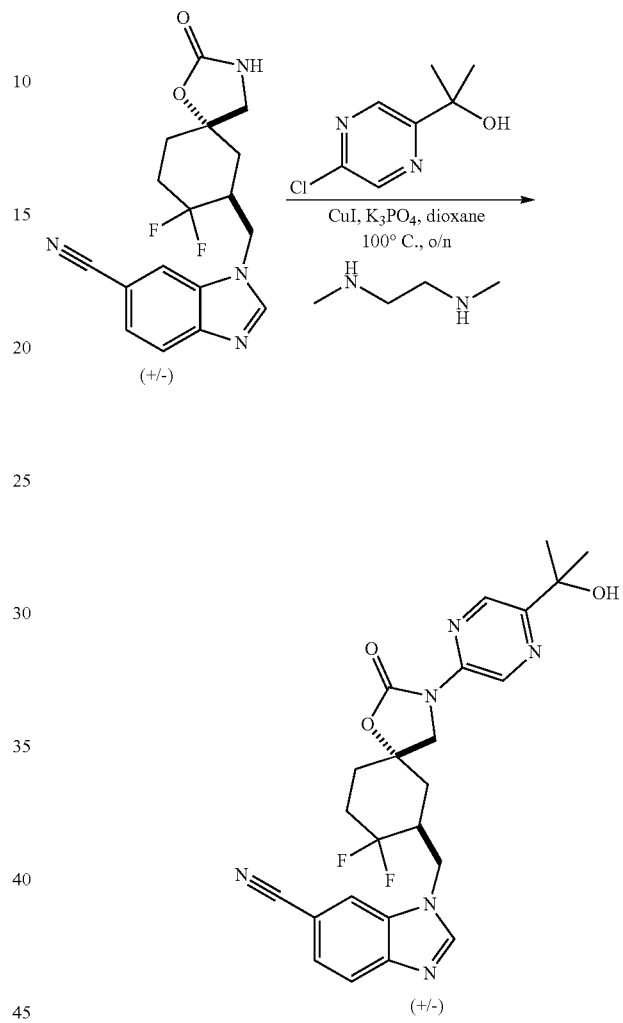

Cuprous iodide (198 mg, 1.03 mmol, 1.2 eq.) was added to a mixture of rac-1-(((5S,7S)-8,8-difluoro-2-oxo-1-oxa-3-azaspiro[4.5]decan-7-yl)methyl)-1H-benzo[d]imidazole-6-carbonitrile (300 mg, 0.87 mmol, 1 eq.), 2-(5-chloropyrazin-2-yl)propan-2-ol (149.5 mg, 0.87 mmol, 1 eq.), $N^1,N^2$-dimethylethane-1,2-diamine (152.7 mg, 1.73 mmol, 2 eq.) and potassium phosphate tribasic (441 mg, 2.08 mmol, 2.4 eq.) in 1,4-dioxane (5 mL) under nitrogen atmosphere. The reaction mixture was stirred at 100° C. for 12 hours. After cooling to room temperature, the reaction mixture was quenched by addition of water (20 mL) and extracted with ethyl acetate (3×20 mL). The combined organic layers were dried over anhydrous sodium sulfate, filtered and the filtrate was concentrated under vacuum to afford the crude products. The residue was purified by silica gel column chromatography, eluted with methanol in dichloromethane from 0% to 10%. The fractions were combined and concentrated under vacuum to afford rac-1-(((5S,7S)-8,8-difluoro-3-(5-(2-hydroxypropan-2-yl)pyrazin-2-yl)-2-oxo-1-oxa-3-azaspiro[4.5]decan-7-yl)methyl)-1H-benzo[d]imidazole-6-carbonitrile (100 mg, 24% yield) as a yellow solid. LCMS (ESI-MS) m/z=483 [M+H]⁺.

1-(((5R,7R)-8,8-Difluoro-3-(5-(2-hydroxypropan-2-yl)pyrazin-2-yl)-2-oxo-1-oxa-3-azaspiro[4.5]decan-7-yl)methyl)-1H-benzo[d]imidazole-6-carbonitrile and 1-(((5S,7S)-8,8-Difluoro-3-(5-(2-hydroxypropan-2-yl)pyrazin-2-yl)-2-oxo-1-oxa-3-azaspiro[4.5]decan-7-yl)methyl)-1H-benzo[d]imidazole-6-carbonitrile

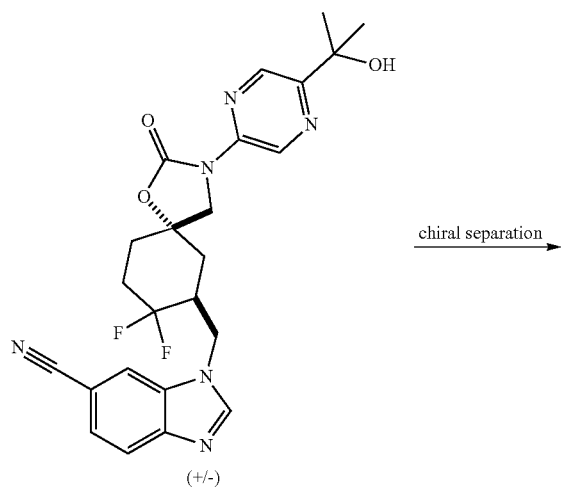
(+/-)

chiral separation →

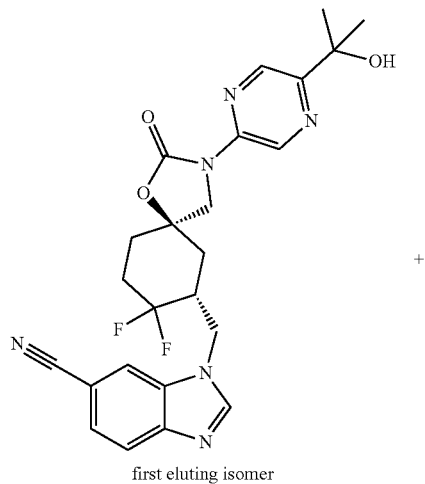
first eluting isomer

+

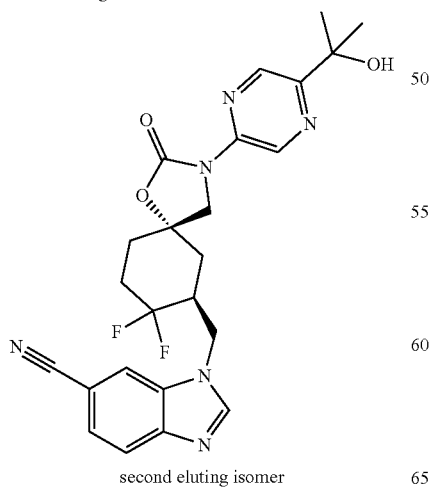
second eluting isomer rac-1-(((5S,7S)-8,8-Difluoro-3-(5-(2-hydroxypropan-2-yl)pyrazin-2-yl)-2-oxo-1-oxa-3-azaspiro[4.5]decan-7-yl)methyl)-1H-benzo[d]imidazole-6-carbonitrile (150 mg, 0.310 mmol) was separated by Prep-Chiral-HPLC with the condition: Column: CHIRALPAK ID, 2*25 cm, 5 μm; Mobile Phase A: Hex: DCM=3:1(0.5% 2M $NH_3$-Methanol)-HPLC, Mobile Phase B: Ethanol-HPLC; Flow rate: 20 mL/min; Gradient: 45% B to 45% B in 17 min; Wave Length: 220 nm. The desired fractions were combined and lyophilized to afford the two products:

First eluting isomer: 1-(((5R,7R)-8,8-Difluoro-3-(5-(2-hydroxypropan-2-yl)pyrazin-2-yl)-2-oxo-1-oxa-3-azaspiro[4.5]decan-7-yl)methyl)-1H-benzo[d]imidazole-6-carbonitrile (26.4 mg, 96.2% purity, 100% ee, 17.6% yield) as a white solid. Confirmed by Xray structure analysis. $^1$H NMR (300 MHz, DMSO-$d_6$) δ 9.17 (s, 1H), 8.57 (d, J=8.0 Hz, 2H), 8.30 (s, 1H), 7.83 (d, J=8.5 Hz, 1H), 7.62 (s, 1H), 5.39-5.37 (m, 1H), 4.66-4.64 (m, 1H), 4.38-4.36 (m, 1H), 3.93-3.91 (m, 2H), 2.90-2.88 (m, 1H), 2.28-1.78 (m, 6H), 1.44 (s, 6H). LCMS (ESI-MS) m/z=483 [M+H]$^+$.

Second eluting isomer: 1-(((5S,7S)-8,8-Difluoro-3-(5-(2-hydroxypropan-2-yl)pyrazin-2-yl)-2-oxo-1-oxa-3-azaspiro[4.5]decan-7-yl)methyl)-1H-benzo[d]imidazole-6-carbonitrile (30.5 mg, 98.7% purity, 97.4% ee, 20.3% yield) as a white solid. Confirmed by Xray structure analysis. $^1$H NMR (300 MHz, DMSO-$d_6$) δ 9.17 (s, 1H), 8.71-8.55 (m, 2H), 8.30 (s, 1H), 7.83 (d, J=8.0 Hz, 1H), 7.65-7.47 (m, 1H), 5.50-5.22 (m, 1H), 4.68 (d, J=9.6 Hz, 1H), 4.39-4.37 (m, 1H), 3.93-3.91 (m, 2H), 2.90-2.89 (m, 1H), 2.31-2.06 (m, 4H), 1.90-1.89 (m, 2H), 1.53-1.37 (m, 6H). LCMS (ESI-MS) m/z=483 [M+H]$^+$.

Example 3. Preparation of: 1-(((4S,6S)-9-(5-(2-Hydroxypropan-2-yl)pyrazin-2-yl)-8-oxo-7-oxa-9-azadispiro[2.2.4$^6$.2$^3$]dodecan-4-yl)methyl)-1H-benzo[d]imidazole-6-carbonitrile

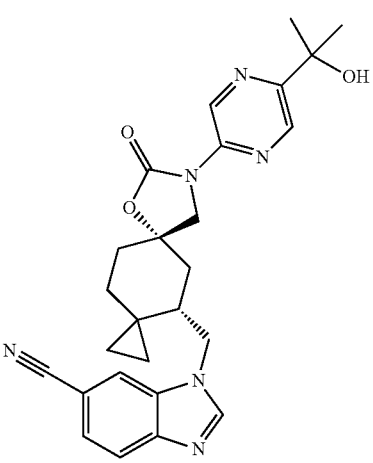 [SMILES: CC(C)(O)c1cnc(N2C[C@@]3(CCC4(CC4)[C@@H](Cn4cnc5ccc(C#N)cc54)C3)OC2=O)cn1]

Reaction Scheme
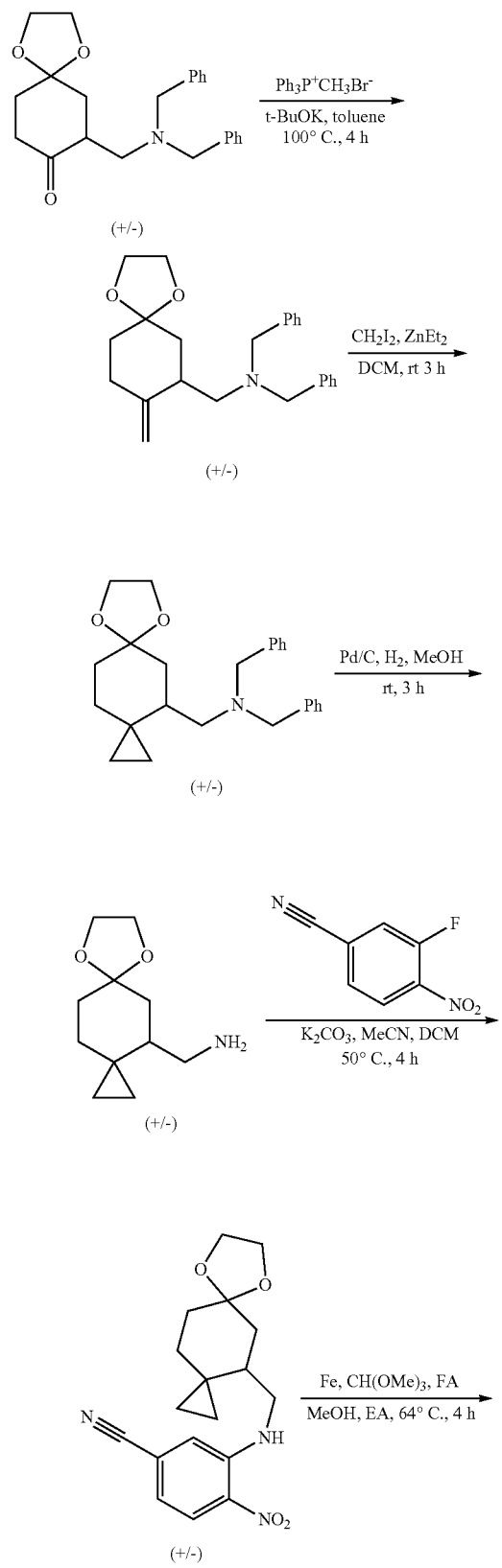
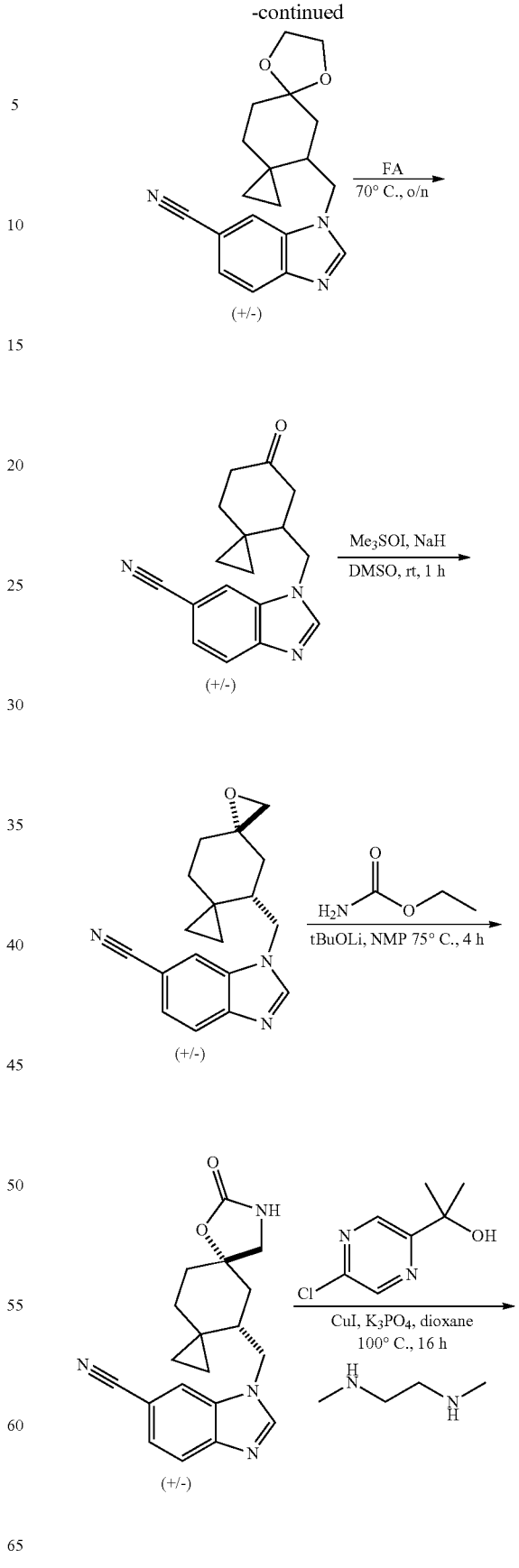

73

-continued

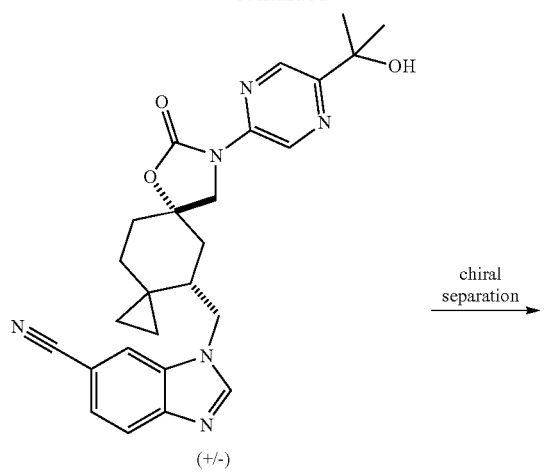
(+/-)

chiral separation

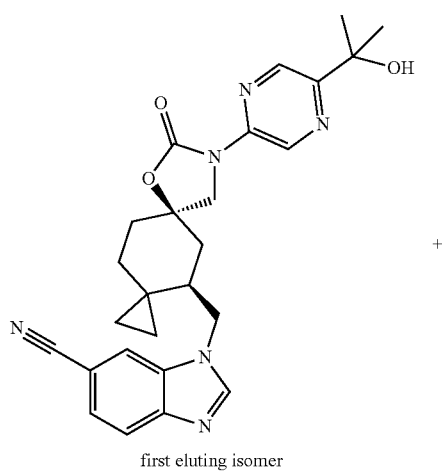
first eluting isomer

+

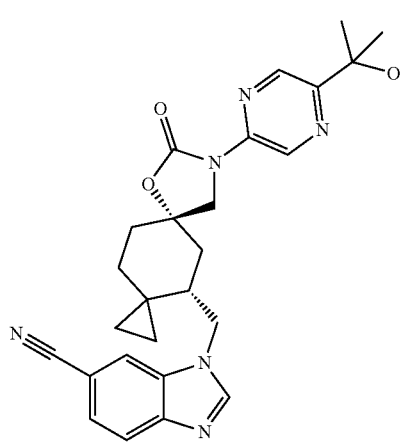
second eluting isomer

74

Detailed Procedure rac-N,N-Dibenzyl-1-(8-methylene-1,4-dioxaspiro[4.5]decan-7-yl)methanamine

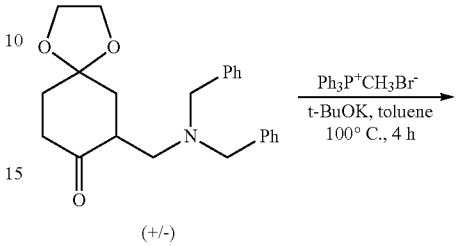
(+/-)

$\xrightarrow{\text{Ph}_3\text{P}^+\text{CH}_3\text{Br}^-}{\text{t-BuOK, toluene} \atop 100°\text{C., 4 h}}$

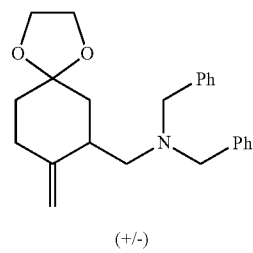
(+/-)

Potassium tert-butoxide (6.1 g, 54.72 mmol, 2 eq.) was added to a mixture of methyltriphenylphosphanium bromide (11.7 g, 32.83 mmol, 1.2 eq.) in toluene (100 mL), followed by addition of rac-7-(((dibenzylamino)methyl)-1,4-dioxaspiro [4.5] decan-8-one (10 g, 27.36 mmol, 1 eq.). The resulting mixture was stirred for 4 hours at 100° C., diluted with water (200 mL) and extracted with dichloromethane (3×100 mL) The combined organic layers were dried over anhydrous sodium sulfate, filtered and the filtrate was concentrated under vacuum to afford the crude product. The residue was purified by silica gel column chromatography, eluted with ethyl acetate in petroleum ether from 0% to 20%. The fractions were combined and concentrated under vacuum to afford the desired product rac-N,N-dibenzyl-1-(8-methylene-1,4-dioxaspiro[4.5]decan-7-yl)methanamine (9.2 g, 92.5% yield) as a yellow solid. LCMS (ESI-MS) m/z=364 [M+H]$^+$.

rac-N-((7,10-Dioxadispiro[2.2.4$^6$.2$^3$]dodecan-4-yl)methyl)-N-benzyl-1-phenylmethanamine

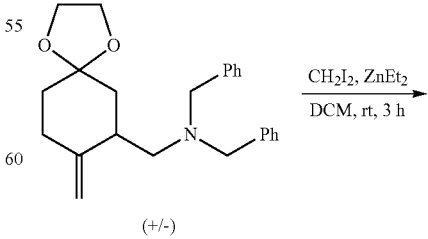
(+/-)

$\xrightarrow{\text{CH}_2\text{I}_2, \text{ZnEt}_2}{\text{DCM, rt, 3 h}}$

76 rac-3-(((7,10-Dioxadispiro[2.2.4⁶.2³]dodecan-4-yl)methyl)amino)-4-nitrobenzonitrile

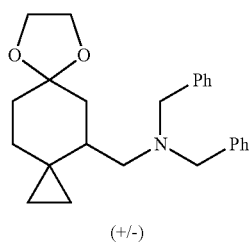

(+/-)

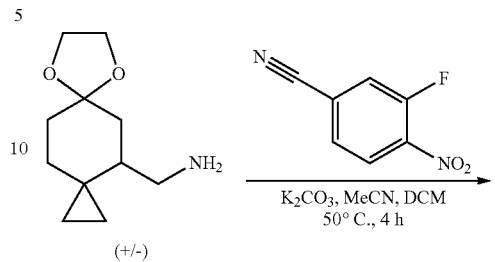

Diiodomethane (1.77 mL, 22 mmol, 2 eq.) and diethylzine (22.01 mL, 22 mmol, 2 eq.) were added to a mixture of rac-N,N-dibenzyl-1-(8-methylene-1,4-dioxaspiro[4.5]decan-7-yl)methanamine (4 g, 11 mmol, 1 eq.) in dichloromethane (50 mL). The resulting mixture was stirred for 3 hours at room temperature, dilute with saturated aqueous ammonium chloride (100 mL) and extracted with dichloromethane (3×60 mL). The combined organic layers were dried over anhydrous sodium sulfate, filtered and the filtrate was concentrated under vacuum to afford the crude product. The residue was purified by reverse phase with water (with 0.1% ammonium bicarbonate) in acetonitrile from 0% to 40% to afford the desired product rac-N-((7,10-dioxadispiro[2.2.4⁶.2³]dodecan-4-yl)methyl)-N-benzyl-1-phenylmethanamine (3 g, 72.2% yield) as a yellow solid. LCMS (ESI-MS) m/z=378 [M+H]⁺.

rac-(7,10-Dioxadispiro[2.2.4⁶.2³]dodecan-4-yl)methanamine

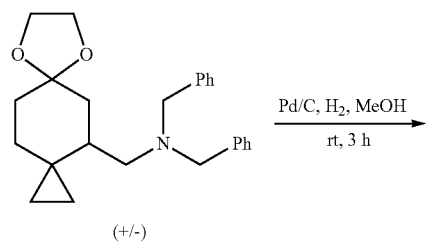

(+/-)

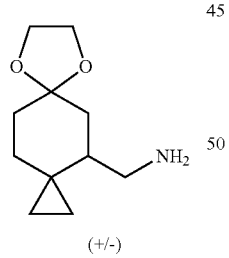

(+/-)

Palladium on carbon (10%, 532.77 mg, 5 mmol, 0.6 eq.) was added to a mixture of rac-N-((7,10-dioxadispiro[2.2.4⁶.2³]dodecan-4-yl) methyl)-N-benzyl-1-phenylmethanamine (3 g, 7.94 mmol, 1 eq.) in methanol (250 mL). The resulting mixture was stirred for 3 hours at room temperature under hydrogen atmosphere. The mixture was filtered through celite and the filtrate was concentrated to afford the crude product rac-(7,10-dioxadispiro[2.2.4⁶.2³]dodecan-4-yl)methanamine (1 g, crude) as yellow oil. LCMS (ESI-MS) m/z=198 [M+H]⁺.

Potassium carbonate (1.12 g, 8.11 mmol, 2 eq.) was added to a mixture of rac-(7,10-dioxadispiro[2.2.4⁶.2³] dodecan-4-yl)methanamine (800 mg, 4.05 mmol, 1 eq.) and 3-fluoro-4-nitrobenzonitrile (0.67 g, 4.05 mmol, 1 eq.) in acetonitrile (20 mL). The resulting mixture was stirred for 4 hours at 50° C., diluted with water (100 mL) and extracted with dichloromethane (3×40 mL). The combined organic layers were dried over anhydrous sodium sulfate, filtered and the filtrate was concentrated under vacuum to afford the crude product. The residue was purified by silica gel column chromatography, eluted with ethyl acetate in petroleum ether from 0% to 15%. The fractions were combined and concentrated under vacuum to afford the desired product rac-3-(((7,10-dioxadispiro[2.2.4⁶.2³]dodecan-4-yl)methyl)amino)-4-nitrobenzonitrile (1.2 g, 86.3% yield) as a yellow solid. LCMS (ESI-MS) m/z=344 [M+H]⁺.

rac-1-((7,10-Dioxadispiro [2.2.4⁶.2³] dodecan-4-yl)methyl)-1H-benzo[d]imidazole-6-carbonitrile

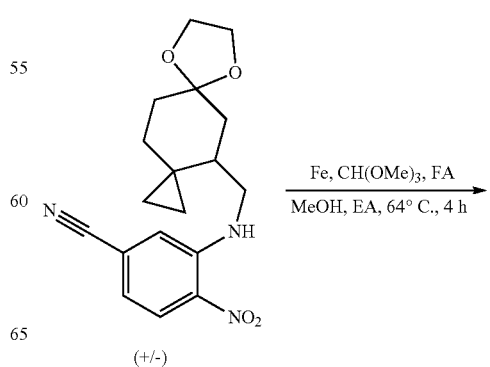

(+/-)

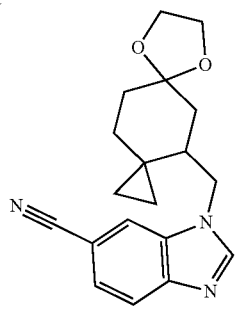

(+/-)

Iron (975.79 mg, 17.47 mmol, 5 eq.) was added to a mixture of rac-3-(((7,10-dioxadispiro [2.2.4⁶.2³] dodecan-4-yl)methyl)amino)-4-nitrobenzonitrile (1.2 g, 3.49 mmol, 1 eq.), trimethoxymethane (370.85 mg, 3.49 mmol, 1 eq.) and formic acid (160.84 mg, 3.49 mmol, 1 eq.) in a mixed solvent of methanol (60 mL) and ethyl acetate (60 mL). The resulting mixture was stirred for 4 hours at 64° C. and concentrated under vacuum. The residue was diluted with water (50 mL), extracted with dichloromethane (3×50 mL). The combined organic layers were dried over anhydrous sodium sulfate, filtered and the filtrate was concentrated under vacuum to afford the crude product. The residue was purified by silica gel column chromatography, eluted with ethyl acetate in petroleum ether from 0% to 50%. The fractions were combined and concentrated under vacuum to afford rac-1-((7,10-dioxadispiro[2.2.4⁶.2³]dodecan-4-yl)methyl)-1H-benzo[d]imidazole-6-carbonitrile (700 mg, 62% yield) as a yellow solid. LCMS (ESI-MS) m/z=324 [M+H]⁺.

rac-1-((6-Oxospiro[2.5]octan-4-yl)methyl)-1H-benzo[d]imidazole-6-carbonitrile

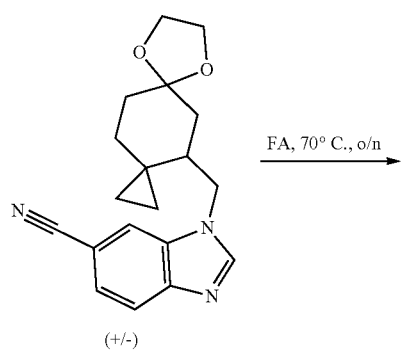

A mixture of rac-1-((7,10-dioxadispiro[2.2.4⁶.2³]dodecan-4-yl)methyl)-1H-benzo[d]imidazole-6-carbonitrile (700 mg, 2.16 mmol, 1 eq.) in formic acid (7 mL) was heated to 70° C., stirred overnight and concentrated under vacuum to afford the crude product. The residue was purified by silica gel column chromatography, eluted with ethyl acetate in petroleum ether from 0% to 70%. The fractions were combined and concentrated under vacuum to afford rac-1-((6-oxospiro[2.5]octan-4-yl)methyl)-1H-benzo[d]imidazole-6-carbonitrile (500 mg, 82.8% yield) as a yellow solid. LCMS (ESI-MS) m/z=280 [M+H]⁺.

rac-1-(((3S,5S)-1-Oxadispiro[2.2.2⁶.2³]decan-5-yl)methyl)-1H-benzo[d]imidazole-6-carbonitrile

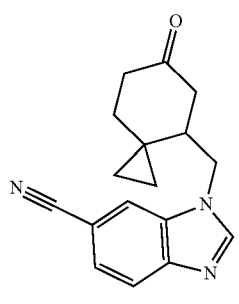

(+/-)

Me₃SOI, NaH
―――――――→
DMSO, rt, 1 h

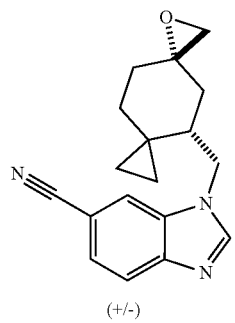

(+/-)

Sodium hydrate (60%, 143.2 mg, 3.58 mmol, 2 eq.) was added to a mixture of rac-1-((6-oxospiro[2.5]octan-4-yl)methyl)-1H-benzo[d]imidazole-6-carbonitrile (500 mg, 1.79 mmol, 1 eq.) and trimethylsulfoxonium iodide (787 mg, 3.58 mmol, 2 eq.) in dimethyl sulfoxide (2 mL). The resulting mixture was stirred for 1 hour at room temperature, diluted with water (40 mL) and extracted with dichloromethane (3×30 mL). The combined organic layers were dried over anhydrous sodium sulfate, filtered and the filtrate was concentrated under vacuum to afford the crude product rac-1-(((3S,5S)-1-oxadispiro[2.2.2⁶.2³]decan-5-yl)methyl)-1H-benzo[d]imidazole-6-carbonitrile (470 mg crude) as a white solid. LCMS (ESI-MS) m/z=294 [M+H]⁺.

79
rac-1-(((4S,6S)-8-Oxo-7-oxa-9-azadispiro[2.2.4⁶.2³]dodecan-4-yl)methyl)-1H-benzo[d]imidazole-6-carbonitrile

80
rac-1-(((4S,6S)-9-(5-(2-Hydroxypropan-2-yl)pyrazin-2-yl)-8-oxo-7-oxa-9-azadispiro[2.2.4⁶.2³]dodecan-4-yl)methyl)-1H-benzo[d]imidazole-6-carbonitrile

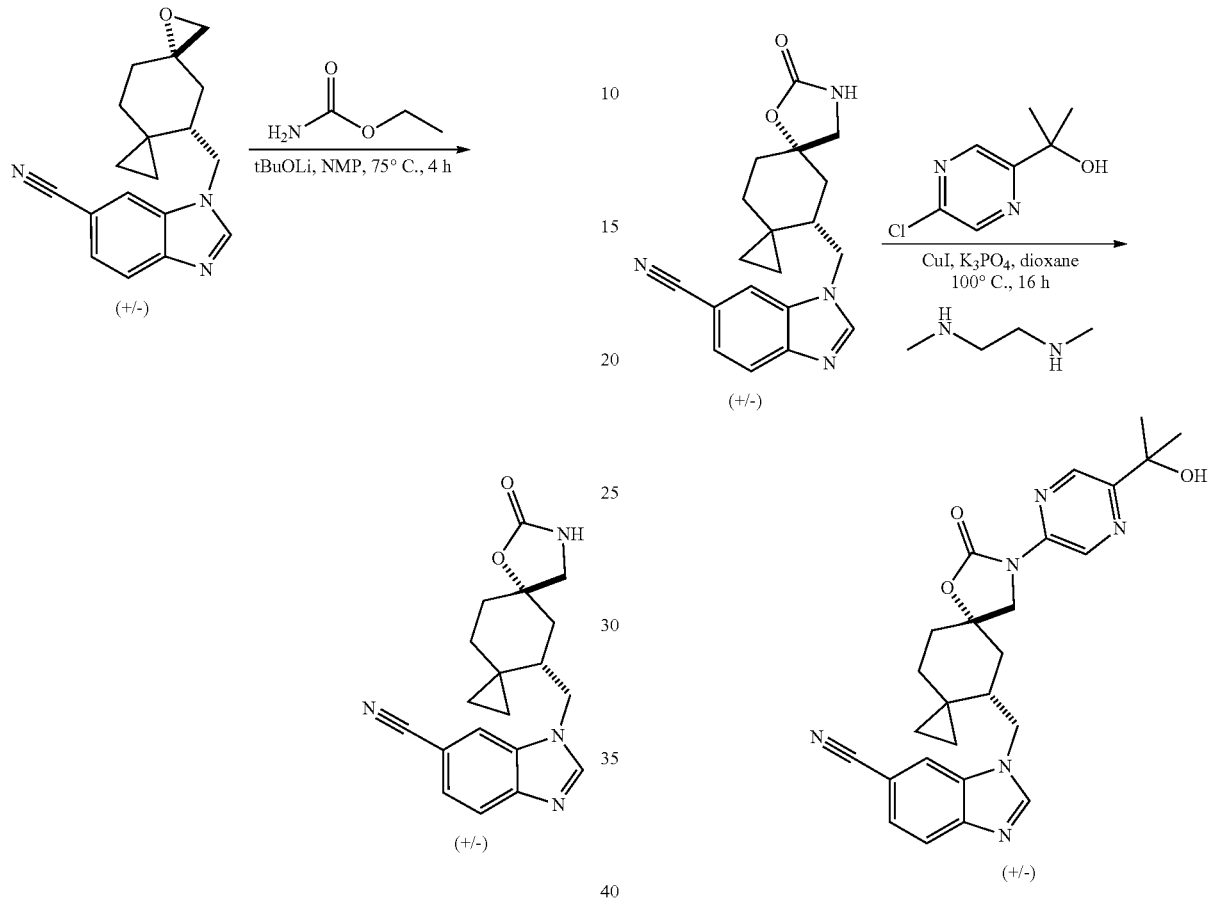

A mixture of lithium tert-butoxide (64.13 mg, 0.8 mmol, 0.5 eq.) and ethyl carbamate (713 mg, 8 mmol, 5 eq.) in N-methyl-2-pyrrolidone (11.75 mL) was stirred for 10 minutes at room temperature, followed by addition of rac-1-(((3S,5S)-1-oxadispiro[2.2.2⁶.2³]decan-5-yl)methyl)-1H-benzo[d]imidazole-6-carbonitrile (470 mg, 1.60 mmol, 1 eq.). The resulting mixture was stirred for 4 hours at 75° C. After cooled to room temperature, the resulting mixture was diluted with water (30 mL) and extracted with dichloromethane (3×30 mL). The combined organic layers were washed with brine (50 mL), dried over anhydrous sodium sulfate, filtered and concentrated under vacuum to afford the crude product rac-1-(((4S,6S)-8-oxo-7-oxa-9-azadispiro[2.2.4⁶.2³]dodecan-4-yl)methyl)-1H-benzo[d]imidazole-6-carbonitrile (420 mg crude) as a white solid. LCMS (ESI-MS) m/z=337 [M+H]+

Cuprous iodide (113.23 mg, 0.59 mmol, 0.5 eq.) was added to a mixture of rac-1-(((4S,6S)-8-oxo-7-oxa-9-azadispiro[2.2.4⁶.2³]dodecan-4-yl)methyl)-1H-benzo[d]imidazole-6-carbonitrile (400 mg, 1.19 mmol, 1 eq.), 2-(5-chloropyrazin-2-yl)propan-2-ol (205.25 mg, 1.19 mmol, 1 eq.), $N^1,N^2$-dimethylethane-1,2-diamine (209.64 mg, 2.38 mmol, 2 eq.) and potassium phosphate tribasic (504.80 mg, 2.38 mmol, 2 eq.) in 1,4-dioxane (15 mL). The resulting mixture was stirred for 16 hours at 100° C. under nitrogen atmosphere. After cooling to room temperature, the reaction mixture was dilute with water (100 mL) and extracted with dichloromethane (3×100 mL). The combined organic layers were dried over anhydrous sodium sulfate, filtered and the filtrate was concentrated under vacuum to afford the crude product. The residue was purified by silica gel column chromatography, eluted with ethyl acetate in petroleum ether from 0% to 60%.

The fractions were combined and concentrated under vacuum to afford the desired product rac-1-(((4S,6S)-9-(5-(2-hydroxypropan-2-yl)pyrazin-2-yl)-8-oxo-7-oxa-9-azadispiro[2.2.4⁶.2³]dodecan-4-yl)methyl)-1H-benzo[d]imidazole-6-carbonitrile (400 mg, 71.3% yield) as a white solid. LCMS (ESI-MS) m/z=473[M+H]⁺.

1-(((4R,6R)-9-(5-(2-Hydroxypropan-2-yl)pyrazin-2-yl)-8-oxo-7-oxa-9-azadispiro[2.2.4⁶.2³]dodecan-4-yl)methyl)-1H-benzo[d]imidazole-6-carbonitrile and 1-(((4S,6S)-9-(5-(2-Hydroxypropan-2-yl)pyrazin-2-yl)-8-oxo-7-oxa-9-azadispiro[2.2.4⁶.2³]dodecan-4-yl)methyl)-1H-benzo[d]imidazole-6-carbonitrile

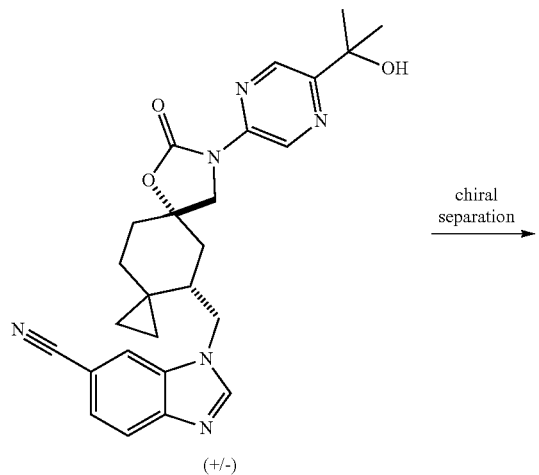

The racemate of rac-1-(((4S,6S)-9-(5-(2-hydroxypropan-2-yl)pyrazin-2-yl)-8-oxo-7-oxa-9-azadispiro-[2.2.4⁶.2³]dodecan-4-yl)methyl)-1H-benzo[d]imidazole-6-carbonitrile (400 mg, 0.84 mmol, 1 eq.) was separated by Prep-Chiral HPLC with the following condition: Column: CHIRALPAK IF, 2*25 cm, 5 µm; Mobile Phase A: MtBE (0.5% 2M NH₃-MeOH)-HPLC, Mobile Phase B: EtOH-HPLC; Flow rate: 15 mL/min; Gradient: 30% B to 30% B in 17 min; Wave Length: 220/254 nm; RT1(min): 10.68; RT2(min): 13.184; Sample Solvent: EtOH-HPLC; Injection Volume: 0.4 mL. The desired fractions were combined and lyophilized to afford the two products:

First eluting isomer: 1-(((4R,6R)-9-(5-(2-Hydroxypropan-2-yl)pyrazin-2-yl)-8-oxo-7-oxa-9-azadispiro [2.2.4⁶.2³] dodecan-4-yl)methyl)-1H benzo[d]imidazole-6-carbonitrile (173.6 mg, 99.1% purity, 100.0% ee) as a white solid. ¹H NMR (300 MHz, DMSO-d₆) δ 9.26 (d, J=1.5 Hz, 1H), 8.60 (d, J=1.5 Hz, 1H), 8.51 (s, 1H), 8.28 (d, J=1.5 Hz, 1H), 7.82 (d, J=8.4 Hz, 1H), 7.58 (dd, J=8.4, 1.5 Hz, 1H), 5.44 (s, 1H), 4.54 (dt, J=16.2, 8.1 Hz, 2H), 3.91 (q, J=10.3 Hz, 2H), 2.49-2.40 (m, 1H), 2.30-2.19 (m, 1H), 2.14-2.00 (m, 1H), 1.93-1.72 (m, 4H), 1.46 (s, 6H), 0.95-0.82 (m, 1H), 0.41-0.17 (m, 3H). LCMS (ESI-MS) m/z=473 [M+H]⁺.

Second eluting isomer: 1-(((4S,6S)-9-(5-(2-Hydroxypropan-2-yl)pyrazin-2-yl)-8-oxo-7-oxa-9-azadispiro [2.2.4⁶.2³] dodecan-4-yl)methyl)-1H-benzo[d]imidazole-6-carbonitrile (159.8 mg, 99.1% purity, 99.0% ee) as a white solid. Absolute configuration confirmed by Xray crystal structure. ¹H NMR (300 MHz, DMSO-d₆) δ 9.26 (d, J=1.5 Hz, 1H), 8.60 (d, J=1.5 Hz, 1H), 8.50 (s, 1H), 8.28 (d, J=1.5 Hz, 1H), 7.82 (d, J=8.4 Hz, 1H), 7.58 (dd, J=8.4, 1.5 Hz, 1H), 5.43 (s, 1H), 4.52 (t, J=8.0 Hz, 2H), 3.91 (q, J=10.3 Hz, 2H), 2.49-2.38 (m, 1H), 2.33-2.20 (m, 1H), 2.15-2.01 (m, 1H), 1.93-1.72 (m, 4H), 1.45 (s, 6H), 0.97-0.80 (m, 1H), 0.38-0.20 (m, 3H). LCMS (ESI-MS) m/z=473 [M+H]⁺.

Example 4. Preparation of: 1-(((5S,7S)-3-(5-(2-Hydroxypropan-2-yl)pyrazin-2-yl)-7-methyl-2,8-dioxo-1-oxa-3-azaspiro[4.5]decan-7-yl)methyl)-1H-benzo[d]imidazole-6-carbonitrile

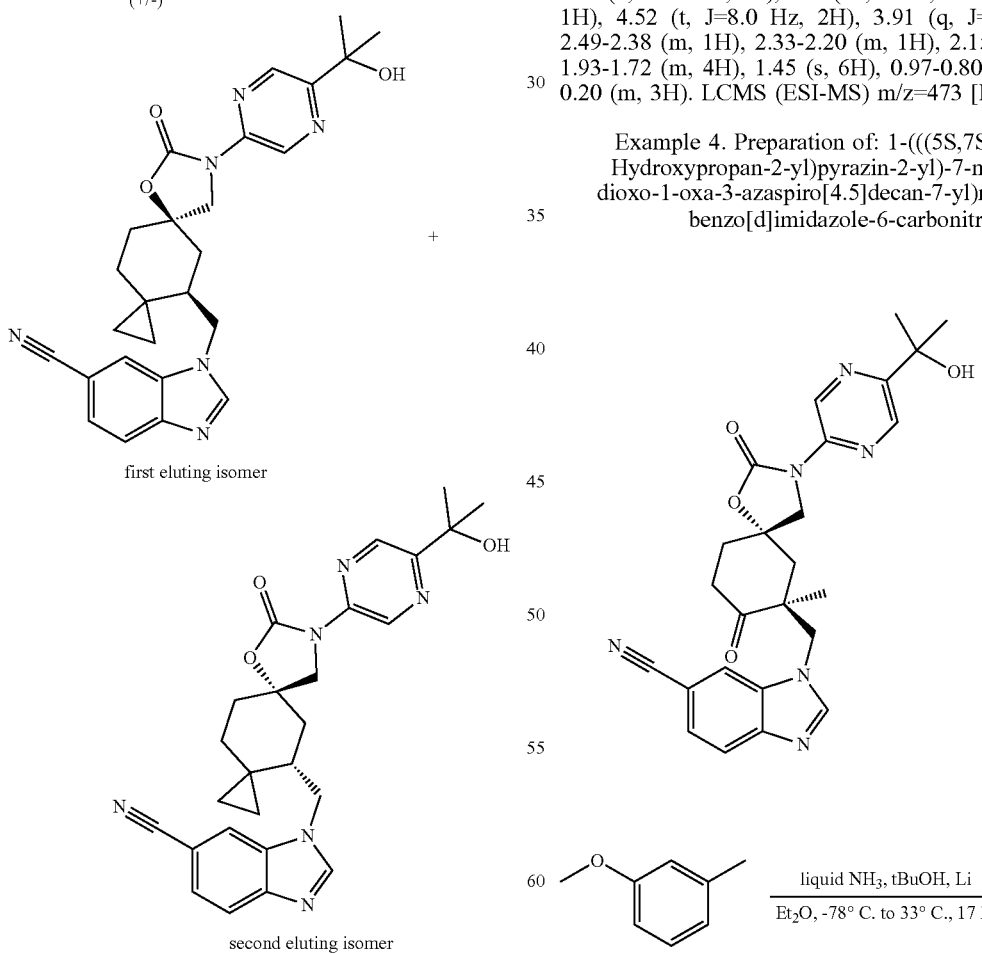

83
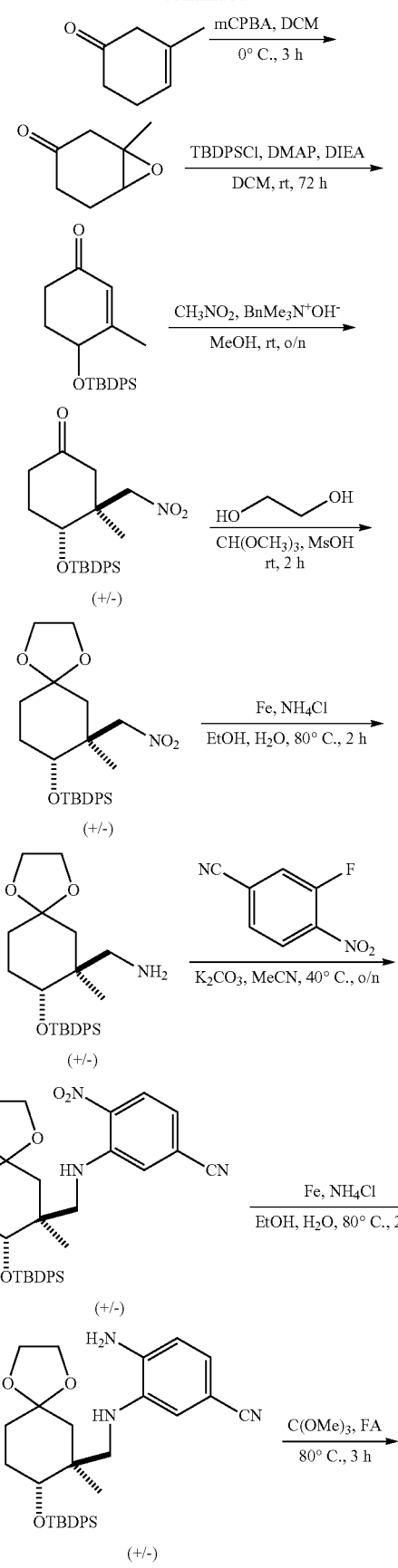
84
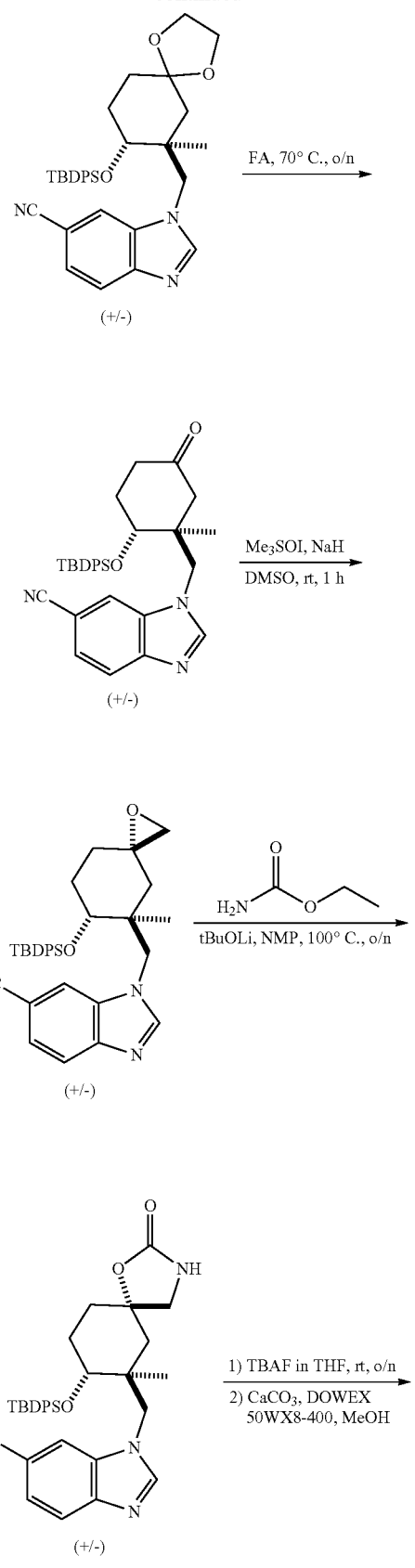

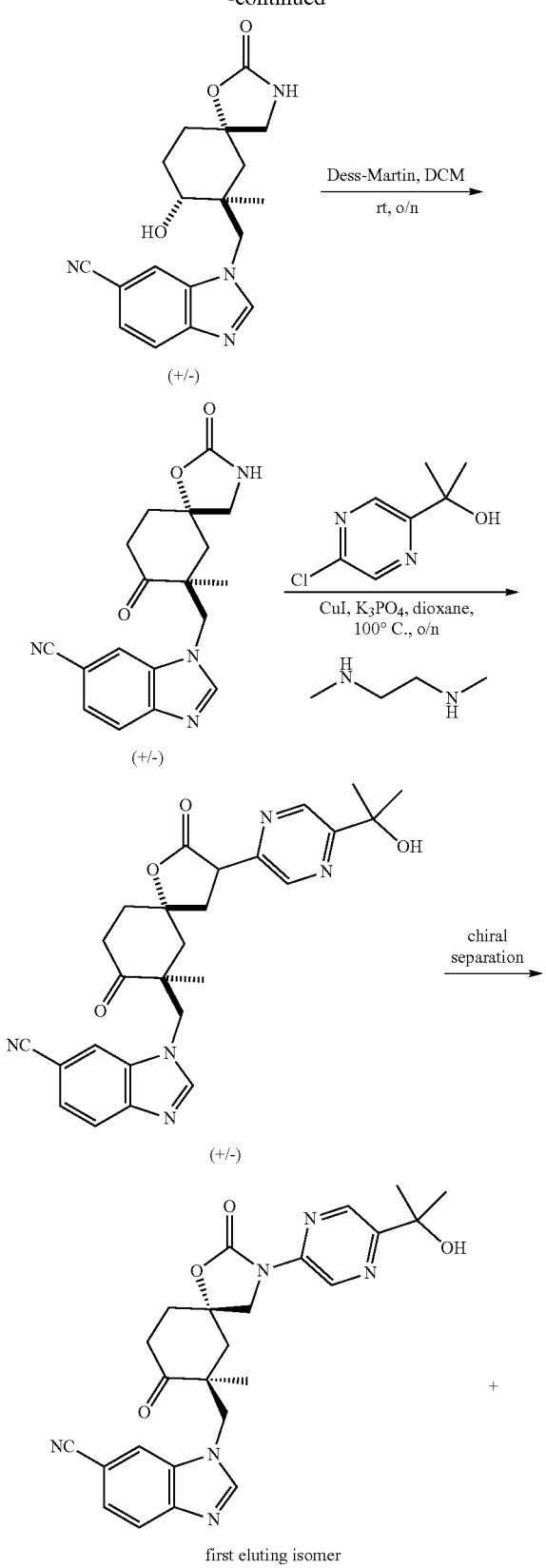

(+/-)

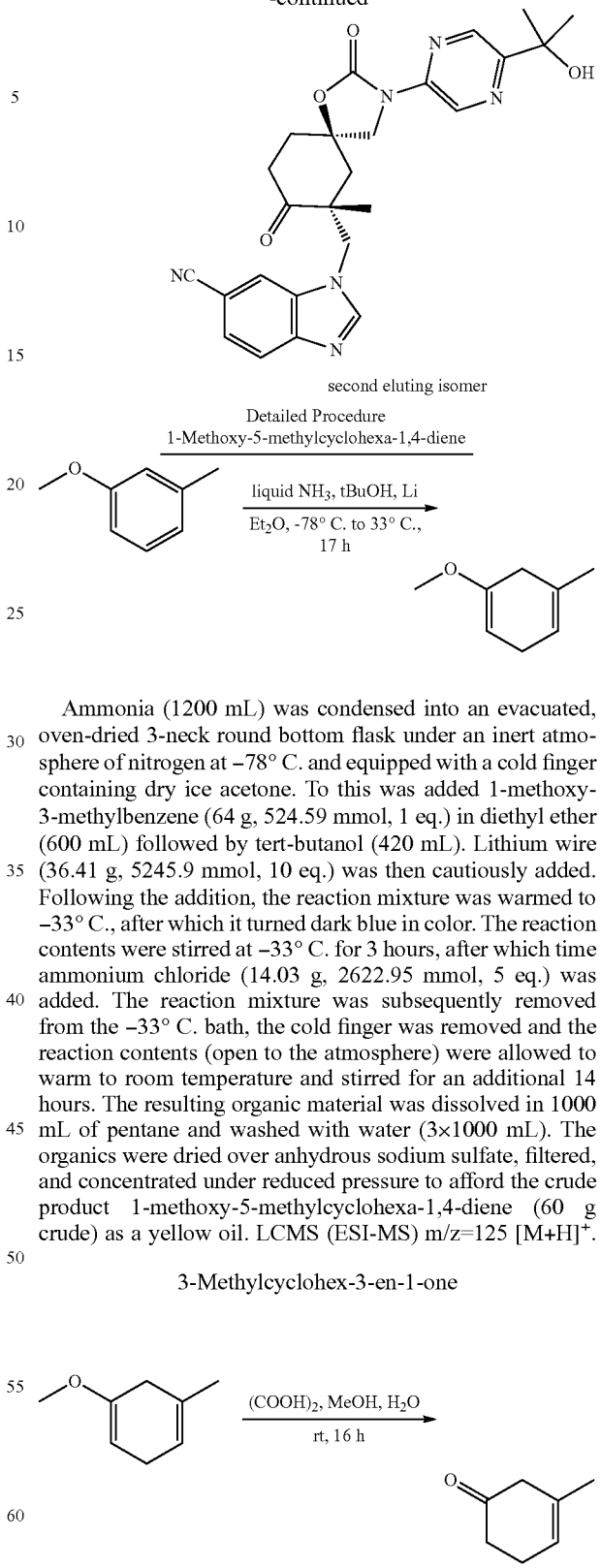

second eluting isomer

Detailed Procedure
1-Methoxy-5-methylcyclohexa-1,4-diene

Ammonia (1200 mL) was condensed into an evacuated, oven-dried 3-neck round bottom flask under an inert atmosphere of nitrogen at −78° C. and equipped with a cold finger containing dry ice acetone. To this was added 1-methoxy-3-methylbenzene (64 g, 524.59 mmol, 1 eq.) in diethyl ether (600 mL) followed by tert-butanol (420 mL). Lithium wire (36.41 g, 5245.9 mmol, 10 eq.) was then cautiously added. Following the addition, the reaction mixture was warmed to −33° C., after which it turned dark blue in color. The reaction contents were stirred at −33° C. for 3 hours, after which time ammonium chloride (14.03 g, 2622.95 mmol, 5 eq.) was added. The reaction mixture was subsequently removed from the −33° C. bath, the cold finger was removed and the reaction contents (open to the atmosphere) were allowed to warm to room temperature and stirred for an additional 14 hours. The resulting organic material was dissolved in 1000 mL of pentane and washed with water (3×1000 mL). The organics were dried over anhydrous sodium sulfate, filtered, and concentrated under reduced pressure to afford the crude product 1-methoxy-5-methylcyclohexa-1,4-diene (60 g crude) as a yellow oil. LCMS (ESI-MS) m/z=125 [M+H]$^+$.

3-Methylcyclohex-3-en-1-one

Oxalic acid (6.53 g, 72.58 mmol, 0.15 eq.) was added to a solution of 1-methoxy-5-methylcyclohexa-1,4-diene (60 g, 483.87 mmol, 1 eq.) in methanol (400 mL) and water (100 mL). The resulting solution was stirred at room temperature for 16 hours. The residue was concentrated under reduced pressure to afford the crude product 3-methylcyclohex-3-en-1-one (50 g crude) as a white solid. LCMS (ESI-MS) m/z=111 I[M+H]$^+$.

1-Methyl-7-Oxabicyclo[4.1.0]heptan-3-one

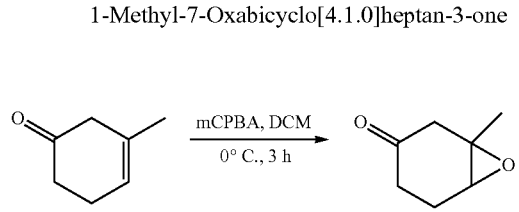

3-Chloroperoxybenzoic acid (101.97 g, 590.90 mmol, 1.3 eq.) was added a solution of 3-methylcyclohex-3-en-1-one (50 g, 454.54 mmol, 1 eq.) in dichloromethane (500 mL) at 0° C. The reaction mixture was stirred for 3 hours at 0° C., the reaction was quenched with 500 mL saturated aqueous sodium thiosulfate and allowed to stir for 5 minutes. The layers were separated, and the aqueous layer was extracted with dichloromethane (2×500 mL). The combined organics were washed with saturated aqueous sodium bicarbonate (3×500 mL), dried over anhydrous sodium sulfate, filtered and concentrated to afford the crude product 1-methyl-7-oxabicyclo[4.1.0]heptan-3-one (54 g crude) as a light yellow oil. $^1$H NMR (400 MHz, Chloroform-d) δ 3.23 (d, J=2.9 Hz, 1H), 2.80 (d, J=19.0 Hz, 1H), 2.59 (dd, J=19.0, 0.9 Hz, 1H), 2.43-2.33 (m, 2H), 2.23-2.14 (m, 2H), 1.38 (s, 3H). LCMS (ESI-MS) m/z=127 [M+H]$^+$.

4-((tert-Butyldiphenylsilyl)oxy)-3-methylcyclohex-2-en-1-one

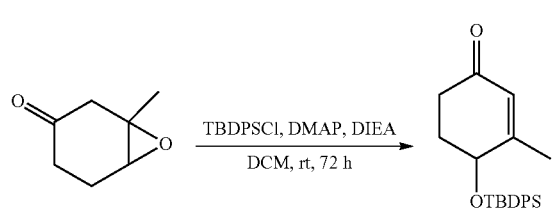

tert-Butyldiphenylsilyl chloride (117.80 g, 428.57 mmol, 1 eq.) was added to a solution of 1-methyl-7-oxabicyclo[4.1.0]heptan-3-one (54 g, 428.57 mmol, 1 eq.), diisopropylethylamine (110.78 g, 857.14 mmol, 2 eq.) and 4-dimethylaminopyridine (10.47 g, 85.71 mmol, 0.2 eq.) in dichloromethane (600 mL) under a nitrogen atmosphere. The reaction mixture was stirred for 72 hours at the room temperature. The reaction mixture was poured into 500 mL of dichloromethane and 500 mL of water and the layers were separated. The organic layer was washed with water, dried over anhydrous sodium sulfate, filtered and concentrated to afford the crude product. The residue was purified by silica gel column chromatography, eluted with ethyl acetate in petroleum ether from 0% to 10%. The fractions with desired mass signal were combined and concentrated under vacuum to afford the desired product 4-((tert-butyldiphenylsilyl)oxy)-3-methylcyclohex-2-en-1-one (60 g, 31.3% yield for 4 steps) as a light yellow oil. LCMS (ESI-MS) m/z=365 [M+H]$^+$.

rac-(3S,4R)-4-((tert-Butyldiphenylsilyl)oxy)-3-methyl-3-(nitromethyl)cyclohexan-1-one

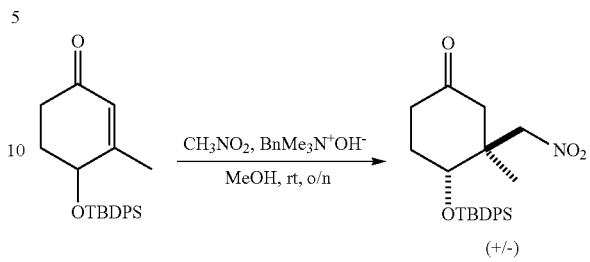

Nitromethane (4.01 g, 65.75 mmol, 1.2 eq.) was added to a solution of 4-((tert-butyldiphenylsilyl)oxy)-3-methylcyclohex-2-en-1-one (20 g, 54.94 mmol, 1 eq.) and benzyltrimethylammonium hydroxide (13.75 g, 82.41 mmol, 1.5 eq.) in methanol (100 mL). The resulting mixture was stirred overnight at the room temperature and concentrated under vacuum to afford the crude product. The residue was purified by silica gel column chromatography, eluted with ethyl acetate in petroleum ether from 0% to 10%. The fractions were combined and concentrated under vacuum to afford the desired product rac-(3S,4R)-4-((tert-butyldiphenylsilyl)oxy)-3-methyl-3-(nitromethyl)cyclohexan-1-one (18 g, 77.1% yield) as a light yellow oil. $^1$H NMR (400 MHz, DMSO-d$_6$) δ 7.62-7.49 (m, 4H), 7.42-7.36 (m, 6H), 4.41-4.33 (m, 2H), 3.65-3.59 (m, 1H), 2.34-1.99 (m, 6H), 1.09-0.98 (m, 12H). LCMS (ESI-MS) m/z=426 [M+H]$^+$.

rac-tert-Butyl(((7S,8R)-7-methyl-7-(nitromethyl)-1,4-dioxaspiro[4.5]decan-8-yl)oxy)diphenylsilane

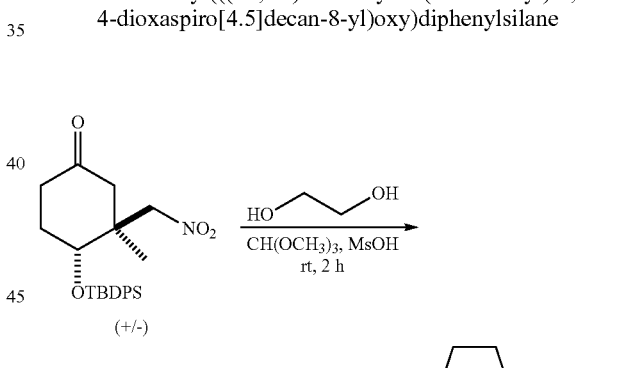

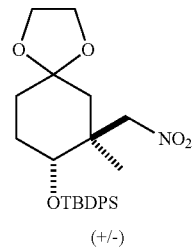

Ethylene glycol (4.33 g, 69.72 mmol, 1.5 eq.) was added to a solution of rac-(3S,4R)-4-((tert-butyldiphenylsilyl)oxy)-3-methyl-3-(nitromethyl)cyclohexan-1-one (19.8 g, 46.58 mmol, 1 eq.) and trimethoxymethane (7.40 g, 69.72 mmol, 1.5 eq.) in dichloromethane (100 mL). The resulting reaction mixture was stirred at room temperature for 5 minutes, then cooled to 0° C. in an ice bath. To this mixture was added methanesulfonic acid (0.67 g, 6.97 mmol, 0.15 eq.) dropwise. The resulting mixture was removed from the bath and allowed to warm to room temperature and stirred for 2 hours. The reaction mixture was concentrated under vacuum. The residue was purified by silica gel column chromatography, eluted with ethyl acetate in petroleum ether from 0% to 10%. The fractions were combined and concentrated under vacuum to afford the desired product rac-tert-butyl(((7S,8R)-7-methyl-7-(nitromethyl)-1,4-dioxaspiro[4.5]decan-8-yl)oxy)diphenylsilane (18.5 g, 84.7% yield) as a light yellow oil. $^1$H NMR (400 MHz, DMSO-$d_6$) δ 7.62-7.49 (m, 4H), 7.42-7.36 (m, 6H), 4.41-4.33 (m, 2H), 3.50-3.34 (m, 4H), 3.25-3.19 (m, 1H), 1.65-1.49 (m, 6H), 1.09 (s, 9H), 0.98 (s, 3H).
LCMS (ESI-MS) m/z=470 [M+H]$^+$.

rac-((7S,8R)-8-((tert-Butyldiphenylsilyl)oxy)-7-methyl-1,4-dioxaspiro[4.5]decan-7-yl)methanamine

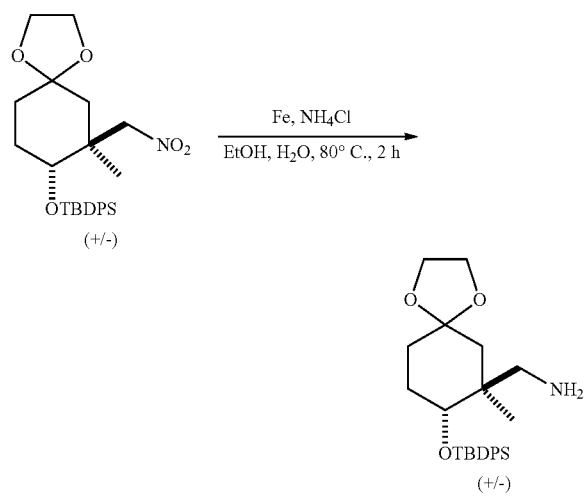

Iron powder (21.75 g, 389.4 mmol, 10 eq.) was added to a solution of rac-tert-butyl(((7S,8R)-7-methyl-7-(nitromethyl)-1,4-dioxaspiro[4.5]decan-8-yl)oxy)diphenylsilane (18.3 g, 39.01 mmol, 1 eq.) and ammonium chloride (8.33 g, 155.76 mmol, 4 eq.) in a mixed solvent of ethanol (120 mL) and water (40 mL). The resulting mixture was heated to 80° C. and stirred for 2 hours. After cooling to room temperature, the resulting mixture was filtered, the filter cake was washed with ethanol (2×200 mL). The filtrate was concentrated under reduced pressure to afford the crude product rac-((7S,8R)-8-((tert-butyldiphenylsilyl)oxy)-7-methyl-1,4-dioxaspiro[4.5]decan-7-yl)methanamine (17 g crude) as a yellow solid. LCMS (ESI-MS) m/z=440 [M+H]$^+$.

rac-3-((((7S,8R)-8-((tert-Butyldiphenylsilyl)oxy)-7-methyl-1,4-dioxaspiro[4.5]decan-7-yl)methyl)amino)-4-nitrobenzonitrile

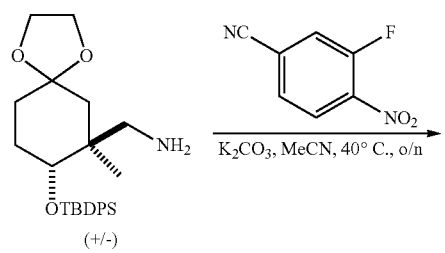

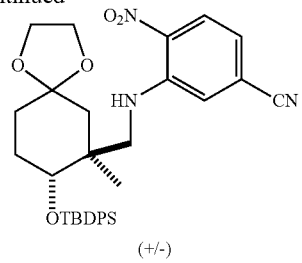

Potassium carbonate (10.68 g, 77.3 mmol, 2 eq.) was added to a solution of rac-((7S,8R)-8-((tert-butyldiphenylsilyl)oxy)-7-methyl-1,4-dioxaspiro[4.5]decan-7-yl)methanamine (17 g, 38.7 mmol, 1 eq.) and 3-fluoro-4-nitrobenzonitrile (6.41 g, 38.7 mmol, 1 eq.) in acetonitrile (150 mL). The resulting mixture was heated to 40° C. and stirred overnight. After cooling to room temperature, the reaction mixture was diluted with water (200 mL) and extracted with ethyl acetate (3×200 mL). The combined organic layers were dried over anhydrous sodium sulfate, filtered and the filtrate was concentrated under vacuum to afford the crude product. The residue was purified by silica gel column chromatography, eluted with ethyl acetate in petroleum ether from 0% to 15%. The fractions with desired mass signal were combined and concentrated under vacuum to afford the desired product rac-3-((((7S,8R)-8-((tert-butyldiphenylsilyl)oxy)-7-methyl-1,4-dioxaspiro[4.5]decan-7-yl)methyl)amino)-4-nitrobenzonitrile (14 g, 61.3% yield for 2 steps) as an orange solid. $^1$H NMR (400 MHz, DMSO-$d_6$) δ 8.30-8.26 (m, 1H), 7.61-7.48 (m, 4H), 7.41-7.34 (m, 7H), 7.15 (dd, J=8.2, 4.6 Hz, 1H), 6.74 (s, 1H), 3.59-3.57 (m, 4H), 3.44-3.34 (m, 1H), 3.02-2.99 (m, 1H), 2.88-2.85 (m, 1H), 1.85-1.30 (m, 6H), 1.07 (s, 9H), 0.94 (s, 3H). LCMS (ESI-MS) m/z=586 [M+H]$^+$.

rac-4-Amino-3-((((7S,8R)-8-((tert-butyldiphenylsilyl)oxy)-7-methyl-1,4-dioxaspiro[4.5]decan-7-yl)methyl)amino)benzonitrile

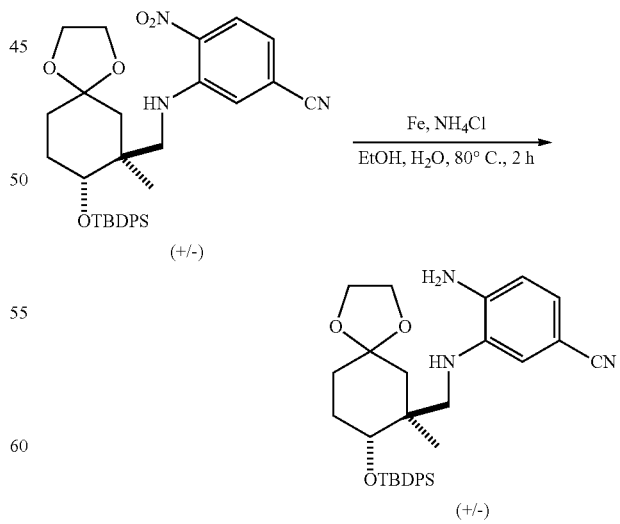

Iron powder (13.34 g, 238.91 mmol, 10 eq.) was added to a solution of rac-3-((((7S,8R)-8-((tert-butyldiphenylsilyl)oxy)-7-methyl-1,4-dioxaspiro[4.5]decan-7-yl)methyl)

amino)-4-nitrobenzonitrile (14 g, 23.93 mmol, 1 eq.) and ammonium chloride (5.11 g, 95.56 mmol, 4 eq.) in a mixed solvent of ethanol (120 mL) and water (40 mL). The resulting mixture was heated to 80° C. and stirred for 2 hours. After cooling to room temperature, the resulting mixture was filtered, the filter cake was washed with ethanol (2×200 mL). The filtrate was concentrated under reduced pressure to afford the crude product rac-4-amino-3-((((7S,8R)-8-((tert-butyldiphenylsilyl)oxy)-7-methyl-1,4-dioxaspiro[4.5]decan-7-yl)methyl)amino)benzonitrile (13 g crude) as a yellow solid. LCMS (ESI-MS) m/z=556 [M+H]+.

rac-1-(((7S,8R)-8-((tert-Butyldiphenylsilyl)oxy)-7-methyl-1,4-dioxaspiro[4.5]decan-7-yl)methyl)-1H-benzo[d]imidazole-6-carbonitrile

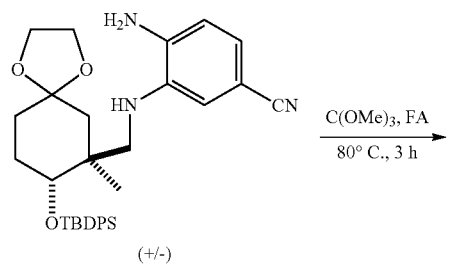

Formic acid (1.08 g, 23.38 mmol, 1 eq.) was added to a solution of rac-4-amino-3-((((7S,8R)-8-((tert-butyldiphenylsilyl)oxy)-7-methyl-1,4-dioxaspiro[4.5]decan-7-yl)methyl)amino)benzonitrile (13 g, 23.4 mmol, 1 eq.) in trimethoxymethane (71.95 g, 678 mmol, 29 eq.). The resulting mixture was heated to 80° C., stirred for 3 hours and concentrated under vacuum to afford the crude product. The residue was purified by silica gel column chromatography, eluted with ethyl acetate in petroleum ether from 0% to 100%. The fractions with desired mass signal were combined and concentrated under vacuum to afford the desired product rac-1-(((7S,8R)-8-((tert-butyldiphenylsilyl)oxy)-7-methyl-1,4-dioxaspiro[4.5]decan-7-yl)methyl)-1H-benzo[d]imidazole-6-carbonitrile (10 g, 73.9% yield for 2 steps) as a pink solid. $^1$H NMR (400 MHz, DMSO-$d_6$) δ 8.40-8.35 (m, 1H), 7.98-7.93 (m, 1H), 7.82-7.79 (m, 1H), 7.63-7.51 (m, 5H), 7.36-7.29 (m, 6H), 3.59-3.46 (m, 6H), 3.44-3.34 (m, 1H), 1.59-1.43 (m, 6H), 1.01 (s, 9H), 0.98 (s, 3H). LCMS (ESI-MS) m/z=566 [M+H]+.

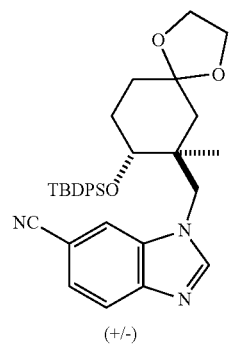

rac-1-(((1S,2R)-2-((tert-Butyldiphenylsilyl)oxy)-1-methyl-5-oxocyclohexyl)methyl)-1H-benzo[d]imidazole-6-carbonitrile

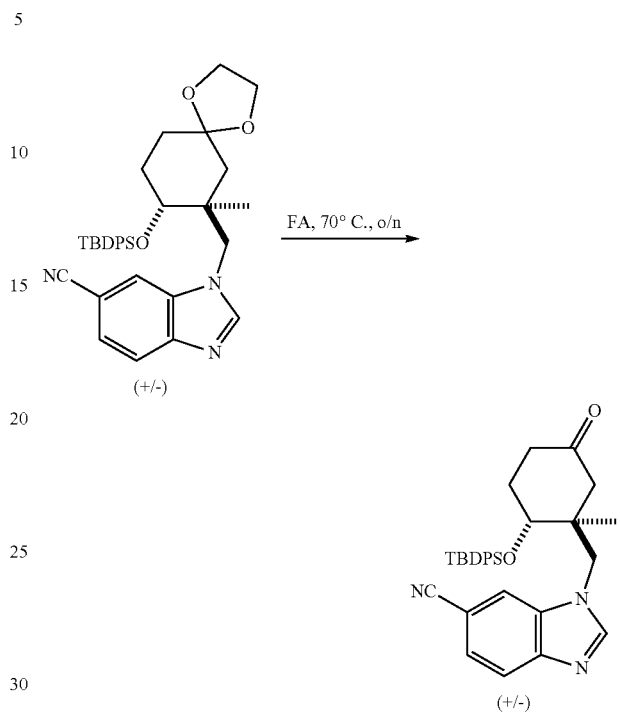

A solution of rac-1-(((7S,8R)-8-((tert-butyldiphenylsilyl)oxy)-7-methyl-1,4-dioxaspiro[4.5]decan-7-yl)methyl)-1H-benzo[d]imidazole-6-carbonitrile (10 g, 17.7 mmol, 1 eq.) in formic acid (100 mL) was stirred overnight at 70° C. The reaction mixture was diluted with saturated sodium bicarbonate aqueous solution (100 mL) and extracted with ethyl acetate (3×100 mL). The combined organic layers were washed with brine, dried over anhydrous sodium sulfate, filtered and concentrated under vacuum to afford the crude product rac-1-(((1S,2R)-2-((tert-butyldiphenylsilyl)oxy)-1-methyl-5-oxocyclohexyl)methyl)-1Hbenzo[d]imidazole-6-carbonitrile (10 g crude) as a yellow solid. LCMS (ESI-MS) m/z=522 [M+H]+.

rac-1-(((3S,5S,6R)-6-((tert-Butyldiphenylsilyl)oxy)-5-methyl-1-oxaspiro[2.5]octan-5-yl)methyl)-1H-benzo[d]imidazole-6-carbonitrile

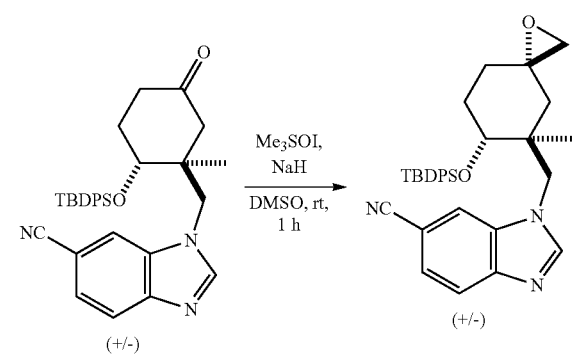

Sodium hydride (60% in mineral oil, 3.07 g, 76.6 mmol, 4 eq.) was added to a solution of trimethylsulfoxonium iodide (16.87 g, 76.6 mmol, 4 eq.) in dimethyl sulfoxide (100 mL) and the resulting mixture was stirred at room temperature for 30 minutes. To this mixture was added a solution of rac-1-(((1S,2R)-2-((tert-butyldiphenylsilyl)oxy)-1-methyl-5-oxocyclohexyl)methyl)-1H-benzo[d]imidazole-6-carbonitrile (10 g, 19.19 mmol, 1 eq.) in dimethyl sulfoxide (100 mL) dropwise. After 8 minutes, the reaction mixture was cooled to 0° C., quenched slowly with 200 mL water and extracted with ethyl acetate (3×200 mL). The combined organic layers were washed with brine, dried over anhydrous sodium sulfate, filtered and concentrated under vacuum to afford the crude product rac-1-(((3S,5S,6R)-6-((tert-butyldiphenylsilyl)oxy)-5-methyl-1-oxaspiro[2.5]octan-5-yl)methyl)-1H-benzo[d]imidazole-6-carbonitrile (10 g crude) as a yellow solid. LCMS (ESI-MS) m/z=536 [M+H]⁺.

rac-1-(((5S,7S,8R)-8-((tert-Butyldiphenylsilyl)oxy)-7-methyl-2-oxo-1-oxa-3-azaspiro[4.5]decan-7-yl)methyl)-1H-benzo[d]imidazole-6-carbonitrile

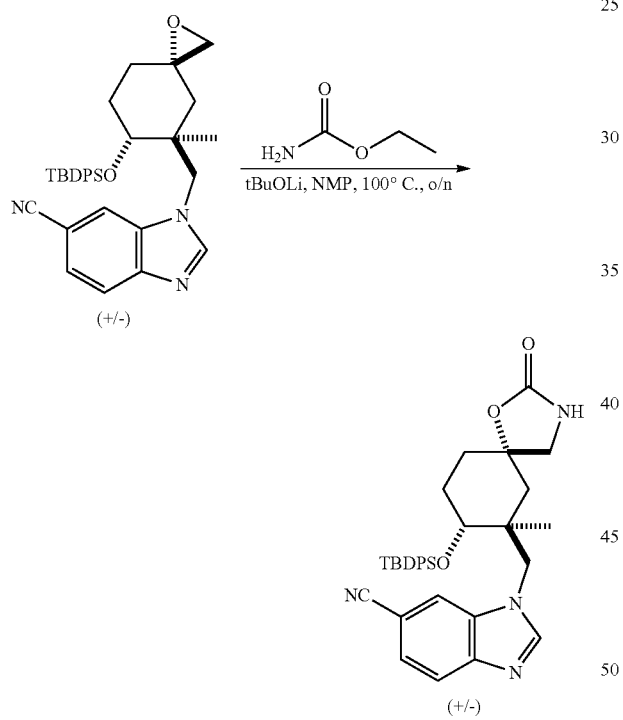

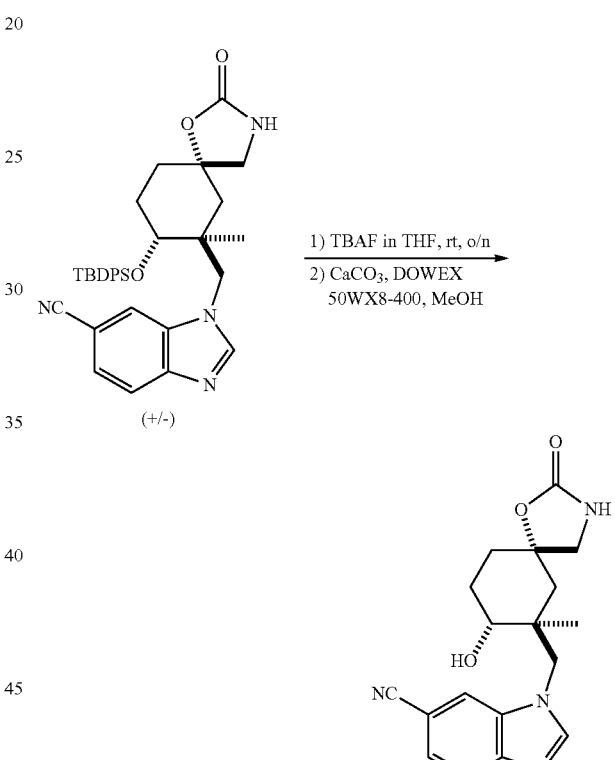

Lithium tert-butoxide (2.99 g, 37.32 mmol, 2 eq.) was added to a solution of ethyl carbamate (33.21 g, 373.20 mmol, 20 eq.) in N-methyl pyrrolidone (100 mL). After stirring for 5 minutes at room temperature, a solution of rac-1-(((3S,5S,6R)-6-((tert-butyldiphenylsilyl)oxy)-5-methyl-1-oxaspiro[2.5]octan-5-yl)methyl)-1H-benzo[d]imidazole-6-carbonitrile (10 g, 18.69 mmol, 1 eq.) in N-methyl pyrrolidone (100 mL) was added dropwise. The reaction mixture was subsequently heated to 100° C. and stirred overnight. After cooled to room temperature, the reaction mixture was diluted with water (200 mL) and extracted with ethyl acetate (3×200 mL). The combined organic layers were dried over anhydrous sodium sulfate, filtered and the filtrate was concentrated under vacuum to afford the crude product. The residue was purified by silica gel column chromatography, eluted with methanol in dichloromethane from 0% to 2%. The fractions with desired mass signal were combined and concentrated under vacuum to afford the desired product rac-1-(((5S,7S,8R)-8-((tert-butyldiphenylsilyl)oxy)-7-methyl-2-oxo-1-oxa-3-azaspiro[4.5]decan-7-yl)methyl)-1H-benzo[d]imidazole-6-carbonitrile (5.5 g, 53.8% yield for 3 steps) as a light pink solid. $^1$H NMR (400 MHz, DMSO-$d_6$) δ 8.40-8.35 (m, 1H), 7.98-7.93 (m, 1H), 7.82-7.79 (m, 1H), 7.63-7.51 (m, 5H), 7.36-7.29 (m, 6H), 6.50 (s, 1H), 3.59-3.46 (m, 2H), 3.44-3.34 (m, 1H), 3.25-3.20 (m, 2H), 1.79-1.45 (m, 6H), 1.22 (s, 9H), 0.97 (s, 3H). LCMS (ESI-MS) m/z=579 [M+H]⁺.

rac-1-(((5S,7S,8R)-8-Hydroxy-7-methyl-2-oxo-1-oxa-3-azaspiro[4.5]decan-7-yl)methyl)-1H-benzo[d]imidazole-6-carbonitrile rac-1-(((5S,7S,8R)-8-((tert-Butyldiphenylsilyl)oxy)-7-methyl-2-oxo-1-oxa-3-azaspiro[4.5]decan-7-yl)methyl)-1H-benzo[d]imidazole-6-carbonitrile (579 mg, 1 mmol, 1 eq.) was added to a solution of tetrabutylammoniumfluoride in tetrahydrofuran (1 M, 1 mL, 1 mmol, 1 eq.). The mixture was stirred overnight at room temperature. The following day, calcium carbonate (200.18 mg, 2 mmol, 2 eq.) and DOWEX 50WX8-400 (800 mg, 1 eq.) were added to the reaction mixture, followed by methanol (2 mL). The resulting mixture was stirred at room temperature for 1 hour and filtered, the filter cake was washed with methanol (2×10 mL). The filtrate was concentrated under reduced pressure. The residue was purified by silica gel column chromatography, eluted with methanol in dichloromethane from 0% to 10%. The fractions with desired mass signal were combined and concentrated under vacuum to afford the desired product rac-1-(((5S,7S,8R)-8-hydroxy-7-methyl-2-oxo-1-oxa-3-azaspiro[4.5]decan-7-yl)methyl)-1H-benzo[d]imidazole-6-carbonitrile (270 mg, 79.4% yield) as a white solid. $^1$H NMR (400 MHz, DMSO-$d_6$) δ 8.30 (s, 1H), 7.98-7.93 (m, 1H), 7.82-7.79 (m, 1H), 7.63-7.51 (m, 1H), 6.45 (s, 1H), 4.75 (s, 1H), 3.63-3.59 (m, 2H), 3.47-3.35 (m, 1H), 3.25-3.20 (m, 2H), 1.81-1.47 (m, 6H), 0.97 (s, 3H). LCMS (ESI-MS) m/z=341 [M+H]$^+$.

rac-1-(((5S,7S)-7-Methyl-2,8-dioxo-1-oxa-3-azaspiro[4.5]decan-7-yl)methyl)-1H-benzo[d]imidazole-6-carbonitrile

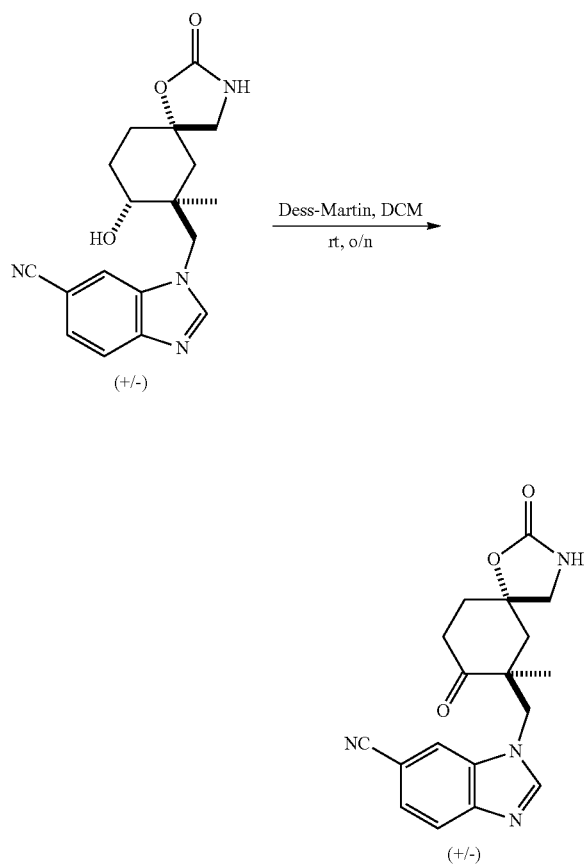

Dess-Martin periodinane (224.45 mg, 0.53 mmol, 1.2 eq.) was added to a solution of rac-1-(((5S,7S,8R)-8-hydroxy-7-methyl-2-oxo-1-oxa-3-azaspiro[4.5]decan-7-yl)methyl)-1H-benzo[d]imidazole-6-carbonitrile (150 mg, 0.44 mmol, 1 eq.) in dichloromethane (2 mL). The resulting mixture was stirred for 3 hours at the room temperature. The residue was purified by silica gel column chromatography, eluted with methanol in dichloromethane from 0% to 2%. The fractions with desired mass signal were combined and concentrated under vacuum to afford the desired product rac-1-(((5S,7S)-7-methyl-2,8-dioxo-1-oxa-3-azaspiro[4.5]decan-7-yl)methyl)-1H-benzo[d]imidazole-6-carbonitrile (130 mg, 87.18% yield) as a white solid. $^1$H NMR (400 MHz, DMSO-$d_6$) δ 8.30 (s, 1H), 7.98-7.93 (m, 1H), 7.82-7.79 (m, 1H), 7.63-7.51 (m, 1H), 6.45 (s, 1H), 3.63-3.59 (m, 2H), 3.25-3.20 (m, 2H), 2.35-2.29 (m, 2H), 2.11-1.85 (m, 4H), 1.12 (s, 3H). LCMS (ESI-MS) m/z=339 [M+H]$^+$.

rac-1-(((5S,7S)-3-(5-(2-Hydroxypropan-2-yl)pyrazin-2-yl)-7-methyl-2,8-dioxo-1-oxa-3-azaspiro[4.5] decan-7-yl)methyl)-1H-benzo[d]imidazole-6-carbonitrile

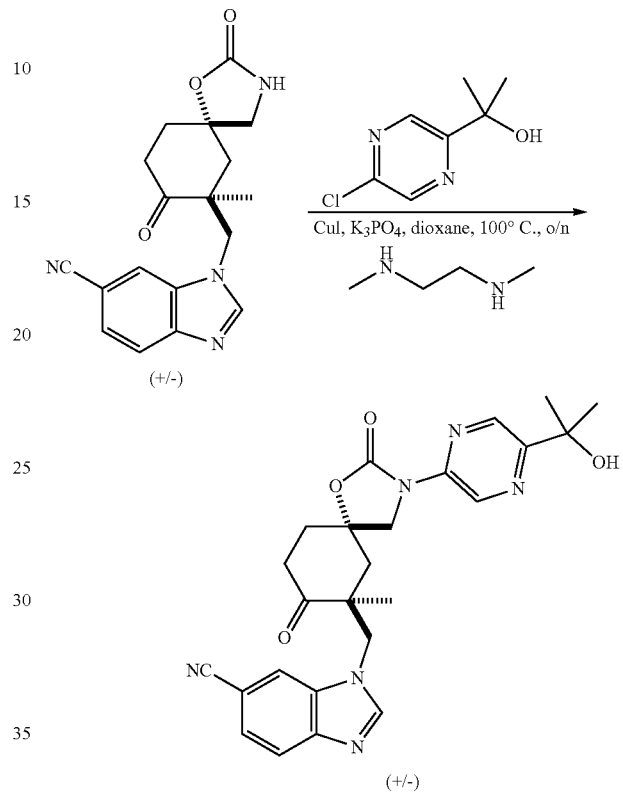

Copper (I) iodide (72.37 mg, 0.38 mmol, 1 eq.) was added to a solution of rac-1-(((5S,7S)-7-methyl-2,8-dioxo-1-oxa-3-azaspiro[4.5]decan-7-yl)methyl)-1H-benzo[d]imidazole-6-carbonitrile (130 mg, 0.38 mmol, 1 eq.), 2-(5-chloropyrazin-2-yl)propan-2-ol (65.74 mg, 0.38 mmol, 1 eq.), N$^1$,N$^2$-dimethylethane-1,2-diamine (66.88 mg, 0.76 mmol, 2 eq.) and tripotassium phosphate (161.32 mg, 0.76 mmol, 2 eq.) in 1,4-dioxane (2 mL) under nitrogen atmosphere. The resulting mixture was heated to 100° C. and stirred overnight. After cooled to room temperature, the resulting mixture was filtered and the filtrate was concentrated under vacuum. The residue was purified by silica gel column chromatography, eluted with methanol in dichloromethane from 0% to 3%. The fractions with desired mass signal were combined and concentrated under vacuum to afford the desired product rac-1-(((5S,7S)-3-(5-(2-hydroxypropan-2-yl)pyrazin-2-yl)-7-methyl-2,8-dioxo-1-oxa-3-azaspiro [4.5] decan-7-yl)methyl)-1H-benzo[d]imidazole-6-carbonitrile (100 mg, 54.7% yield) as a light yellow solid. $^1$H NMR (300 MHz, DMSO-$d_6$) δ 9.27 (s, 1H), 8.64 (d, J=4.0 Hz, 1H), 8.32 (d, J=10.1 Hz, 2H), 7.86-7.79 (m, 1H), 7.60 (t, J=5.6 Hz, 1H), 5.44 (d, J=3.3 Hz, 1H), 4.85 (d, J=14.7 Hz, 1H), 4.60 (d, J=14.9 Hz, 1H), 4.16 (d, J=10.1 Hz, 1H), 4.05 (d, J=10.5 Hz, 1H), 3.19 (s, 1H), 2.58 (d, J=12.4 Hz, 2H), 2.46-2.19 (m, 3H), 1.47 (t, J=3.2 Hz, 6H), 0.95 (d, J=3.6 Hz, 3H). LCMS (ESI-MS) m/z=475 [M+H]$^+$.

1-(((5S,7S)-3-(5-(2-Hydroxypropan-2-yl)pyrazin-2-yl)-7-methyl-2,8-dioxo-1-oxa-3-azaspiro[4.5]decan-7-yl)methyl)-1H-benzo[d]imidazole-6-carbonitrile and 1-(((5R,7R)-3-(5-(2-Hydroxypropan-2-yl)pyrazin-2-yl)-7-methyl-2,8-dioxo-1-oxa-3-azaspiro[4.5]decan-7-yl)methyl)-1H-benzo[d] imidazole-6-carbonitrile

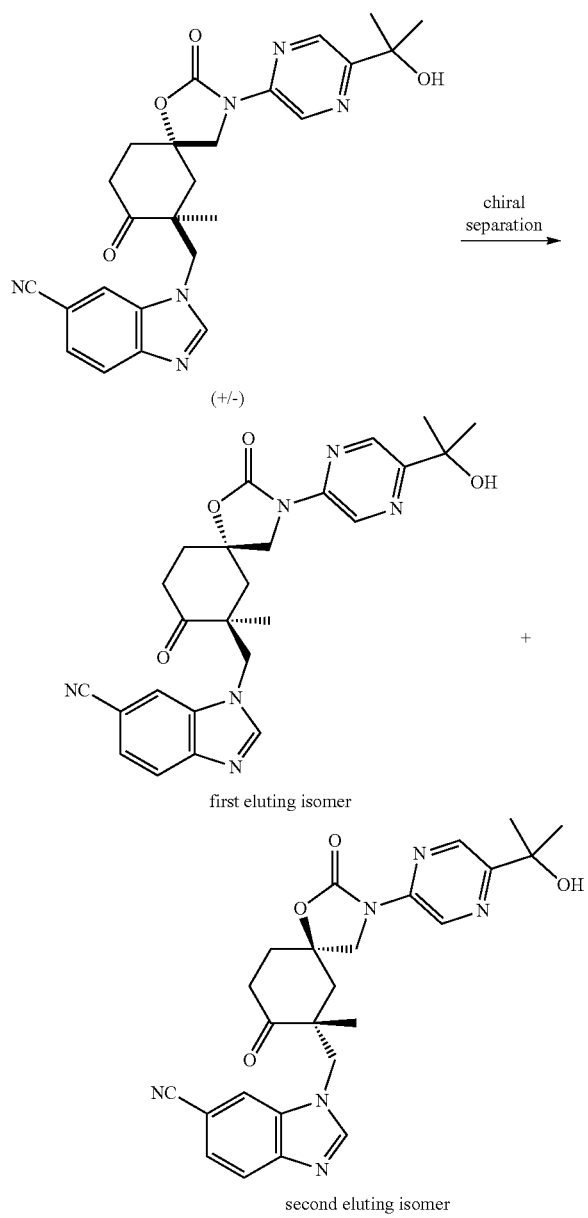

rac-1-(((5S,7S)-3-(5-(2-Hydroxypropan-2-yl)pyrazin-2-yl)-7-methyl-2,8-dioxo-1-oxa-3-azaspiro[4.5]decan-7-yl)methyl)-1H-benzo[d]imidazole-6-carbonitrile (100 mg, 0.21 mmol, 1 eq.) was separated by Prep-Chiral-HPLC with the condition: Column: CHIRALPAK ID, 2*25 cm, 5 μm; Mobile Phase A: EtOH-HPLC, Mobile Phase B: MtBE (0.5% 2M NH$_3$-MeOH)-HPLC; Flow rate: 13 mL/min; Gradient: 50% B to 50% B in 13 min; Wave Length: 220/254 nm; RT1(min): 8.31; RT2(min): 23.51; Sample Solvent: EtOH: DCM=1:1-HPLC; Injection Volume: 2 mL. The desired fractions were combined and lyophilized to afford the products:

First eluting isomer: 1-(((5S,7S)-3-(5-(2-Hydroxypropan-2-yl)pyrazin-2-yl)-7-methyl-2,8-dioxo-1-oxa-3-azaspiro[4.5]decan-7-yl)methyl)-1H-benzo[d]imidazole-6-carbonitrile (25.6 mg, 98.8% purity, 98.5% ee, 25.6% yield) as a white solid. $^1$H NMR (300 MHz, DMSO-d$_6$) δ 9.27 (s, 1H), 8.64 (d, J=4.0 Hz, 1H), 8.32 (d, J=10.1 Hz, 2H), 7.86-7.79 (m, 1H), 7.60 (t, J=5.6 Hz, 1H), 5.44 (d, J=3.3 Hz, 1H), 4.85 (d, J=14.7 Hz, 1H), 4.60 (d, J=14.9 Hz, 1H), 4.16 (d, J=10.1 Hz, 1H), 4.05 (d, J=10.5 Hz, 1H), 3.19 (s, 1H), 2.58 (d, J=12.4 Hz, 2H), 2.46-2.19 (m, 3H), 1.47 (t, J=3.2 Hz, 6H), 0.95 (d, J=3.6 Hz, 3H). LCMS (ESI-MS) m/z=475 [M+H]$^+$.

Second eluting isomer: 1-(((5R,7R)-3-(5-(2-Hydroxypropan-2-yl)pyrazin-2-yl)-7-methyl-2,8-dioxo-1-oxa-3-azaspiro[4.5]decan-7-yl)methyl)-1H-benzo[d]imidazole-6-carbonitrile (22.7 mg, 99.6% purity, 100% ee, 22.7% yield) as a white solid. $^1$H NMR (300 MHz, DMSO-d$_6$) δ 9.27 (s, 1H), 8.64 (d, J=4.0 Hz, 1H), 8.32 (d, J=10.1 Hz, 2H), 7.86-7.79 (m, 1H), 7.60 (t, J=5.6 Hz, 1H), 5.44 (d, J=3.3 Hz, 1H), 4.85 (d, J=14.7 Hz, 1H), 4.60 (d, J=14.9 Hz, 1H), 4.16 (d, J=10.1 Hz, 1H), 4.05 (d, J=10.5 Hz, 1H), 3.19 (s, 1H), 2.58 (d, J=12.4 Hz, 2H), 2.46-2.19 (m, 3H), 1.47 (t, J=3.2 Hz, 6H), 0.95 (d, J=3.6 Hz, 3H). LCMS (ESI-MS) m/z=475 [M+H]$^+$.

Example 5. Preparation of: 1-(((5S,7S,8R)-8-Fluoro-3-(5-(2-hydroxypropan-2-yl)pyrazin-2-yl)-7-methyl-2-oxo-1-oxa-3-azaspiro[4.5]decan-7-yl)methyl)-1H-benzo[d]imidazole-6-carbonitrile

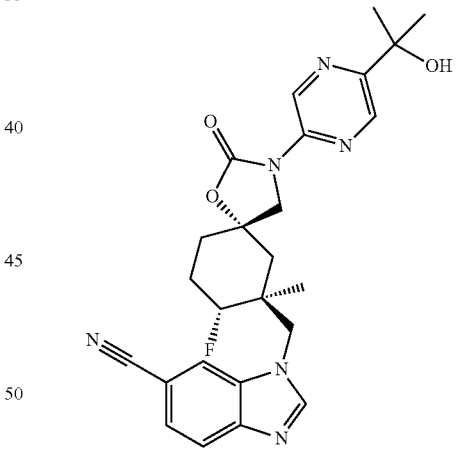

Reaction Scheme

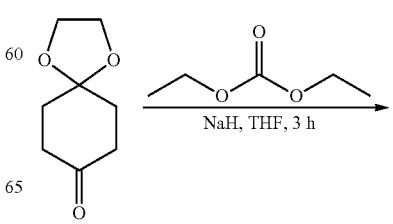

-continued
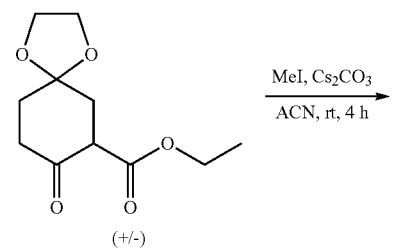
MeI, Cs2CO3
ACN, rt, 4 h
(+/-)
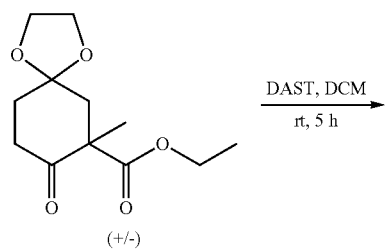
DAST, DCM
rt, 5 h
(+/-)
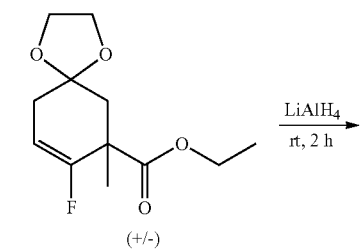
LiAlH4
rt, 2 h
(+/-)
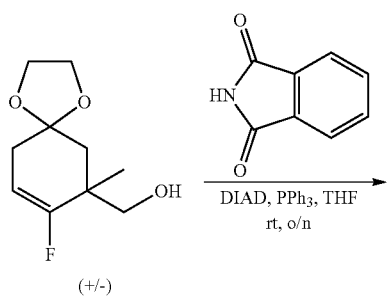
DIAD, PPh3, THF
rt, o/n
(+/-)
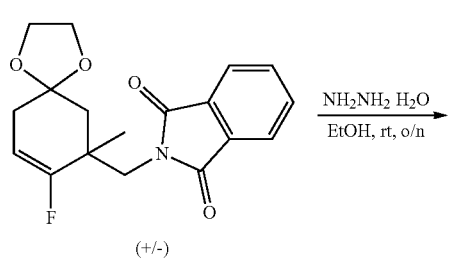
NH2NH2 H2O
EtOH, rt, o/n
(+/-)
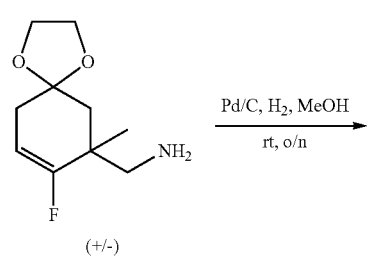
Pd/C, H2, MeOH
rt, o/n
(+/-)
-continued
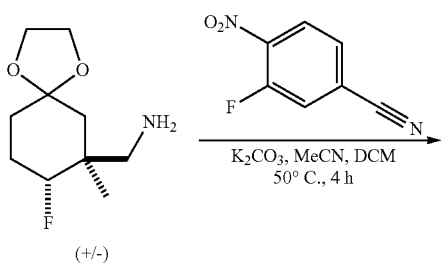
K2CO3, MeCN, DCM
50° C., 4 h
(+/-)
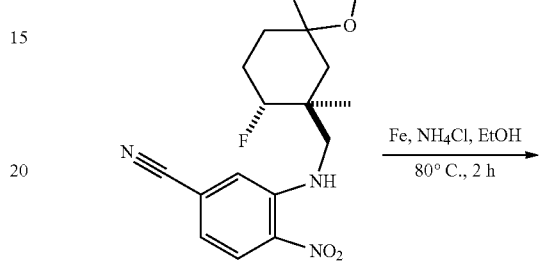
Fe, NH4Cl, EtOH
80° C., 2 h
(+/-)
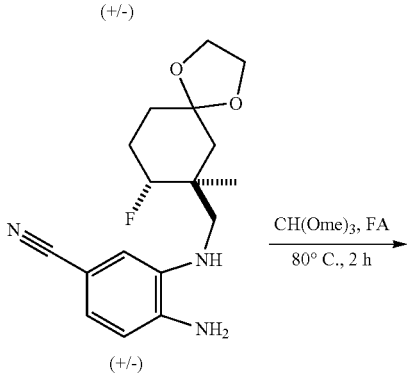
CH(OMe)3, FA
80° C., 2 h
(+/-)
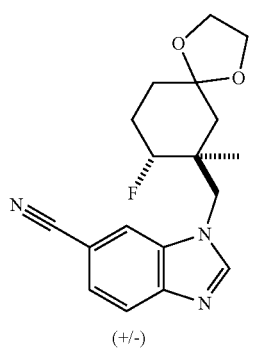
FA, 70° C
o/n
(+/-)
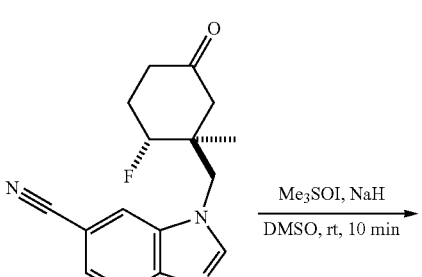
Me3SOI, NaH
DMSO, rt, 10 min
(+/-)

rac-Ethyl 8-fluoro-7-methyl-1,4-dioxaspiro[4.5]dec-8-ene-7-carboxylate

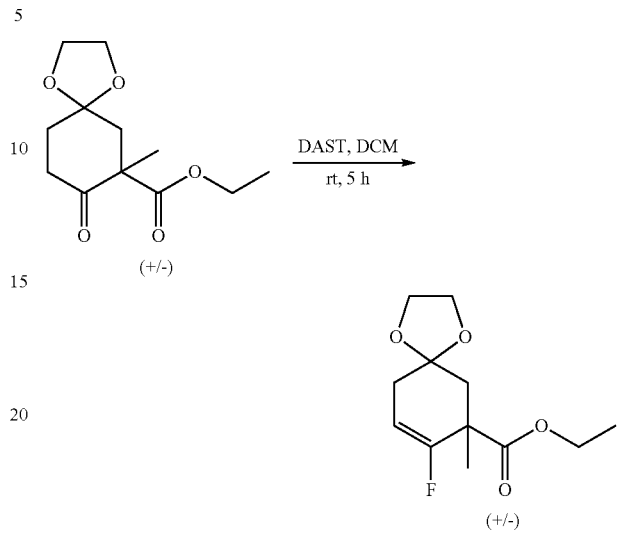

To a mixture of rac-ethyl 7-methyl-8-oxo-1,4-dioxaspiro[4.5]decane-7-carboxylate (30 g, 124 mmol) in dichloromethane (500 mL) was added diethylaminosulfur trifluoride (39.9 g, 248 mmol) at 0° C. The solution was warmed to room temperature and stirred for 5 hours. The mixture was then slowly added to stirred aq. sodium bicarbonate (600 mL) at 0° C., and the resulting solution was extracted with dichloromethane (3×300 mL). The organic layer was dried over sodium sulfate, filtered and concentrated to afford rac-ethyl 8-fluoro-7-methyl-1,4-dioxaspiro [4.5]dec-8-ene-7-carboxylate (35 g crude). LCMS (ESI-MS) m/z=245.1 [M+H]$^+$.

rac-(8-Fluoro-7-methyl-1,4-dioxaspiro[4.5]dec-8-en-7-yl)methanol

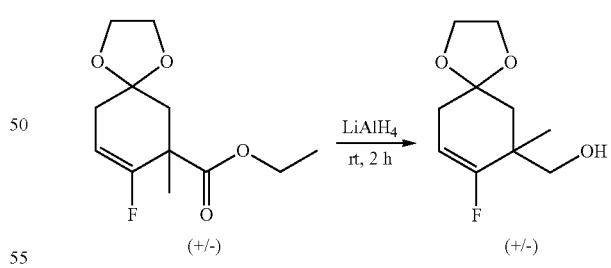

To a mixture of rac-ethyl 8-fluoro-7-methyl-1,4-dioxaspiro[4.5]dec-8-ene-7-carboxylate (35 g, 143 mmol) in tetrahydrofuran (600 mL) was added lithium aluminum hydride (115 mL, 286 mmol) at 0° C., the mixture was stirred for 2 hours at room temperature, then the mixture was quenched with cold ethanol. The resulting mixture was filtered and the filtrate was concentrated to afford crude product rac-(8-fluoro-7-methyl-1,4-dioxaspiro[4.5]dec-8-en-7-yl)methanol (30 g crude). LCMS (ESI-MS) m/z=203.1 [M+H]$^+$.

A mixture of diethyl carbonate (94 g, 79.6 mmol) and sodium hydride (60% in mineral oil, 37.5 g, 93.8 mmol) in tetrahydrofuran (800 mL) was heated to reflux, then a solution of 1,4-dioxaspiro[4.5]decan-8-one (50.0 g, 32.0 mmol) in tetrahydrofuran (230 mL) was added. The resulting mixture was stirred for 3 hours and then allowed to cool to room temperature. Water (500 mL) and acetic acid (500 mL) were added to quench the reaction. The resulting solution was then extracted with ethyl acetate (3×500 mL), the organic layer was dried over sodium sulfate, filtered, and concentrated to afford rac-ethyl 8-oxo-1,4-dioxaspiro[4.5]decane-7-carboxylate (52 g, 0.23 mol) as yellow oil. This was used without further purification. LCMS (ESI-MS) m/z=229.1 [M+H]$^+$.

rac-Ethyl 7-methyl-8-oxo-1,4-dioxaspiro[4.5]decane-7-carboxylate

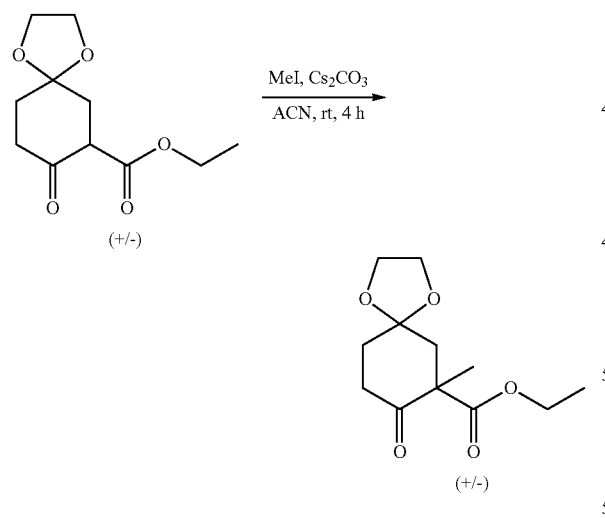

Iodomethane (48.5 g, 341 mmol) was added to a mixture of rac-ethyl 8-oxo-1,4-dioxaspiro[4.5]decane-7-carboxylate (52 g, 228 mmol) and cesium carbonate (149 g, 456 mmol) in acetonitrile (600 mL). The resulting mixture was stirred for 4 hours at room temperature. The mixture was filtered and the filtrate was concentrated to afford the crude product. The residue was purified by silica gel column chromatography, and eluted with ethyl acetate in petroleum ether from 0% to 30% to afford the product rac-ethyl 7-methyl-8-oxo-1,4-dioxaspiro[4.5]decane-7-carboxylate (45 g, 81.5%) as light yellow oil. LCMS (ESI-MS) m/z=243.1 [M+H]$^+$.

103 rac-2-((8-Fluoro-7-methyl-1,4-dioxaspiro[4.5]dec-8-en-7-yl)methyl)isoindoline-1,3-dione

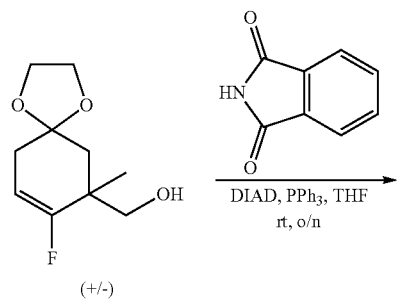

To a mixture of rac-(8-fluoro-7-methyl-1,4-dioxaspiro[4.5]dec-8-en-7-yl)methanol (25 g, 124 mmol), isoindoline-1,3-dione (20 g, 136 mmol) and triphenyl phosphate (48.6 g, 185 mmol) in tetrahydrofuran (300 mL) was added diisopropyl azodiformate (37.5 g, 185 mmol). The mixture was stirred overnight at room temperature and the following morning the mixture was poured into ice water (200 mL). The resulting solution was extracted with ethyl acetate (3×200 mL), the organic layer was dried over sodium sulfate, filtered and concentrated to afford the crude product. The residue was purified by silica gel column chromatography, and eluted with ethyl acetate in petroleum ether from 0% to 40% to afford the product rac-2-((8-fluoro-7-methyl-1,4-dioxaspiro[4.5]dec-8-en-7-yl)methyl)isoindoline-1,3-dione (18 g, 43.9%) as yellow oil. LCMS (ESI-MS) m/z=332.1 [M+H]$^+$.

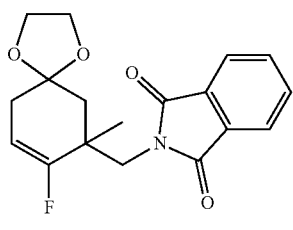

rac-(8-Fluoro-7-methyl-1,4-dioxaspiro[4.5]dec-8-en-7-yl)methanamine

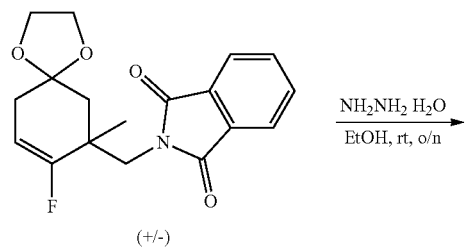

104

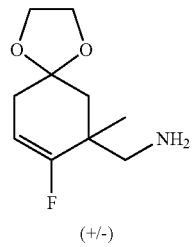

To a mixture of rac-2-((8-fluoro-7-methyl-1,4-dioxaspiro[4.5]dec-8-en-7-yl)methyl)isoindoline-1,3-dione (18 g, 54 mmol) in ethanol (100 mL) was added hydrazine (17 g, 272 mmol, 80%). The mixture was stirred overnight at room temperature, then diluted with water (300 mL). The resulting solution was extracted with ethyl acetate (3×200 mL), the organic layer was dried over sodium sulfate, filtered and concentrated to afford the product rac-(8-fluoro-7-methyl-1,4-dioxaspiro[4.5]dec-8-en-7-yl)methanamine (8 g crude). LCMS (ESI-MS) m/z=202.1 [M+H]$^+$.

rac-((7S,8R)-8-Fluoro-7-methyl-1,4-dioxaspiro[4.5]decan-7-yl)methanamine

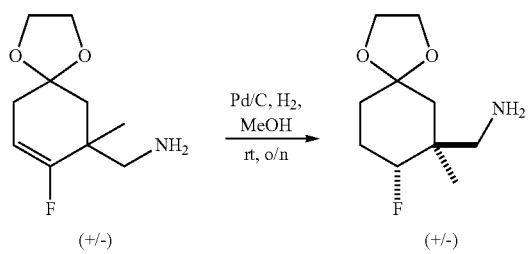

To a mixture of rac-(8-fluoro-7-methyl-1,4-dioxaspiro[4.5]dec-8-en-7-yl)methanamine (8 g, 39.8 mmol) in methanol (80 mL) was added palladium carbon (4 g, 50% wt, 10% on carbon). The mixture was stirred overnight at room temperature under hydrogen atmosphere (2 atm). The suspension was filtered and the filtrate was concentrated under vacuum to afford rac-((7S,8R)-8-fluoro-7-methyl-1,4-dioxaspiro[4.5]decan-7-yl)methanamine (7.2 g crude) as yellow oil. LCMS (ESI-MS) m/z=204.1 [M+H]$^+$.

rac-3-((((7S,8R)-8-Fluoro-7-methyl-1,4-dioxaspiro[4.5]decan-7-yl)methyl)amino)-4-nitrobenzonitrile

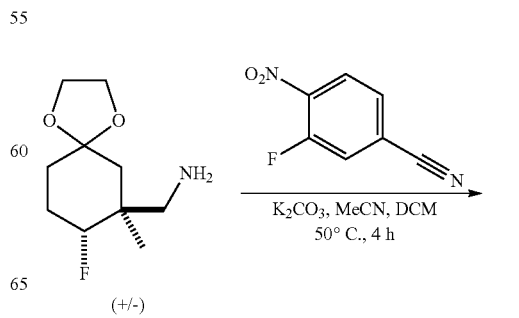

-continued

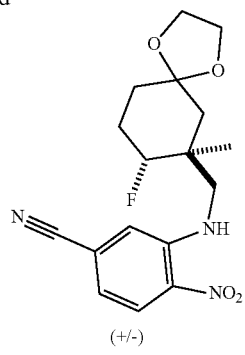
(+/-)

To a mixture of rac-((7S,8R)-8-fluoro-7-methyl-1,4-dioxaspiro[4.5]decan-7-yl)methanamine (7.2 g, 35.4 mmol) and 3-fluoro-4-nitrobenzonitrile (5.88 g, 35.4 mmol) in acetonitrile (100 mL) was added potassium carbonate (9.79 g, 70.8 mmol), and the resulting mixture was stirred for 4 hours at 50° C. The suspension was filtered and the filtrate was diluted with water (200 mL), then the resulting solution was extracted with dichloromethane (3×200 mL), the organic layer was dried over sodium sulfate, filtered and concentrated to afford the crude product. The residue was purified by silica gel column chromatography, and eluted with ethyl acetate in petroleum ether from 0% to 15% to afford the product rac-3-((((7S,8R)-8-fluoro-7-methyl-1,4-dioxaspiro[4.5]decan-7-yl)methyl)amino)-4-nitrobenzonitrile (6 g, 48.4%) as an orange solid. LCMS (ESI-MS) m/z=350.1 [M+H]⁺.

rac-4-Amino-3-((((7S,8R)-8-fluoro-7-methyl-1,4-dioxaspiro[4.5]decan-7-yl)methyl)amino)benzonitrile

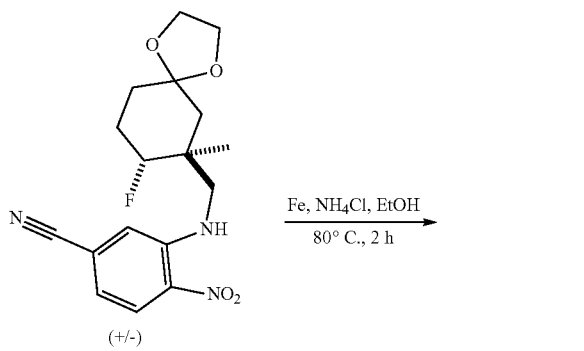

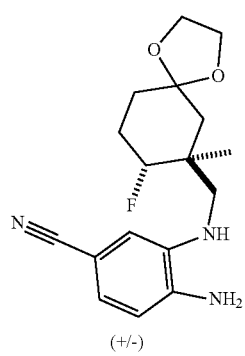
(+/-)

To a mixture of rac-3-((((7S,8R)-8-fluoro-7-methyl-1,4-dioxaspiro[4.5]decan-7-yl)methyl)amino)-4-nitrobenzonitrile (5.5 g, 15.7 mmol) and ammonium chloride (4.21 g, 78.7 mmol) in ethanol (100 mL) and water (30 mL) was added iron (4.40 g, 78.7 mmol), the mixture was stirred for 2 hours at 80° C. The mixture was cooled to room temperature and filtered. The filtrate was concentrated under vacuum to afford rac-4-amino-3-((((7S,8R)-8-fluoro-7-methyl-1,4-dioxaspiro[4.5]decan-7-yl)methyl)amino)benzonitrile (4.2 g crude) as a yellow solid. LCMS(ESI-MS) m/z=320.2 [M+H]⁺.

rac-1-(((7S,8R)-8-Fluoro-7-methyl-1,4-dioxaspiro [4.5]decan-7-yl)methyl)-1H-benzo[d]imidazole-6-carbonitrile

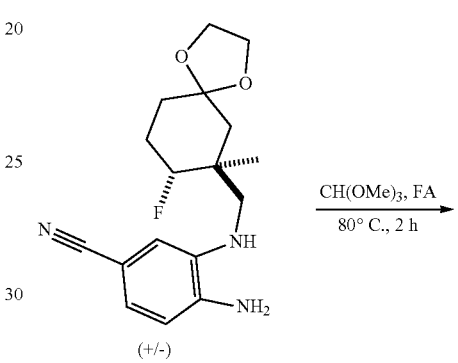
(+/-)

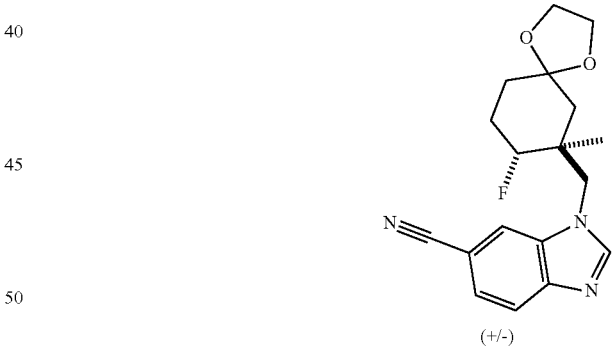
(+/-)

To a mixture of rac-4-amino-3-((((7S,8R)-8-fluoro-7-methyl-1,4-dioxaspiro[4.5]decan-7-yl)methyl)amino)benzonitrile (4.2 g, 13.2 mmol) and trimethoxymethane (2.09 g, 19.7 mmol) in acetonitrile (20 mL) was added formic acid (0.91 g, 19.7 mmol). The mixture was stirred for 2 hours at 80° C. and then cooled to room temperature. The resulting solution was concentrated under vacuum to afford the crude product. The residue was purified by silica gel column chromatography, and eluted with ethyl acetate in petroleum ether from 0% to 45% to afford the product rac-1-(((7S,8R)-8-fluoro-7-methyl-1,4-dioxaspiro[4.5]decan-7-yl)methyl)-1H-benzo[d]imidazole-6-carbonitrile (4 g, 92.3%) as a yellow solid. LCMS (ESI-MS) m/z=330.2 [M+H]⁺.

rac-1-(((1S,2R)-2-Fluoro-1-methyl-5-oxocyclohexyl)methyl)-1H-benzo[d]imidazole-6-carbonitrile

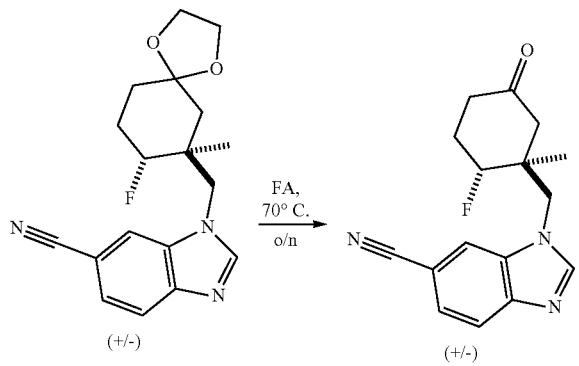

Formic acid (15 mL) was added to rac-1-(((7S,8R)-8-fluoro-7-methyl-1,4-dioxaspiro[4.5]decan-7-yl)methyl)-1H-benzo[d]imidazole-6-carbonitrile (4 g, 12.1 mmol). The mixture was stirred overnight at 70° C. and concentrated to afford the product rac-1-(((1S,2R)-2-fluoro-1-methyl-5-oxocyclohexyl)methyl)-1H-benzo[d]imidazole-6-carbonitrile (3.6 g crude) as yellow oil. LCMS (ESI-MS) m/z=286.1 [M+H]$^+$.

rac-1-(((3S,5S,6R)-6-Fluoro-5-methyl-1-oxaspiro[2.5]octan-5-yl)methyl)-1H-benzo[d]imidazole-6-carbonitrile and rac-1-(((3R,5S,6R)-6-fluoro-5-methyl-1-oxaspiro[2.5]octan-5-yl)methyl)-1H-benzo[d]imidazole-6-carbonitrile

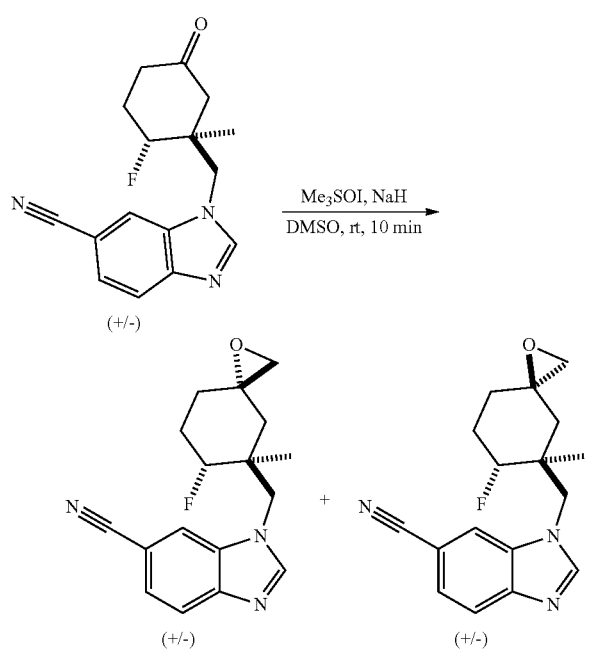

To a mixture of trimethylsulfoxonium iodide (5.24 g, 23.8 mmol) in DMSO (50 mL) was added sodium hydrogen (60% in mineral oil, 1.43 g, 35.7 mmol). The mixture was stirred for 10 min at 10° C., then rac-1-(((1S,2R)-2-fluoro-1-methyl-5-oxocyclohexyl)methyl)-1H-benzo[d]imidazole-6-carbonitrile (3.4 g, 11.9 mmol) was added followed, the mixture was stirred for 10 min at room temperature and then quenched with aqueous ammonium chloride (200 mL). The resulting solution was extracted with ethyl acetate (3×100 mL), the organic layer was dried over sodium sulfate, filtered and concentrated to afford the crude product. To separate the diastereomers, the residue was purified by reverse phase chromatography, eluted with acetonitrile in water from 0% to 45% to afford the more polar rac-1-(((3R,5S,6S)-6-fluoro-5-methyl-1-oxaspiro[2.5]octan-5-yl)methyl)-1H-benzo[d]imidazole-6-carbonitrile (600 mg) as a light yellow solid. Further elution with acetonitrile in water (55%) afforded less polar rac-1-(((3S,5S,6R)-6-fluoro-5-methyl-1-oxaspiro[2.5]octan-5-yl)methyl)-1H-benzo[d]imidazole-6-carbonitrile (1.2 g) as a light yellow solid. LCMS (ESI-MS) m/z=300.1 [M+H]$^+$.

rac-1-(((5S,7S,8R)-8-Fluoro-7-methyl-2-oxo-1-oxa-3-azaspiro[4.5]decan-7-yl)methyl)-1H-benzo[d]imidazole-6-carbonitrile

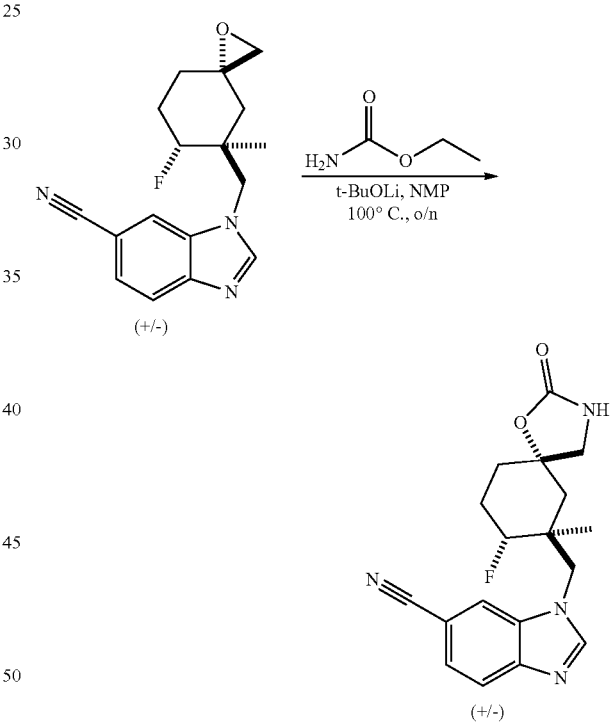

A mixture of ethyl carbamate (1.49 g, 16.7 mmol) and lithium tert-butoxide (401 mg, 5.01 mmol) in N-methyl pyrrolidone (10 mL) was stirred for 10 min at room temperature, then rac-1-(((3S,5S,6R)-6-fluoro-5-methyl-1-oxaspiro[2.5]octan-5-yl)methyl)-1H-benzo[d]imidazole-6-carbonitrile (500 mg, 1.67 mmol) was added and the mixture was stirred overnight at 100° C. The following day the mixture was quenched with water (60 mL) and solution was extracted with ethyl acetate (3×30 mL). The organic layer was dried over sodium sulfate, filtered and concentrated to afford the crude product. The residue was purified by silica gel column chromatography, and eluted with ethyl acetate in petroleum ether from 0% to 100% to afford the product rac-1-(((5S,7S,8R)-8-fluoro-7-methyl-2-oxo-1-oxa-3- azaspiro[4.5]decan-7-yl)methyl)-1H-benzo[d]imidazole-6-carbonitrile (400 mg) as colorless oil. LCMS (ESI-MS) m/z=343.1[M+H]$^+$.

rac-1-(((5S,7S,8R)-8-Fluoro-3-(5-(2-hydroxypropan-2-yl)pyrazin-2-yl)-7-methyl-2-oxo-1-oxa-3-azaspiro[4.5]decan-7-yl)methyl)-1H-benzo[d]imidazole-6-carbonitrile

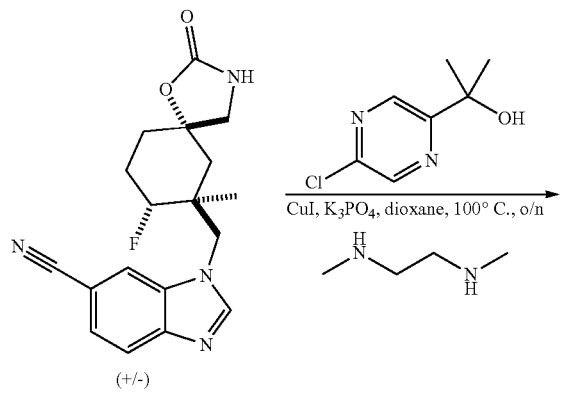

Copper (I) iodide (110.46 mg, 0.58 mmol, 1 eq.) was added to a solution of rac-1-(((5S,7S,8R)-8-fluoro-7-methyl-2-oxo-1-oxa-3-azaspiro[4.5]decan-7-yl)methyl)-1H-benzo[d]imidazole-6-carbonitrile (200 mg, 0.58 mmol, 1 eq.), 2-(5-chloropyrazin-2-yl)propan-2-ol (100.34 mg, 0.58 mmol, 1 eq.), N$^1$,N$^2$-dimethylethane-1,2-diamine (102.08 mg, 1.16 mmol, 2 eq.) and tripotassium phosphate (246.23 mg, 1.16 mmol, 2 eq.) in 1,4-dioxane (2 mL) under a nitrogen atmosphere. The resulting mixture was heated to 100° C. and stirred overnight. After cooling to room temperature, the resulting mixture was filtered and the filtrate was concentrated under vacuum. The residue was purified by silica gel column chromatography, eluted with methanol in dichloromethane from 0% to 3%. The fractions with desired mass signal were combined and concentrated under vacuum to afford the desired product rac-1-(((5S,7S,8R)-8-fluoro-3-(5-(2-hydroxypropan-2-yl)pyrazin-2-yl)-7-methyl-2-oxo-1-oxa-3-azaspiro[4.5]decan-7-yl)methyl)-1H-benzo[d]imidazole-6-carbonitrile (200 mg, 71.43% yield) as a light yellow solid. $^1$H NMR (400 MHz, DMSO-d$_6$) δ 9.18 (d, J=1.5 Hz, 1H), 8.59 (d, J=1.5 Hz, 1H), 8.45 (s, 1H), 8.26 (d, J=1.5 Hz, 1H), 7.84 (d, J=8.4 Hz, 1H), 7.60 (dd, J=8.3, 1.5 Hz, 1H), 5.42 (s, 1H), 4.67-4.50 (m, 1H), 4.38-4.25 (m, 2H), 3.83 (d, J=2.0 Hz, 2H), 2.12-1.99 (m, 2H), 1.97-1.88 (m, 2H), 1.80-1.69 (m, 2H), 1.44 (d, J=2.3 Hz, 6H), 1.19 (s, 3H). LCMS (ESI-MS) m/z=479 [M+H]$^+$.

1-(((5S,7S,8R)-8-Fluoro-3-(5-(2-hydroxypropan-2-yl)pyrazin-2-yl)-7-methyl-2-oxo-1-oxa-3-azaspiro[4.5]decan-7-yl)methyl)-1H-benzo[d]imidazole-6-carbonitrile and 1-(((5R,7R,8S)-8-Fluoro-3-(5-(2-hydroxypropan-2-yl)pyrazin-2-yl)-7-methyl-2-oxo-1-oxa-3-azaspiro[4.5]decan-7-yl)methyl)-1H-benzo[d]imidazole-6-carbonitrile

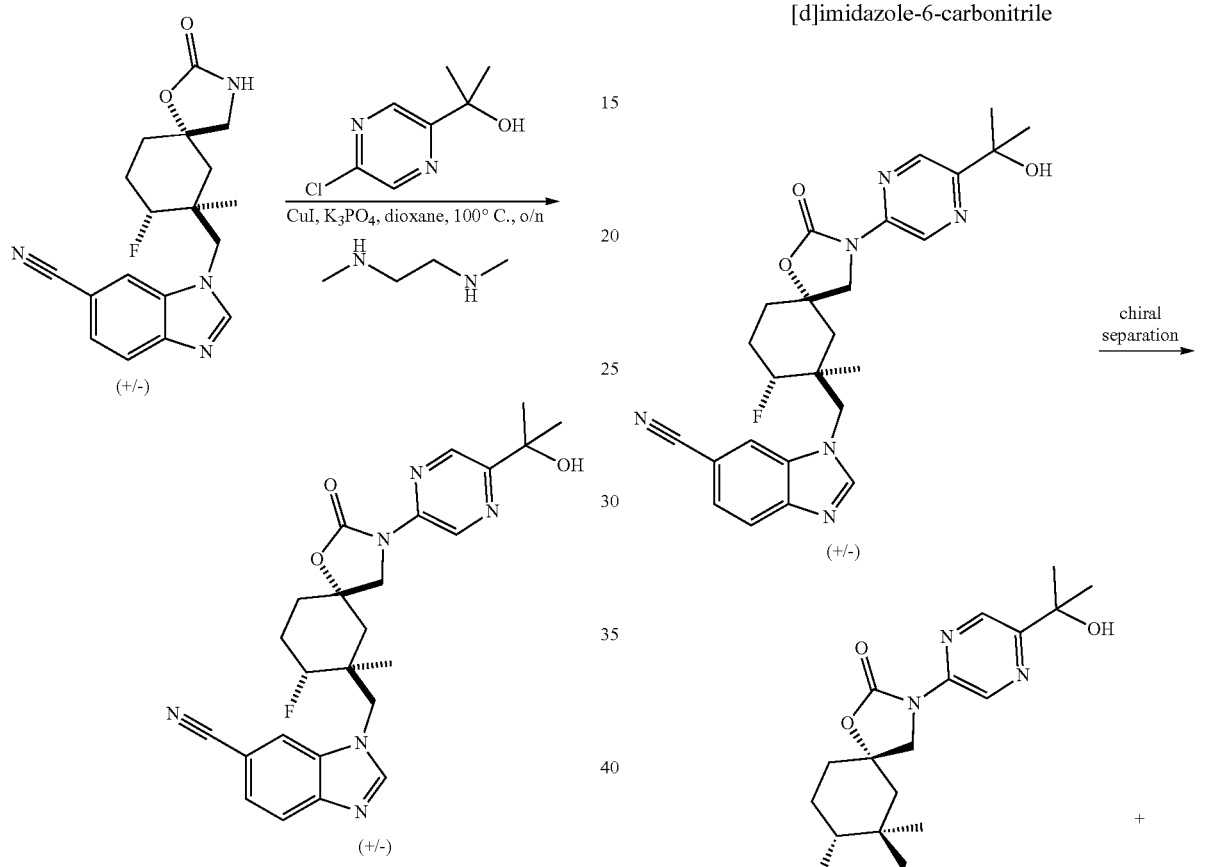

rac-1-(((5S,7S,8R)-8-Fluoro-3-(5-(2-hydroxypropan-2-yl)pyrazin-2-yl)-7-methyl-2-oxo-1-oxa-3-azaspiro[4.5]decan-7-yl)methyl)-1H-benzo[d]imidazole-6-carbonitrile (200 mg, 0.42 mmol, 1 eq.) was separated by Prep-Chiral-HPLC with the condition: Column: CHIRALPAK IF, 2*25 cm, 5 μm; Mobile Phase A: MtBE (0.5% 2M NH₃-MeOH)-HPLC, Mobile Phase B: EtOH-HPLC; Flow rate: 14 mL/min; Gradient: 30% B to 30% B in 29 min; Wave Length: 220/254 nm; RT1(min): 13.529; RT2(min): 21.063; Sample Solvent: EtOH-HPLC; Injection Volume: 0.8 mL. The desired fractions were combined and lyophilized to afford the products:

Example 5A (first eluting isomer): 1-(((5S,7S,8R)-8-Fluoro-3-(5-(2-hydroxypropan-2-yl)pyrazin-2-yl)-7-methyl-2-oxo-1-oxa-3-azaspiro[4.5]decan-7-yl)methyl)-1H-benzo[d]imidazole-6-carbonitrile (77.3 mg, 97.0% purity, 100% ee, 38.65% yield) as a white solid. $^1$H NMR (400 MHz, DMSO-$d_6$) δ 9.18 (d, J=1.5 Hz, 1H), 8.59 (d, J=1.5 Hz, 1H), 8.45 (s, 1H), 8.26 (d, J=1.5 Hz, 1H), 7.84 (d, J=8.4 Hz, 1H), 7.60 (dd, J=8.3, 1.5 Hz, 1H), 5.42 (s, 1H), 4.67-4.50 (m, 1H), 4.38-4.25 (m, 2H), 3.83 (d, J=2.0 Hz, 2H), 2.12-1.99 (m, 2H), 1.97-1.88 (m, 2H), 1.80-1.69 (m, 2H), 1.44 (d, J=2.3 Hz, 6H), 1.19 (s, 3H). LCMS (ESI-MS) m/z=479 [M+H]$^+$.

Example 5B (second eluting isomer): 1-(((5R,7R,8S)-8-Fluoro-3-(5-(2-hydroxypropan-2-yl)pyrazin-2-yl)-7-methyl-2-oxo-1-oxa-3-azaspiro[4.5]decan-7-yl)methyl)-1H-benzo[d]imidazole-6-carbonitrile (76.5 mg, 99.5% purity, 100% ee, 38.25% yield) as a white solid. $^1$H NMR (400 MHz, DMSO-$d_6$) δ 9.18 (d, J=1.5 Hz, 1H), 8.59 (d, J=1.5 Hz, 1H), 8.45 (s, 1H), 8.26 (d, J=1.5 Hz, 1H), 7.84 (d, J=8.4 Hz, 1H), 7.60 (dd, J=8.3, 1.5 Hz, 1H), 5.42 (s, 1H), 4.67-4.50 (m, 1H), 4.38-4.25 (m, 2H), 3.83 (d, J=2.0 Hz, 2H), 2.12-1.99 (m, 2H), 1.97-1.88 (m, 2H), 1.80-1.69 (m, 2H), 1.44 (d, J=2.3 Hz, 6H), 1.19 (s, 3H). LCMS (ESI-MS) m/z=479 [M+H]$^+$. Structure confirmed by Xray crystal structure analysis.

Example 6. Preparation of: 1-(((4R,6S)-9-(5-(2-Hydroxypropan-2-yl)pyrazin-2-yl)-4-methyl-8-oxo-7-oxa-9-azadispiro[2.2.4⁶.2³]dodecan-4-yl)methyl)-1H-benzo[d]imidazole-6-carbonitrile

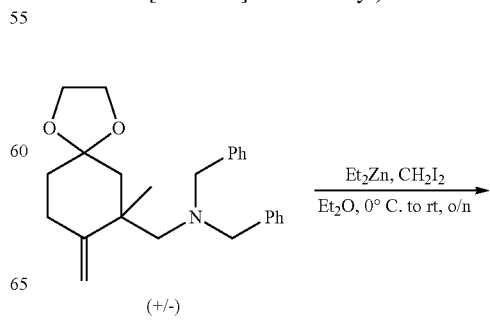

Detailed Procedure rac-N,N-Dibenzyl-1-(7-methyl-8-methylene-1,4-dioxaspiro[4.5]decan-7-yl)methan amine

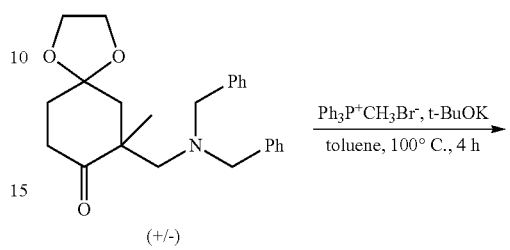

To a mixture of methyltriphenylphosphonium bromide (70.6 g, 198 mmol) in toluene (600 mL) was added potassium 2-methylpropan-2-olate (22.2 g, 198 mmol), the mixture was stirred for 10 minutes at room temperature, then rac-7-((dibenzylamino)methyl)-7-methyl-1,4-dioxaspiro[4.5]decan-8-one (50 g, 132 mmol) was added. The mixture was stirred for 4 hours at 100° C. and then cooled to room temperature. The mixture was quenched with water (600 mL) and the resulting solution was extracted with ethyl acetate (3×400 mL). The organic layer was dried over sodium sulfate, filtered, and concentrated to afford the crude product. The residue was purified by silica gel column chromatography, and eluted with ethyl acetate in petroleum ether from 0% to 10% to afford rac-N,N-dibenzyl-1-(7-methyl-8-methylene-1,4-dioxaspiro[4.5]decan-7-yl)methanamine (45 g) as colorless oil. LCMS (ESI-MS) m/z=378.2 [M+H]$^+$.

rac-N,N-Dibenzyl-1-(4-methyl-7,10-dioxadispiro[2.2.4⁶.2³]dodecan-4-yl)methanamine

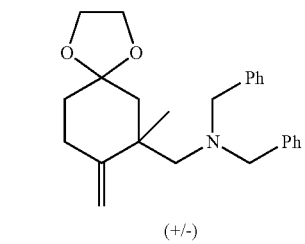

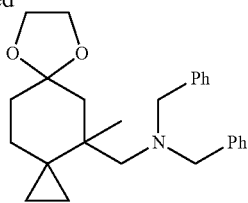

(+/-)

To a mixture of rac-N,N-dibenzyl-1-(7-methyl-8-methylene-1,4-dioxaspiro[4.5]decan-7-yl)methanamine (45 g, 119 mmol) in diethyl ether (600 mL) was added diethylzinc (1M in THF, 358 mL, 358 mmol) at 0° C. The mixture was stirred for 30 minutes, then diiodomethane (95.8 g, 358 mmol) was added, and the resulting solution was warmed to room temperature and stirred overnight. The mixture was quenched by aq. ammonium chloride (600 mL) slowly, then the resulting solution was extracted with DCM (3×200 mL), the organic layer was dried over sodium sulfate, filtered and concentrated to afford the crude product. The residue was purified by silica gel column chromatography, and eluted with ethyl acetate in petroleum ether from 0% to 10% to afford rac-N,N-dibenzyl-1-(4-methyl-7,10-dioxadispiro[2.2.4$^6$.2$^3$]dodecan-4-yl)methanamine (5 g) as colorless oil. LCMS (ESI-MS) m/z=392.3 [M+H]$^+$.

rac-(4-Methyl-7,10-dioxadispiro[2.2.4$^6$.2$^3$]dodecan-4-yl)methanamine

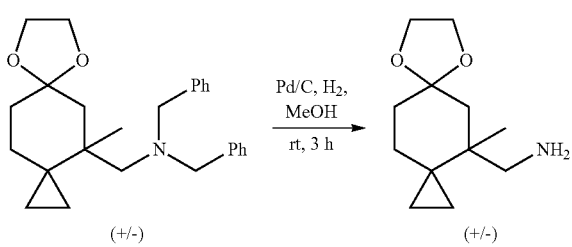 [SMILES: CC1(CN(Cc2ccccc2)Cc2ccccc2)CC2(CCC13CC3)OCCO2 ; CC1(CN)CC2(CCC13CC3)OCCO2]

To a solution of rac-N,N-dibenzyl-1-(4-methyl-7,10-dioxadispiro[2.2.4$^6$.2$^3$]dodecan-4-yl)methanamine (4 g, 10.2 mmol) in methanol (100 mL) was added palladium (2 g, 50% wt, 10% on carbon). The suspension was stirred for 3 hours under hydrogen atmosphere and then filtered. The filtrate was concentrated to afford the crude product rac-(4-methyl-7,10-dioxadispiro[2.2.4$^6$.2$^3$]dodecan-4-yl)methanamine (2 g crude) as yellow oil. LCMS (ESI-MS) m/z=212.2 [M+H]$^+$.

rac-3-(((4-Methyl-7,10-dioxadispiro[2.2.4$^6$.2$^3$]dodeca-4-yl)methyl)amino)-4-nitrobenzonitrile

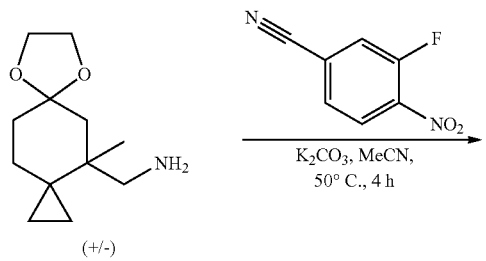

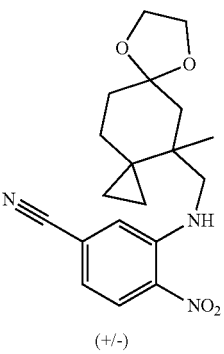

(+/-)

To a mixture of rac-(4-methyl-7,10-dioxadispiro [2.2.4$^6$.2$^3$]dodecan-4-yl)methanamine (2.2 g, 10.4 mmol) and 3-fluoro-4-nitrobenzonitrile (1.73 g, 10.4 mmol) in acetonitrile (30 mL) was added potassium carbonate (4.32 g, 31.2 mmol). The mixture was stirred for 4 hours at 50° C. and the cooled to room temperature. The mixture was filtered and the filtrate was concentrated to afford the crude product. The residue was purified by silica gel column chromatography and eluted with ethyl acetate in petroleum ether from 0% to 18% to afford rac-3-(((4-methyl-7,10-dioxadispiro[2.2.4$^6$.2$^3$]dodecan-4-yl)methyl)amino)-4-nitrobenzonitrile (3.7 g, 99.4%) as an orange solid. LCMS (ESI-MS) m/z=358.2 [M+H]$^+$.

rac-4-Amino-3-(((4-methyl-7,10-dioxadispiro [2.2.4$^6$.2$^3$]dodecan-4-yl)methyl)amino)-benzonitrile

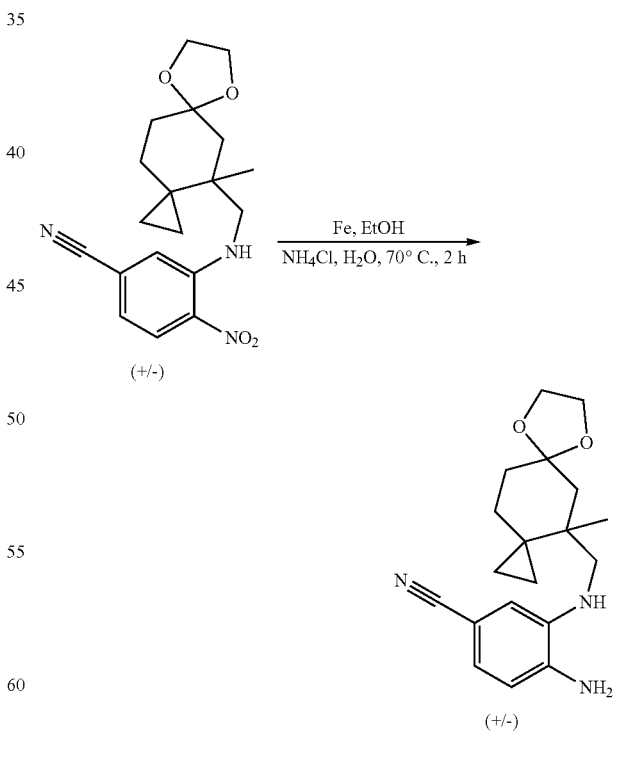

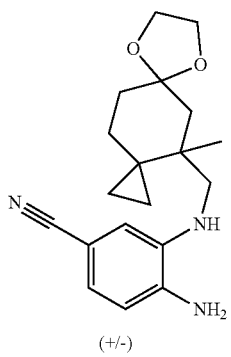

(+/-)

To a mixture of rac-3-(((4-methyl-7,10-dioxadispiro [2.2.4$^6$.2$^3$]dodecan-4-yl)methyl)amino)-4-nitrobenzonitrile (3.7 g, 10.4 mmol) and ammonium chloride (2.77 g, 51.8 mmol) in ethanol (50 mL) was added iron (2.89 g, 51.8 mmol), the mixture was stirred for 2 hours at 70° C. and then cooled to room temperature. The mixture was then filtered and the filtrate was diluted with water (50 mL), extracted with ethyl acetate (3×30 mL), dried over sodium sulfate, filtered, and concentrated to afford the product rac-4-amino-3-(((4-methyl-7,10-dioxadispiro[2.2.4$^6$.2$^3$]dodecan-4-yl)methyl)amino)benzonitrile (3.3 g, 97.3%) as a yellow solid. LCMS (ESI-MS) m/z=328.2 [M+H]$^+$.

rac-1-((4-Methyl-7,10-dioxadispiro[2.2.4$^6$.2$^3$]dodecan-4-yl)methyl)-1H-benzo[d]imidazole-6-carbonitrile

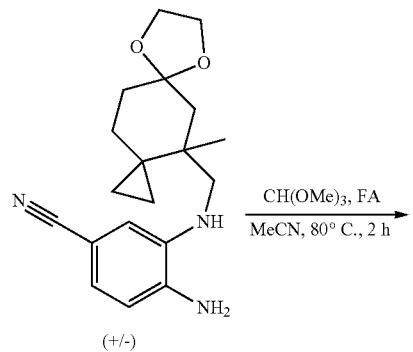

To a mixture of rac-4-amino-3-(((4-methyl-7,10-dioxadispiro[2.2.4$^6$.2$^3$]dodecan-4-yl)methyl)amino)benzonitrile (3.2 g, 9.77 mmol) in acetonitrile (30 mL) was added trimethoxymethane (1.56 g, 14.7 mmol) and formic acid (0.67 g, 14.7 mmol), the resulting mixture was stirred for 2 hours at 80° C. and cooled to room temperature. The mixture was concentrated to afford the crude product and the residue was purified by silica gel column chromatography and eluted with ethyl acetate in petroleum ether from 0% to 30% to afford rac-1-((4-methyl-7,10-dioxadispiro[2.2.4$^6$.2$^3$]dodecan-4-yl)methyl)-1H-benzo[d]imidazole-6-carbonitrile (3 g, 90.9%) as a yellow solid. LCMS (ESI-MS) m/z=338.2 [M+H]$^+$.

rac-1-((4-Methyl-6-oxospiro[2.5]octan-4-yl)methyl)-1H-benzo[d]imidazole-6-carbonitrile

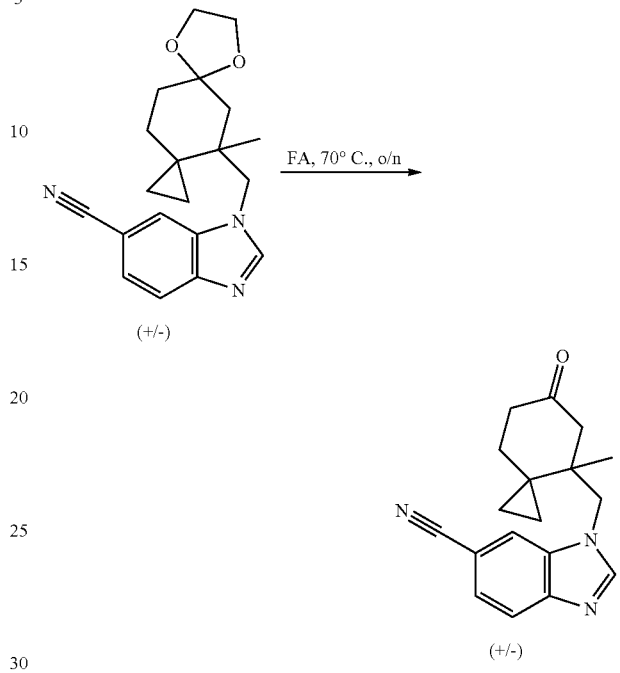

Formic acid (20 mL) was added to rac-1-((4-methyl-7,10-dioxadispiro[2.2.4$^6$.2$^3$]dodecan-4-yl)methyl)-1H-benzo[d]imidazole-6-carbonitrile (3 g, 8.89 mmol), the mixture was stirred overnight at 70° C. and then cooled to room temperature. The solution was concentrated to afford the product rac-1-((4-methyl-6-oxospiro[2.5]octan-4-yl)methyl)-1H-benzo[d]imidazole-6-carbonitrile (2.3 g) as yellow oil. LCMS (ESI-MS) m/z=294.2 [M+H]$^+$. 1-(5-methyl-1-oxadispiro[2.2.2$^6$.2$^3$]decan-5-yl)methyl)-1H-benzo[d]imidazole-6-carbonitrile

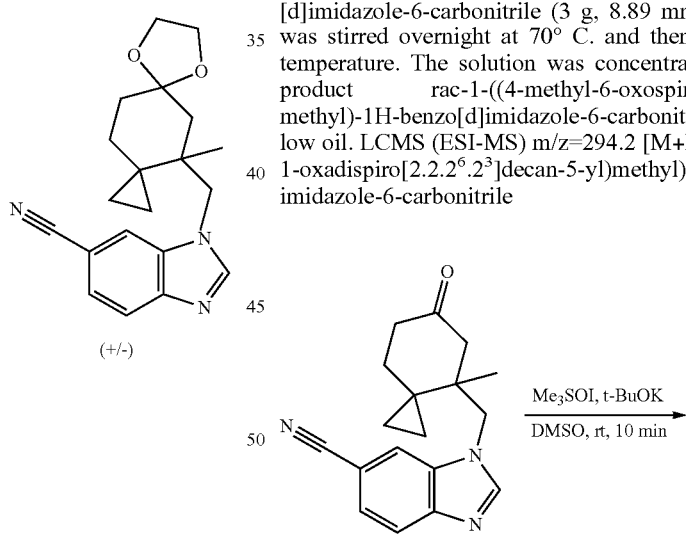

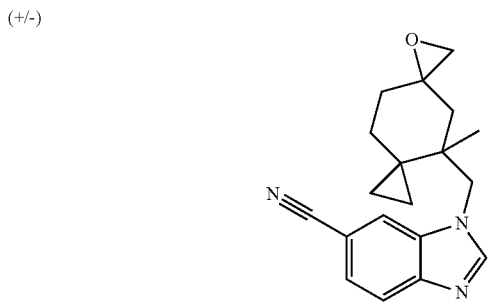

To a mixture of rac-1-((4-methyl-6-oxospiro[2.5]octan-4-yl)methyl)-1H-benzo[d]imidazole-6-carbonitrile (2 g, 6.82 mmol) and trimethylsulfoxonium iodide (1.95 g, 8.86 mmol) in methyl sulfoxide (30 mL) was added potassium tert-butoxide (0.99 g, 8.86 mmol). The mixture was stirred for 10 min at room temperature and then quenched with aqueous ammonium chloride (50 mL), the resulting solution was extracted with dichloromethane (3×30 mL). The combined organic layers were dried over sodium sulfate, filtered and concentrated to afford the crude product, the residue was purified by silica gel column chromatography and eluted with ethyl acetate in petroleum ether from 0% to 80% to afford 1-((5-methyl-1-oxadispiro[2.2.26.23]decan-5-yl)methyl)-1H-benzo[d]imidazole-6-carbonitrile (1.7 g) as a white solid. LCMS (ESI-MS) m/z=308.2 [M+H]$^+$.

1-((6-hydroxy-6-(hydroxymethyl)-4-methylspiro[2.5]octan-4-yl)methyl)-1H-benzo[d]imidazole-6-carbonitrile rac-1-(((3S,5R)-5-Methyl-1-oxadispiro[2.2.2$^6$.2$^3$]decan-5-yl)methyl)-1H-benzo[d]imidazole-6-carbonitrile and rac-1-(((3R,5R)-5-methyl-1-oxadispiro[2.2.2$^6$.2$^3$]decan-5-yl)methyl)-1H-benzo[d]imidazole-6-carbonitrile

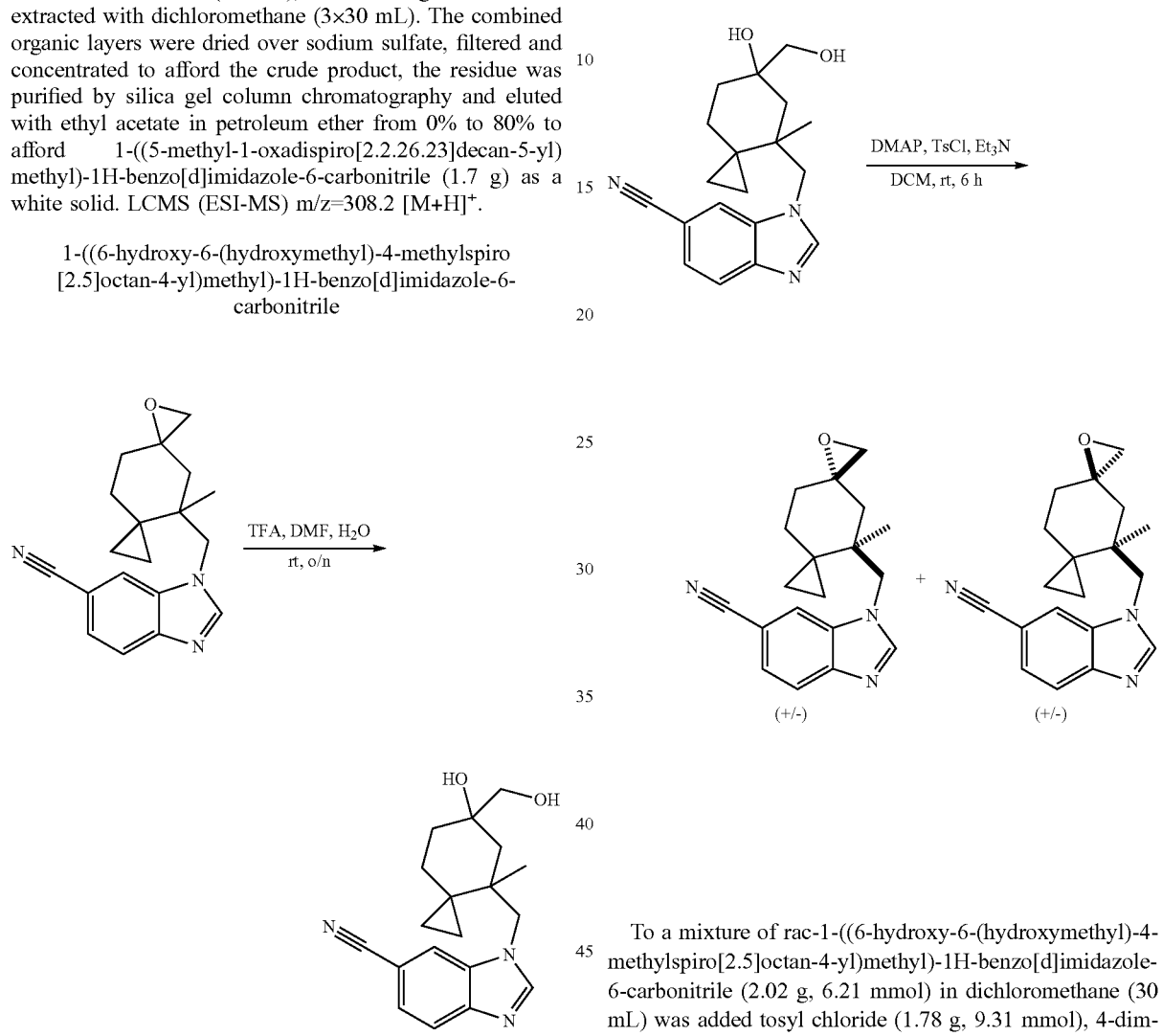

To a mixture of 1-((5-methyl-1-oxadispiro[2.2.26.23]decan-5-yl)methyl)-1H-benzo[d]imidazole-6-carbonitrile (1.7 g, 5.53 mmol) in N,N-dimethylformamide (10 mL) and water (10 mL) was added trifluoroacetic acid (1.26 g, 11.1 mmol). The mixture was stirred overnight at room temperature and diluted with aqueous sodium bicarbonate (50 mL). The resulting solution was extracted with dichloromethane (3×30 mL), dried over sodium sulfate, filtered, and concentrated to afford the crude product 1-((6-hydroxy-6-(hydroxymethyl)-4-methylspiro[2.5]octan-4-yl)methyl)-1H-benzo[d]imidazole-6-carbonitrile (2.02 g) as yellow oil. LCMS (ESI-MS) m/z=326.2 [M+H]$^+$.

To a mixture of rac-1-((6-hydroxy-6-(hydroxymethyl)-4-methylspiro[2.5]octan-4-yl)methyl)-1H-benzo[d]imidazole-6-carbonitrile (2.02 g, 6.21 mmol) in dichloromethane (30 mL) was added tosyl chloride (1.78 g, 9.31 mmol), 4-dimethylaminopyridine (0.38 g, 3.10 mmol) and triethylamine (1.88 g, 18.6 mmol). The mixture was stirred for 6 hours at room temperature and then quenched with water (50 mL). The resulting solution was extracted with dichloromethane (3×30 mL), the organic layer was dried over sodium sulfate, filtered and concentrated to afford the crude intermediates. The residue was dissolved in acetonitrile (20 mL), potassium carbonate (1.72 g, 12.4 mmol) was added, the mixture was stirred for 3 hours at 50° C. and filtered, the filtrate was concentrated to afford the crude product. The residue was purified by Prep-TLC (EA), Rf=0.5 to afford the products rac-1-(((3S,5R)-5-methyl-1-oxadispiro[2.2.2$^6$.2$^3$]decan-5-yl)methyl)-1H-benzo[d]imidazole-6-carbonitrile (210 mg, 11%) as a white solid and Rf=0.3 to afford rac-1-(((3R,5R)-5-methyl-1-oxadispiro[2.2.2$^6$.2$^3$]decan-5-yl)methyl)-1H-benzo[d]imidazole-6-carbonitrile (350 mg, 18.3%) as a white solid. LCMS (ESI-MS) m/z=308.2 [M+H]$^+$.

rac-1-(((4R,6S)-4-Methyl-8-oxo-7-oxa-9-azadispiro[2.2.4⁶.2³]dodecan-4-yl)methyl)-1H-benzo[d]imidazole-6-carbonitrile

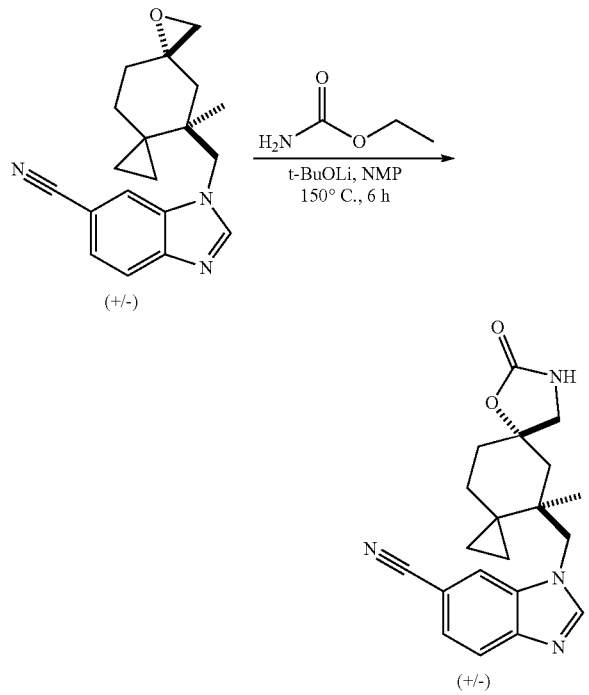

A mixture of ethyl carbamate (1.01 g, 11.4 mmol) and lithium tert-butoxide (182 mg, 2.28 mmol) in 1-methyl-2-pyrrolidinone (10 mL) was stirred for 10 min at room temperature, then rac-1-(((3S,5R)-5-methyl-1-oxadispiro[2.2.2⁶.2³]decan-5-yl)methyl)-1H-benzo[d]imidazole-6-carbonitrile (350 mg, 1.14 mmol) was added. The mixture was stirred for 6 hours at 150° C., then cooled to room temperature. The mixture was quenched with water (50 mL) and extracted with ethyl acetate (3×30 mL). The organic layer was dried over sodium sulfate, filtered, and concentrated to afford the crude product. The residue was purified by silica gel column chromatography and eluted with ethyl acetate in petroleum ether from 0% to 100% to afford rac-1-(((4R,6S)-4-methyl-8-oxo-7-oxa-9-azadispiro[2.2.4⁶.2³]dodecan-4-yl)methyl)-1H-benzo[d]imidazole-6-carbonitrile (330 mg, 82.7%) as a yellow solid. LCMS (ESI-MS) m/z=351.2 [M+H]⁺.

rac-1-(((4R,6S)-9-(5-(2-Hydroxypropan-2-yl)pyrazin-2-yl)-4-methyl-8-oxo-7-oxa-9-azadispiro[2.2.4⁶.2³]dodecan-4-yl)methyl)-1H-benzo[d]imidazole-6-carbonitrile

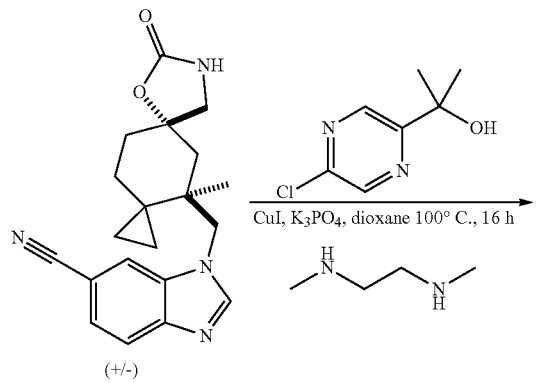

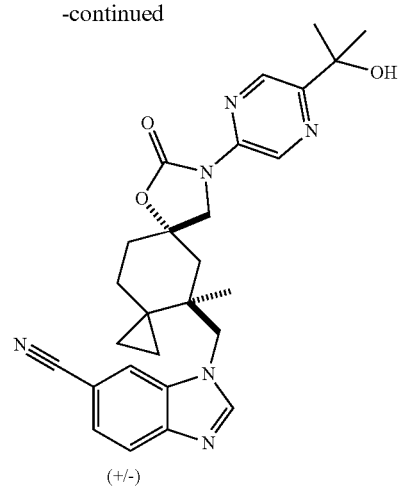

To a mixture of rac-1-(((4R,6S)-4-methyl-8-oxo-7-oxa-9-azadispiro[2.2.4⁶.2³]dodecan-4-yl)methyl)-1H-benzo[d]imidazole-6-carbonitrile (330 mg, 0.94 mmol) in 1,4-dioxane (15 mL) was added 2-(5-chloropyrazin-2-yl)propan-2-ol (244 mg, 1.41 mmol), N¹,N²-dimethylethane-1,2-diamine (165 mg, 1.88 mmol), potassium phosphate tribasic (399 mg, 1.88 mmol) and copper (I) iodide (90 mg, 0.47 mmol). The mixture was stirred for 16 hours at 100° C. under nitrogen atmosphere and then cooled to room temperature. The mixture was diluted with water (50 mL), extracted with ethyl acetate (3×30 mL), dried over sodium sulfate, filtered and concentrated to afford the crude product. The residue was purified by silica gel column chromatography and eluted with methanol in chloromethane from 0% to 7% to afford rac-1-(((4R,6S)-9-(5-(2-hydroxypropan-2-yl)pyrazin-2-yl)-4-methyl-8-oxo-7-oxa-9-azadispiro[2.2.4⁶.2³]dodecan-4-yl)methyl)-1H-benzo[d]imidazole-6-carbonitrile (350 mg) as a white solid. LCMS (ESI-MS) m/z=487.2 [M+H]⁺.

1-(((4R,6S)-9-(5-(2-Hydroxypropan-2-yl)pyrazin-2-yl)-4-methyl-8-oxo-7-oxa-9-azadispiro[2.2.4⁶.2³]dodecan-4-yl)methyl)-1H-benzo[d]imidazole-6-carbonitrile and 1-(((4S,6R)-9-(5-(2-Hydroxypropan-2-yl)pyrazin-2-yl)-4-methyl-8-oxo-7-oxa-9-azadispiro[2.2.4⁶.2³]dodecan-4-yl)methyl)-1H-benzo[d]imidazole-6-carbonitrile

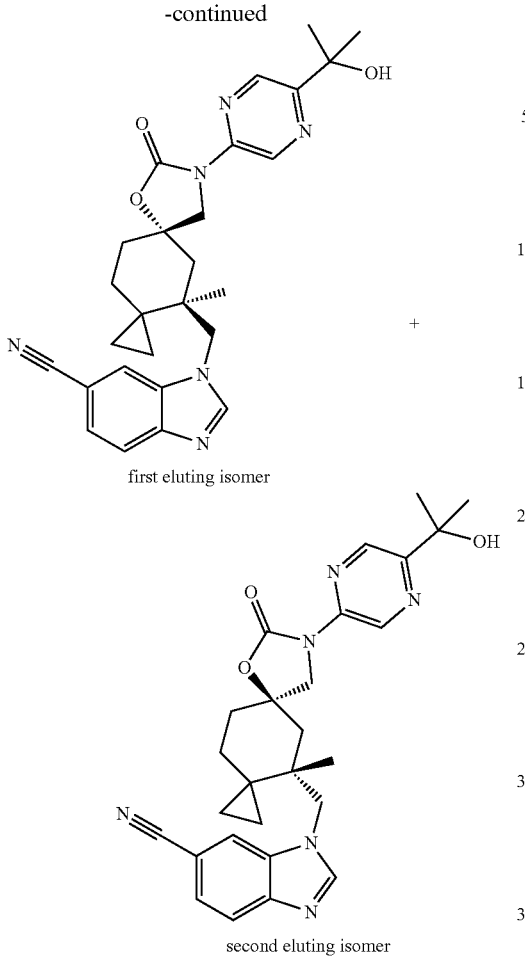

first eluting isomer second eluting isomer

The mixture of rac-1-(((4R,6S)-9-(5-(2-hydroxypropan-2-yl)pyrazin-2-yl)-4-methyl-8-oxo-7-oxa-9-azadispiro[2.2.4⁶.2³]dodecan-4-yl)methyl)-1H-benzo[d]imidazole-6-carbonitrile (350 mg, 0.72 mmol) was separated by Prep-Chiral-HPLC with the following condition: Column: CHIRALPAK ID, 2×25 cm, 5 μm; Mobile Phase A: MTBE (0.5% 2M NH₃-MeOH)-HPLC, Mobile Phase B: EtOH-HPLC; Flow rate: 12 mL/min; Gradient: 20% B to 20% B in 25 min; Wave Length: 220/254 nm; RT1(min): 11.542; Sample Solvent: EtOH-HPLC; Injection Volume: 0.7 mL. The desired fractions were combined and lyophilized to afford the two products:

First eluting isomer:1-(((4R,6S)-9-(5-(2-Hydroxypropan-2-yl)pyrazin-2-yl)-4-methyl-8-oxo-7-oxa-9-azadispiro[2.2.4⁶.2³]dodecan-4-yl)methyl)-1H-benzo[d]imidazole-6-carbonitrile (113.6 mg, 95.3% purity, 100% ee) as a light yellow solid. ¹H NMR (400 MHz, DMSO-d₆) δ 9.17 (d, J=1.5 Hz, 1H), 8.60 (d, J=1.5 Hz, 1H), 8.44 (s, 1H), 8.36 (d, J=1.5 Hz, 1H), 7.81 (d, J=8.4 Hz, 1H), 7.57 (dd, J=8.4, 1.5 Hz, 1H), 5.41 (s, 1H), 4.20-4.06 (m, 3H), 3.95 (d, J=10.2 Hz, 1H), 2.17 (d, J=13.9 Hz, 1H), 1.97-1.74 (m, 4H), 1.52-1.34 (m, 7H), 0.91 (s, 3H), 0.81-0.79 (m, 1H), 0.59-0.49 (m, 1H), 0.31-0.17 (m, 2H). LCMS (ESI-MS) m/z=487.2 [M+H]⁺.

Second eluting isomer: 1-(((4S,6R)-9-(5-(2-Hydroxypropan-2-yl)pyrazin-2-yl)-4-methyl-8-oxo-7-oxa-9-azadispiro[2.2.4⁶.2³]dodecan-4-yl)methyl)-1H-benzo[d]imidazole-6-carbonitrile (111.0 mg, 99.5% purity, 100% ee) as a white solid. ¹H NMR (400 MHz, DMSO-d₆) δ 9.17 (d, J=1.5 Hz, 1H), 8.60 (d, J=1.6 Hz, 1H), 8.44 (s, 1H), 8.38-8.33 (m, 1H), 7.81 (d, J=8.4 Hz, 1H), 7.57 (dd, J=8.4, 1.4 Hz, 1H), 5.41 (s, 1H), 4.20-4.04 (m, 3H), 3.95 (d, J=10.2 Hz, 1H), 2.17 (d, J=13.9 Hz, 1H), 2.01-1.71 (m, 4H), 1.54-1.37 (m, 7H), 0.91 (s, 3H), 0.837-0.77 (m, 1H), 0.59-0.47 (m, 1H), 0.32-0.17 (m, 2H). LCMS (ESI-MS) m/z=487.2 [M+H]⁺.

Example 7. Preparation of: 1-(((5S,7R)-7-(Fluoromethyl)-3-(5-(2-hydroxypropan-2-yl)pyrazin-2-yl)-2-oxo-1-oxa-3-azaspiro[4.5]decan-7-yl)methyl)-1H-benzo[d]imidazole-6-carbonitrile

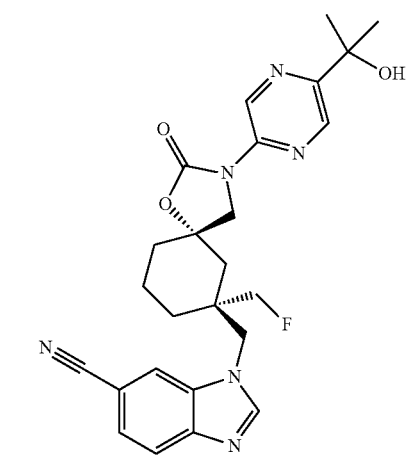 [SMILES: CC(C)(O)c1cnc(N2C[C@@]3(CCC[C@](CF)(Cn4cnc5ccc(C#N)cc54)C3)OC2=O)cn1]

Detailed Procedure (1,4-Dioxaspiro[4.5]dec-6-en-7-yl)methanol

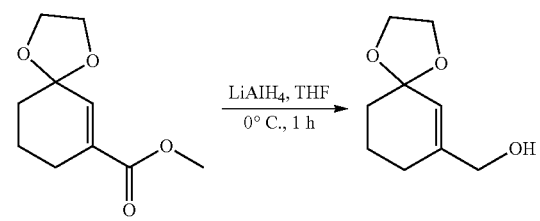

A solution of methyl 1,4-dioxaspiro[4.5]dec-6-ene-7-carboxylate (19.5 g, 98.4 mmol) and lithium aluminum hydride (3.73 g, 98.8 mmol) in tetrahydrofuran (400 mL) was stirred for 1 hour at 0° C. The resulting mixture was quenched with water, aq. sodium hydroxide, then the resulting mixture was filtered, the filter cake was washed with tetrahydrofuran (2×100 mL). The filtrate was concentrated under reduced pressure to afford the crude product (1,4-dioxaspiro[4.5]dec-6-en-7-yl)methanol (7 g) as yellow oil. ¹H NMR (400 MHz, DMSO-d6) δ 5.48 (s, 1H), 3.92-3.79 (m, 6H), 1.92-1.83 (m, 2H), 1.71-1.61 (m, 4H).

7-(Fluoromethyl)-1,4-dioxaspiro[4.5]dec-6-ene

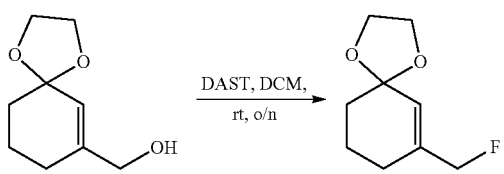 [SMILES: OCC1=CC2(CCC1)OCCO2 ; FCC1=CC2(CCC1)OCCO2]

A solution of (1,4-dioxaspiro[4.5]dec-6-en-7-yl)methanol (7.0 g, 41.1 mmol) and diethylaminosulfur trifluoride (7.95 g, 49.3 mmol) in dichloromethane (140 mL) was stirred overnight at room temperature. The mixture was quenched with aq. sodium carbonate (200 mL), then the resulting mixture was extracted with dichloromethane (3×100 mL). The organic layers were dried, filtered and concentrated to afford the crude product. The residue was purified by silica gel column chromatography and eluted with dichloromethane (100%) to afford 7-(fluoromethyl)-1,4-dioxaspiro[4.5]dec-6-ene (6.0 g) as brown oil. $^1$H NMR (400 MHz, DMSO-$d_6$) δ 5.90 (s, 1H), 5.08 (d, J=4.0 Hz, 1H), 2.52-2.48 (m, 1H), 2.42-2.16 (m, 5H), 2.08-1.84 (m, 3H), 1.73-1.59 (m, 1H), 1.44-1.31 (m, 1H).

3-(Fluoromethyl)cyclohex-2-en-1-one

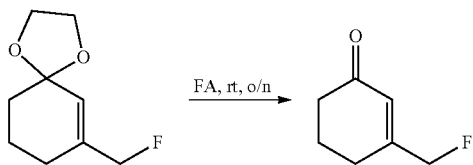 [SMILES: FCC1=CC2(CCC1)OCCO2 ; O=C1C=C(CF)CCC1]

A solution of 7-(fluoromethyl)-1,4-dioxaspiro[4.5]dec-6-ene (6.0 g, 34.8 mmol) in formic acid (10 mL) was stirred for 1 hour at 80° C. The resulting mixture was concentrated under vacuum. The residue was purified by silica gel column chromatography and eluted with ethyl acetate in petroleum ether from 0% to 10% to afford 3-(fluoromethyl)cyclohex-2-en-1-one (2.0 g) as colorless oil.

rac-3-(Fluoromethyl)-3-(nitromethyl)cyclohexan-1-one

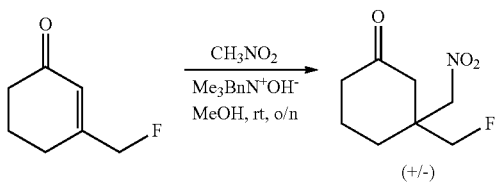 [SMILES: O=C1C=C(CF)CCC1 ; "CH3NO2" ; O=C1CCCC(CF)(C[N+](=O)[O-])C1]

A solution of 3-(fluoromethyl)cyclohex-2-en-1-one (2.0 g, 15.6 mmol) and nitromethane (1.14 g, 18.7 mmol) in benzyltrimethylazanium methanolate (3 mL) was stirred overnight at room temperature. The resulting mixture was concentrated under vacuum. The residue was purified by silica gel column chromatography and eluted with ethyl acetate in petroleum ether from 0% to 20% to afford to afford rac-3-(fluoromethyl)-3-(nitromethyl)cyclohexan-1-one (1.0 g) as colorless oil. $^1$H NMR (400 MHz, DMSO-d6) δ 4.69-4.30 (m, 4H), 2.45-2.21 (m, 4H), 1.95-1.70 (m, 4H).

rac-7-(Fluoromethyl)-7-(nitromethyl)-1,4-dioxaspiro[4.5]decane

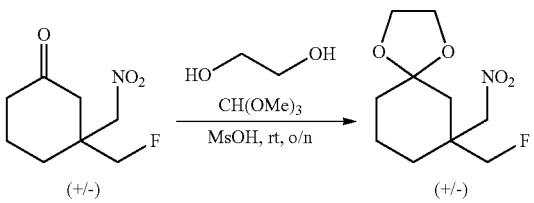

A solution of rac-3-(fluoromethyl)-3-(nitromethyl)cyclohexan-1-one (1.0 g, 5.3 mmol), ethylene glycol (0.49 g, 7.9 mmol) and trimethoxymethane (0.84 g, 7.9 mmol) in dichloromethane (20 mL) was stirred for 5 min at room temperature. The solution was cooled to 0° C. and methanesulfonic acid (80 mg, 0.79 mmol) was added. The resulting mixture was warmed to room temperature and stirred overnight. The solution was concentrated under vacuum and the residue was purified by silica gel column chromatography and eluted with ethyl acetate in petroleum ether from 0% to 10% to afford rac-7-(fluoromethyl)-7-(nitromethyl)-1,4-dioxaspiro[4.5]decane (950 mg) as colorless oil. LCMS (ESI-MS) m/z=234.2 [M+H]$^+$.

rac-(7-(Fluoromethyl)-1,4-dioxaspiro[4.5]decan-7-yl)methanamine

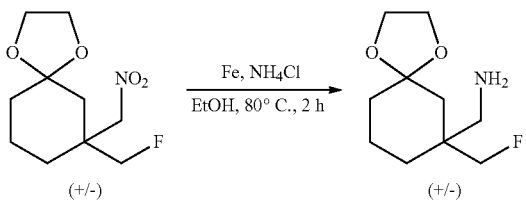 [SMILES: O=[N+]([O-])CC1(CF)CCCC2(C1)OCCO2 ; NCC1(CF)CCCC2(C1)OCCO2]

A solution of rac-7-(fluoromethyl)-7-(nitromethyl)-1,4-dioxaspiro[4.5]decane (950 mg, 4.6 mmol), iron (2.56 g, 46.7 mmol) and ammonium chloride (990 mg, 18.7 mmol) in ethanol (10 mL) and water (3 mL) was stirred for 2 hours at 80° C. The resulting mixture was filtered, and the filter cake was washed with ethanol (3×50 mL). The filtrate was concentrated under reduced pressure to afford rac-(7-(fluoromethyl)-1,4-dioxaspiro[4.5]decan-7-yl)methanamine (950 mg crude) as yellow oil. LCMS (ESI-MS) m/z=204.2 [M+H]$^+$.

rac-3-(((7-(Fluoromethyl)-1,4-dioxaspiro[4.5]decan-7-yl)methyl)amino)-4-nitrobenzonitrile

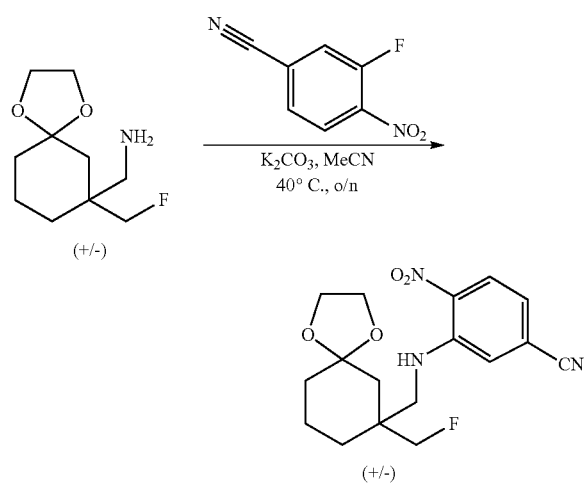

A solution of rac-(7-(fluoromethyl)-1,4-dioxaspiro[4.5]decan-7-yl)methanamine (950 mg, 4.7 mmol), 3-fluoro-4-nitrobenzonitrile (776 mg, 4.7 mmol) and potassium carbonate (1.29 g, 9.3 mmol) in acetonitrile (15 mL) was stirred overnight at 40° C. The resulting mixture was concentrated under vacuum. The residue was purified by silica gel column chromatography and eluted with ethyl acetate in petroleum ether from 0% to 50% to afford rac-3-(((7-(fluoromethyl)-1,4-dioxaspiro[4.5]decan-7-yl)methyl)amino)-4-nitrobenzonitrile (1.0 g) as a yellow solid. LCMS (ESI-MS) m/z=350.3 [M+H]$^+$.

rac-4-Amino-3-(((7-(fluoromethyl)-1,4-dioxaspiro[4.5]decan-7-yl)methyl)amino)benzonitrile

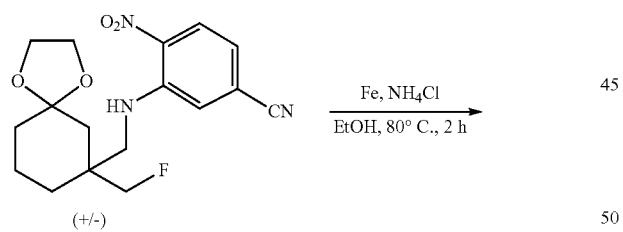

A solution of rac-3-(((7-(fluoromethyl)-1,4-dioxaspiro[4.5]decan-7-yl)methyl)amino)-4-nitrobenzonitrile (1.0 g, 2.9 mmol), iron (1.60 g, 28.6 mmol) and ammonium chloride (0.61 g, 11.4 mmol) in ethanol (12 mL) and water (4 mL) was stirred for 2 hours at 80° C. The resulting mixture was concentrated under vacuum to afford the crude product rac-4-amino-3-(((7-(fluoromethyl)-1,4-dioxaspiro[4.5]decan-7-yl)methyl)amino)benzonitrile (1.0 g) as yellow oil. LCMS (ESI-MS) m/z=320.3 [M+H]$^+$.

rac-1-((7-(Fluoromethyl)-1,4-dioxaspiro[4.5]decan-7-yl)methyl)-1H-benzo[d]imidazole-6-carbonitrile

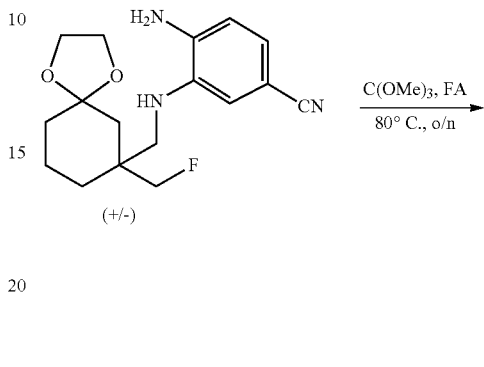

A solution of rac-4-amino-3-(((7-(fluoromethyl)-1,4-dioxaspiro[4.5]decan-7-yl)methyl)amino)benzonitrile (1.0 g, 3.1 mmol) and formic acid (143 mg, 3.1 mmol) in trimethoxymethane (3 mL) was stirred overnight at 80° C. The resulting mixture was concentrated under vacuum. The residue was purified by Prep-TLC (ethyl acetate) to afford rac-1-((7-(fluoromethyl)-1,4-dioxaspiro[4.5]decan-7-yl)methyl)-1H-benzo [d]imidazole-6-carbonitrile (900 mg) as colorless oil. LCMS (ESI-MS) m/z=330.3 [M+H]$^+$.

rac-1-((1-(Fluoromethyl)-3-oxocyclohexyl)methyl)-1H-benzo[d]imidazole-6-carbonitrile

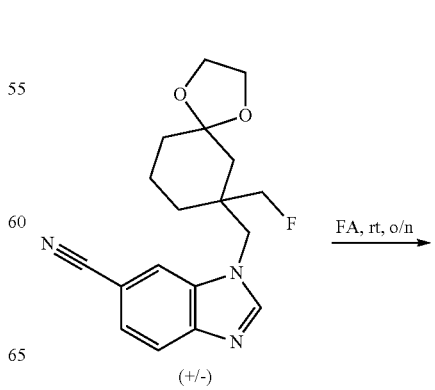

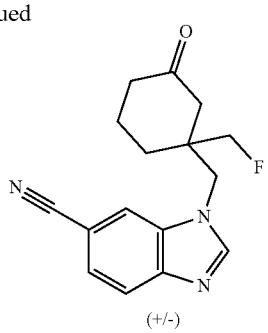

A solution of rac-1-((7-(fluoromethyl)-1,4-dioxaspiro[4.5]decan-7-yl)methyl)-1H-benzo[d]imidazole-6-carbonitrile (900 mg, 2.7 mmol) in formic acid (5 mL) was stirred overnight at room temperature. The resulting mixture was concentrated under vacuum. The residue was purified by Prep-TLC (100% ethyl acetate) to afford rac-1-((1-(fluoromethyl)-3-oxocyclohexyl)methyl)-1H-benzo[d]imidazole-6-carbonitrile (500 mg) as a white solid. LCMS (ESI-MS) m/z=286.3 [M+H]$^+$.

rac-1-(((3S,5R)-5-(Fluoromethyl)-1-oxaspiro[2.5]octan-5-yl)methyl)-1H-benzo[d]imidazole-6-carbonitrile and rac-1-(((3R,5R)-5-(Fluoromethyl)-1-oxaspiro[2.5]octan-5-yl)methyl)-1H-benzo[d]imidazole-6-carbonitrile

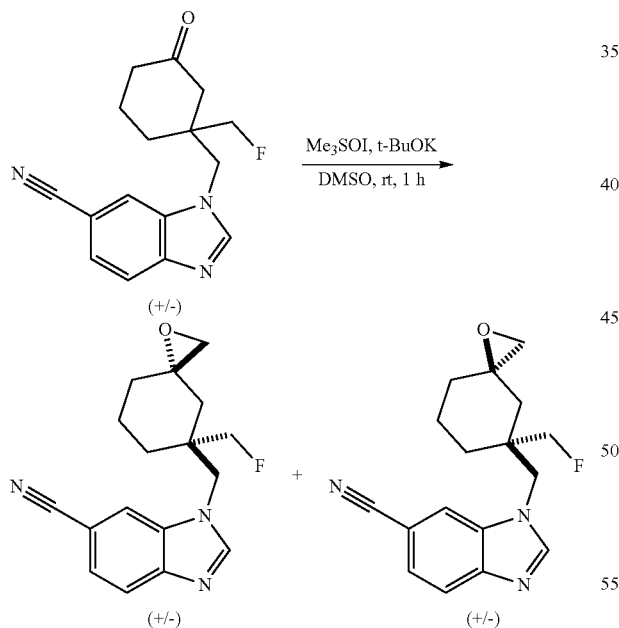

A solution of rac-1-((1-(fluoromethyl)-3-oxocyclohexyl)methyl)-1H-benzo[d]imidazole-6-carbonitrile (500 mg, 1.7 mmol) and dimethylmethanesulfinic iodide (424 mg, 1.9 mmol) in dimethyl sulfoxide (5 mL) was stirred for 5 minutes at room temperature. The solution was cooled to 0° C. and tert-butoxypotassium (216 mg, 1.9 mmol) was added dropwise over 2 minutes. The resulting mixture was stirred for an additional 1 hour at 0° C. The reaction was quenched with water at 0° C. The aqueous phase was extracted with ethyl acetate (3×100 mL). The resulting mixture was concentrated under vacuum. The residue was purified by Prep-TLC (ethyl acetate=100%) to afford rac-1-(((3S,5R)-5-(fluoromethyl)-1-oxaspiro[2.5]octan-5-yl)methyl)-1H-benzo[d]imidazole-6-carbonitrile (200 mg) as a white solid and rac-1-(((3R,5R)-5-(fluoromethyl)-1-oxaspiro[2.5]octan-5-yl)methyl)-1H-benzo[d]imidazole-6-carbonitrile (180 mg) as a white solid. LCMS (ESI-MS) m/z=300.3 [M+H]$^+$.

rac-1-(((5S,7R)-7-(Fluoromethyl)-2-oxo-1-oxa-3-azaspiro[4.5]decan-7-yl)methyl)-1H-benzo[d]imidazole-6-carbonitrile

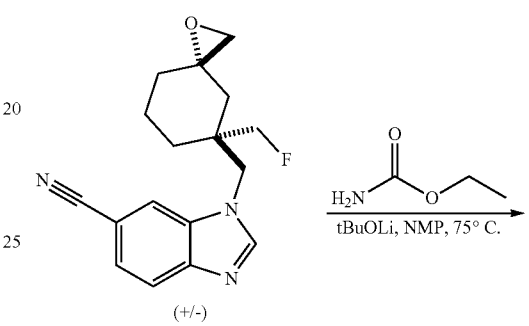

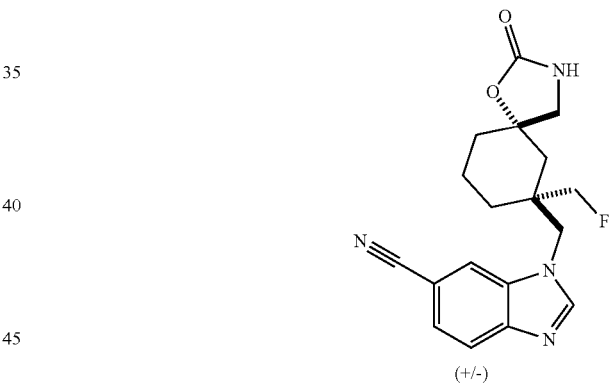

A solution of ethyl carbamate (1.1 g, 13.3 mmol) and tert-butoxylithium (107 mg, 1.3 mmol) in N-methyl-2-pyrrolidone (3 mL) was stirred for 5 minutes at room temperature. rac-1-(((3S,5R)-5-(Fluoromethyl)-1-oxaspiro[2.5]octan-5-yl)methyl)-1H-benzo[d]imidazole-6-carbonitrile (200 mg, 0.7 mmol) was added dropwise over 10 minutes. The resulting mixture was stirred overnight at 75° C. The resulting mixture was cooled to room temperature and concentrated under vacuum to afford the crude product. The residue was purified by Prep-TLC (dichloromethane: methanol=10:1) to afford rac-1-((((5S,7R)-7-(fluoromethyl)-2-oxo-1-oxa-3-azaspiro[4.5]decan-7-yl)methyl)-1H-benzo[d]imidazole-6-carbonitrile (200 mg) as a white solid. LCMS (ESI-MS) m/z=343.3 [M+H]$^+$.

129 rac-1-(((5S,7R)-7-(Fluoromethyl)-3-(5-(2-hydroxy-propan-2-yl)pyrazin-2-yl)-2-oxo-1-oxa-3-azaspiro[4.5]decan-7-yl)methyl)-1H-benzo[d]imidazole-6-carbonitrile

130

1-(((5S,7R)-7-(Fluoromethyl)-3-(5-(2-hydroxypropan-2-yl)pyrazin-2-yl)-2-oxo-1-oxa-3-azaspiro[4.5]decan-7-yl)methyl)-1H-benzo[d]imidazole-6-carbonitrile and 1-(((5R,7S)-7-(fluoromethyl)-3-(5-(2-hydroxypropan-2-yl)pyrazin-2-yl)-2-oxo-1-oxa-3-azaspiro[4.5]decan-7-yl)methyl)-1H-benzo[d]imidazole-6-carbonitrile

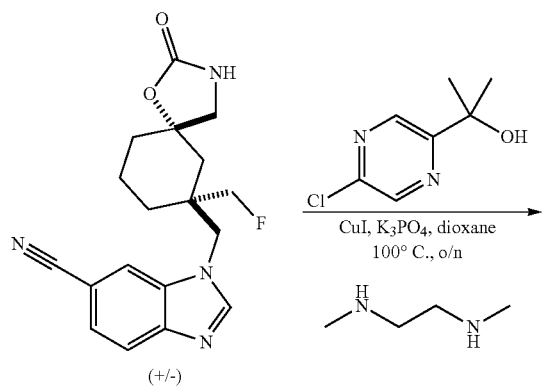

A solution of rac-1-((((5S,7R)-7-(fluoromethyl)-2-oxo-1-oxa-3-azaspiro[4.5]decan-7-yl)methyl)-1H-benzo[d]imidazole-6-carbonitrile (200 mg, 0.6 mmol), 2-(5-chloropyrazin-2-yl)propan-2-ol (151 mg, 0.9 mmol), N1,N2-dimethylethane-1,2-diamine (103 mg, 1.1 mmol), copper(I) iodide (111 mg, 0.6 mmol) and potassium phosphate tribasic (248 mg, 1.2 mmol) in dioxane (3 mL) was stirred overnight at 100° C. under nitrogen atmosphere. The resulting mixture was concentrated under vacuum. The residue was purified by Prep-TLC (dichloromethane: methanol=10:1) to afford rac-1-(((5S,7R)-7-(fluoromethyl)-3-(5-(2-hydroxypropan-2-yl)pyrazin-2-yl)-2-oxo-1-oxa-3-azaspiro[4.5]decan-7-yl)methyl)-1H-benzo[d]imidazole-6-carbonitrile (180 mg) as a white solid. LCMS (ESI-MS) m/z=479.2 [M+H]$^+$.

The mixture of rac-1-(((5S,7R)-7-(fluoromethyl)-3-(5-(2-hydroxypropan-2-yl)pyrazin-2-yl)-2-oxo-1-oxa-3-azaspiro[4.5]decan-7-yl)methyl)-1H-benzo[d]imidazole-6-carbonitrile (180 mg, 0.4 mmol) was separated by Prep-chiral-HPLC with the following conditions: Column: CHIRALPAK IE, 2×25 cm, 5 μm; Mobile Phase A: MtBE (0.5% 2M NH$_3$-MeOH)-HPLC, Mobile Phase B: EtOH-HPLC; Flow rate: 20 m/min; Gradient: 15% B to 15% B in 19 min; Wave Length: 220/254 nm; RT1(min): 12.796; RT2(min): 15.536; Sample Solvent: MtBE (0.5% 2M NH$_3$-MeOH)-HPLC; Injection Volume: 0.4 mL. The desired fractions were combined and lyophilized to afford the two products:

First eluting isomer: 1-(((5R,7S)-7-(Fluoromethyl)-3-(5-(2-hydroxypropan-2-yl)pyrazin-2-yl)-2-oxo-1-oxa-3-azaspiro[4.5]decan-7-yl)methyl)-1H-benzo[d]imidazole-6-carbonitrile (62.2 mg, 98.2% purity, 100% ee) as a white solid. $^1$H NMR (400 MHz, Dimethyl sulfoxide-d$_6$) δ: 9.25 (s, 1H), 8.61 (s, 1H), 8.46 (s, 1H), 8.24 (s, 1H), 7.85 (d, J=8.0 Hz, 1H), 7.61 (d, J=8.4 Hz, 1H), 5.42 (s, 1H), 4.55-4.46 (m, 2H), 4.18-3.89 (m, 4H), 2.12-1.76 (m, 6H), 1.46 (s, 8H). LCMS (ESI-MS) m/z=479.2 [M+H]$^+$.

Second eluting isomer: 1-(((5S,7R)-7-(Fluoromethyl)-3-(5-(2-hydroxypropan-2-yl)pyrazin-2-yl)-2-oxo-1-oxa-3-azaspiro[4.5]decan-7-yl)methyl)-1H-benzo[d]imidazole-6-carbonitrile (63.0 mg, 90.9% purity, 100% ee) as a white solid. NMR (400 MHz, Dimethyl sulfoxide-d$_6$) δ: 9.25 (s, 1H), 8.62 (s, 1H), 8.47 (s, 1H), 8.24 (s, 1H), 7.85 (d, J=8.4 Hz, 1H), 7.61 (d, J=8.4 Hz, 1H), 5.44 (s, 1H), 4.56-4.46 (m, 2H), 4.19 (s, 1H), 4.07-4.03 (m, 2H), 3.90 (d, J=10.0 Hz, 1H), 2.12-2.03 (m, 1H), 2.02-1.96 (m, 1H), 1.95-1.89 (m, 1H), 1.89-1.76 (m, 2H), 1.46 (s, 9H). LCMS (ESI-MS) m/z=479.2 [M+H]$^+$.

Example 8. Preparation of: 1-(((1R,3S,6S)-3'-(5-(2-Hydroxypropan-2-yl)pyrazin-2-yl)-2'-oxospiro[bicyclo[4.1.0]heptane-3,5'-oxazolidin]-1-yl)methyl)-1H-benzo[d]imidazole-6-carbonitrile

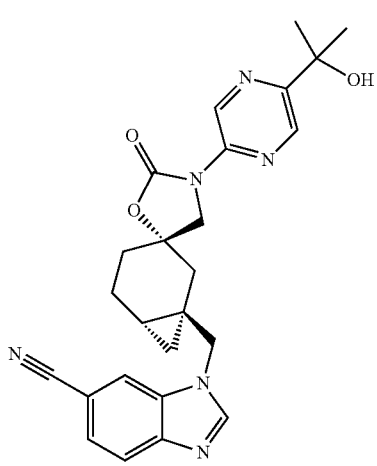 [SMILES: CC(C)(O)c1cnc(N2C[C@@]3(CC[C@H]4C[C@@]4(Cn4cnc5ccc(C#N)cc54)C3)OC2=O)cn1]

Detailed Procedure

3-Methoxycyclohexa-1,4-diene-1-carboxylic acid

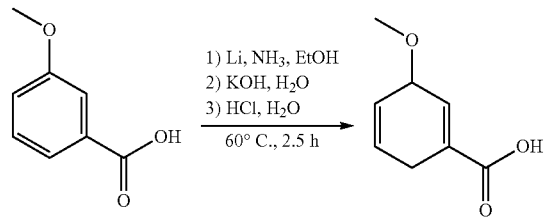

In a 3-necked flask is placed m-anisic acid (50.0 g. 0.33 mol) and H$_2$O (75 mL). The flask is equipped with a mechanical stirrer, an ammonia inlet, and a cold-finger condenser containing solid carbon dioxide and acetone. Ammonia is admitted above the solution through a sintered glass filter; about 1 liter of ammonia is collected. The ammonia inlet is replaced with a nitrogen inlet, and a slow stream of nitrogen is introduced above the surface. Vigorous stirring is begun (caution: exothermic reaction), and lithium wire (7.0 g, 1.0 mol) is added in small pieces over a period of 20-30 min to carry out the Bitch reduction. Vigorous stirring is continued until the blue color completely disappears. The stirring is stopped, the condenser is removed, and the ammonia is allowed to evaporate completely under a steady stream of nitrogen. Then a 1M potassium hydroxide solution (500 mL) (thoroughly purged with nitrogen) is added, and stirring is again started. The solution is heated for 2.5 h with a water bath maintained at 60° C. The water bath is replaced with an ice bath, and the solution is cooled to 10° C. With the ice bath still in place, concentrated HCl (100 mL) is added without allowing the temperature to go over 70° C. Stirring is continued until the solution temperature falls to about 15° C. The ice bath is removed, and stirring is continued until a homogeneous solution is achieved. The aqueous solution is transferred to a separatory funnel and extracted with CH$_2$Cl$_2$ (3×200 mL). The combined organic extracts are dried and evaporated on a rotary evaporator under reduced pressure. A sample of the product is recrystallized from toluene. LCMS (ESI-MS) m/z=155.2 [M+H]$^+$.

5-Oxocyclohex-1-ene-1-carboxylic acid

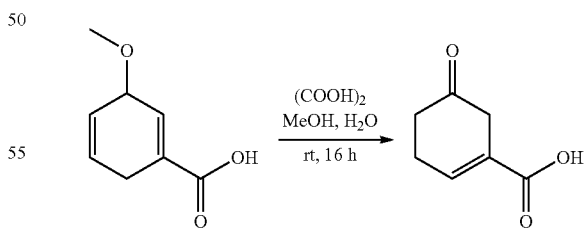

Into a solution of 3-methoxycyclohexa-1,4-diene-1-carboxylic acid (14.5 g, 94.1 mmol) in methanol (200 mL) was added oxalic acid (1.27 g, 14.1 mmol) and water (50 mL). The resulting solution was stirred at room temperature for 16 h. The residue was concentrated and purified by silica gel column (EA:PE=2:1) to give 5-oxocyclohex-1-ene-1-carboxylic acid (3 g) as a white solid. LCMS (ESI-MS) m/z=141.0 [M+H]$^+$.

Methyl 5-oxocyclohex-1-ene-1-carboxylate

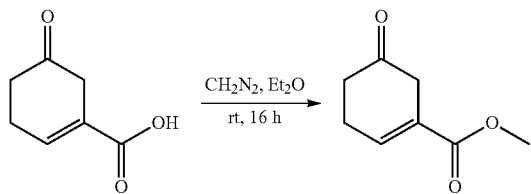

Into a solution of 5-oxocyclohex-1-ene-1-carboxylic acid (30 g, 214 mmol) in diethyl ether (300 mL) was added diazomethane (27.0 g, 642 mmol). The resulting solution was stirred at room temperature for 16 h. The residue was concentrated and purified with silica gel column (EA:PE=1:1) to give the desired product methyl 5-oxocyclohex-1-ene-1-carboxylate (11.0 g) as a light yellow oil. LCMS (ESI-MS) m/z=155.1 [M+H]$^+$.

Methyl 1,4-dioxaspiro[4.5]dec-7-ene-7-carboxylate

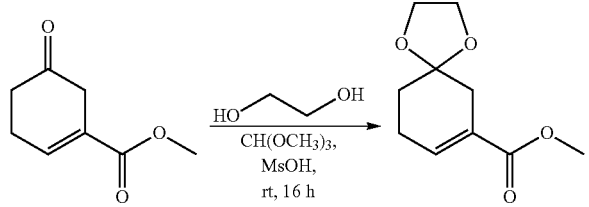

Into a solution of methyl 5-oxocyclohex-1-ene-1-carboxylate (2.3 g, 14.9 mmol) in methylene chloride (50 mL) was added ethylene glycol (1.39 g, 22.4 mmol), trimethyl orthoformate (2.37 g, 224 mmol), and methanesulfonic acid (220 mg, 2.24 mmol). The resulting solution was stirred at room temperature for 16 h. The residue was evaporated and purified by silica gel column (EA:PE=1:1) to give methyl 1,4-dioxaspiro[4.5]dec-7-ene-7-carboxylate (2.30 g) as a light yellow oil. LCMS (ESI-MS) m/z=199.0 [M+H]$^+$.

(1,4-Dioxaspiro[4.5]dec-7-en-7-yl)methanol

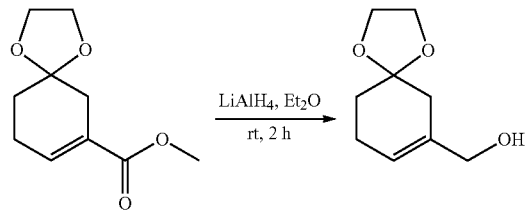

Into a solution of methyl 1,4-dioxaspiro[4.5]dec-7-ene-7-carboxylate (2.10 g, 10.6 mmol) in diethyl ether (20 mL) was added lithium aluminum hydride (302 mg, 7.95 mmol). The resulting solution was stirred at room temperature for 2 h. The reaction was quenched with KOH (15%, 1 mL), water (1 mL). The residue was extracted with Et$_2$O (20.0 mL×2). The organic phase was combined, evaporated and purified with silica gel column (EA:PE=1:1) to give (1,4-dioxaspiro[4.5]dec-7-en-7-yl)methanol (1.6 g) as a light yellow oil.

rac-Spiro[bicyclo[4.1.0]heptane-3,2'-[1,3]dioxolan]-1-ylmethanol

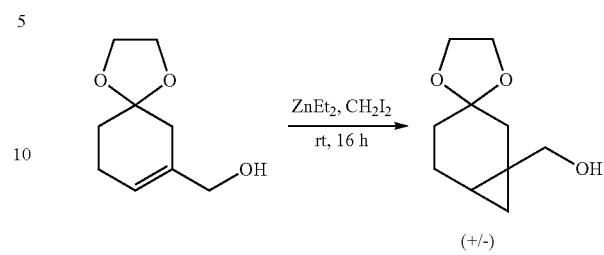

Into a solution of 1,4-dioxaspiro[4.5]dec-7-en-7-ylmethanol (1.60 g, 9.40 mmol) in methylene chloride (30 mL) was added diethylzinc (2.90 g, 23.5 mmol), diiodomethane (6.29 g, 23.5 mmol) and trifluoroacetic acid (2.68 g, 23.5 mmol) at 0° C. The resulting solution was stirred at room temperature for 16 h. The residue was evaporated and purified by silica gel column (EA:PE=1:1) to give rac-spiro[bicyclo[4.1.0]heptane-3,2'-[1,3]dioxolan]-1-ylmethanol (1.00 g) as a light yellow oil.

rac-2-(Spiro[bicyclo[4.1.0]heptane-3,2'-[1,3]dioxolan]-1-ylmethyl)isoindoline-1,3-dione

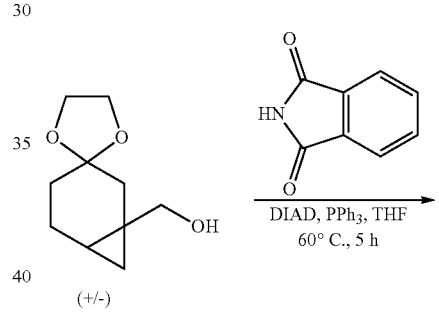

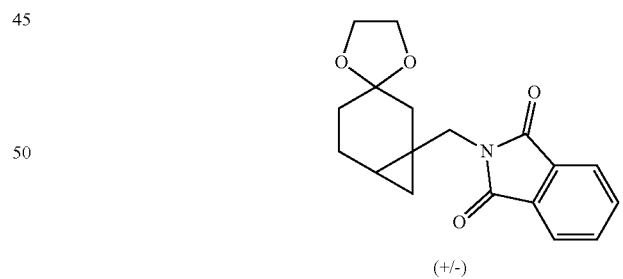

Into a solution of rac-spiro[bicyclo[4.1.0]heptane-3,2'-[1,3]dioxolan]-1-ylmethanol (1.0 g, 5.43 mmol) in tetrahydrofuran (20 mL) was added phthalimide (1.2 g, 8.16 mmol), diisopropyl azodicarboxylate (1.65 g, 8.14 mmol) and triphenylphosphine (2.14 g, 8.14 mmol). The resulting solution was stirred at 60° C. for 5 h. The solution was cooled to room temperature and the residue was concentrated and purified by silica gel column (EA:PE=1:1) to give rac-2-(spiro[bicyclo[4.1.0]heptane-3,2'-[1,3]dioxolan]-1-ylmethyl)isoindoline-1,3-dione (1.40 g, 60.8%) as a white solid. LCMS (ESI-MS) m/z=314.1 [M+H]$^+$.

rac-Spiro[bicyclo[4.1.0]heptane-3,2'-[1,3]dioxolan]-1-ylmethanamine

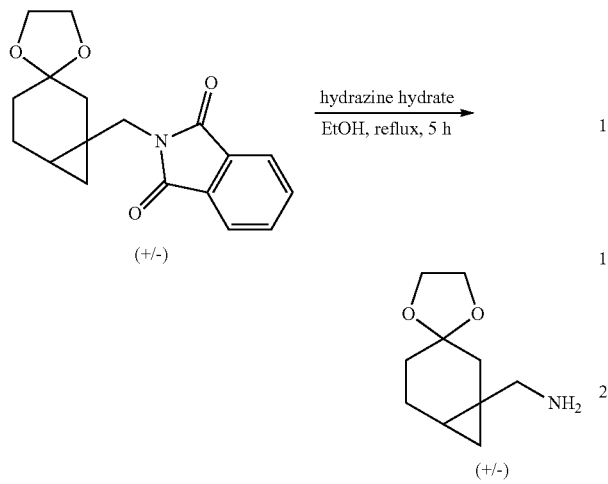

To a solution of rac-2-(spiro[bicyclo[4.1.0]heptane-3,2'-[1,3]dioxolan]-1-ylmethyl)isoindole-1,3-dione (1.30 g, 4.15 mmol) in ethyl alcohol (20 mL) was added hydrazinium hydroxide (830 mg, 16.6 mmol). The resulting solution was stirred at reflux for 5 h. The mixture was cooled to room temperature, concentrated, and purified by silica gel column (DCM: MeOH=10:1) to give rac-spiro[bicyclo[4.1.0]heptane-3,2'-[1,3]dioxolan]-1-ylmethanamine (450 mg) as a light yellow oil.

rac-4-Nitro-3-((spiro[bicyclo[4.1.0]heptane-3,2'-[1,3]dioxolan]-1-ylmethyl)amino)benzonitrile

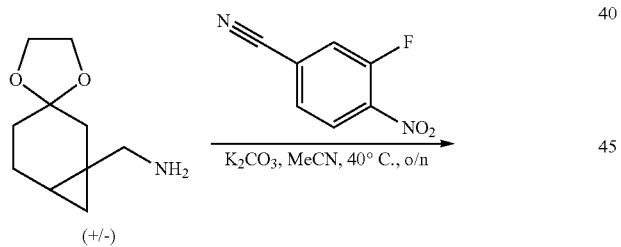

To a solution of rac-spiro[bicyclo[4.1.0]heptane-3,2'-[1,3]dioxolan]-1-ylmethanamine (400 mg, 2.18 mmol) in acetonitrile (5 mL) was added 3-fluoro-4-nitrobenzonitrile (363 mg, 2.18 mmol) and potassium carbonate (649 mg, 6.55 mmol). The resulting solution was stirred at 40° C. for 4 h. The mixture was cooled to room temperature, concentrated, and purified by silica gel column (EA:PE=1:1) to give rac-4-nitro-3-((spiro[bicyclo[4.1.0]heptane-3,2'-[1,3]dioxolan]-1-ylmethyl)amino)benzonitrile (650 mg) as a yellow solid. LCMS (ESI-MS) m/z=330.1 [M+H]$^+$.

rac-4-Amino-3-((spiro[bicyclo[4.1.0]heptane-3,2'-[1,3]dioxolan]-1-ylmethyl)amino)benzonitrile

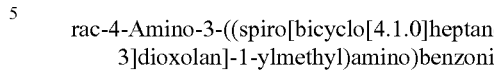

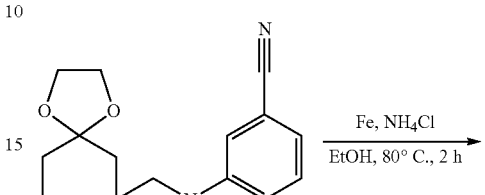

Into a solution of rac-4-nitro-3-((spiro[bicyclo[4.1.0]heptane-3,2'-[1,3]dioxolan]-1-ylmethyl)amino)benzonitrile (600 mg, 1.82 mmol) in ethyl alcohol (10 mL) and water (3 mL) was added iron (1.02 g, 18.2 mmol) and ammonium chloride (390 mg, 7.29 mmol). The resulting solution was stirred at 80° C. for 4 h. The mixture was cooled to room temperature, concentrated, and purified by silica gel column (DCM:MeOH=10:1) to give rac-4-amino-3-((spiro[bicyclo[4.1.0]heptane-3,2'-[1,3]dioxolan]-1-ylmethyl)amino)benzonitrile (500 mg) as a yellow oil. LCMS (ESI-MS) m/z=300.0 [M+H]$^+$.

rac-1-(Spiro[bicyclo[4.1.0]heptane-3,2'-[1,3]dioxolan]-1-ylmethyl)-1H-benzo[d]imidazole-6-carbonitrile

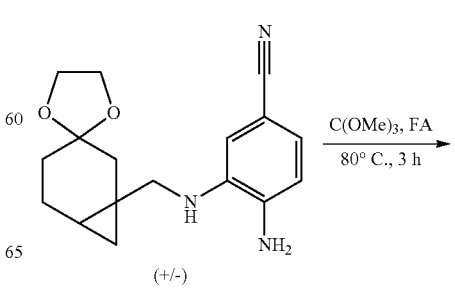

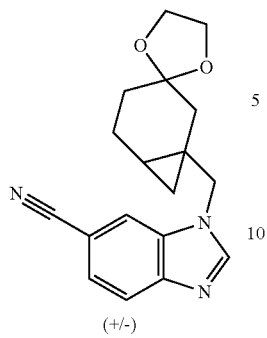

(+/-)

To a solution of rac-4-amino-3-((spiro[bicyclo[4.1.0]heptane-3,2'-[1,3]dioxolan]-1-ylmethyl)amino)benzonitrile (450 mg, 1.5 mmol) in trimethyl orthoformate (5 mL) was added formic acid (69.2 mg, 1.5 mmol). The resulting solution was stirred at 80° C. for 16 h. The mixture was cooled to room temperature, concentrated, and purified by silica gel column (EA:PE=1:1) to give rac-1-(spiro[bicyclo[4.1.0]heptane-3,2'-[1,3]dioxolan]-1-ylmethyl)-1H-benzo[d]imidazole-6-carbonitrile (350 mg) as a light yellow solid. LCMS (ESI-MS) m/z=310.1 [M+H]⁺.

rac-1-((3-Oxobicyclo[4.1.0]heptan-1-yl)methyl)-1H-benzo[d]imidazole-6-carbonitrile

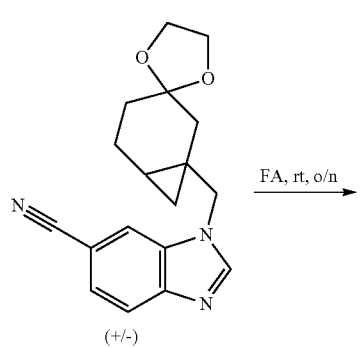

(+/-)

rac-1-(Spiro[bicyclo[4.1.0]heptane-3,2'-[1,3]dioxolan]-1-ylmethyl)-1H-benzo [d]imidazole-6-carbonitrile (350 mg, 1.13 mmol) and formic acid (5.0 mL, 0.04 mmol) were combined in a 25 mL round bottom flask. The resulting solution was stirred at room temperature for 2 h. The reaction was quenched with saturated NaHCO₃, extracted with EA (20 mL×2). The organic phase was combined, dried with anhydrous Na₂SO₄, and evaporated to give rac-1-((3-oxobicyclo[4.1.0]heptan-1-yl)methyl)-1H-benzo[d]imidazole-6-carbonitrile (300 mg) as a light yellow solid. LCMS (ESI-MS) m/z=266.2 [M+H]⁺.

rac-1-(((1R,3S,6S)-Spiro[bicyclo[4.1.0]heptane-3,2'-oxiran]-1-yl)methyl)-1H-benzo[d]imidazole-6-carbonitrile and rac-1-(((1R,3R,6S)-Spiro[bicyclo[4.1.0]heptane-3,2'-oxiran]-1-yl)methyl)-1H-benzo[d]imidazole-6-carbonitrile

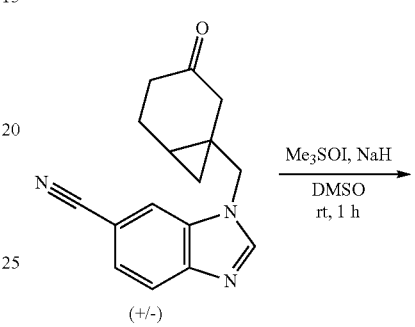

(+/-)

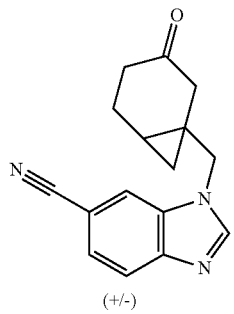

(+/-)

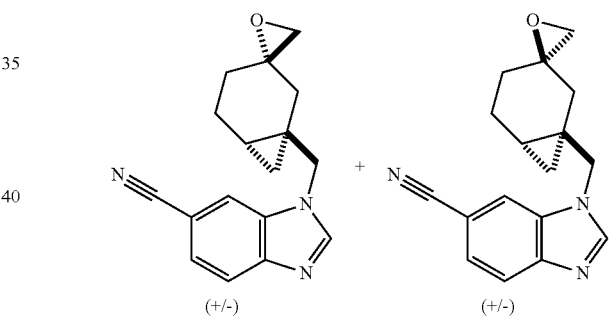

(+/-)   (+/-)

To a solution of trimethylsulfoxonium iodide (3.77 mmol) in dimethyl sulfoxide (5 mL) was added iodotrimethyl-lambda6-sulfanone (3.77 mmol) at 0° C. After stirring for 30 min, rac-1-((3-oxobicyclo[4.1.0]heptan-1-yl)methyl)-1H-benzo[d]imidazole-6-carbonitrile (3.77 mmol) was added. The resulting solution was stirred at room temperature for 1 h and then quenched with water. The resulting mixture was extracted with EtOAc (3×5.0 mL). The combined organic layers were washed with brine (3×5.0 mL), dried over anhydrous Na₂SO₄, and concentrated under reduced pressure to afford a mixture of rac-1-(((1R,3S,6S)-spiro[bicyclo[4.1.0]heptane-3,2'-oxiran]-1-yl)methyl)-1H-benzo[d]imidazole-6-carbonitrile & rac-1-(((1R,3R,6S)-spirol[bicyclol[4.1.0]heptane-3,2'-oxiran]-1-yl)methyl)-1H-benzo[d]imidazole-6-carbonitrile (210 mg) as a light yellow solid. LCMS (ESI-MS) m/z=280.1 [M+H]⁺.

139 rac-1-(((1R,3S,6S)-2'-Oxospiro[bicyclo[4.1.0]heptane-3,5'-oxazolidin]-1-yl)methyl)-1H-benzo[d]imidazole-6-carbonitrile and rac-1-(((1R,3R,6S)-2'-Oxospiro[bicyclo[4.1.0]heptane-3,5'-oxazolidin]-1-yl)methyl)-1H-benzo[d]imidazole-6-carbonitrile

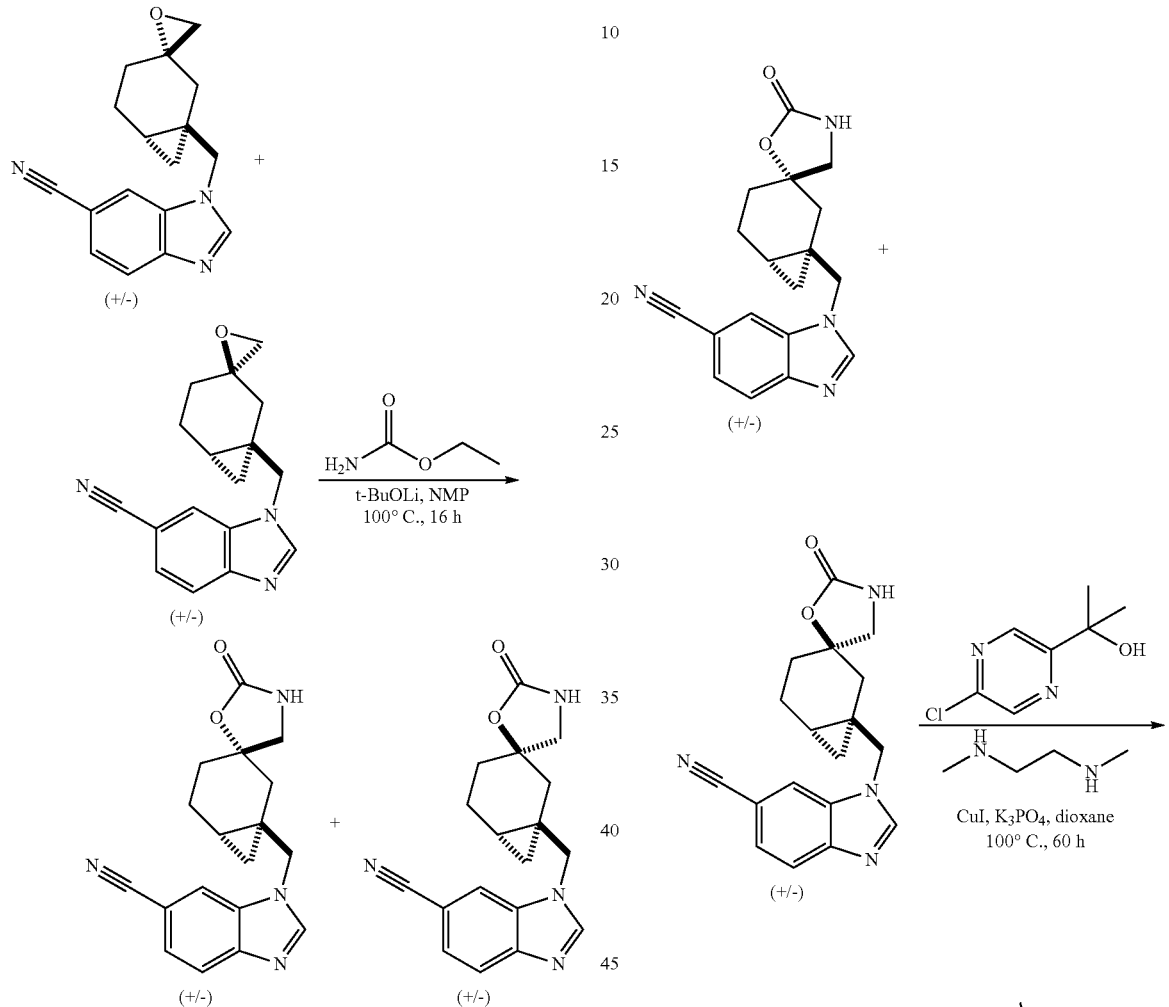

To a solution of a mixture of rac-1-(((1R,3S,6S)-spiro[bicyclo[4.1.0]heptane-3,2'-oxiran]-1-yl)methyl)-1H-benzo[d]imidazole-6-carbonitrile & rac-1-(((1R,3R,6S)-spiro[bicyclo[4.1.0]heptane-3,2'-oxiran]-1-yl)methyl)-1H-benzo[d]imidazole-6-carbonitrile (200 mg, 0.716 mmol) in methylpyrrolidone (5 mL) was added urethane (319 mg, 3.58 mmol) and tert-butoxylithium (143 mg, 1.79 mmol). The resulting solution was stirred at 100° C. for 16 h. The resulting mixture was cooled to room temperature, diluted with EtOAc (10 mL), washed with brine (3×10 mL), dried with anhydrous Na$_2$SO$_4$, concentrated and purified with silica gel column (DCM:MeOH=10:1) to afford a mixture of rac-1-(((1R,3S,6S)-2'-oxospiro[bicyclo[4.1.0]heptane-3,5'-oxazolidin]-1-yl)methyl)-1H-benzo[d]imidazole-6-carbonitrile & rac-1-(((1R,3R,6S)-2'-oxospiro[bicyclo[4.1.0]heptane-3,5'-oxazolidin]-1-yl)methyl)-1H-benzo[d]imidazole-6-carbonitrile (200 mg) as a light yellow solid. LCMS (ESI-MS) m/z=323.1 [M+H]$^+$.

140 rac-1-(((1R,3S,6S)-3'-(5-(2-Hydroxypropan-2-yl)pyrazin-2-yl)-2'-oxospiro[bicyclo[4.1.0]heptane-3,5'-oxazolidin]-1-yl)methyl)-1H-benzo[d]imidazole-6-carbonitrile and rac-1-(((1R,3R,6S)-3'-(5-(2-hydroxypropan-2-yl)pyrazin-2-yl)-2'-oxospiro[bicyclo[4.1.0]heptane-3,5'-oxazolidin]-1-yl)methyl)-1H-benzo[d]imidazole-6-carbonitrile

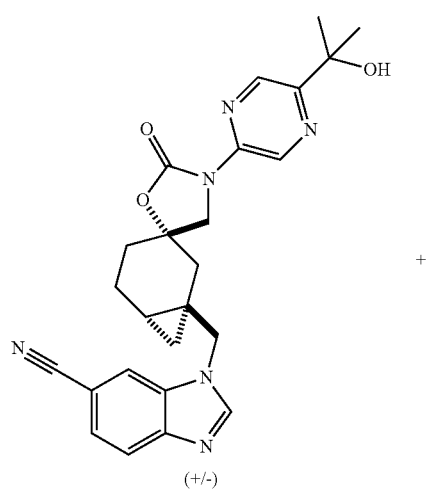

141
-continued

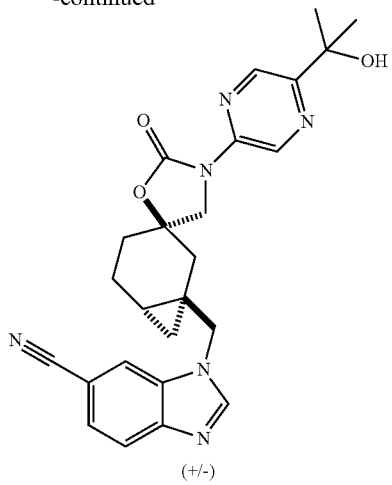

(+/-)

Into a solution of a mixture of rac-1-(((1R,3S,6S)-2'-oxospiro[bicyclo[4.1.0]heptane-3,5'-oxazolidin]-1-yl)methyl)-1H-benzo[d]imidazole-6-carbonitrile & rac-1-(((1R,3R,6S)-2'-oxospiro[bicyclo[4.1.0]heptane-3,5'-oxazolidin]-1-yl)methyl)-1H-benzo[d]imidazole-6-carbonitrile (200 mg, 0.62 mmol) in dioxane (5.0 mL) was added 2-(5-bromopyrazin-2-yl)propan-2-ol (135 mg, 0.62 mmol), N1,N2-dimethylethane-1,2-diamine (109 mg, 1.24 mmol), tripotassium phosphate (263 mg, 1.24 mmol) and copper(I) iodide (118 mg, 0.62 mmol). The resulting solution was stirred at 100° C. for 16 h. The residue was evaporated and purified with silica gel column (DCM:MeOH=10:1) to afford a mixture of rac-1-(((1R,3S,6S)-3'-(5-(2-hydroxypropan-2-yl)pyrazin-2-yl)-2'-oxospiro[bicyclo[4.1.0]heptane-3,5'-oxazolidin]-1-yl)methyl)-1H-benzo[d]imidazole-6-carbonitrile and rac-1-(((1R,3R,6S)-3'-(5-(2-hydroxypropan-2-yl)pyrazin-2-yl)-2'-oxospiro[bicyclo[4.1.0]heptane-3,5'-oxazolidin]-1-yl)methyl)-1H-benzo[d]imidazole-6-carbonitrile (100 mg) as a light yellow solid. LCMS (ESI-MS) m/z=459.2 [M+H]$^+$.

Achiral Separation: A mixture of rac-1-(((1R,3S,6S)-3'-(5-(2-hydroxypropan-2-yl)pyrazin-2-yl)-2'-oxospiro[bicycle[4.1.0]heptane-3,5'-oxazolidin]-1-yl)methyl)-1H-benzo[d]imidazole-6-carbonitrile & rac-1-(((1R,3R,6S)-3'-(5-(2-hydroxypropan-2-yl)pyrazin-2-yl)-2'-oxospiro[bicyclo[4.1.0]heptane-3,5'-oxazolidin]-1-yl)methyl)-1H-benzo[d]imidazole-6-carbonitrile (100 mg, 0.22 mmol) was separated by Prep-Achiral-HPLC with the condition: Column: CHIRALPAK IF-3, 4.6*50 mm, 3 μm; Mobile Phase A: MTBE (0.1% DEA): ethanol=70:30; Flow rate: 1 mL/min; Gradient: 0% B to 0% B; Injection Volume: 5 μl to afford the first eluting isomer: rac-1-(((1R,3S,6S)-3'-(5-(2-hydroxypropan-2-yl)pyrazin-2-yl)-2'-oxospiro[bicyclo[4.1.0]heptane-3,5'-oxazolidin]-1-yl)methyl)-1H-benzo[d]imidazole-6-carbonitrile (10 mg) as a white solid and the second eluting isomer: rac-1-(((1R,3R,6S)-3'-(5-(2-hydroxypropan-2-yl)pyrazin-2-yl)-2'-oxospiro[bicyclo[4.1.0]heptane-3,5'-oxazolidin]-1-yl)methyl)-1H-benzo[d]imidazole-6-carbonitrile (15 mg) as a white solid.

142

1-(((1R,3S,6S)-3'-(5-(2-Hydroxypropan-2-yl)pyrazin-2-yl)-2'-oxospiro[bicyclo[4.1.0]heptane-3,5'-oxazolidin]-1-yl)methyl)-1H-benzo[d]imidazole-6-carbonitrile & 1-(((1S,3R,6R)-3'-(5-(2-hydroxypropan-2-yl)pyrazin-2-yl)-2'-oxospiro[bicyclo[4.1.0]heptane-3,5'-oxazolidin]-1-yl)methyl)-1H-benzo[d]imidazole-6-carbonitrile

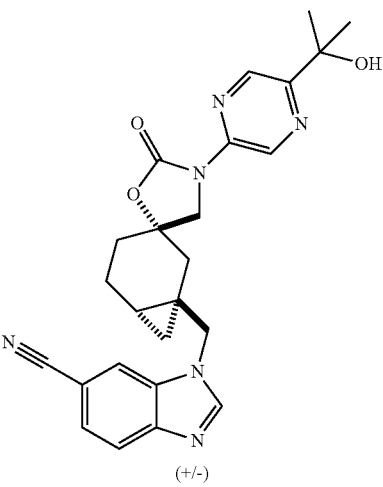

(+/-) → chiral separation

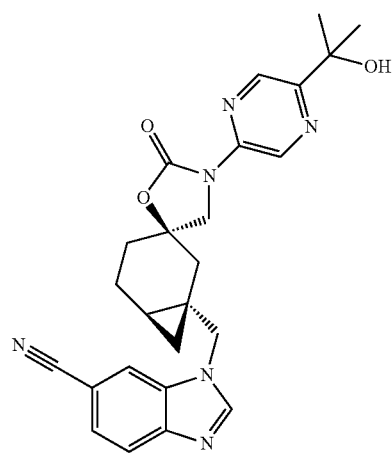

first eluting isomer

+

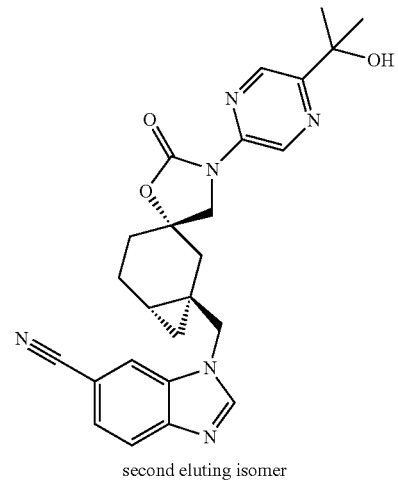

second eluting isomer rac-1-(((1R,3S,6S)-3'-(5-(2-Hydroxypropan-2-yl)pyrazin-2-yl)-2'-oxospiro[bicyclo[4.1.0]heptane-3,5'-oxazolidin]-1-yl)methyl)-1H-benzo[d]imidazole-6-carbonitrile (10.0 mg, 0.0220 mmol) was separated by Prep-Chiral-HPLC with the condition: Column: CHIRALPAK IF-3, 4.6*50 mm, 3 um; Mobile Phase A: MTBE (0.1% DEA): ethanol=70:30; Flow rate: 1 mL/min; Injection Volume: 5 μl. The desired fractions were combined and lyophilized to afford the two products:

First eluting isomer: 1-(((1S,3R,6R)-3'-(5-(2-Hydroxypropan-2-yl)pyrazin-2-yl)-2'-oxospiro[bicycle[4.1.0]heptane-3,5'-oxazolidin]-1-yl)methyl)-1H-benzo[d]imidazole-6-carbonitrile (4.10 mg) as a white solid. $^1$H NMR (400 MHz, DMSO-$d_6$) δ 8.95 (s, 1H), 8.61 (s, 1H), 8.48 (s, 1H), 8.35 (s, 1H), 7.65 (d, J=8.4 Hz, 1H), 7.32 (d, J=10.0 Hz, 1H), 5.44 (s, 1H), 4.37-4.33 (m, 1H), 4.09-4.05 (m, 1H), 3.66-3.64 (m, 1H), 2.93-2.91 (m, 1H), 2.18-2.14 (m, 1H), 2.01-1.87 (m, 3H), 1.65-1.56 (m, 2H), 1.52 (s, 3H), 1.45 (s, 3H), 1.43-1.37 (m, 1H), 0.97-0.94 (m, 1H), 0.68-0.66 (m, 1H). LCMS (ESI-MS) m/z=459.2 [M+H]$^+$.

The second eluting isomer: 1-(((1R,3S,6S)-3'-(5-(2-Hydroxypropan-2-yl)pyrazin-2-yl)-2'-oxospiro[bicycle[4.1.0]heptane-3,5'-oxazolidin]-1-yl)methyl)-1H-benzo[d]imidazole-6-carbonitrile (3.60 mg) as a white solid. $^1$H NMR (400 MHz, DMSO-$d_6$) δ 8.95 (s, 1H), 8.61 (s, 1H), 8.48 (s, 1H), 8.35 (s, 1H), 7.65 (d, J=8.4 Hz, 1H), 7.32 (d, J=10.0 Hz, 1H), 5.44 (s, 1H), 4.37-4.33 (m, 1H), 4.09-4.05 (m, 1H), 3.66-3.64 (m, 1H), 2.93-2.91 (m, 1H), 2.18-2.14 (m, 1H), 1.91-1.87 (m, 3H), 1.61-1.58 (m, 2H), 1.52 (s, 3H), 1.45 (s, 3H), 1.43-1.39 (m, 1H), 0.97-0.95 (m, 1H), 0.71-0.65 (m, 1H). LCMS (ESI-MS) m/z=459.3 [M+H]$^+$.

Example 9. Preparation of: 1-(((5S,7R)-3-(5-(2-Hydroxypropan-2-yl)pyrazin-2-yl)-7-methoxy-2-oxo-1-oxa-3-azaspiro[4.5]decan-7-yl)methyl)-1H-benzo[d]imidazole-6-carbonitrile

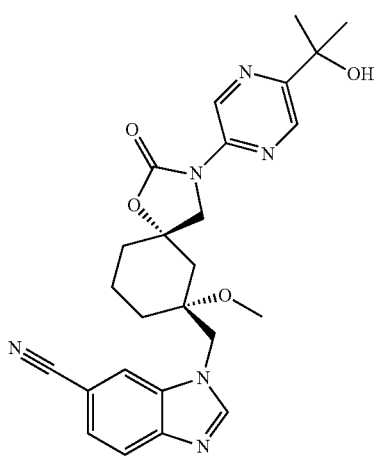 [SMILES: CO[C@]1(Cn2cnc3ccc(C#N)cc32)CCC[C@@]2(CN(c3cnc(C(C)(C)O)cn3)C(=O)O2)C1]

Detailed Procedure 1,4-Dioxaspiro[4.5]decan-7-one

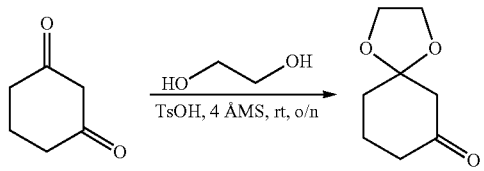

p-Toluenesulfonic acid (13.8 g, 80.3 mmol) was added to a mixture of cyclohexane-1,3-dione (30 g, 268 mmol), molecular sieves (4 Å) (30 g) and magnesium sulfate (30 g) in ethylene glycol (300 mL). The resulting mixture was stirred overnight at room temperature. The reaction mixture was diluted with water (300 mL), and the resulting mixture extracted with ethyl acetate (3×300 mL). The combined organic layers were washed with brine, dried over anhydrous sodium sulfate, filtered and concentrated under vacuum to afford the crude product 1,4-dioxaspiro [4.5]decan-7-one (28 g crude) as light yellow oil. LCMS (ESI-MS) m/z=157.1 [M+H]$^+$.

rac-1,6,9-Trioxadispiro[2.1.4$^5$.3$^3$]dodecane

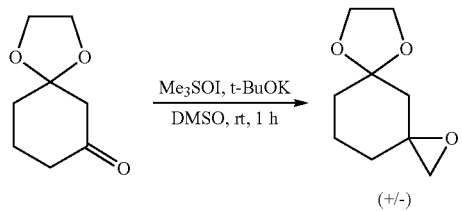

Potassium tert-butoxide (22.1 g, 197 mmol) was added to a solution of 1,4-dioxaspiro [4.5]decan-7-one (28 g, 179 mmol) and trimethylsulfoxonium iodide (39.5 g, 179 mmol) in dimethyl sulfoxide (280 mL). The reaction mixture was stirred for 1 hour at the room temperature. The reaction mixture was diluted with water (300 mL) and the resulting solution was extracted with ethyl acetate (3×300 mL). The combined organic layers were washed with brine, dried over anhydrous sodium sulfate, filtered and concentrated under vacuum to afford the crude product rac-1,6,9-trioxadispiro [2.1.4$^5$.3$^3$]dodecane (28 g crude) as light yellow oil. LCMS (ESI-MS) m/z=171.1 [M+H]$^+$.

rac-7-(Aminomethyl)-1,4-dioxaspiro[4.5]decan-7-ol

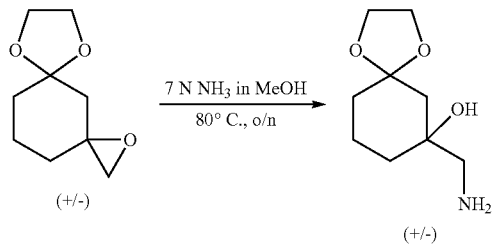 [SMILES: C1CC2(CO2)CC2(C1)OCCO2 ; "7 N NH3 in MeOH" ; NCC1(O)CCCC2(C1)OCCO2]

A solution of rac-1,6,9-trioxadispiro[2.1.4⁵.3³]dodecane (28 g, 165 mmol) in ammonia in methanol (7 N, 280 mL, 1.96 mol). The resulting mixture was heated to 80° C. and stirred overnight. The reaction mixture was concentrated under vacuum to afford the crude product rac-7-(aminomethyl)-1,4-dioxaspiro[4.5]decan-7-ol (28 g crude) as light yellow oil. LCMS (ESI-MS) m/z=188.1 [M+H]⁺.

rac-3-(((7-Hydroxy-1,4-dioxaspiro[4.5]decan-7-yl)methyl)amino)-4-nitrobenzonitrile

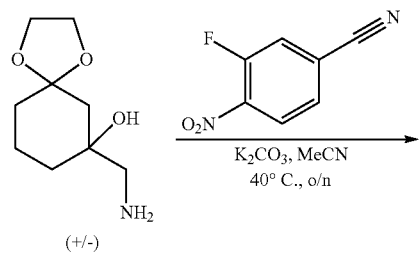

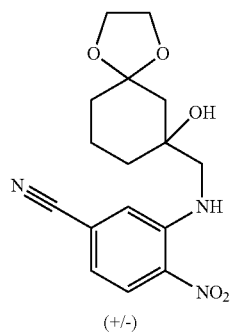

Potassium carbonate (41.3 g, 299 mmol) was added to a solution of rac-7-(aminomethyl)-1,4-dioxaspiro[4.5]decan-7-ol (28 g, 150 mmol) and 3-fluoro-4-nitrobenzonitrile (24.8 g, 150 mmol) in acetonitrile (200 mL). The resulting mixture was heated to 40° C. and stirred overnight. After cooling to room temperature, the resulting mixture was purified by silica gel column chromatography, and eluted with ethyl acetate in petroleum ether from 0% to 15% to afford the desired product rac-3-(((7-hydroxy-1,4-dioxaspiro[4.5]decan-7-yl)methyl)amino)-4-nitrobenzonitrile (12 g) as an orange solid. LCMS (ESI-MS) m/z=334.1 [M+H]⁺.

rac-4-Amino-3-(((7-hydroxy-1,4-dioxaspiro[4.5]decan-7-yl)methyl)amino)benzonitrile

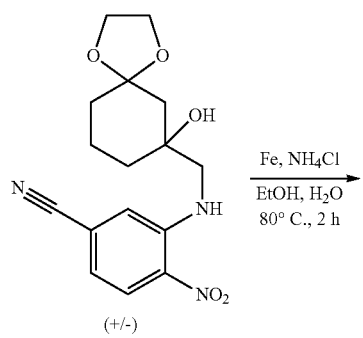

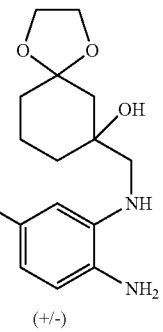

Iron powder (20.1 g, 360 mmol) was added to a solution of rac-3-(((7-hydroxy-1,4-dioxaspiro[4.5]decan-7-yl)methyl)amino)-4-nitrobenzonitrile (12 g, 36.0 mmol), ammonium chloride (7.7 g, 144 mmol), ethanol (120 mL) and water (40 mL). The resulting mixture was heated to 80° C. and stirred for 2 hours. After cooling to room temperature, the resulting mixture was filtered and the filter cake was washed with ethanol (2×200 mL). The filtrate was concentrated under reduced pressure to afford the crude product rac-4-amino-3-(((7-hydroxy-1,4-dioxaspiro[4.5]decan-7-yl)methyl)amino)benzonitrile (12 g crude) as a yellow soild. LCMS (ESI-MS) m/z=304.2 [M+H]⁺.

rac-1-((7-Hydroxy-1,4-dioxaspiro[4.5]decan-7-yl)methyl)-1H-benzo[d]imidazole-6-carbonitrile

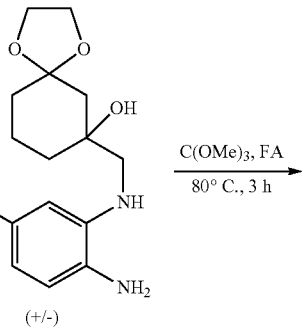

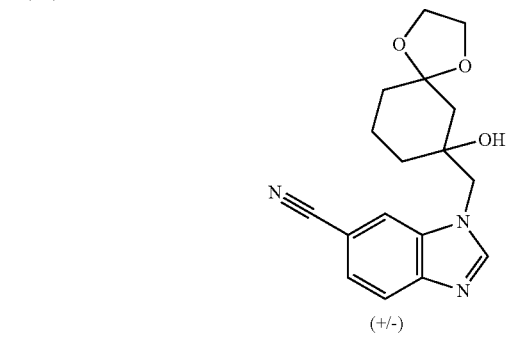

Formic acid (1.82 g, 39.6 mmol) was added to a solution of rac-4-amino-3-(((7-hydroxy-1,4-dioxaspiro[4.5]decan-7-yl)methyl)amino)benzonitrile (12 g, 39.6 mmol) in trimethoxymethane (83.9 g, 791 mmol). The resulting mixture was heated to 80° C. and stirred for 3 hours. The mixture was cooled to room temperature and concentrated to afford the crude product. The residue was purified by silica gel column chromatography, eluted with ethyl acetate in petroleum ether from 0% to 70% to afford the desired product rac-1-((7-hydroxy-1,4-dioxaspiro[4.5]decan-7-yl)methyl)-1H-benzo[d]imidazole-6-carbonitrile (9 g) as a white solid. LCMS (ESI-MS) m/z=314.1 [M+H]⁺.

rac-1-((1-Hydroxy-3-oxocyclohexyl)methyl)-1H-benzo[d]imidazole-6-carbonitrile rac-1-(((3S,5R)-5-Hydroxy-1-oxaspiro[2.5]octan-5-yl)methyl)-1H-benzo[d]imidazole-6-carbonitrile

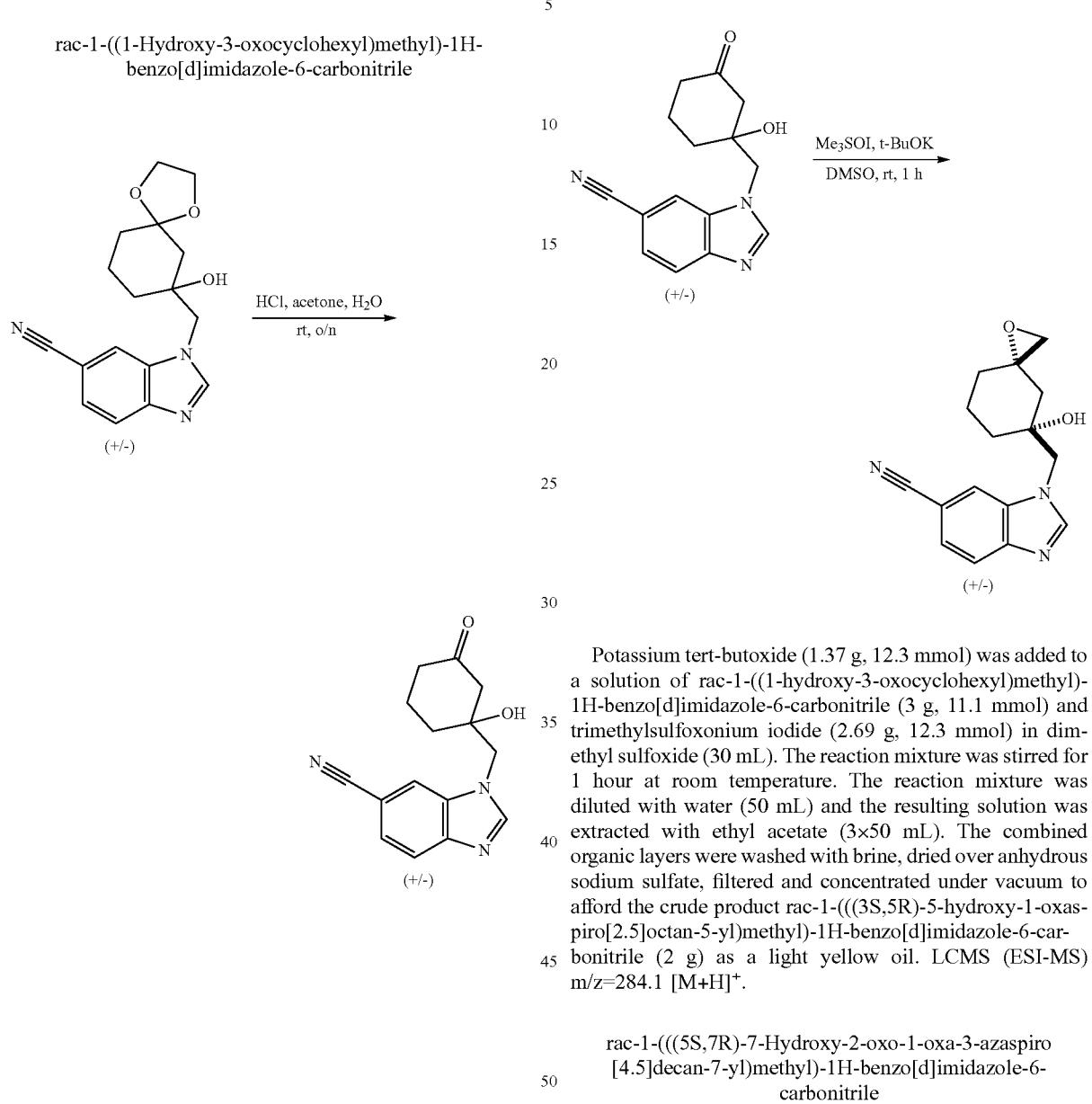

Potassium tert-butoxide (1.37 g, 12.3 mmol) was added to a solution of rac-1-((1-hydroxy-3-oxocyclohexyl)methyl)-1H-benzo[d]imidazole-6-carbonitrile (3 g, 11.1 mmol) and trimethylsulfoxonium iodide (2.69 g, 12.3 mmol) in dimethyl sulfoxide (30 mL). The reaction mixture was stirred for 1 hour at room temperature. The reaction mixture was diluted with water (50 mL) and the resulting solution was extracted with ethyl acetate (3×50 mL). The combined organic layers were washed with brine, dried over anhydrous sodium sulfate, filtered and concentrated under vacuum to afford the crude product rac-1-(((3S,5R)-5-hydroxy-1-oxaspiro[2.5]octan-5-yl)methyl)-1H-benzo[d]imidazole-6-carbonitrile (2 g) as a light yellow oil. LCMS (ESI-MS) m/z=284.1 [M+H]⁺.

rac-1-(((5S,7R)-7-Hydroxy-2-oxo-1-oxa-3-azaspiro[4.5]decan-7-yl)methyl)-1H-benzo[d]imidazole-6-carbonitrile

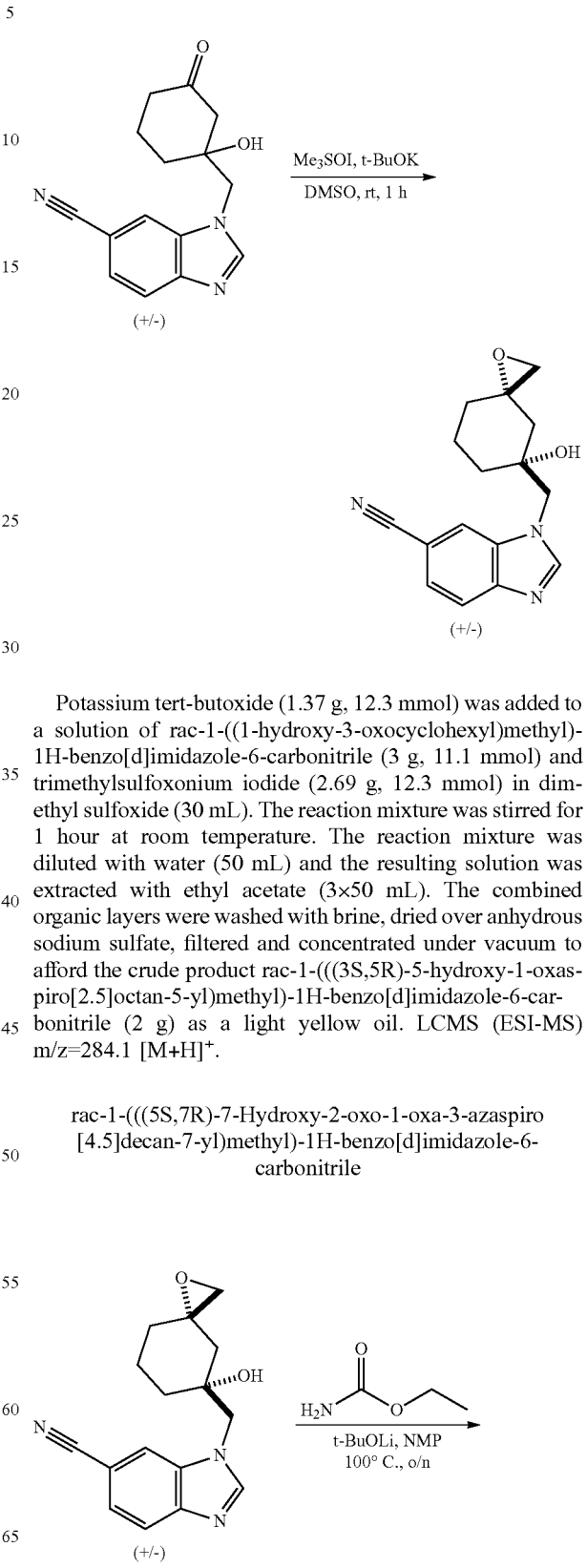

A solution of rac-1-((7-hydroxy-1,4-dioxaspiro[4.5]decan-7-yl)methyl)-1H-benzo[d]imidazole-6-carbonitrile (5 g, 17.7 mmol) in acetone (30 mL) and water (10 mL) was treated with 1 M aqueous hydrochloric acid (8.66 mL, 8.66 mmol), the resulting mixture was stirred overnight at the room temperature. The reaction mixture was diluted with water (100 mL) and then extracted with ethyl acetate (3×100 mL). The combined organic layers were washed with brine, dried over anhydrous sodium sulfate, filtered and concentrated under vacuum to afford the crude product. The residue was purified by silica gel column chromatography, eluted with ethyl acetate in petroleum ether from 0% to 80% to afford the desired product rac-1-((1-hydroxy-3-oxocyclohexyl)methyl)-1H-benzo[d]imidazole-6-carbonitrile (3 g) as a yellow solid. LCMS (ESI-MS) m/z=270.1 [M+H]⁺.

149
-continued

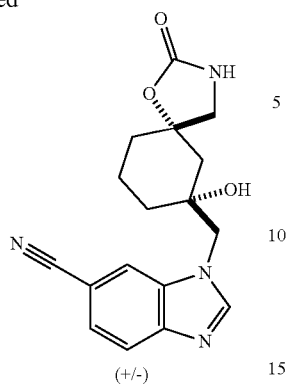

(+/-)

Lithium tert-butoxide (1.13 g, 14.1 mmol) was added to a solution of ethyl carbamate (12.6 g, 141 mmol) in N-methyl pyrrolidone (10 mL). After stirred for 5 minutes at room temperature, a solution of rac-1-(((3S,5R)-5-hydroxy-1-oxaspiro[2.5]octan-5-yl)methyl)-1H-benzo[d]imidazole-6-carbonitrile (2 g, 7.06 mmol) in N-methyl pyrrolidone (5 mL) was added dropwise. The reaction mixture was subsequently heated to 100° C. and stirred overnight. After cooling to room temperature, the residue was purified by reversed-phase flash chromatography with the following conditions: column, $C_{18}$ silica gel; mobile phase, ACN in water (10 mmol/L $NH_4HCO_3$), 0% to 30% gradient in 10 min; detector, UV 254 nm to afford the desired product rac-1-(((5S,7R)-7-hydroxy-2-oxo-1-oxa-3-azaspiro[4.5]decan-7-yl)methyl)-1H-benzo[d]imidazole-6-carbonitrile (1 g) as a white solid. $^1$H NMR (400 MHz, DMSO-d$_6$) δ 9.21 (d, J=1.6 Hz, 1H), 8.60 (d, J=1.6 Hz, 1H), 8.35 (d, J=1.6 Hz, 1H), 8.29 (s, 1H), 6.45 (s, 1H), 4.50 (s, 1H), 3.80 (dd, J=8.3, 8.3 Hz, 2H), 3.10 (dd, J=8.1, 8.1 Hz, 2H), 2.10-2.00 (m, 2H), 1.60-1.48 (m, 2H), 1.45-1.43 (m, 4H). LCMS (ESI-MS) m/z=327.1 [M+H]$^+$.

rac-1-(((5S,7R)-7-Hydroxy-3-(5-(2-((4-methoxybenzyl)oxy)propan-2-yl)pyrazin-2-yl)-2-oxo-1-oxa-3-azaspiro[4.5]decan-7-yl)methyl)-1H-benzo[d]imidazole-6-carbonitrile 150
-continued

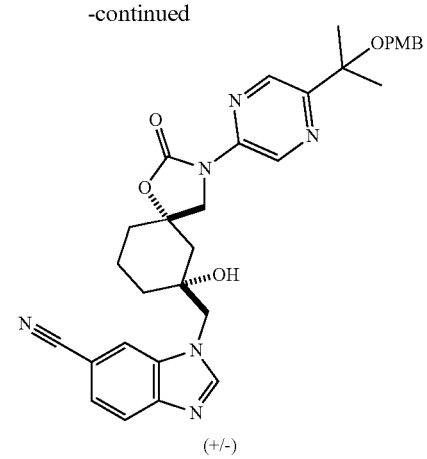

(+/-)

Copper(I) iodide (582 mg, 3.06 mmol) was added to a mixture of rac-1-(((5S,7R)-7-hydroxy-2-oxo-1-oxa-3-azaspiro[4.5]decan-7-yl)methyl)-1H-benzo[d]imidazole-6-carbonitrile (1 g, 3.06 mmol), 2-chloro-5-(2-((4-methoxybenzyl)oxy)propan-2-yl)pyrazine (896 mg, 3.06 mmol), $N^1,N^2$-dimethylethane-1,2-diamine (540 mg, 6.12 mmol) and tripotassium phosphate (1.3 g, 6.12 mmol) in 1,4-dioxane (10 mL) under a nitrogen atmosphere. The resulting mixture was heated to 100° C. and stirred overnight. After cooling to room temperature, the resulting mixture was filtered and concentrated under vacuum. The residue was purified by silica gel column chromatography, and eluted with methanol in dichloromethane from 0% to 3% to afford the desired product rac-1-(((5S,7R)-7-hydroxy-3-(5-(2-((4-methoxybenzyl)oxy)propan-2-yl)pyrazin-2-yl)-2-oxo-1-oxa-3-azaspiro[4.5]decan-7-yl)methyl)-1H-benzo [d]imidazole-6-carbonitrile (700 mg) as a light yellow solid. $^1$H NMR (300 MHz, DMSO-d$_6$) δ 9.21 (d, J=1.6 Hz, 1H), 8.60 (d, J=1.6 Hz, 1H), 8.35 (d, J=1.6 Hz, 1H), 8.29 (s, 1H), 7.84 (d, J=8.3 Hz, 1H), 7.59 (dd, J=8.3, 1.5 Hz, 1H), 6.89 (d, J=7.2 Hz, 2H), 6.79 (d, J=7.2 Hz, 2H), 4.81 (s, 2H), 4.50 (s, 1H), 4.44 (d, J=15.1 Hz, 1H), 4.36 (d, J=15.0 Hz, 1H), 3.92 (d, J=10.2 Hz, 1H), 3.84 (d, J=10.2 Hz, 1H), 3.79 (s, 3H), 2.27 (d, J=15.1 Hz, 1H), 2.00 (d, J=13.4 Hz, 1H), 1.80 (d, J=15.1 Hz, 1H), 1.69 (t, J=12.9 Hz, 1H), 1.61-1.47 (m, 1H) 1.47-1.43 (m, 9H). LCMS (ESI-MS) m/z=583.3 [M+H]$^+$.

rac-1-(((5S,7R)-7-Methoxy-3-(5-(2-((4-methoxybenzyl)oxy)propan-2-yl)pyrazin-2-yl)-2-oxo-1-oxa-3-azaspiro[4.5]decan-7-yl)methyl)-1H-benzo[d]imidazole-6-carbonitrile

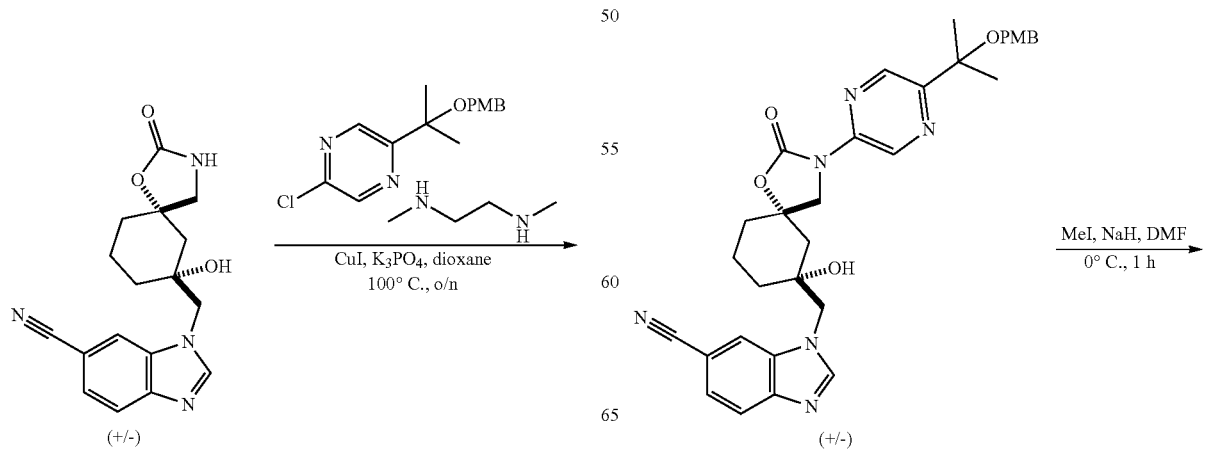

151

-continued

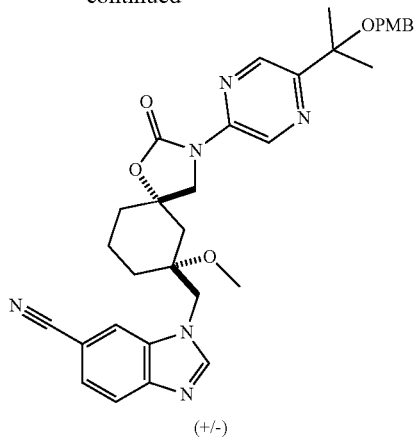

(+/-)

Iodomethane (170.33 mg, 1.20 mmol) was added to a mixture of rac-1-(((5S,7R)-7-hydroxy-3-(5-(2-((4-methoxybenzyl)oxy)propan-2-yl)pyrazin-2-yl)-2-oxo-1-oxa-3-azaspiro[4.5]decan-7-yl)methyl)-1H-benzo[d]imidazole-6-carbonitrile (700 mg, 1.20 mmol) and sodium hydride (60% in mineral oil, 48 mg, 1.20 mmol) in N,N-Dimethylformamide (5 mL) at 0° C. The mixture was stirred for 1 hour at 0° C. The mixture was quenched slowly with water (10 mL) and extracted with ethyl acetate (3×10 mL). The combined organic layers were washed with brine, dried over anhydrous sodium sulfate, filtered, and concentrated under vacuum to afford the crude product. The residue was purified by silica gel column chromatography and eluted with methanol in dichloromethane from 0% to 2% to afford the desired product rac-1-(((5S,7R)-7-methoxy-3-(5-(2-((4-methoxybenzyl)oxy)propan-2-yl)pyrazin-2-yl)-2-oxo-1-oxa-3-azaspiro[4.5]decan-7-yl)methyl)-1H-benzo[d]imidazole-6-carbonitrile (400 mg) as a white solid. $^1$H NMR (400 MHz, DMSO-$d_6$) δ 9.21 (d, J=1.6 Hz, 1H), 8.60 (d, J=1.6 Hz, 1H), 8.35 (d, J=1.6 Hz, 1H), 8.29 (s, 1H), 7.84 (d, J=8.3 Hz, 1H), 7.59 (dd, J=8.3, 1.5 Hz, 1H), 6.89 (d, J=7.2 Hz, 2H), 6.79 (d, J=7.2 Hz, 2H), 4.70 (s, 2H), 4.44 (d, J=15.1 Hz, 1H), 4.36 (d, J=15.0 Hz, 1H), 3.92 (d, J=10.2 Hz, 1H), 3.84 (d, J=10.2 Hz, 1H), 3.79 (s, 3H), 3.39 (s, 3H), 2.27 (d, J=15.1 Hz, 1H), 2.00 (d, J=13.4 Hz, 1H), 1.80 (d, J=15.1 Hz, 1H), 1.69 (t, J=12.9 Hz, 1H), 1.61-1.47 (m, 1H) 1.47-1.43 (m, 9H). LCMS (ESI-MS) m/z=597.3 [M+H]$^+$.

rac-1-(((5S,7R)-3-(5-(2-hydroxypropan-2-yl)pyrazin-2-yl)-7-methoxy-2-oxo-1-oxa-3-azaspiro[4.5]decan-7-yl)methyl)-1H-benzo[d]imidazole-6-carbonitrile

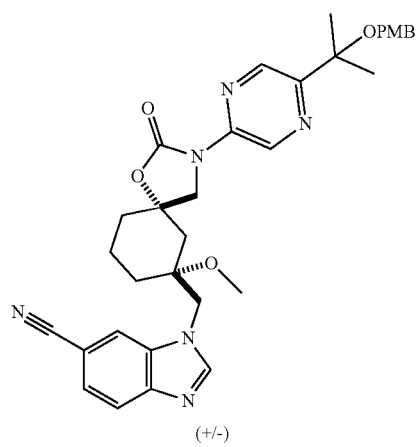

(+/-)

152

-continued

Trifluoroacetic acid (229 mg, 2.01 mmol) was added to a solution of rac-1-(((5S,7R)-7-methoxy-3-(5-(2-((4-methoxybenzyl)oxy)propan-2-yl)pyrazin-2-yl)-2-oxo-1-oxa-3-azaspiro[4.5]decan-7-yl)methyl)-1H-benzo[d]imidazole-6-carbonitrile (400 mg, 0.67 mmol) in dichloromethane (3 mL). The resulting mixture was stirred for 1 hour at room temperature. The reaction mixture was concentrated under vacuum and purified by silica gel column chromatography, eluted with methanol in dichloromethane from 0% to 3% to afford the desired product rac-1-(((5S,7R)-3-(5-(2-hydroxypropan-2-yl)pyrazin-2-yl)-7-methoxy-2-oxo-1-oxa-3-azaspiro[4.5]decan-7-yl)methyl)-1H-benzo[d]imidazole-6-carbonitrile (200 mg) as yellow oil. $^1$H NMR (300 MHz, DMSO-$d_6$) δ 9.21 (d, J=1.6 Hz, 1H), 8.60 (d, J=1.6 Hz, 1H), 8.35 (d, J=1.6 Hz, 1H), 8.29 (s, 1H), 7.84 (d, J=8.3 Hz, 1H), 7.59 (dd, J=8.3, 1.5 Hz, 1H), 5.40 (s, 1H), 4.44 (d, J=15.1 Hz, 1H), 4.36 (d, J=15.0 Hz, 1H), 3.92 (d, J=10.2 Hz, 1H), 3.84 (d, J=10.2 Hz, 1H), 3.39 (s, 3H), 2.27 (d, J=15.1 Hz, 1H), 2.00 (d, J=13.4 Hz, 1H), 1.80 (d, J=15.1 Hz, 1H), 1.69 (t, J=12.9 Hz, 1H), 1.61-1.47 (m, 1H) 1.47-1.43 (m, 9H). LCMS (ESI-MS) m/z=477.2 [M+H]$^+$.

1-(((5S,7R)-3-(5-(2-Hydroxypropan-2-yl)pyrazin-2-yl)-7-methoxy-2-oxo-1-oxa-3-azaspiro[4.5]decan-7-yl)methyl)-1H-benzo[d]imidazole-6-carbonitrile and 1-(((5R,7S)-3-(5-(2-Hydroxypropan-2-yl)pyrazin-2-yl)-7-methoxy-2-oxo-1-oxa-3-azaspiro[4.5]decan-7-yl)methyl)-1H-benzo[d]imidazole-6-carbonitrile

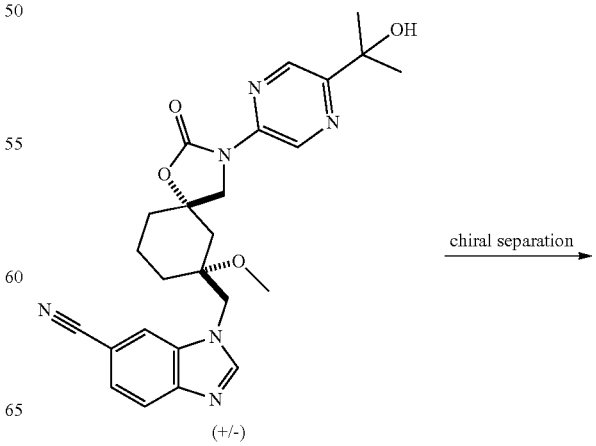

(+/-)

J=10.2 Hz, 1H), 3.84 (d, J=10.2 Hz, 1H), 3.39 (s, 3H), 2.27 (d, J=15.1 Hz, 1H), 2.00 (d, J=13.4 Hz, 1H), 1.80 (d, J=15.1 Hz, 1H), 1.69 (t, J=12.9 Hz, 1H), 1.61-1.47 (m, 1H) 1.47-1.43 (m, 9H). LCMS (ESI-MS) m/z=477.2 [M+H]+.

Example 10. Preparation of: 1-(((5S,7S,8R)-3-(5-(2-Hydroxypropan-2-yl)pyrazin-2-yl)-8-methoxy-7-methyl-2-oxo-1-oxa-3-azaspiro[4.5]decan-7-yl)methyl)-1H-benzo[d]imidazole-6-carbonitrile

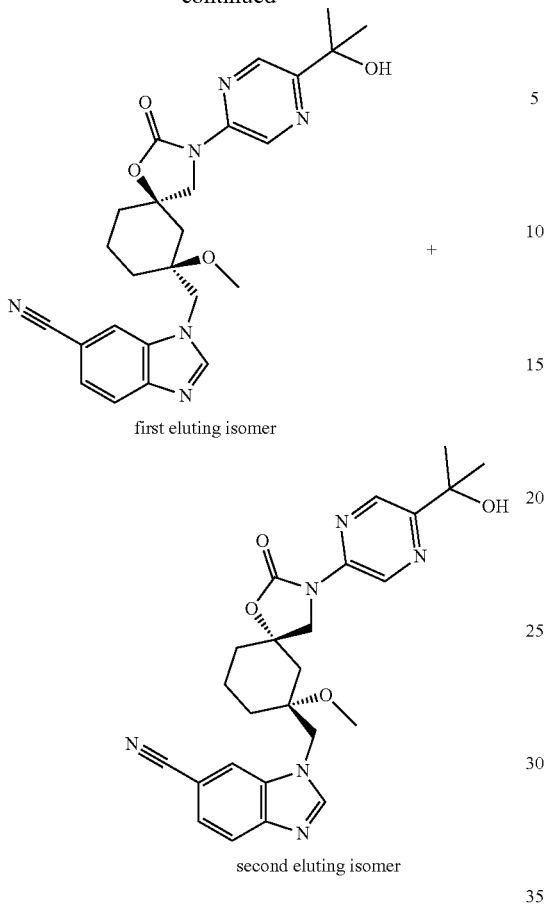

first eluting isomer second eluting isomer

The mixture of rac-1-(((5S,7R)-3-(5-(2-hydroxypropan-2-yl)pyrazin-2-yl)-7-methoxy-2-oxo-1-oxa-3-azaspiro[4.5]decan-7-yl)methyl)-1H-benzo[d]imidazole-6-carbonitrile (200 mg, 0.42 mmol) was separated by Prep-Chiral-HPLC with the condition: Column: CHIRALPAK IE, 2×25 cm, 5 μm; Mobile Phase A: MTBE (0.5% 2M NH₃-MeOH)-HPLC, Mobile Phase B: EtOH-HPLC; Flow rate: 17 m/min; Gradient: 10% B to 10% B in 24 min; Wave Length: 220/254 nm; RT1(min): 14.661; RT2(min): 20.017; Sample Solvent: EtOH-HPLC; Injection Volume: 0.5 mL. The desired fraction was combined and lyophilized to afford the products:

First eluting isomer: 1-(((5R,7S)-3-(5-(2-Hydroxypropan-2-yl)pyrazin-2-yl)-7-methoxy-2-oxo-1-oxa-3-azaspiro[4.5]decan-7-yl)methyl)-1H-benzo[d]imidazole-6-carbonitrile (44.6 mg, 99.7% purity, 100% ee) as a white solid. ¹H NMR (300 MHz, DMSO-d₆) δ 9.21 (d, J=1.6 Hz, 1H), 8.60 (d, J=1.6 Hz, 1H), 8.35 (d, J=1.6 Hz, 1H), 8.29 (s, 1H), 7.84 (d, J=8.3 Hz, 1H), 7.59 (dd, J=8.3, 1.5 Hz, 1H), 5.40 (s, 1H), 4.44 (d, J=15.1 Hz, 1H), 4.36 (d, J=15.0 Hz, 1H), 3.92 (d, J=10.2 Hz, 1H), 3.84 (d, J=10.2 Hz, 1H), 3.39 (s, 3H), 2.27 (d, J=15.1 Hz, 1H), 2.00 (d, J=13.4 Hz, 1H), 1.80 (d, J=15.1 Hz, 1H), 1.69 (t, J=12.9 Hz, 1H), 1.61-1.47 (m, 1H) 1.47-1.43 (m, 9H). LCMS (ESI-MS) m/z=477.2 [M+H]+.

Second eluting isomer: 1-(((5S,7R)-3-(5-(2-Hydroxypropan-2-yl)pyrazin-2-yl)-7-methoxy-2-oxo-1-oxa-3-azaspiro[4.5]decan-7-yl)methyl)-1H-benzo[d]imidazole-6-carbonitrile (41.0 mg, 98.6% purity, 100% ee) as a white solid. ¹H NMR (300 MHz, DMSO-d₆) δ 9.21 (d, J=1.6 Hz, 1H), 8.60 (d, J=1.6 Hz, 1H), 8.35 (d, J=1.6 Hz, 1H), 8.29 (s, 1H), 7.84 (d, J=8.3 Hz, 1H), 7.59 (dd, J=8.3, 1.5 Hz, 1H), 5.40 (s, 1H), 4.44 (d, J=15.1 Hz, 1H), 4.36 (d, J=15.0 Hz, 1H), 3.92 (d,

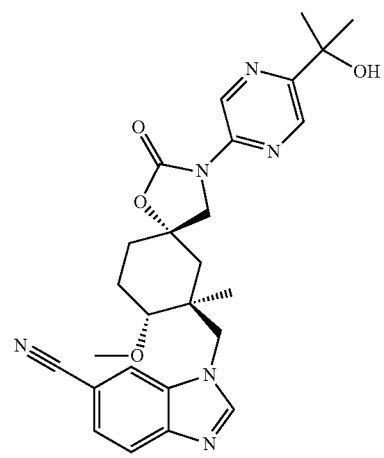

Detailed Procedure rac-1-(((5S,7S,8R)-8-Hydroxy-3-(5-(2-((4-methoxybenzyl)oxy)propan-2-yl)pyrazin-2-yl)-7-methyl-2-oxo-1-oxa-3-azaspiro[4.5]decan-7-yl)methyl)-1H-benzo[d]imidazole-6-carbonitrile

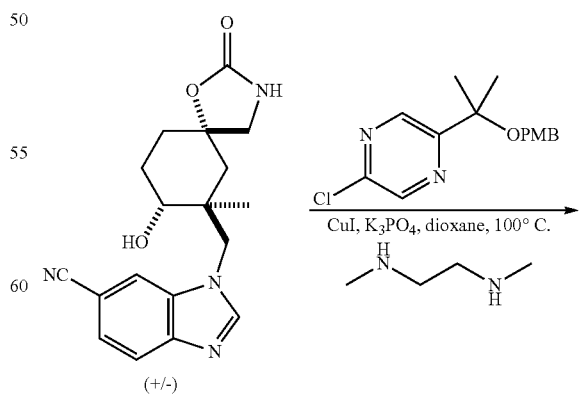

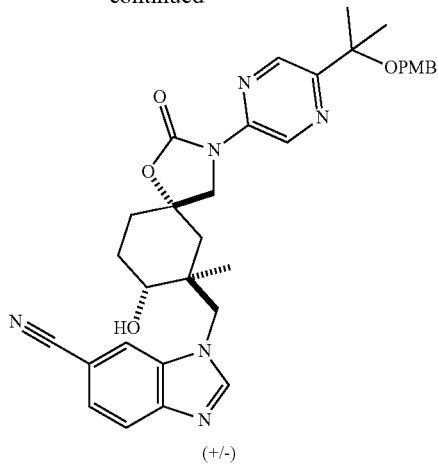

(+/-)

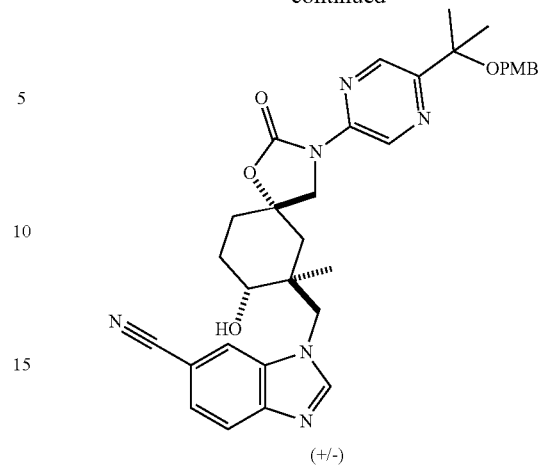

(+/-)

Copper(I) iodide (448 mg, 2.35 mmol) was added to a solution of rac-1-(((5S,7S,8R)-8-hydroxy-7-methyl-2-oxo-1-oxa-3-azaspiro[4.5]decan-7-yl)methyl)-1H-benzo[d]imidazole-6-carbonitrile (800 mg, 2.35 mmol), 2-chloro-5-(2-((4-methoxybenzyl)oxy)propan-2-yl)pyrazine (686 mg, 2.35 mmol), $N^1,N^2$-dimethylethane-1,2-diamine (414 mg, 4.70 mmol) and tripotassium phosphate (996 mg, 4.70 mmol) in 1,4-dioxane (10 mL) under a nitrogen atmosphere. The resulting mixture was heated to 100° C. and stirred overnight. After cooling to room temperature, the resulting mixture was filtered and concentrated under vacuum. The residue was purified by silica gel column chromatography, and eluted with methanol in dichloromethane from 0% to 3% to afford the desired product rac-1-(((5S,7S,8R)-8-hydroxy-3-(5-(2-((4-methoxybenzyl)oxy)propan-2-yl)pyrazin-2-yl)-7-methyl-2-oxo-1-oxa-3-azaspiro[4.5]decan-7-yl)methyl)-1H-benzo[d]imidazole-6-carbonitrile (1 g) as a light yellow solid. LCMS (ESI-MS) m/z=597.3 [M+H]$^+$.

rac-1-(((5S,7S,8R)-8-Hydroxy-3-(5-(2-((4-methoxybenzyl)oxy)propan-2-yl)pyrazin-2-yl)-7-methyl-2-oxo-1-oxa-3-azaspiro[4.5]decan-7-yl)methyl)-1H-benzo[d]imidazole-6-carbonitrile and rac-1-(((5R,7S,8R)-8-Hydroxy-3-(6-(2-((4-methoxybenzyl)oxy)propan-2-yl)pyridin-3-yl)-7-methyl-2-oxo-1-oxa-3-azaspiro[4.5]decan-7-yl)methyl)-1H-benzo[d]imidazole-6-carbonitrile

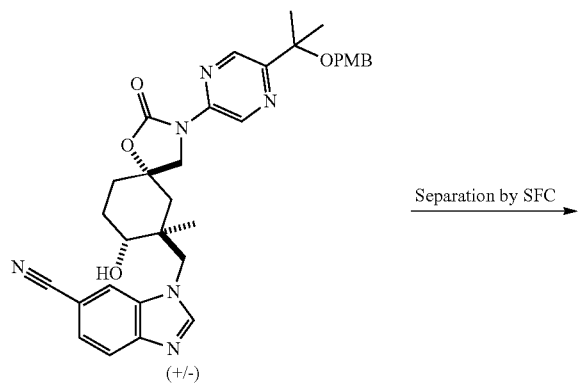

(+/-)

Separation by SFC →

The mixture of rac-1-(((5S,7S,8R)-8-hydroxy-3-(5-(2-((4-methoxybenzyl)oxy)propan-2-yl)pyrazin-2-yl)-7-methyl-2-oxo-1-oxa-3-azaspiro[4.5]decan-7-yl)methyl)-1H-benzo[d]imidazole-6-carbonitrile (1 g, 1.68 mmol) was separated by Prep-Chiral-HPLC with the condition: Column: CHIRALPAK IE, 2×25 cm, 5 μm; Mobile Phase A: Hex: DCM=3: 1(0.5% 2M NH$_3$-MeOH)-HPLC, Mobile Phase B: IPA-HPLC; Flow rate: 20 mL/min; Gradient: 20% B to 20% B in 21 min; Wave Length: 220/254 nm; RT1 (min): 10.051; RT2(min): 16.651; Sample Solvent: EtOH-HPLC; Injection Volume: 1 mL. The desired fraction was combined and lyophilized to afford the products.

First eluting isomer: rac-1-(((5S,7S,8R)-8-Hydroxy-3-(5-(2-((4-methoxybenzyl)oxy)propan-2-yl)pyrazin-2-yl)-7-methyl-2-oxo-1-oxa-3-azaspiro[4.5]decan-7-yl)methyl)-1H-benzo[d]imidazole-6-carbonitrile (200 mg) as a light yellow solid. $^1$H NMR (400 MHz, DMSO-d$_6$) δ 9.25 (d, J=1.5 Hz, 1H), 8.56 (d, J=1.5 Hz, 1H), 8.35 (d, J=15.2 Hz, 1H), 8.23 (d, J=1.6 Hz, 1H), 7.84 (d, J=8.4 Hz, 1H), 7.59 (dd, J=8.3, 1.5 Hz, 1H), 7.29-7.20 (m, 2H), 6.94-6.84 (m, 2H), 4.35-4.24 (m, 1H), 4.27-4.17 (m, 2H), 3.88-3.70 (m, 2H), 3.74 (s, 3H), 3.36-3.30 (m, 3H), 2.08-1.91 (m, 4H), 1.65-1.50 (m, 8H), 1.11 (s, 3H). LCMS (ESI-MS) m/z=597.3 [M+H]$^+$.

Second eluting isomer: rac-1-(((5R,7S,8R)-8-Hydroxy-3-(6-(2-((4-methoxybenzyl)oxy)propan-2-yl)pyridin-3-yl)-7-methyl-2-oxo-1-oxa-3-azaspiro[4.5]decan-7-yl)methyl)-1H-benzo[d]imidazole-6-carbonitrile (400 mg, 40.0% yield) as a light yellow solid. $^1$H NMR (400 MHz, DMSO-d$_6$) δ

9.30 (d, J=1.5 Hz, 1H), 8.59 (d, J=1.5 Hz, 1H), 8.42 (s, 1H), 8.25 (s, 1H), 7.83 (d, J=8.1 Hz, 1H), 7.64-7.55 (m, 1H), 7.28-7.20 (m, 2H), 6.93-6.86 (m, 2H), 4.41-4.32 (m, 1H), 4.25 (s, 2H), 3.91-3.81 (m, 2H), 3.79 (s, 3H), 3.37-3.34 (m, 3H), 2.00-1.83 (m, 4H), 1.75-1.59 (m, 8H), 0.91 (s, 3H). LCMS (ESI-MS) m/z=597.3 [M+H]+.

rac-1-(((5S,7S,8R)-8-Methoxy-3-(5-(2-((4-methoxybenzyl)oxy)propan-2-yl)pyrazin-2-yl)-7-methyl-2-oxo-1-oxa-3-azaspiro[4.5]decan-7-yl)methyl)-1H-benzo[d]imidazole-6-carbonitrile methyl-2-oxo-1-oxa-3-azaspiro[4.5]decan-7-yl)methyl)-1H-benzo[d]imidazole-6-carbonitrile (80 mg) as a white solid. 1H NMR (400 MHz, DMSO-d6) δ 9.25 (d, J=1.5 Hz, 1H), 8.56 (d, J=1.5 Hz, 1H), 8.35 (d, J=15.2 Hz, 1H), 8.23 (d, J=1.6 Hz, 1H), 7.84 (d, J=8.4 Hz, 1H), 7.59 (dd, J=8.3, 1.5 Hz, 1H), 7.29-7.20 (m, 2H), 6.94-6.84 (m, 2H), 4.30-4.17 (m, 4H), 3.88-3.70 (m, 2H), 3.74 (s, 3H), 3.39 (s, 3H), 3.10-3.03 (m, 1H), 2.08-1.91 (m, 4H), 1.65-1.50 (m, 8H), 1.11 (s, 3H). LCMS (ESI-MS) m/z=611.3 [M+H]+.

rac-1-(((5S,7S,8R)-3-(5-(2-Hydroxypropan-2-yl)pyrazin-2-yl)-8-methoxy-7-methyl-2-oxo-1-oxa-3-azaspiro[4.5]decan-7-yl)methyl)-1H-benzo[d]imidazole-6-carbonitrile

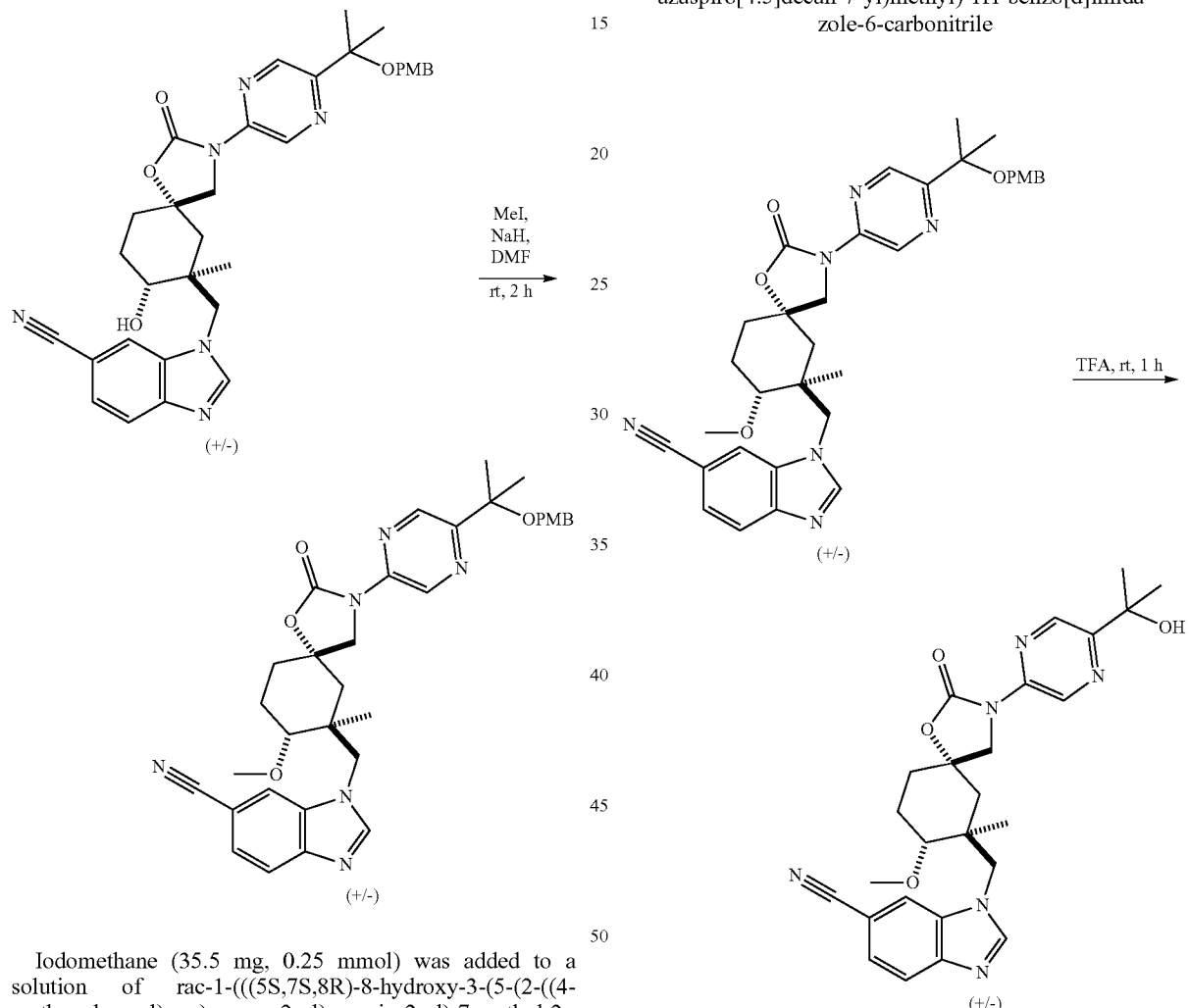

Iodomethane (35.5 mg, 0.25 mmol) was added to a solution of rac-1-(((5S,7S,8R)-8-hydroxy-3-(5-(2-((4-methoxybenzyl)oxy)propan-2-yl)pyrazin-2-yl)-7-methyl-2-oxo-1-oxa-3-azaspiro[4.5]decan-7-yl)methyl)-1H-benzo[d]imidazole-6-carbonitrile (150 mg, 0.25 mmol) and sodium hydride (60% in mineral oil, 10 mg, 0.25 mmol) in N,N-Dimethylformamide (2 mL) at 0° C. The resulting mixture was warmed to room temperature and stirred for 2 hours. The mixture was quenched slowly with 5 mL water, and the resulting solution was extracted with ethyl acetate (3×5 mL). The combined organic layers were washed with brine, dried over anhydrous sodium sulfate, filtered and concentrated under vacuum to afford the crude product. The residue was purified by silica gel column chromatography, and eluted with methanol in dichloromethane from 0% to 2% to afford the desired product rac-1-(((5S,7S,8R)-8-methoxy-3-(5-(2-((4-methoxybenzyl)oxy)propan-2-yl)pyrazin-2-yl)-7-

Trifluoroacetic acid (44 mg, 0.39 mmol) was added to a solution of rac-1-(((5S,7S,8R)-8-methoxy-3-(5-(2-((4-methoxybenzyl)oxy)propan-2-yl)pyrazin-2-yl)-7-methyl-2-oxo-1-oxa-3-azaspiro[4.5]decan-7-yl)methyl)-1H-benzo[d]imidazole-6-carbonitrile (80 mg, 0.13 mmol) in dichloromethane (1 mL). The resulting mixture was stirred for 1 hour at room temperature. The reaction mixture was concentrated under vacuum to afford crude product rac-1-(((5S,7S,8R)-3-(5-(2-hydroxypropan-2-yl)pyrazin-2-yl)-8-methoxy-7-methyl-2-oxo-1-oxa-3-azaspiro[4.5]decan-7-yl)methyl)-1H-benzo[d]imidazole-6-carbonitrile (70 mg crude) as yellow oil. LCMS (ESI-MS) m/z=491.2 [M+H]+.

1-(((5S,7S,8R)-3-(5-(2-Hydroxypropan-2-yl)pyrazin-2-yl)-8-methoxy-7-methyl-2-oxo-1-oxa-3-azaspiro[4.5]decan-7-yl)methyl)-1H-benzo[d]imidazole-6-carbonitrile and 1-(((5R,7R,8S)-3-(5-(2-Hydroxypropan-2-yl)pyrazin-2-yl)-8-methoxy-7-methyl-2-oxo-1-oxa-3-azaspiro[4.5]decan-7-yl)methyl)-1H-benzo[d]imidazole-6-carbonitrile

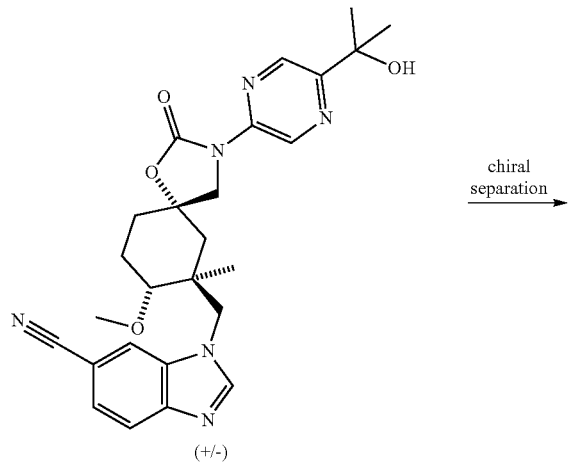

(+/-)

chiral separation →

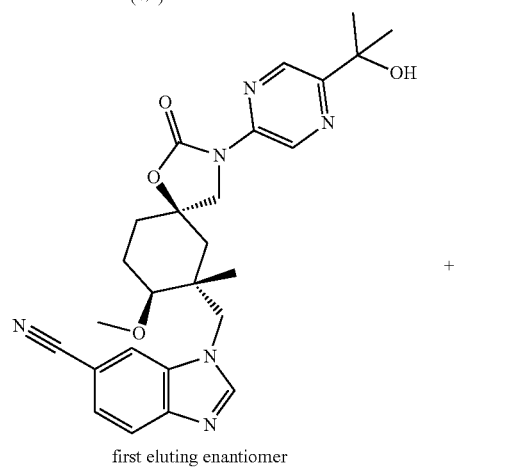

first eluting enantiomer

+

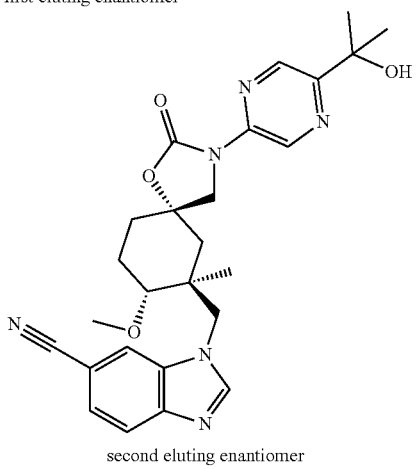

second eluting enantiomer

The mixture of rac-1-(((5S,7S,8R)-3-(5-(2-hydroxypropan-2-yl)pyrazin-2-yl)-8-methoxy-7-methyl-2-oxo-1-oxa-3-azaspiro[4.5]decan-7-yl)methyl)-1H-benzo[d]imidazole-6-carbonitrile (70 mg, 0.14 mmol) was separated by Prep-Chiral-HPLC with the condition: Column: CHIRAL ART Cellulose-SC, 2×25 cm, 5 μm; Mobile Phase A: Hex:DCM=3:1(0.5% 2M NH₃-MeOH)-HPLC, Mobile Phase B: EtOH-HPLC; Flow rate: 20 m/min; Gradient: 30% B to 30% B in 14 min; Wave Length: 220/254 nm; RT1(min): 9.92; RT2(min): 12.16; Sample Solvent: EtOH-HPLC; Injection Volume: 0.8 mL. The desired fraction was combined and lyophilized to afford the products.

First eluting isomer: 1-(((5R,7R,8S)-3-(5-(2-hydroxypropan-2-yl)pyrazin-2-yl)-8-methoxy-7-methyl-2-oxo-1-oxa-3-azaspiro[4.5]decan-7-yl)methyl)-1H-benzo[d]imidazole-6-carbonitrile (14.0 mg, 99.7% purity, 100% ee) as a white solid. $^1$H NMR (300 MHz, DMSO-$d_6$) δ 9.18 (d, J=1.5 Hz, 1H), 8.58 (d, J=1.5 Hz, 1H), 8.37 (s, 1H), 8.25-8.20 (m, 1H), 7.84 (d, J=8.3 Hz, 1H), 7.60 (dd, J=8.3, 1.5 Hz, 1H), 5.42 (s, 1H), 4.31 (d, J=14.5 Hz, 1H), 4.21 (d, J=14.5 Hz, 1H), 3.81 (q, J=10.3 Hz, 2H), 3.31 (s, 3H), 3.07-3.00 (m, 1H), 2.04 (d, J=9.7 Hz, 2H), 1.95 (d, J=15.0 Hz, 1H), 1.72 (d, J=14.6 Hz, 1H), 1.65-1.48 (m, 2H), 1.44 (d, J=2.3 Hz, 6H), 1.11 (s, 3H). LCMS (ESI-MS) m/z=491.2 [M+H]⁺.

Second eluting isomer: 1-(((5S,7S,8R)-3-(5-(2-hydroxypropan-2-yl)pyrazin-2-yl)-8-methoxy-7-methyl-2-oxo-1-oxa-3-azaspiro[4.5]decan-7-yl)methyl)-1H-benzo[d]imidazole-6-carbonitrile (14.8 mg, 99.6% purity, 99.5% ee) as a white solid. $^1$H NMR (300 MHz, DMSO-$d_6$) δ 9.18 (d, J=1.5 Hz, 1H), 8.58 (d, J=1.5 Hz, 1H), 8.37 (s, 1H), 8.25-8.20 (m, 1H), 7.84 (d, J=8.3 Hz, 1H), 7.60 (dd, J=8.3, 1.5 Hz, 1H), 5.42 (s, 1H), 4.31 (d, J=14.5 Hz, 1H), 4.21 (d, J=14.5 Hz, 1H), 3.81 (q, J=10.3 Hz, 2H), 3.31 (s, 3H), 3.07-3.00 (m, 1H), 2.04 (d, J=9.7 Hz, 2H), 1.95 (d, J=15.0 Hz, 1H), 1.72 (d, J=14.6 Hz, 1H), 1.65-1.48 (m, 2H), 1.44 (d, J=2.3 Hz, 6H), 1.11 (s, 3H). LCMS (ESI-MS) m/z=491.2 [M+H]⁺.

Example 11. Preparation of: 1-(((5S,7S)-8,8-Difluoro-3-neopentyl-2-oxo-1-oxa-3-azaspiro[4.5]decan-7-yl)methyl)-1H-benzo[d]imidazole-6-carbonitrile

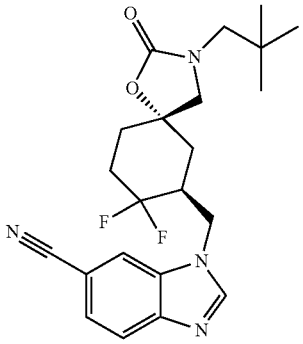 [SMILES: CC(C)(C)CN1C[C@@]2(CCC(F)(F)[C@H](Cn3cnc4ccc(C#N)cc43)C2)OC1=O]

Detailed Procedure rac-1-(((5S,7S)-8,8-Difluoro-3-neopentyl-2-oxo-1-oxa-3-azaspiro[4.5]decan-7-yl)methyl)-1H-benzo[d]imidazole-6-carbonitrile

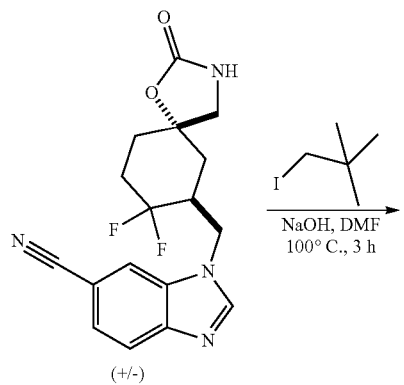

1-(((5S,7S)-8,8-Difluoro-3-neopentyl-2-oxo-1-oxa-3-azaspiro[4.5]decan-7-yl)methyl)-1H-benzo[d]imidazole-6-carbonitrile and 1-(((5R,7R)-8,8-difluoro-3-neopentyl-2-oxo-1-oxa-3-azaspiro[4.5]decan-7-yl)methyl)-1H-benzo[d]imidazole-6-carbonitrile

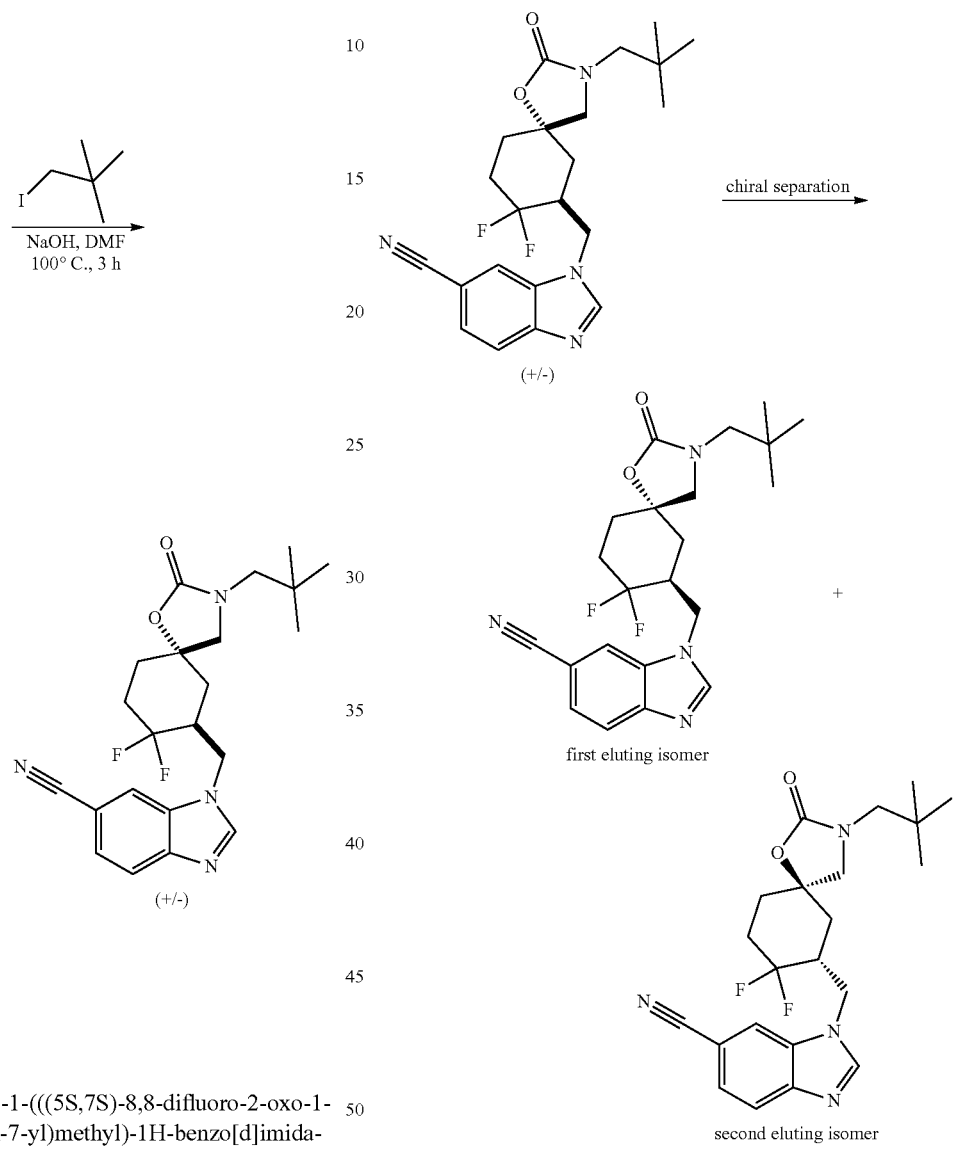

To a mixture of rac-1-(((5S,7S)-8,8-difluoro-2-oxo-1-oxa-3-azaspiro[4.5]decan-7-yl)methyl)-1H-benzo[d]imidazole-6-carbonitrile (1 g, 2.89 mmol) and 1-iodo-2,2-dimethylpropane (859 mg, 4.34 mmol) in N,N-Dimethylformamide (10 mL) was added sodium hydroxide (347 mg, 8.67 mmol). The reaction mixture was stirred for 3 hours at 100° C. and cooled to room temperature. The mixture was quenched with aqueous ammonium chloride (50 mL), extracted with ethyl acetate (3×30 mL), dried over sodium sulfate, filtered and concentrated to afford the crude product. The residue was purified by silica gel column chromatography, and eluted with ethyl acetate in petroleum ether from 0% to 60% to afford the product rac-1-(((5S,7S)-8,8-difluoro-3-neopentyl-2-oxo-1-oxa-3-azaspiro[4.5]decan-7-yl)methyl)-1H-benzo[d]imidazole-6-carbonitrile (200 mg) as a white solid. LCMS (ESI-MS) m/z=417.2 [M+H]$^+$.

The mixture of rac-1-(((5S,7S)-8,8-difluoro-3-neopentyl-2-oxo-1-oxa-3-azaspiro[4.5]decan-7-yl)methyl)-1H-benzo[d]imidazole-6-carbonitrile (200 mg, 0.48 mmol) was separated by Prep-Chiral-HPLC with the following condition: Column: CHIRALPAK IH, 2×25 cm, 5 μm; Mobile Phase A: MTBE (0.5% 2M NH$_3$-MeOH)-HPLC, Mobile Phase B: IPA-HPLC; Flow rate: 20 mL/min; Gradient: 40% B to 40% B in 12 min; Wave Length: 220/254 nm; RT1(min): 7.342; RT2(min): 9.486; Sample Solvent: EtOH-HPLC; Injection Volume: 0.3 mL. The desired fractions were combined and lyophilized to afford the two products:

First eluting isomer:1-(((5S,7S)-8,8-Difluoro-3-neopentyl-2-oxo-1-oxa-3-azaspiro[4.5]decan-7-yl)methyl)-1H-benzo[d]imidazole-6-carbonitrile (76.5 mg, 99.8% purity, 100% ee) as a white solid. ¹H NMR (400 MHz, DMSO-d₆) δ 8.56 (s, 1H), 8.31 (d, J=1.5 Hz, 1H), 7.83 (d, J=8.5 Hz, 1H), 7.61 (dd, J=8.4, 1.5 Hz, 1H), 4.65 (dd, J=14.6, 6.1 Hz, 1H), 4.41 (dd, J=14.6, 7.7 Hz, 1H), 3.46-3.37 (m, 2H), 2.90-2.71 (m, 3H), 2.15-1.93 (m, 3H), 1.88-1.63 (m, 3H), 0.82 (s, 9H). LCMS (ESI-MS) m/z=417.2 [M+H]⁺.

Second eluting isomer: 1-(((5R,7R)-8,8-Difluoro-3-neopentyl-2-oxo-1-oxa-3-azaspiro[4.5]decan-7-yl)methyl)-1H-benzo[d]imidazole-6-carbonitrile (19.9 mg, 99.0% purity, 98.4% ee) as a white solid. ¹H NMR (400 MHz, DMSO-d₆) δ 8.56 (s, 1H), 8.31 (d, J=1.5 Hz, 1H), 7.83 (d, J=8.3 Hz, 1H), 7.61 (dd, J=8.4, 1.5 Hz, 1H), 4.65 (dd, J=14.7, 6.0 Hz, 1H), 4.41 (dd, J=14.6, 7.7 Hz, 1H), 3.44-3.35 (m, 2H), 2.91-2.80 (m, 3H), 2.16-1.93 (m, 3H), 1.86-1.70 (m, 3H), 0.82 (s, 9H). LCMS (ESI-MS) m/z=417.2 [M+H]⁺.

Example 12. Preparation of: 1-((((5S,7S)-3-(2-Chlorophenyl)-8,8-difluoro-2-oxo-1-oxa-3-azaspiro[4.5]decan-7-yl)methyl)-1H-benzo[d]imidazole-6-carbonitrile

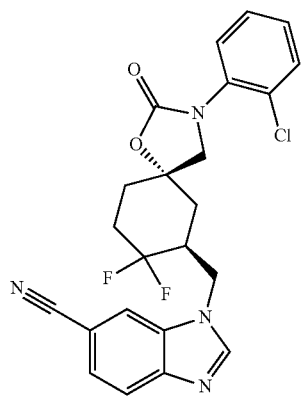 [SMILES: N#Cc1ccc2ncn(C[C@@H]3C[C@@]4(CCC3(F)F)CN(c3ccccc3Cl)C(=O)O4)c2c1]

Detailed Procedure 1-((3-(2-chlorophenyl)-8,8-difluoro-2-oxo-1-oxa-3-azaspiro[4.5]decan-7-yl)methyl)-1H-benzo[d]imidazole-6-carbonitrile

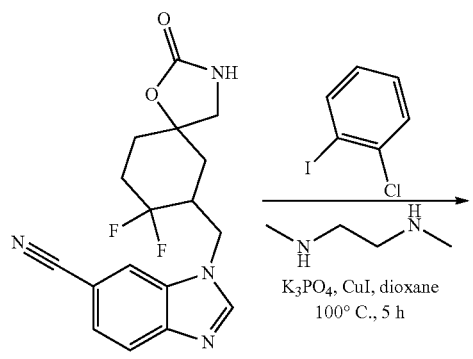

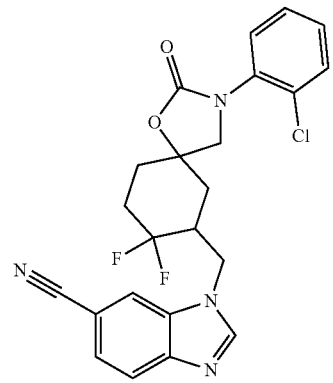

To a diastereomeric mixture of 1-((8,8-difluoro-2-oxo-1-oxa-3-azaspiro[4.5]decan-7-yl)methyl)-1H-benzo[d]imidazole-6-carbonitrile (500 mg, 1.45 mmol) and 1-chloro-2-iodobenzene (519 mg, 2.18 mmol) in 1,4-dioxane (10 mL) was added N1,N2-dimethylethane-1,2-diamine (255 mg, 2.9 mmol), potassium phosphate tribasic (615 mg, 2.9 mmol) and copper (I) iodide (139 mg, 0.73 mmol). The resulting mixture was stirred for 5 hours at 100° C. under nitrogen atmosphere and then cooled to room temperature. The mixture was quenched with aqueous ammonium chloride (50 mL), extracted with ethyl acetate (3×30 mL), dried over sodium sulfate, filtered, and concentrated to afford the crude product. The residue was purified by silica gel column chromatography, then eluted with ethyl acetate in petroleum ether from 0% to 55% to afford the product 1-((3-(2-chlorophenyl)-8,8-difluoro-2-oxo-1-oxa-3-azaspiro[4.5]decan-7-yl)methyl)-1H-benzo[d]imidazole-6-carbonitrile (400 mg) as a white solid. LCMS (ESI-MS) m/z=457.1 [M+H]⁺.

rac-1-((((5S,7S)-3-(2-Chlorophenyl)-8,8-difluoro-2-oxo-1-oxa-3-azaspiro[4.5]decan-7-yl)methyl)-1H-benzo[d]imidazole-6-carbonitrile and rac-1-((((5R,7S)-3-(2-Chlorophenyl)-8,8-difluoro-2-oxo-1-oxa-3-azaspiro[4.5]decan-7-yl)methyl)-1H-benzo[d]imidazole-6-carbonitrile

166

1-(((5R,7R)-3-(2-Chlorophenyl)-8,8-difluoro-2-oxo-1-oxa-3-azaspiro[4.5]decan-7-yl)methyl)-1H-benzo[d]imidazole-6-carbonitrile and 1-(((5S,7S)-3-(2-chlorophenyl)-8,8-difluoro-2-oxo-1-oxa-3-azaspiro[4.5]decan-7-yl)methyl)-1H-benzo[d]imidazole-6-carbonitrile

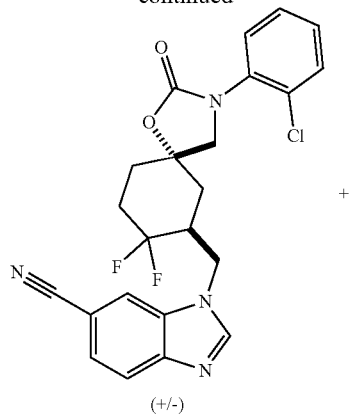

The diastereomeric mixture of 1-((3-(2-chlorophenyl)-8,8-difluoro-2-oxo-1-oxa-3-azaspiro[4.5]decan-7-yl)methyl)-1H-benzo[d]imidazole-6-carbonitrile (400 mg, 0.88 mmol) was separated by Prep-Achiral SFC with the following condition: Column: YMC-Actus Triart Diol-HILIC, 3×25 cm, 5 μm; Mobile Phase A: CO$_2$, Mobile Phase B: MeOH (0.1% 2M NH$_3$-MeOH); Flow rate: 75 mL/min; Gradient: isocratic 24% B; Column Temperature (° C.): 35; Back Pressure (bar): 100; Wave Length: 220 nm; RT1(min): 4.26; Sample Solvent: MeOH-HPLC; Injection Volume: 3 mL. The desired fractions were combined and lyophilized to afford the two products:

First eluting isomer: rac-1-(((5S,7S)-3-(2-Chlorophenyl)-8,8-difluoro-2-oxo-1-oxa-3-azaspiro[4.5]decan-7-yl)methyl)-1H-benzo[d]imidazole-6-carbonitrile (240 mg) as a white solid.

Second eluting isomer: rac-1-(((5R,7S)-3-(2-Chlorophenyl)-8,8-difluoro-2-oxo-1-oxa-3-azaspiro[4.5]decan-7-yl)methyl)-1H-benzo[d]imidazole-6-carbonitrile (20 mg) as a white solid.

The mixture of rac-1-(((5S,7S)-3-(2-chlorophenyl)-8,8-difluoro-2-oxo-1-oxa-3-azaspiro[4.5]decan-7-yl)methyl)-1H-benzo[d]imidazole-6-carbonitrile (240 mg, 0.88 mmol) was separated by Prep-Chiral HPLC with the following condition: Column: CHIRALPAK IF, 2×25 cm, 5 μm; Mobile Phase A: MTBE (0.5% 2M NH$_3$-MeOH)-HPLC, Mobile Phase B: EtOH-HPLC; Flow rate: 20 mL/min; Gradient: 20% B to 20% B in 23 min; Wave Length: 220/254 nm; RT1(min): 11.816; RT2(min): 16.483; Sample Solvent:

EtOH-HPLC; Injection Volume: 2 mL. The desired fractions were combined and lyophilized to afford the two products:

First eluting isomer: 1-(((5R,7R)-3-(2-Chlorophenyl)-8,8-difluoro-2-oxo-1-oxa-3-azaspiro[4.5]decan-7-yl)methyl)-1H-benzo[d]imidazole-6-carbonitrile (10.6 mg, 99.5% purity, 100% ee) as a white solid. $^1$H NMR (400 MHz, DMSO-d$_6$) δ 8.59 (s, 1H), 8.35 (s, 1H), 7.85 (d, J=8.4 Hz, 1H), 7.63 (dd, J=8.4, 1.5 Hz, 1H), 7.60-7.51 (m, 2H), 7.45-7.36 (m, 2H), 4.70 (dd, J=14.6, 5.9 Hz, 1H), 4.45 (dd, J=14.6, 8.0 Hz, 1H), 3.77-3.66 (m, 2H), 3.02-2.82 (m, 1H), 2.26-2.12 (m, 3H), 2.09-1.93 (m, 2H), 1.91-1.78 (m, 1H). LCMS (ESI-MS) m/z=457.1 [M+H]$^+$.

Second eluting isomer: 1-(((5S,7S)-3-(2-Chlorophenyl)-8,8-difluoro-2-oxo-1-oxa-3-azaspiro[4.5]decan-7-yl)methyl)-1H-benzo[d]imidazole-6-carbonitrile (31.6 mg, 99.2% purity, 100% ee) as a white solid. $^1$H NMR (400 MHz, DMSO-d$_6$) δ 8.59 (s, 1H), 8.35 (d, J=1.5 Hz, 1H), 7.85 (d, J=8.3 Hz, 1H), 7.63 (dd, J=8.3, 1.5 Hz, 1H), 7.59-7.50 (m, 2H), 7.45-7.34 (m, 2H), 4.70 (dd, J=14.6, 5.9 Hz, 1H), 4.45 (dd, J=14.6, 8.0 Hz, 1H), 3.77-3.66 (m, 2H), 3.00-2.84 (m, 1H), 2.27-2.12 (m, 3H), 2.03-1.89 (m, 2H), 1.89-1.78 (m, 1H). LCMS (ESI-MS) m/z=457.1 [M+H]$^+$.

Example 13. Preparation of: 1-(((5S,7S)-3-(2-Ethoxyphenyl)-8,8-difluoro-2-oxo-1-oxa-3-azaspiro[4.5]decan-7-yl)methyl)-1H-benzo[d]imidazole-6-carbonitrile

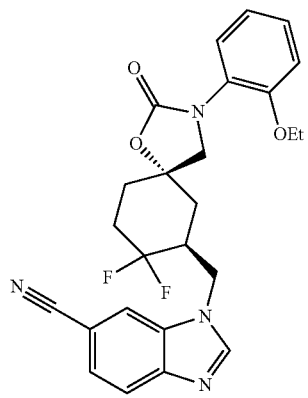 [SMILES: CCOc1ccccc1N1C[C@@]2(CCC(F)(F)[C@H](Cn3cnc4ccc(C#N)cc43)C2)OC1=O]

Detailed Procedure 1-((3-(2-Ethoxyphenyl)-8,8-difluoro-2-oxo-1-oxa-3-azaspiro[4.5]decan-7-yl)methyl)-1H-benzo[d]imidazole-6-carbonitrile

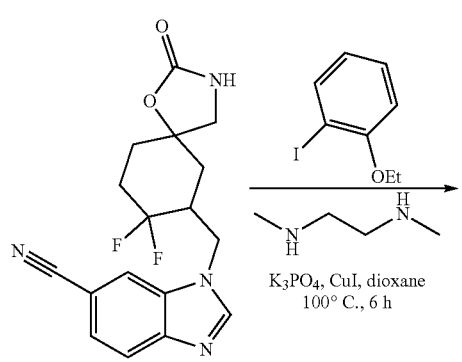

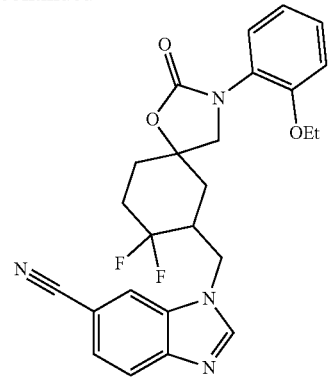

To a diastereomeric mixture of 1-((8,8-difluoro-2-oxo-1-oxa-3-azaspiro[4.5]decan-7-yl)methyl)-1H-benzo[d]imidazole-6-carbonitrile (250 mg, 0.72 mmol) and 1-bromo-2-ethoxybenzene (217 mg, 1.08 mmol) in 1,4-dioxane (10 mL) was added N1,N2-dimethylethane-1,2-diamine (127 mg, 1.44 mmol), potassium phosphate tribasic (305 mg, 1.44 mmol) and copper (I) iodide (69 mg, 0.36 mmol). The resulting mixture was stirred for 6 hours at 100° C. under nitrogen atmosphere and cooled to room temperature, the mixture was quenched with aqueous ammonium chloride (50 mL), the resulting solution was extracted with ethyl acetate (3×30 mL), the organic layer was dried over sodium sulfate, filtered and concentrated to afford the crude product, the residue was purified by silica gel column chromatography, and eluted with ethyl acetate in petroleum ether from 0% to 58% to afford the 1-((3-(2-ethoxyphenyl)-8,8-difluoro-2-oxo-1-oxa-3-azaspiro[4.5]decan-7-yl)methyl)-1H-benzo[d]imidazole-6-carbonitrile (220 mg) as a white solid.

LCMS (ESI-MS) m/z=467.2 [M+H]$^+$.

rac-1-(((5S,7S)-3-(2-Ethoxyphenyl)-8,8-difluoro-2-oxo-1-oxa-3-azaspiro[4.5]decan-7-yl)methyl)-1H-benzo[d]imidazole-6-carbonitrile and rac-1-(((5R,7S)-3-(2-Ethoxyphenyl)-8,8-difluoro-2-oxo-1-oxa-3-azaspiro[4.5]decan-7-yl)methyl)-1H-benzo[d]imidazole-6-carbonitrile

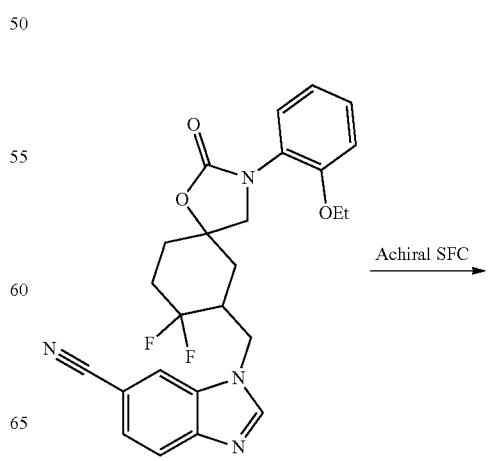

-continued

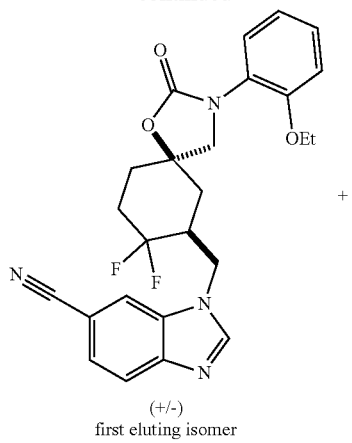

(+/-)
first eluting isomer

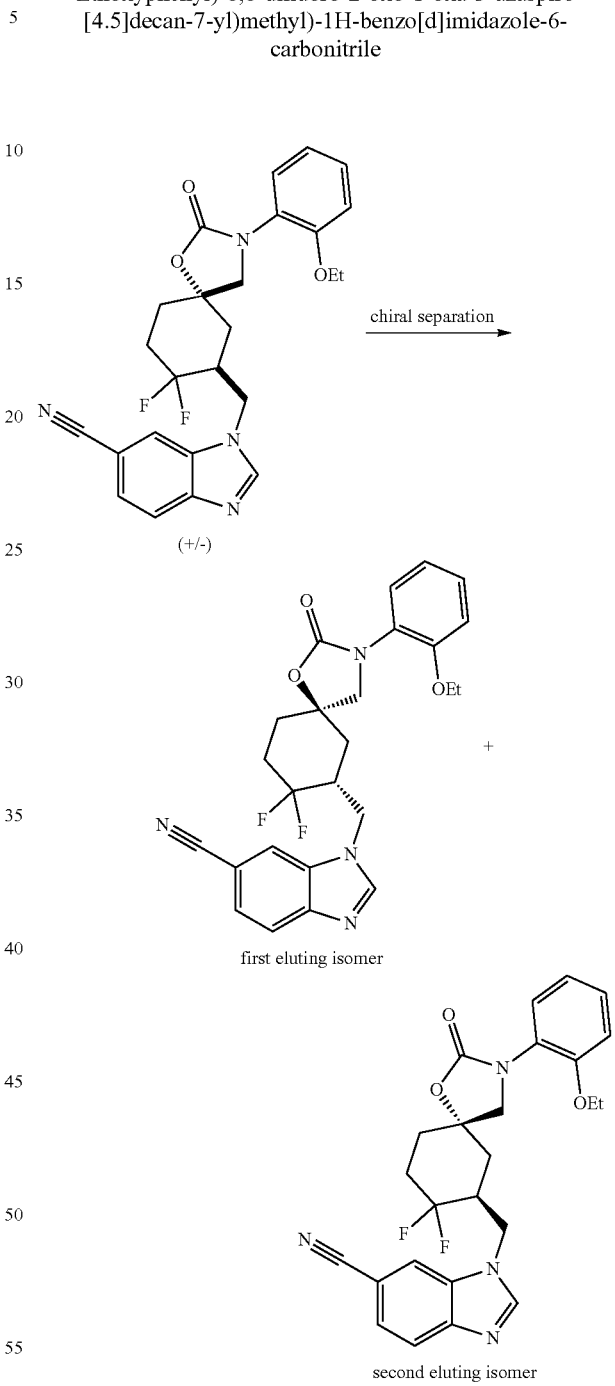

1-(((5R,7R)-3-(2-Ethoxyphenyl)-8,8-difluoro-2-oxo-1-oxa-3-azaspiro[4.5]decan-7-yl)methyl)-1H-benzo[d]imidazole-6-carbonitrile and 1-(((5S,7S)-3-(2-Ethoxyphenyl)-8,8-difluoro-2-oxo-1-oxa-3-azaspiro[4.5]decan-7-yl)methyl)-1H-benzo[d]imidazole-6-carbonitrile The diastereomeric mixture of 1-((3-(2-ethoxyphenyl)-8,8-difluoro-2-oxo-1-oxa-3-azaspiro[4.5]decan-7-yl)methyl)-1H-benzo[d]imidazole-6-carbonitrile (220 mg, 0.47 mmol) was separated by Prep-Achiral SFC with the following condition: Column: GreenSep Naphthyl, 3×25 cm, 5 μm; Mobile Phase A: $CO_2$, Mobile Phase B: MeOH (0.1% 2M $NH_3$-MeOH); Flow rate: 75 mL/min; Gradient: isocratic 25% B; Column Temperature (° C.): 35; Back Pressure (bar): 100; Wave Length: 220 nm; RT1(min): 5.99; RT2 (min): 6.51; Sample Solvent: MeOH-HPLC; Injection Volume: 1 mL. The desired fractions were combined and lyophilized to afford the two products.

First eluting isomer: rac-1-(((5R,7S)-3-(2-Ethoxyphenyl)-8,8-difluoro-2-oxo-1-oxa-3-azaspiro[4.5]decan-7-yl)methyl)-1H-benzo[d]imidazole-6-carbonitrile (30 mg) as a white solid.

Second eluting isomer: rac-1-(((5S,7S)-3-(2-Ethoxyphenyl)-8,8-difluoro-2-oxo-1-oxa-3-azaspiro[4.5]decan-7-yl)methyl)-1H-benzo[d]imidazole-6-carbonitrile (140 mg) as a white solid.

The mixture of rac-1-(((5S,7S)-3-(2-Ethoxyphenyl)-8,8-difluoro-2-oxo-1-oxa-3-azaspiro[4.5]decan-7-yl)methyl)-1H-benzo[d]imidazole-6-carbonitrile (140 mg, 0.3 mmol) was separated by Prep-Chiral HPLC with the following condition: Column: CHIRALPAK ID, 2×25 cm, 5 μm; Mobile Phase A: MTBE (2 mM $NH_3$-MeOH)-HPLC, Mobile Phase B: EtOH-HPLC; Flow rate: 20 mL/min; Gradient: 8% B to 8% B in 31 min; Wave Length: 220/254 nm; RT1(min): 20.16; RT2(min): 26.092; Sample Solvent:

EtOH-HPLC; Injection Volume: 0.4 mL. The desired fractions were combined and lyophilized to afford the two products.

First eluting isomer: 1-(((5R,7R)-3-(2-Ethoxyphenyl)-8,8-difluoro-2-oxo-1-oxa-3-azaspiro[4.5]decan-7-yl)methyl)-1H-benzo[d]imidazole-6-carbonitrile (18.0 mg, 98.9% purity, 100% ee) as a white solid. ¹H NMR (400 MHz, DMSO-d₆) δ 8.59 (s, 1H), 8.34 (s, 1H), 7.85 (d, J=8.4 Hz, 1H), 7.63 (dd, J=8.4, 1.5 Hz, 1H), 7.32-7.25 (m, 2H), 7.06 (d, J=8.4 Hz, 1H), 6.94 (t, J=7.6 Hz, 1H), 4.69 (dd, J=14.7, 5.9 Hz, 1H), 4.44 (dd, J=14.6, 8.0 Hz, 1H), 4.04-3.93 (m, 2H), 3.64 (s, 2H), 3.01-2.84 (m, 1H), 2.23-2.08 (m, 3H), 1.96-1.78 (m, 3H), 1.17 (t, J=6.9 Hz, 3H). LCMS (ESI-MS) m/z=467.2 [M+H]⁺.

Second eluting isomer: 1-(((5S,7S)-3-(2-Ethoxyphenyl)-8,8-difluoro-2-oxo-1-oxa-3-azaspiro[4.5]decan-7-yl)methyl)-1H-benzo[d]imidazole-6-carbonitrile (40.4 mg, 99.8% purity, 100% ee) as a white solid. ¹H NMR (400 MHz, DMSO-d₆) δ 8.59 (s, 1H), 8.34 (s, 1H), 7.85 (d, J=8.4 Hz, 1H), 7.62 (dd, J=8.4, 1.5 Hz, 1H), 7.31-7.24 (m, 2H), 7.10-7.04 (m, 1H), 6.94 (td, J=7.7, 1.3 Hz, 1H), 4.69 (dd, J=14.6, 5.9 Hz, 1H), 4.44 (dd, J=14.6, 8.1 Hz, 1H), 4.01-3.92 (m, 2H), 3.64 (s, 2H), 3.00-2.82 (m, 1H), 2.23-2.12 (m, 3H), 1.96-1.82 (m, 3H), 1.17 (t, J=6.9 Hz, 3H). LCMS (ESI-MS) m/z=467.2 [M+H]⁺.

Example 14. Preparation of: 1-(((5S,7S)-3-(5-(tert-Butyl)pyrazin-2-yl)-8,8-difluoro-2-oxo-1-oxa-3-azaspiro[4.5]decan-7-yl)methyl)-1H-benzo[d]imidazole-6-carbonitrile

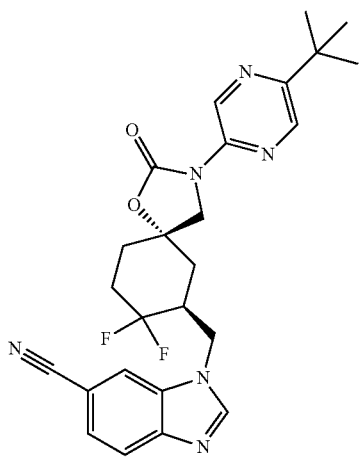

Detailed Procedure

2-Bromo-N-(3,3-dimethyl-2-oxobutyl)acetamide

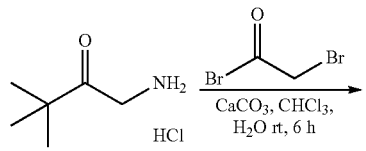

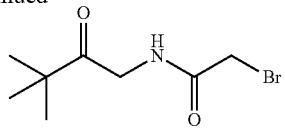

To a mixture of calcium carbonate (7.15 g, 93.8 mmol) in chloroform (30 mL) was added 1-amino-3,3-dimethylbutan-2-one hydrochloride (1.8 g, 15.6 mmol) in water (10 mL) at 5° C. under nitrogen atmosphere. Subsequently, 2-bromoacetyl bromide (5.90 g, 39.1 mmol) was added at 5° C. The resulting mixture was warmed to room temperature and then stirred for 6 hours. The reaction was filtered and washed with aqueous sodium carbonate (30 mL). The organic layer was dried over sodium sulfate, filtered and concentrated to afford the crude product 2-bromo-N-(3,3-dimethyl-2-oxobutyl)acetamide (2.4 g) as yellow oil. LCMS (ESI-MS) m/z=236.0 [M+H]⁺.

5-(tert-Butyl)pyrazin-2-ol

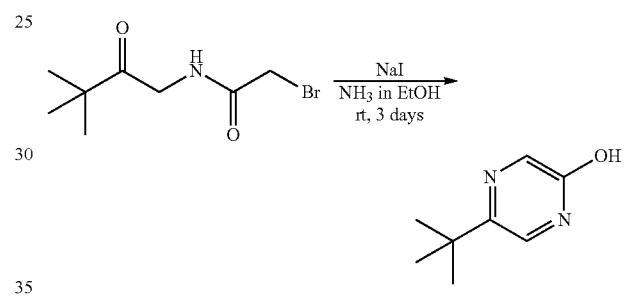

To a mixture of 2-bromo-N-(3,3-dimethyl-2-oxobutyl)acetamide (2.3 g, 9.74 mmol) in ammonia (20 ml, 7 N in MeOH) was added sodium iodide (0.26 g, 1.75 mmol). The resulting mixture was stirred for 3 days at room temperature. The mixture was quenched with aqueous ammonium chloride (50 mL), extracted with ethyl acetate (3×30 mL), dried over sodium sulfate, filtered and concentrated to afford the crude product 5-(tert-butyl)pyrazin-2-ol (740 mg) as yellow oil. LCMS (ESI-MS) m/z=153.1 [M+H]⁺.

5-(tert-Butyl)pyrazin-2-yl trifluoromethanesulfonate

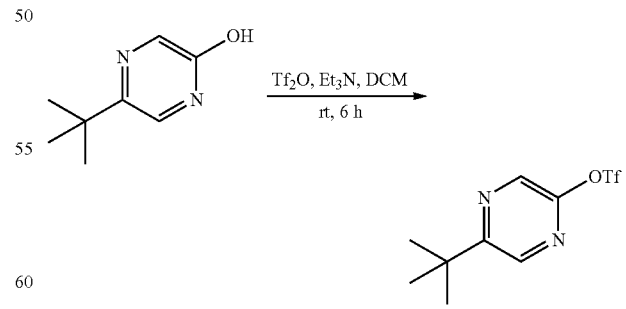

To a mixture of 5-tert-butylpyrazin-2-ol (730 mg, 4.80 mmol) in dichloromethane (10 mL) at 0° C. under nitrogen atmosphere was added triethylamine (1.46 g, 14.4 mmol) and trifluoromethanesulfonic anhydride (2.03 g, 7.19 mmol), the mixture was warmed to room temperature and stirred for 6 hours. The mixture was quenched with water (50 mL), extracted with ethyl acetate (3×30 mL), dried over sodium sulfate, filtered and concentrated to afford the crude product. The residue was purified by silica gel column chromatography, and eluted with ethyl acetate in petroleum ether from 0% to 30% to afford the product 5-(tert-butyl)pyrazin-2-yl trifluoromethanesulfonate (500 mg) as yellow oil. LCMS (ESI-MS) m/z=285.0 [M+H]⁺.

1-((3-(5-(tert-Butyl)pyrazin-2-yl)-8,8-difluoro-2-oxo-1-oxa-3-azaspiro[4.5]decan-7-yl)methyl)-1H-benzo[d]imidazole-6-carbonitrile

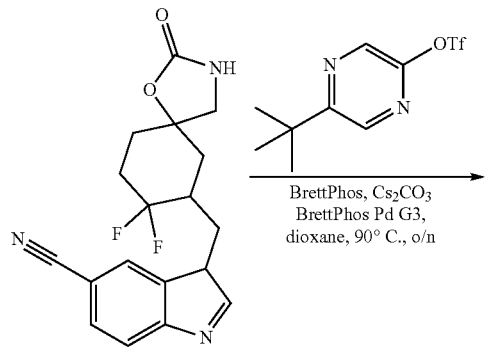

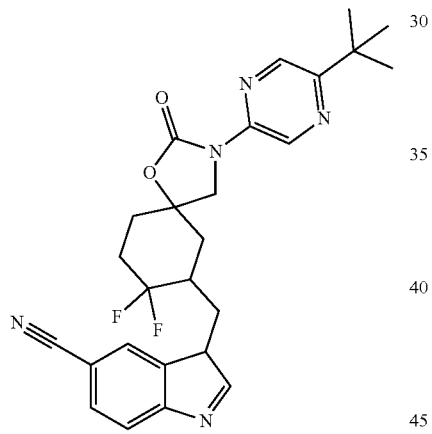

To a diastereomeric mixture of 1-((8,8-difluoro-2-oxo-1-oxa-3-azaspiro[4.5]decan-7-yl)methyl)-1H-benzo[d]imidazole-6-carbonitrile (600 mg, 1.73 mmol) and 5-(tert-butyl)pyrazin-2-yl trifluoromethanesulfonate (738 mg, 2.60 mmol) in 1,4-dioxane (10 mL) was added BrettPhos (93 mg, 0.173 mmol), BrettPhos Pd G3 (157 mg, 0.173 mmol) and cesium carbonate (1.69 g, 5.19 mmol). The resulting mixture was stirred overnight at 90° C. under nitrogen atmosphere and cooled to room temperature. The reaction was quenched with aqueous ammonium chloride (50 mL), extracted with ethyl acetate (3×30 mL), dried over sodium sulfate, filtered and concentrated to afford the crude product. The residue was purified by silica gel column chromatography, and eluted with ethyl acetate in petroleum ether from 0% to 70% to afford the product 1-((3-(5-(tert-butyl)pyrazin-2-yl)-8,8-difluoro-2-oxo-1-oxa-3-azaspiro[4.5]decan-7-yl)methyl)-1H-benzo[d]imidazole-6-carbonitrile (420 mg) as a light yellow solid. LCMS (ESI-MS) m/z=481.2 [M+H]⁺.

rac-1-(((5R,7S)-3-(5-(tert-Butyl)pyrazin-2-yl)-8,8-difluoro-2-oxo-1-oxa-3-azaspiro[4.5]decan-7-yl)methyl)-1H-benzo[d]imidazole-6-carbonitrile and rac-1-(((5S,7S)-3-(5-(tert-Butyl)pyrazin-2-yl)-8,8-difluoro-2-oxo-1-oxa-3-azaspiro[4.5]decan-7-yl)methyl)-1H-benzo[d]imidazole-6-carbonitrile

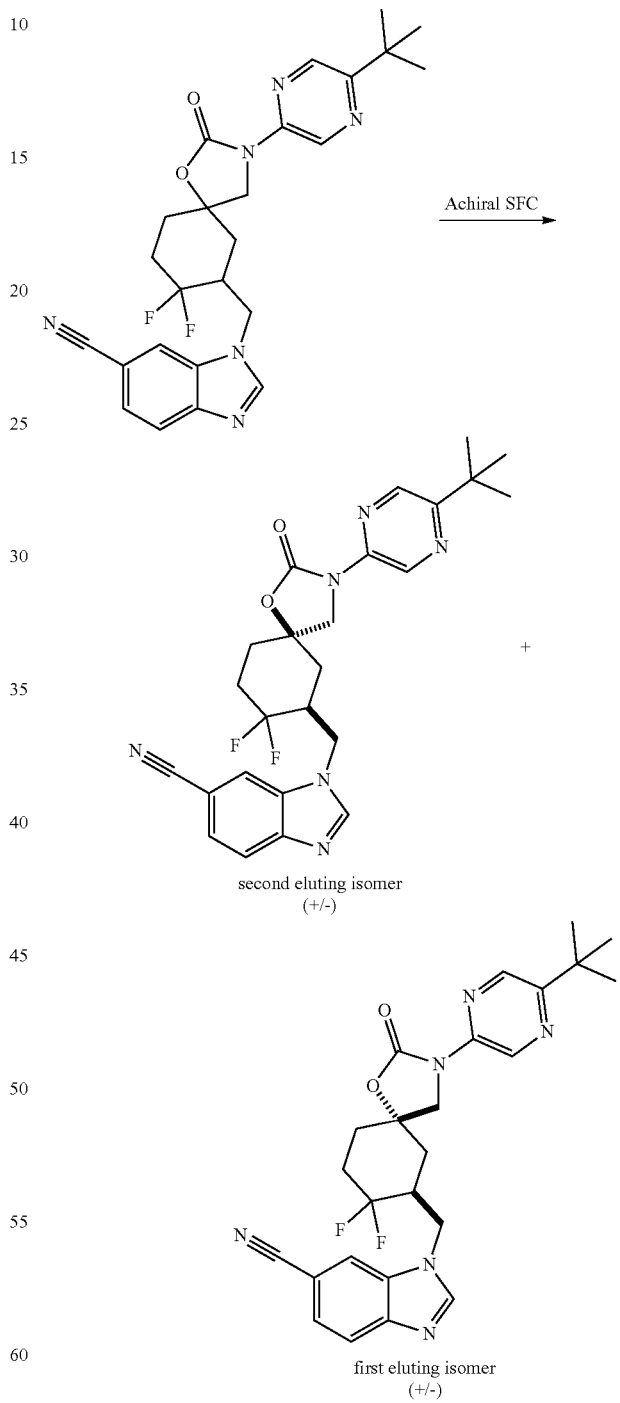

The diastereomeric mixture of 1-((3-(5-(tert-butyl)pyrazin-2-yl)-8,8-difluoro-2-oxo-1-oxa-3-azaspiro[4.5]decan-7-yl)methyl)-1H-benzo[d]imidazole-6-carbonitrile (420 mg, 0.87 mmol) was separated by Prep-Achiral SFC with the following condition: Column: DAICEL DCpak P4VP, 3×25 cm, 5 μm; Mobile Phase A: $CO_2$, Mobile Phase B: MeOH (0.1% 2M $NH_3$-MeOH); Flow rate: 60 mL/min; Gradient: isocratic 17% B; Column Temperature (25° C.): 35; Back Pressure (bar): 100; Wave Length: 254 nm; RT1 (min): 7.62; RT2(min): 9; Sample Solvent: MeOH-HPLC; Injection Volume: 2.5 mL. The desired fractions were combined and lyophilized to afford the two products:

First eluting isomer: rac-1-(((5R,7S)-3-(5-(tert-Butyl) pyrazin-2-yl)-8,8-difluoro-2-oxo-1-oxa-3-azaspiro[4.5]decan-7-yl)methyl)-1H-benzo[d]imidazole-6-carbonitrile (300 mg) as a white solid.

Second eluting isomer: rac-1-(((5S,7S)-3-(5-(tert-Butyl) pyrazin-2-yl)-8,8-difluoro-2-oxo-1-oxa-3-azaspiro[4.5]decan-7-yl)methyl)-1H-benzo[d]imidazole-6-carbonitrile (50 mg) as a white solid.

1-(((5S,7S)-3-(5-(tert-Butyl)pyrazin-2-yl)-8,8-difluoro-2-oxo-1-oxa-3-azaspiro[4.5]decan-7-yl) methyl)-1H-benzo[d]imidazole-6-carbonitrile and
1-(((5R,7R)-3-(5-(tert-Butyl)pyrazin-2-yl)-8,8-difluoro-2-oxo-1-oxa-3-azaspiro[4.5]decan-7-yl) methyl)-1H-benzo[d]imidazole-6-carbonitrile

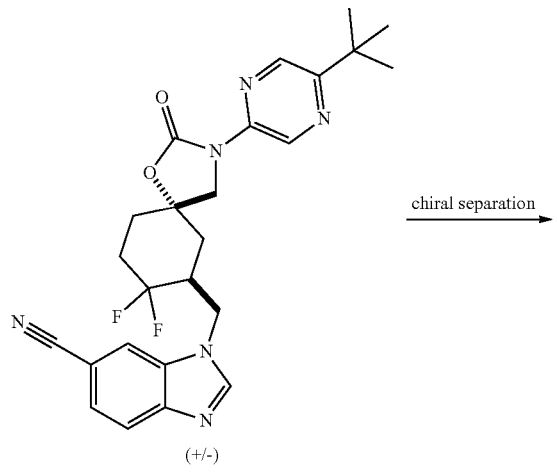

(+/-)

chiral separation

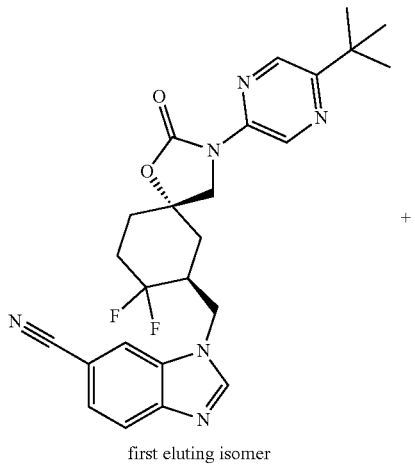

first eluting isomer

+

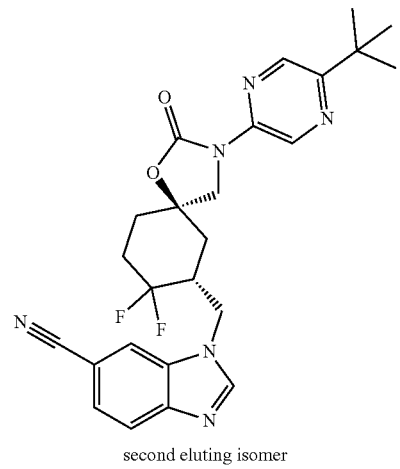

second eluting isomer

The mixture of rac-1-(((5S,7S)-3-(5-(tert-butyl)pyrazin-2-yl)-8,8-difluoro-2-oxo-1-oxa-3-azaspiro[4.5]decan-7-yl) methyl)-1H-benzo[d]imidazole-6-carbonitrile (300 mg, 0.62 mmol) was separated by Prep-Chiral HPLC with the following condition: Column: CHIRALPAK IE, 2×25 cm, 5 μm; Mobile Phase A: MTBE (0.5% 2M $NH_3$-MeOH)-HPLC, Mobile Phase B: EtOH-HPLC; Flow rate: 16 m/min; Gradient: 50% B to 50% B in 12 min; Wave Length: 220/254 nm; RT1(min): 7.528; RT2(min): 9.869; Sample Solvent: EtOH; Injection Volume: 0.4 mL. The desired fractions were combined and lyophilized to afford the two products:

First eluting isomer: 1-(((5S,7S)-3-(5-(tert-Butyl)pyrazin-2-yl)-8,8-difluoro-2-oxo-1-oxa-3-azaspiro[4.5]decan-7-yl) methyl)-1H-benzo[d]imidazole-6-carbonitrile (143.5 mg, 98.6% purity, 100% ee) as a white solid. $^1$H NMR (400 MHz, DMSO-$d_6$) δ 9.20 (d, J=1.6 Hz, 1H), 8.56 (s, 1H), 8.45 (d, J=1.5 Hz, 1H), 8.30 (d, J=1.4 Hz, 1H), 7.83 (d, J=8.3 Hz, 1H), 7.61 (dd, J=8.4, 1.5 Hz, 1H), 4.72-4.64 (m, 1H), 4.40 (dd, J=14.7, 7.7 Hz, 1H), 3.91 (q, J=10.4 Hz, 2H), 3.00-2.80 (m, 1H), 2.26-2.02 (m, 4H), 2.01-1.89 (m, 2H), 1.32 (s, 9H). LCMS (ESI-MS) m/z=481.2 [M+H]$^+$ Second eluting isomer: 1-(((5R,7R)-3-(5-(tert-Butyl) pyrazin-2-yl)-8,8-difluoro-2-oxo-1-oxa-3-azaspiro[4.5]decan-7-yl)methyl)-1H-benzo[d]imidazole-6-carbonitrile (51.7 mg, 99.8% purity, 100% ee) as a white solid. $^1$H NMR (400 MHz, DMSO-$d_6$) δ 9.20 (d, J=1.6 Hz, 1H), 8.56 (s, 1H), 8.45 (d, J=1.6 Hz, 1H), 8.35-8.28 (m, 1H), 7.83 (d, J=8.4 Hz, 1H), 7.61 (dd, J=8.4, 1.5 Hz, 1H), 4.67 (dd, J=14.7, 5.9 Hz, 1H), 4.40 (dd, J=14.7, 7.7 Hz, 1H), 3.91 (q, J=10.4 Hz, 2H), 3.02-2.82 (m, 1H), 2.24-2.04 (m, 4H), 1.99-1.83 (m, 2H), 1.32 (s, 9H). LCMS (ESI-MS) m/z=481.2 [M+H]$^+$.

Example 15. Preparation of: 1-(((5S,7S)-8,8-Difluoro-3-(5-(2-hydroxypropan-2-yl)pyrazin-2-yl)-7-methyl-2-oxo-1-oxa-3-azaspiro[4.5]decan-7-yl)methyl)-1H-benzo[d]imidazole-6-carbonitrile

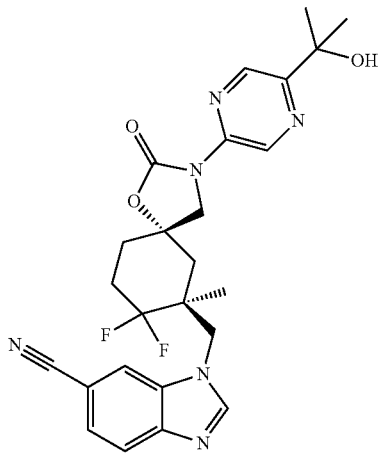 [SMILES: CC(C)(O)c1cnc(N2C[C@@]3(CCC(F)(F)[C@](C)(Cn4cnc5ccc(C#N)cc54)C3)OC2=O)cn1]

Detailed Procedure 4,4-Difluoro-3-methylcyclohexa-2,5-dien-1-one

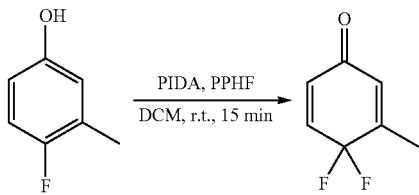

To a solution of 4-fluoro-3-methylphenol (25.2 g, 1 eq, 200 mmol) in DCM (1.5 L) at r.t. was added pyridine hydrofluoride (20 mL, 70% Wt, 0.78 eq, 156 mmol) dropwise over 10 min. Then, phenyl-13-iodanediyl diacetate (77.3 g, 1.2 eq, 240 mmol) was added in one portion and the reaction was stirred at r.t. for 15 min. Potassium carbonate (138 g, 5 eq, 1.00 mol) was added and the resulting mixture was stirred under the same conditions for 10 min. The mixture was filtered, and the filtrate was washed with HCl 1M (3x) and brine (1x), dried over $Na_2SO_4$, filtered and concentrated under reduced pressure (45° C., not below 850 mbar because the product is volatile) down to around 200 mL. The crude solution was used in the next step without further purification. $^1$H NMR (400 MHz, $CDCl_3$) δ 6.80 (dt, J=10.2, 5.5 Hz, 1H), 6.32-6.26 (m, 1H), 6.15-6.09 (m, J=1.5 Hz, 1H), 2.09 (dt, J=1.9, 1.0 Hz, 3H). $^{19}$F NMR (376 MHz, $CDCl_3$) δ −102.58.

4,4-Difluoro-3-methylcyclohex-2-en-1-one

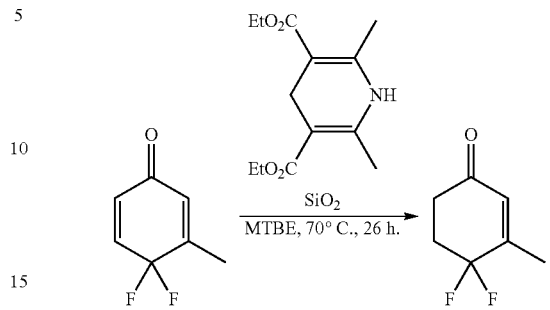

Crude 4,4-difluoro-3-methylcyclohexa-2,5-dien-1-one (28.8 g, 1 eq, 200 mmol) in tert-butyl methyl ether (1.33 L) was mechanically stirred under reflux with 3,5-pyridinedicarboxylic acid, 1,4-dihydro-2,6-dimethyl-diethyl ester (HEH; 111 g, 2.2 eq, 440 mmol) in the presence of silicon dioxide (400 g, 33.3 eq, 6.66 mol) at 60° C. overnight. Then, as there was not full conversion (by crude $^{19}$F NMR of an aliquot), 0.2 eq of HEH was added and the mixture was stirred at 60° C. for an additional 5 h. The mixture was cooled to r.t. and filtered to remove silica, and the volume of the filtrate reduced with the rotavapor down to 400 mL. 1.6 L of pentane were added and the mixture was filtered through a pad of silica and concentrated to 200 mL (Fraction A), the pad was washed with 1 L of pentane:MTBE 4:1 and concentrated to 250 mL (Fraction B) (Remark: most of the unreacted HEH can be removed through this filtration). NMR showed still impurities of HEH in both fractions which were stored in the freezer overnight. Both fractions had precipitated HEH that was filtered off. Each of the fractions were washed with 5% aq. CuSO4 (x2) (Remark: this was done to remove any residue of HEH) and 3 M HCl (aq) (x3) (Remark: this is needed to remove the Hantzsch pyridine). Afterwards, qNMR showed that 4,4-difluoro-3-methylcyclohex-2-en-1-one (14.6 g, 100 mmol, 50%) was obtained as a solution in MTBE, which was used without further purification in the next step. $^1$H NMR (400 MHz, $CDCl_3$) δ 6.00 (h, J=1.5 Hz, 1H), 2.63 (dd, J=7.2, 6.0 Hz, 2H), 2.52-2.41 (m, 2H), 2.05 (dt, J=1.5, 0.8 Hz, 3H). $^{19}$F NMR (376 MHz, $CDCl_3$) δ −100.50 (t, J=13.3 Hz).

(S)-4,4-Difluoro-3-methyl-3-(nitromethyl)cyclohexan-1-one

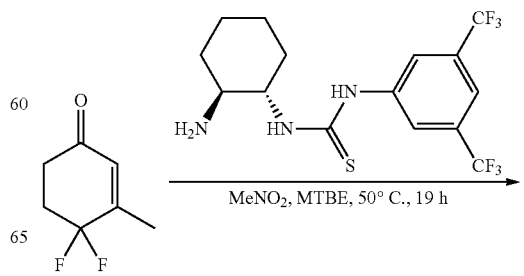

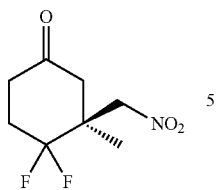

In a 1 L flask, a solution of crude 4,4-difluoro-3-methyl-cyclohex-2-en-1-one (7.98 g, 210 mL, 0.26 molar, 1 eq, 54.6 mmol) in MTBE was diluted to a total volume of MTBE (546 mL). 1-((1S,2S)-2-aminocyclohexyl)-3-(3,5-bis(trifluoromethyl)phenyl)thiourea (2.10 g, 0.1 eq, 5.46 mmol) and nitromethane (33.3 g, 29.4 mL, 10 eq, 546 mmol) were added and the mixture was stirred at 50° C. under N₂ for 2 days. The flask was cooled to room temperature. The mixture was washed with KHSO₄ sat. (3×), NaHCO₃ sat. (3×), H₂O (1×) and brine (1×). Dried (Na₂SO₄), filtered and concentrated. The crude product was purified by silica chromatography (220 g) using a 0-25% EtOAc in c-hexane gradient (2 CV 0%, 10 CV 0-10%, 2 CV 10%, 10 CV 10-20%, 4 CV 20-25%, 2 CV 25%) to afford (S)-4,4-difluoro-3-methyl-3-(nitromethyl)cyclohexan-1-one (4.11 g, 19.8 mmol, 36.3%) as a yellow oil. ¹H NMR (400 MHz, CDCl₃) δ 4.63 (d, J=11.1 Hz, 1H), 4.58 (d, J=11.1 Hz, 1H), 2.88-2.80 (m, 1H), 2.72-2.62 (m, 1H), 2.56-2.47 (m, 2H), 2.45-2.30 (m, 2H), 1.28 (d, J=1.0 Hz, 3H). ¹⁹F NMR (376 MHz, CDCl₃) δ −110.17 (dd, J=24.0, 12.9 Hz), −110.31 (td, J=10.4, 3.5 Hz).

(S)-8,8-Difluoro-7-methyl-7-(nitromethyl)-1,4-dioxaspiro[4.5]decane

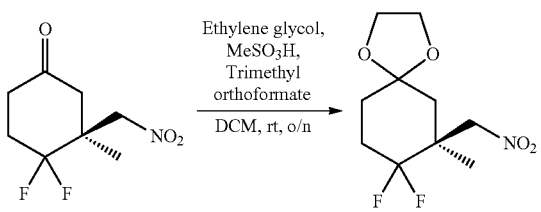 [SMILES: C[C@@]1(C[N+](=O)[O-])CC(=O)CCC1(F)F ; C[C@@]1(C[N+](=O)[O-])CC2(CCC1(F)F)OCCO2]

To a solution of (S)-4,4-difluoro-3-methyl-3-(nitromethyl)cyclohexan-1-one (4.0 g, 1 eq, 19.3 mmol) in dry DCM (3.8 M) were added ethylene glycol (1.59 mL, 1.48 eq, 28.6 mmol) and trimethyl ortho formate (3.2 mL, 1.5 eq, 29.0 mmol). The resulting reaction mixture was stirred at RT for 5 minutes and then cooled to 0° C. in an ice bath. To this mixture was added methanesulfonic acid (186 µL, 0.148 eq, 2.86 mmol) dropwise. The reaction mixture was removed from the ice bath and allowed to warm to RT and stirred overnight. The reaction was cooled back to 0° C., quenched with 100 mL of water and partitioned with 100 mL DCM. The layers were separated, and the aqueous layer was extracted with DCM (3×50 mL). The combined organic layers were dried over anhydrous Na₂SO₄, filtered, and concentrated to give (S)-8,8-difluoro-7-methyl-7-(nitromethyl)-1,4-dioxaspiro[4.5]decane (4.2 g, 87%) as a clear, orange-yellowish oil. ¹H NMR (400 MHz, CDCl₃) δ 4.82 (d, J=11.0 Hz, 1H), 4.51 (d, J=11.1 Hz, 1H), 4.02-3.92 (m, 4H), 2.29-2.15 (m, 1H), 2.15-2.09 (m, 1H), 2.08-1.95 (m, 1H), 1.91-1.79 (m, 3H), 1.30 (d, J=1.4 Hz, 3H). ¹⁹F NMR (376 MHz, CDCl₃) δ −109.08 (ddd, J=244.3, 20.7, 7.2 Hz), −110.28 (dddd, J=243.9, 21.2, 7.6, 3.0 Hz).

(S)-(8,8-Difluoro-7-methyl-1,4-dioxaspiro[4.5]decan-7-yl)methanamine

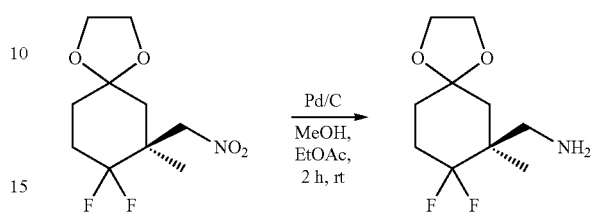

To Pd (10% in charcoal; 0.075 eq) under inert atmosphere was added a solution of (S)-8,8-difluoro-7-methyl-7-(nitromethyl)-1,4-dioxaspiro[4.5]decane (1 eq) in EtOAc. To this mixture was added MeOH (MeOH:EtOAc 2:1, 0.1M) and the reaction vessel was evacuated and back-filled with H₂ from a balloon. The reaction was stirred at r.t. overnight. Full conversion was observed by TLC (TLC 5% MeOH in DCM shows full conversion, ninhydrin as the stain). The reaction vessel was evacuated and back-filled with nitrogen. The reaction contents were filtered through Celite, washed with EtOAc and concentrated in vacuo obtaining (S)-(8,8-difluoro-7-methyl-1,4-dioxaspiro[4.5]decan-7-yl)methanamine (3.7 g, quant.) as a yellowish clear oil, which was used in the next step without further purification. ¹H NMR (400 MHz, CDCl₃) δ 3.97-3.91 (m, 4H), 2.87 (d, J=13.3 Hz, 1H), 2.77 (d, J=13.4 Hz, 1H), 2.13-2.01 (m, 2H), 1.84-1.79 (m, 3H), 1.64-1.58 (m, 1H), 1.12 (d, J=1.5 Hz, 3H). ¹⁹F NMR (376 MHz, CDCl₃) δ −106.57−−107.45 (m), −111.32−−112.12 (m).

(S)-3-(((8,8-Difluoro-7-methyl-1,4-dioxaspiro[4.5]decan-7-yl)methyl)amino)-4-nitrobenzonitrile

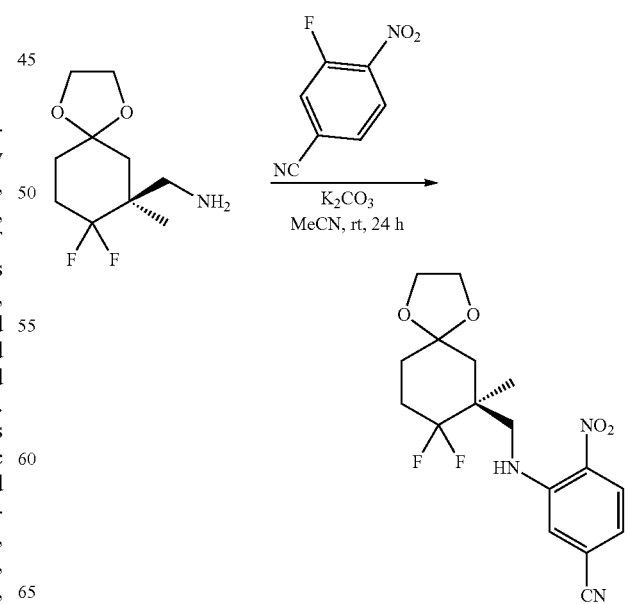

(S)-(8,8-Difluoro-7-methyl-1,4-dioxaspiro[4.5]decan-7-yl)methanamine (S)-(8,8-Difluoro-7-methyl-1,4-dioxaspiro[4.5]decan-7-yl)methanamine (1.00 eq) was dissolved in MeCN (0.35 M). K₂CO₃ (2.00 eq) and 3-fluoro-4-nitrobenzonitrile (1.00 eq) were added and the resulting orange mixture was stirred at room temperature for 24 h. The reaction was filtered through a frit, the filtrate was concentrated and purified on a silica gel column (0-1% MeOH/DCM) to afford (S)-3-(((8,8-difluoro-7-methyl-1,4-dioxaspiro[4.5]decan-7-yl)methyl)amino)-4-nitrobenzonitrile (5.4 g, 88%). ¹H NMR (400 MHz, CDCl₃) δ 8.41 (s, 1H), 8.30-8.22 (m, 1H), 6.85 (dd, J=8.7, 1.6 Hz, 1H), 4.07-3.90 (m, 4H), 3.56-3.44 (m, 2H), 2.22-2.09 (m, 2H), 1.93-1.82 (m, 3H), 1.76 (dd, J=14.0, 2.6 Hz, 1H), 1.30-1.18 (m, 4H). ¹⁹F NMR (376 MHz, CDCl₃) δ −107.02−−107.96 (m), −110.15−−111.12 (m).

(S)-4-Amino-3-(((8,8-difluoro-7-methyl-1,4-dioxaspiro[4.5]decan-7-yl)methyl)amino)benzonitrile

(S)-1-((8,8-Difluoro-7-methyl-1,4-dioxaspiro[4.5]decan-7-yl)methyl)-1H-benzo[d]imidazole-6-carbonitrile

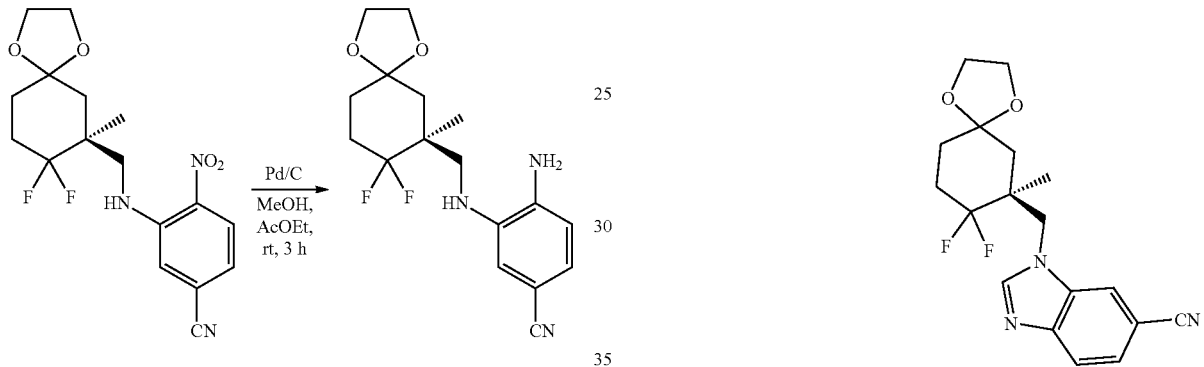

To Pd (10% on charcoal; 0.05 eq) under inert atmosphere was added a solution of (S)-3-(((8,8-difluoro-7-methyl-1,4-dioxaspiro[4.5]decan-7-yl)methyl)amino)-4-nitrobenzonitrile (1 eq) in ethyl acetate. To this mixture was added MeOH (MeOH:AcOEt 2:1, 0.1 M) and the reaction vessel was evacuated and back-filled with H₂ from a balloon. The reaction was stirred at r.t. for 2 h, until full conversion was observed by TLC (TLC: 100% DCM, ninhydrin as the stain). The reaction vessel was evacuated and back-filled with nitrogen. The reaction contents were filtered through Celite, washed with EtOAc and concentrated in vacuo obtaining (S)-4-amino-3-(((8,8-difluoro-7-methyl-1,4-dioxaspiro[4.5]decan-7-yl)methyl)amino)benzonitrile (4.9 g, 99%). ¹H NMR (400 MHz, CDCl₃) δ 7.02 (dd, J=8.0, 1.8 Hz, 1H), 6.89 (d, J=1.8 Hz, 1H), 6.67 (d, J=7.9 Hz, 1H), 4.02-3.91 (m, 4H), 3.22-3.15 (m, 2H), 2.25-2.08 (m, 2H), 1.95 (dd, J=14.2, 2.7 Hz, 1H), 1.85 (d, J=6.5 Hz, 2H), 1.73 (dt, J=14.2, 2.2 Hz, 1H), 1.27 (d, J=1.5 Hz, 3H). ¹⁹F NMR (376 MHz, CDCl₃) δ −105.99−−106.88 (m), −109.87 (ddd, J=242.6, 19.3, 10.3 Hz).

(S)-4-Amino-3-(((8,8-difluoro-7-methyl-1,4-dioxaspiro[4.5]decan-7-yl)methyl)amino)benzonitrile (4.9 g, 1 eq, 15 mmol) was added to trimethyl orthoformate (46 mL, 29 eq, 420 mmol) followed by formic acid (0.56 mL, 1 eq, 15 mmol). The resulting mixture was allowed to stir at room temperature. Additional formic acid (0.56 mL, 1 eq, 15 mmol) was added at t=90 min, 120 min and 180 min following the initiation of the reaction after which the mixture was allowed to stir overnight. The reaction contents were partitioned with 500 mL of EtOAc and 300 mL of sat aq NaHCO₃ and the layers were separated. The aqueous layer was back extracted with EtOAc (3×150 mL). The combined organics were dried over anhydrous Na₂SO₄, filtered and concentrated in vacuo. The crude material was purified by silica gel chromatography (80 g SiO₂, 0-70% EtOAc:Hexanes) to obtain (S)-1-((8,8-difluoro-7-methyl-1,4-dioxaspiro[4.5]decan-7-yl)methyl)-1H-benzo[d]imidazole-6-carbonitrile (4.4 g, 13 mmol, 87%) as a white solid. ¹H NMR (400 MHz, CDCl₃) δ 8.17 (s, 1H), 7.86 (dd, J=8.4, 0.7 Hz, 1H), 7.80 (d, J=1.5 Hz, 1H), 7.54 (dd, J=8.4, 1.5 Hz, 1H), 4.47 (d, J=14.8 Hz, 1H), 4.31 (d, J=14.9 Hz, 1H), 4.04-3.90 (m, 4H), 2.29-2.07 (m, 2H), 1.97-1.82 (m, 3H), 1.73-1.65 (m, 1H), 1.13-1.09 (m, 3H). ¹⁹F NMR (376 MHz, CDCl₃) δ −107.43−−108.46 (m), −110.25 (ddd, J=243.6, 22.9, 7.7 Hz).

(S)-1-((2,2-Difluoro-1-methyl-5-oxocyclohexyl)methyl)-1H-benzo[d]imidazole-6-carbonitrile

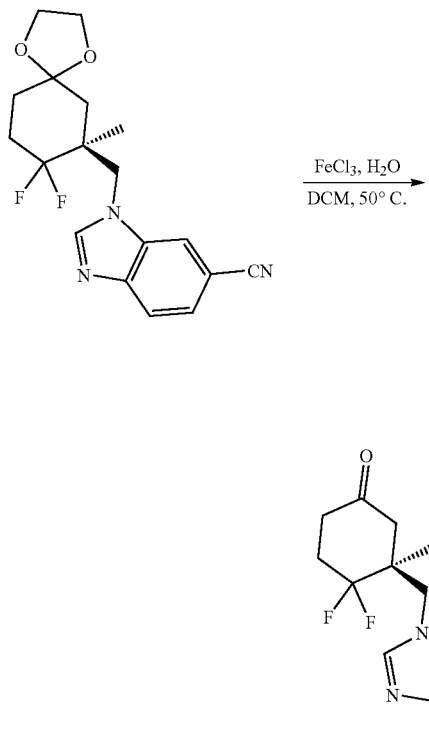

To iron (III) chloride (3.27 g, 3.5 eq, 20.2 mmol) and water (2.18 g, 2.18 mL, 21 eq, 121 mmol), was added a solution of (S)-1-((8,8-difluoro-7-methyl-1,4-dioxaspiro[4.5]decan-7-yl)methyl)-1H-benzo[d]imidazole-6-carbonitrile (2.00 g, 1 eq, 5.76 mmol) in CH$_2$Cl$_2$ (19.2 mL) at room temperature. The resulting yellow to amber colored suspension was heated at 50° C. and iron(III) chloride (3.27 g, 3.5 eq, 20.2 mmol) in water (2.18 g, 2.18 mL, 21 eq, 121 mmol) was added at t=1, 2 and 3 hours maintaining the temperature at 50° C. over the whole process. The reaction was quenched by addition of saturated aqueous NaHCO$_3$. The aqueous layer was extracted three times with CH$_2$Cl$_2$, and the combined organics were washed with brine, dried over Na$_2$SO$_4$, and concentrate under reduced pressure. NMR shows conversion was not complete. The reaction was restarted with the same conditions as before adding iron(III) chloride (3.27 g, 3.5 eq, 20.2 mmol) in water (2.18 g, 2.18 mL, 21 eq, 121 mmol) at t=2, 16, 19 and 25 hours. Conversion was not full (70%). The reaction was quenched by addition of saturated aqueous NaHCO$_3$. The aqueous layer was extracted three times with CH$_2$Cl$_2$, and the combined organics were washed with brine, dried over Na$_2$SO$_4$, and concentrate under reduced pressure. The reaction was restarted adding ferric chloride hexahydrate (5.4 g, 3.0 mL, 3.5 eq, 20 mmol) this time. The reaction was heated during 2 h and afterwards more ferric chloride hexahydrate (5.4 g, 3.0 mL, 3.5 eq, 20 mmol) was added, 1 hour later full conversion was reached (determined by LCMS analysis). The reaction was quenched by addition of saturated aqueous NaHCO$_3$. The aqueous layer was extracted three times with CH$_2$Cl$_2$, and the combined organics were washed with brine, dried over Na$_2$SO$_4$, and concentrate under reduced pressure to obtain (S)-1-((2,2-difluoro-1-methyl-5-oxocyclohexyl)methyl)-1H-benzo[d]imidazole-6-carbonitrile (993 mg, 3.27 mmol, 57%) as a light brown foam. $^1$H NMR (400 MHz, CDCl$_3$) δ 8.07 (s, 1H), 7.89 (d, J=8.4 Hz, 1H), 7.75 (s, 1H), 7.56 (dd, J=8.3, 1.4 Hz, 1H), 4.38 (q, J=15.3 Hz, 2H), 2.77-2.62 (m, 2H), 2.54 (d, J=15.7 Hz, 1H), 2.50-2.32 (m, 2H), 2.25 (d, J=14.0 Hz, 1H), 1.15 (s, 3H). $^{19}$F NMR (376 MHz, CDCl$_3$) δ −109.71−−109.83 (m), −109.83−−109.94 (m).

(S)-1-((2,2-Difluoro-1-methyl-5-methylenecyclohexyl)methyl)-1H-benzo[d]imidazole-6-carbonitrile

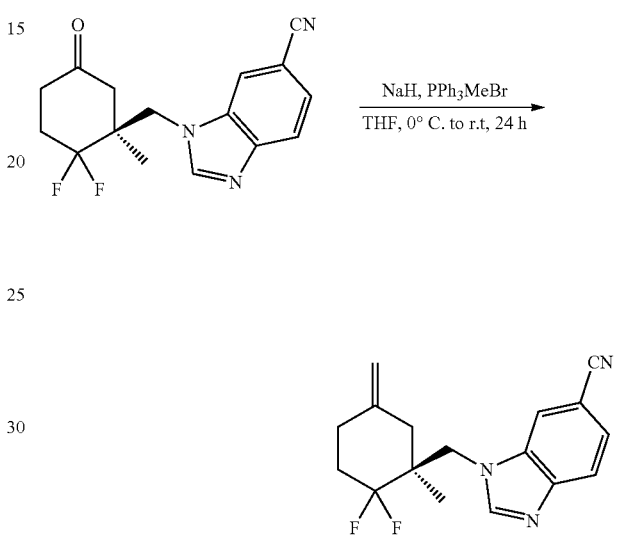

Under N$_2$ atmosphere, NaH (60% in mineral oil) (183 mg, 4.58 mmol, 1.4 eq) was added portionwise to a stirred suspension of methyltriphenylphosphonium bromide (1.64 g, 4.58 mmol, 1.4 eq.) in dry THF (14.6 mL) at 0° C. The mixture was stirred at 0° C. for 5 min, then allowed to warm to r.t. and stirred at this temperature for 1 hour. A solution of (S)-1-((2,2-difluoro-1-methyl-5-oxocyclohexyl)methyl)-1H-benzo[d]imidazole-6-carbonitrile (0.993 g, 3.27 mmol), in dry THF (7.28 mL) was added slowly at 0° C. and allowed to reach room temperature overnight. TLC (CyH/EtOAC: 1/1) indicated complete conversion. The reaction mixture was concentrated under reduced pressure and the residue was suspended in sat. aq. NH$_4$Cl and extracted with EtOAc 3 times. The combined organic phases were washed with H$_2$O and brine, dried over Na$_2$SO$_4$, filtered, and concentrated under reduced pressure. The residue was purified by column chromatography on silica gel (20 g SiO$_2$, 10 to 100% EtOAc in cHex) to give (S)-1-((2,2-difluoro-1-methyl-5-methylenecyclohexyl)methyl)-1H-benzo[d]imidazole-6-carbonitrile (473 mg, 3.27 mmol, 48%) as a white crystalline solid. LC-MS: m/z: 302 [M+H]$^+$ $^1$H NMR (400 MHz, CDCl$_3$) δ 8.08 (s, 1H), 7.87 (d, J=8.3 Hz, 1H), 7.81-7.77 (m, 1H), 7.54 (dd, J=8.3, 1.5 Hz, 1H), 4.92 (p, J=1.2 Hz, 1H), 4.76 (t, J=1.7 Hz, 1H), 4.42 (d, J=15.1 Hz, 1H), 4.29 (d, J=15.1 Hz, 1H), 2.44-2.33 (m, 3H), 2.15-2.05 (m, 2H), 2.02-1.91 (m, 2H), 1.42 (d, J=1.3 Hz, 1H), 1.34 (d, J=15.1 Hz, 1H), 1.02 (s, 4H), 0.95 (dd, J=8.1, 6.2 Hz, 1H). $^{19}$F NMR (376 MHz, CDCl$_3$) δ −105.09−−105.83 (m), −105.86−−106.80 (m), −108.95 (dd, J=32.0, 11.1 Hz), −109.60 (dd, J=31.7, 11.4 Hz).

1-(((3R,5S)-6,6-difluoro-5-methyl-1-oxaspiro[2.5] octan-5-yl)methyl)-1H-benzo[d]imidazole-6-carbonitrile and 1-(((3S,5S)-6,6-Difluoro-5-methyl-1-oxaspiro[2.5]octan-5-yl)methyl)-1H-benzo[d]imidazole-6-carbonitrile

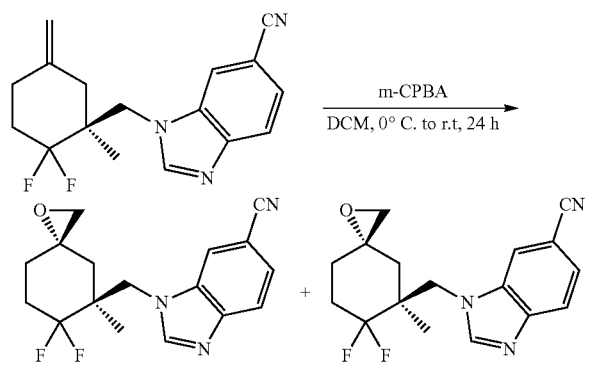

To a solution of (S)-1-((2,2-difluoro-1-methyl-5-methylenecyclohexyl)methyl)-1H-benzo[d]imidazole-6-carbonitrile (327 mg, 1.09 mmol, 1 eq.) in DCM (7.2 mL) at 0° C. was added m-CPBA (340 mg, 1.52 mmol, 1.4 eq. 77% WT). The mixture was allowed to warm to r.t. and stirred for 4 hours. LCMS showed the reaction was not complete, m-CPBA (340 mg, 1.52 mmol, 1.4 eq. 77% WT) was then added to the reaction mixture which was stirred at room temperature overnight. The reaction was quenched with a 1/1 mixture of sat. aq. Na₂S₂O₃/sat. aq. NaHCO₃, extracted with DCM three times. The combined organic layers were washed with NaHCO₃ sat. and brine, dried (Na₂SO₄), filtered and concentrated under reduced pressure. The residue was purified by column chromatography on silica gel (40 g SiO2, DCM/EtOAc 100/0 to 85/15 10 CV, then 85/15 for 20 CV then up to 75/25) to give the first diastereomer (undesired) 1-(((3R,5S)-6,6-difluoro-5-methyl-1-oxaspiro[2.5]octan-5-yl)methyl)-1H-benzo[d]imidazole-6-carbonitrile (96 mg, 0.3 mmol, 28%), and the second diastereomer (desired) 1-(((3S,5S)-6,6-difluoro-5-methyl-1-oxaspiro[2.5]octan-5-yl)methyl)-1H-benzo[d]imidazole-6-carbonitrile (64 mg, 0.2 mmol, 19%). LC-MS: m/z: 318 [M+H]⁺ ¹H NMR (400 MHz, CDCl₃) δ 8.11 (s, 1H), 7.88 (d, J=8.4 Hz, 1H), 7.76 (d, J=1.3 Hz, 1H), 7.60-7.54 (m, 1H), 4.42 (d, J=15.2 Hz, 1H), 4.30 (d, J=15.2 Hz, 1H), 2.61 (t, J=4.3 Hz, 1H), 2.57 (d, J=4.4 Hz, 1H), 2.38-2.22 (m, 4H), 1.37 (dt, J=11.8, 2.6 Hz, 2H), 1.30 (s, 3H), 1.07 (ddd, J=13.8, 5.4, 2.6 Hz, 1H).

1-(((5S,7S)-8,8-Difluoro-7-methyl-2-oxo-1-oxa-3-azaspiro[4.5]decan-7-yl)methyl)-1H-benzo[d]imidazole-6-carbonitrile

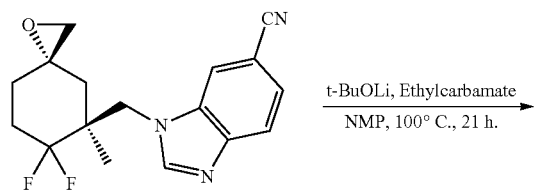

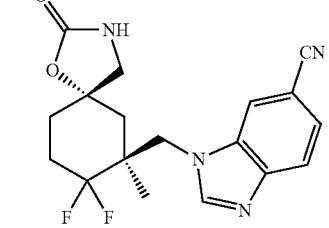

Lithium 2-methyl-2-propanolate (0.51 mL, 1.0 molar in THF, 0.51 mmol, 2.7 eq,) was added to a solution of aminoformic acid ethyl ester (0.23 g, 2.6 mmol, 13.5 eq) in NMP (1.3 mL). After stirring for 10 min at room temperature, a solution of 1-(((3S,5S)-6,6-difluoro-5-methyl-1-oxaspiro[2.5]octan-5-yl)methyl)-1H-benzo[d]imidazole-6-carbonitrile (60 mg, 0.46 mmol, 1.00 eq.) in NMP (1.3 mL) was added dropwise. The reaction mixture was subsequently heated to 100° C. and stirred at this temperature for 21 h until full conversion by TLC (100% DCM). The reaction mixture was cooled to room temperature, poured into H₂O and extracted with EtOAc (×4). The combined organic extract was washed with NH₄Cl (×3), H₂O and brine, dried, filtered and concentrated under reduced pressure. The crude product was purified by silica chromatography (4 g SiO2, 0 to 7% MeOH in DCM) to provide 1-(((5S,7S)-8,8-difluoro-7-methyl-2-oxo-1-oxa-3-azaspiro[4.5]decan-7-yl)methyl)-1H-benzo[d]imidazole-6-carbonitrile (48 mg, 0.13 mmol, 70%) as a thick colorless oil. LC-MS: m/z: 361 [M+H]⁺

1-(((5S,7S)-8,8-Difluoro-3-(5-(2-hydroxypropan-2-yl)pyrazin-2-yl)-7-methyl-2-oxo-1-oxa-3-azaspiro[4.5]decan-7-yl)methyl)-1H-benzo[d]imidazole-6-carbonitrile

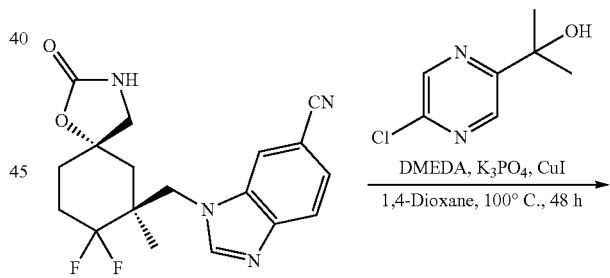

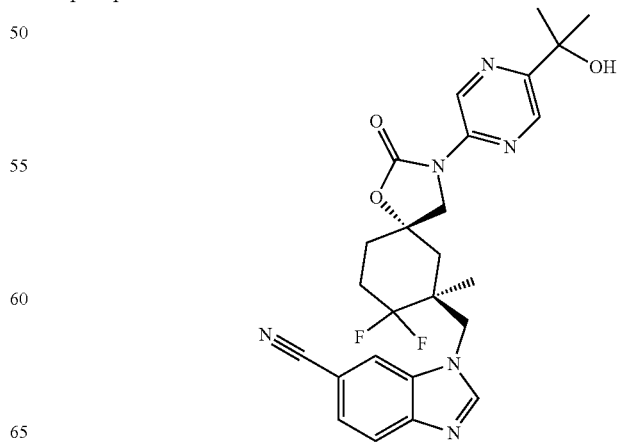

In a sealed tube, to 2-(5-chloropyrazin-2-yl)propan-2-ol (29 mg, 0.17 mmol, 1.25 eq.) was added potassium phosphate, tribasic (57 mg, 0.27 mmol, 2.0 eq,), 1-(((5S,7S)-8,8-difluoro-7-methyl-2-oxo-1-oxa-3-azaspiro[4.5]decan-7-yl)methyl)-1H-benzo[d]imidazole-6-carbonitrile (48 mg, 0.13 mmol, 1 eq), 1,4-dioxane (0.67 mL), methyl[2-(methylamino)ethyl]amine (12.0 mg, 0.28 mmol, 1.00 eq) and CuI (26.9 mg, 0.14 mmol, 0.50 eq). The reaction mixture was placed under a nitrogen atmosphere and heated to 100° C. for 32 h. The reaction mixture was cooled to room temperature, diluted with DCM, water and 7M $NH_3$ in MeOH and stirred for 10 min. The organic layer was separated, and the aqueous layer was extracted with DCM (×2). The combined organic extracts were washed with water (2×), dried, filtered and concentrated under reduced pressure giving an orange oil. The residue was purified by FCC (MeOH 0-10% in DCM) and concentrated to give 1-(((5S,7S)-8,8-difluoro-3-(5-(2-hydroxypropan-2-yl)pyrazin-2-yl)-7-methyl-2-oxo-1-oxa-3-azaspiro[4.5]decan-7-yl)methyl)-1H-benzo[d]imidazole-6-carbonitrile (26 mg, 0.13 mmol, 39%) as an off white solid. LC-MS: m/z: 497 [M+H]$^+$ $^1$H NMR (400 MHz, CDCl$_3$) δ 9.37 (d, J=1.6 Hz, 1H), 8.43 (d, J=1.6 Hz, 1H), 8.37 (s, 1H), 7.90 (dd, J=8.4, 0.7 Hz, 1H), 7.80 (d, J=1.3 Hz, 1H), 7.57 (dd, J=8.4, 1.4 Hz, 1H), 4.46 (d, J=15.2 Hz, 1H), 4.35 (d, J=15.2 Hz, 1H), 3.99 (d, J=10.8 Hz, 1H), 3.91 (d, J=10.8 Hz, 1H), 2.45 (dddd, J=35.7, 18.0, 9.0, 3.9 Hz, 1H), 2.30-2.10 (m, 2H), 2.09-1.93 (m, 3H), 1.63-1.57 (m, 6H), 1.43 (s, 3H). $^{19}$F NMR (376 MHz, CDCl$_3$) δ −107.42 (d, J=242.5 Hz), −109.03 (ddd, J=242.8, 35.6, 10.3 Hz).

Example 16. Preparation of: 1-(((5S,7R)-3-(5-(2-Hydroxypropan-2-yl)pyrazin-2-yl)-7-methyl-8-methylene-2-oxo-1-oxa-3-azaspiro[4.5]decan-7-yl)methyl)-1H-benzo[d]imidazole-6-carbonitrile

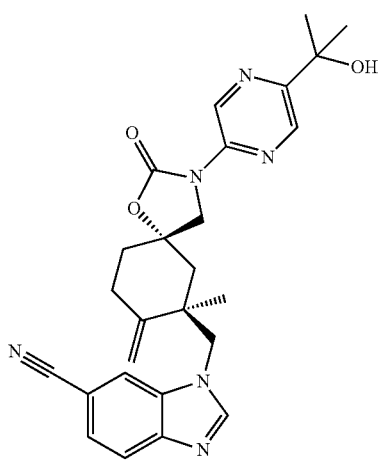 [SMILES: C=C1CC[C@@]2(CN(c3cnc(C(C)(C)O)cn3)C(=O)O2)C[C@@]1(C)Cn1cnc2ccc(C#N)cc21]

Detailed Procedure rac-1-(((5S,7S)-3-(5-(2-Hydroxypropan-2-yl)pyrazin-2-yl)-7-methyl-2,8-dioxo-1-oxa-3-azaspiro [4.5] decan-7-yl)methyl)-1H-benzo[d]imidazole-6-carbonitrile

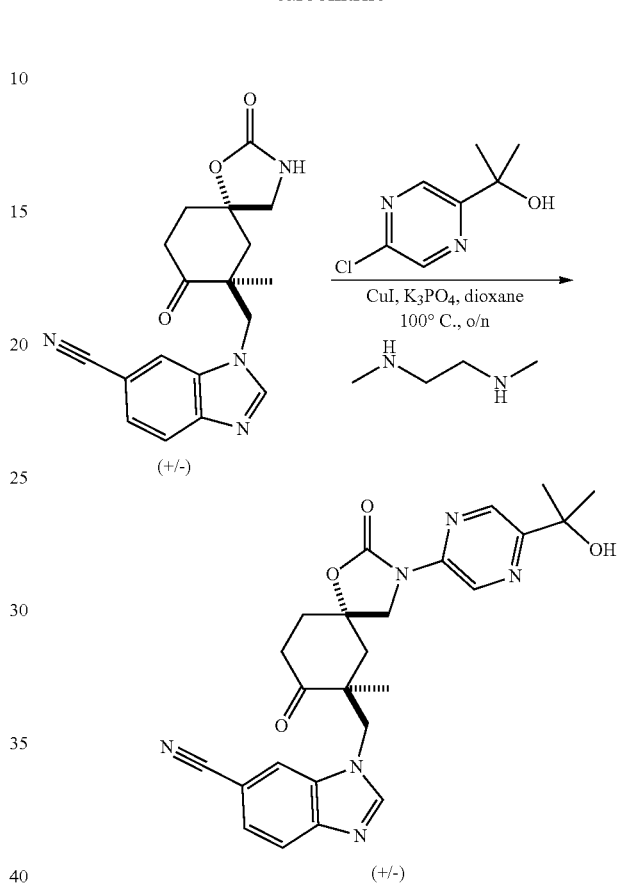

Copper(I) iodide (281.87 mg, 1.48 mmol) was added to a solution of rac-1-(((5S,7S)-7-methyl-2,8-dioxo-1-oxa-3-azaspiro[4.5]decan-7-yl)methyl)-1H-benzo[d]imidazole-6-carbonitrile (500 mg, 1.48 mmol), 2-(5-chloropyrazin-2-yl)propan-2-ol (254.43 mg, 1.48 mmol, 1 eq), $N^1,N^2$-dimethylethane-1,2-diamine (260.35 mg, 2.96 mmol) and tripotassium phosphate (628.3 mg, 2.96 mmol) in 1,4-dioxane (5 mL) under nitrogen atmosphere. The resulting mixture was heated to 100° C. and stirred overnight. The reaction mixture was allowed to cool to room temperature, filtered and the filtrate was concentrated under vacuum. The residue was purified by silica gel column chromatography, eluted with methanol in dichloromethane from 0% to 3% to afford the desired product rac-1-(((5S,7S)-3-(5-(2-hydroxypropan-2-yl)pyrazin-2-yl)-7-methyl-2,8-dioxo-1-oxa-3-azaspiro[4.5]decan-7-yl)methyl)-1H-benzo[d]imidazole-6-carbonitrile (300 mg) as a light yellow solid. LCMS (ESI-MS) m/z=475 [M+H]$^+$. $^1$H NMR (400 MHz, DMSO-d$_6$) δ(ppm) 9.27 (s, 1H), 8.64 (d, J=4.0 Hz, 1H), 8.32 (d, J=10.1 Hz, 2H), 7.86-7.79 (m, 1H), 7.60 (t, J=5.6 Hz, 1H), 5.44 (d, J=3.3 Hz, 1H), 4.85 (d, J=14.7 Hz, 1H), 4.60 (d, J=14.9 Hz, 1H), 4.16 (d, J=10.1 Hz, 1H), 4.05 (d, J=10.5 Hz, 1H), 3.19 (s, 1H), 2.58 (d, J=12.4 Hz, 2H), 2.46-2.19 (m, 3H), 1.47 (t, J=3.2 Hz, 6H), 0.95 (d, J=3.6 Hz, 3H).

189 rac-1-(((5S,7R)-3-(5-(2-Hydroxypropan-2-yl) pyrazin-2-yl)-7-methyl-8-methylene-2-oxo-1-oxa-3-aza spiro[4.5]decan-7-yl)methyl)-1H-benzo[d]imidazole-6-carbonitrile

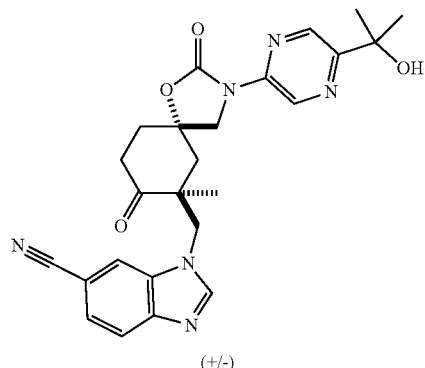

190

1-(((5S,7R)-3-(5-(2-Hydroxypropan-2-yl)pyrazin-2-yl)-7-methyl-8-methylene-2-oxo-1-oxa-3-azaspiro [4.5]decan-7-yl)methyl)-1H-benzo[d]imidazole-6-carbonitrile and 1-(((5R,7S)-3-(5-(2-Hydroxypropan-2-yl)pyrazin-2-yl)-7-methyl-8-methylene-2-oxo-1-oxa-3-azaspiro [4.5]decan-7-yl)methyl)-1H-benzo[d]imidazole-6-carbonitrile

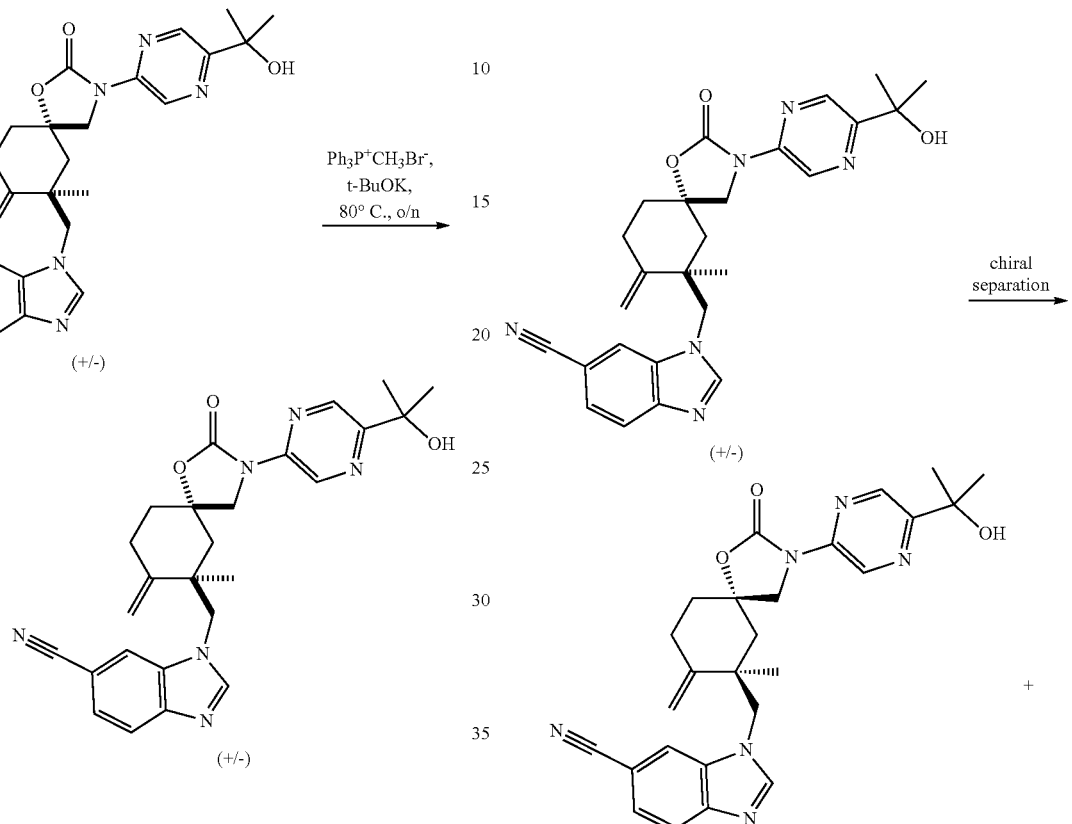

Potassium tert-butoxide (106.38 mg, 0.95 mmol) was added to a solution of methyltriphenylphosphanium bromide (337.36 mg, 0.95 mmol) in benzene (3 mL). To this mixture was added a solution of rac-1-(((5S,7S)-3-(5-(2-hydroxypropan-2-yl)pyrazin-2-yl)-7-methyl-2,8-dioxo-1-oxa-3-azaspiro[4.5]decan-7-yl)methyl)-1H-benzo[d]imidazole-6-carbonitrile (300 mg, 0.63 mmol) in benzene (3 mL) dropwise. The reaction mixture was stirred overnight at 80° C. The reaction mixture was allowed to cool to room temperature, diluted with water (10 mL) and extracted with ethyl acetate (3×10 mL). The combined organic layers were washed with brine (30 mL), dried over anhydrous sodium sulfate, and filtered. The filtrate was concentrated under vacuum to afford the crude product. The residue was purified by silica gel column chromatography, eluted with methanol in dichloromethane from 0% to 3% to afford rac-1-(((5S,7R)-3-(5-(2-hydroxypropan-2-yl)pyrazin-2-yl)-7-methyl-8-methylene-2-oxo-1-oxa-3-azaspiro[4.5]decan-7-yl)methyl)-1H-benzo[d]imidazole-6-carbonitrile (100 mg) as a yellow solid. LCMS (ESI-MS) m/z=473 [M+H]⁺. $^1$H NMR (400 MHz, DMSO-d$_6$) δ (ppm) 9.28 (d, J=1.5 Hz, 1H), 8.64 (d, J=1.5 Hz, 1H), 8.37 (d, J=1.4 Hz, 1H), 8.21 (s, 1H), 7.80 (d, J=8.3 Hz, 1H), 7.57 (dd, J=8.3, 1.4 Hz, 1H), 5.44 (s, 1H), 5.00 (s, 1H), 4.76 (d, J=14.6 Hz, 1H), 4.49 (s, 1H), 4.44 (d, J=14.6 Hz, 1H), 4.03-3.92 (m, 2H), 2.97 (dd, J=15.2, 11.1 Hz, 1H), 2.40 (ddd, J=24.0, 14.3, 3.4 Hz, 2H), 2.28 (d, J=13.1 Hz, 1H), 1.86-1.74 (m, 2H), 1.50-1.45 (m, 6H), 0.90 (s, 3H).

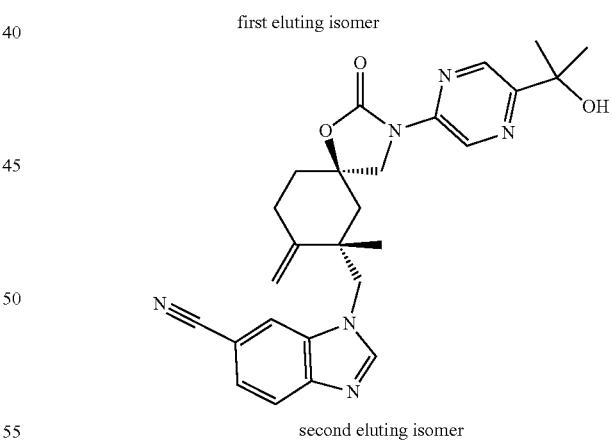

rac-1-(((5S,7R)-3-(5-(2-Hydroxypropan-2-yl)pyrazin-2-yl)-8,8-dimethyl-2-oxo-1-oxa-3-azaspiro[4.5]decan-7-yl)methyl)-1H-benzo[d]imidazole-6-carbonitrile (100 mg, 0.21 mmol) was separated by Prep-Chiral-HPLC with the condition: Column: CHIRAL ART Amylose-SA, 2*25 cm, 5 μm; Mobile Phase A: MtBE (0.5% 2M NH$_3$-MeOH)-HPLC, Mobile Phase B: EtOH-HPLC; Flow rate: 20 mL/min; Gradient: 20% B to 20% B in 22 min; Wave Length: 220/254 nm; RT1(min): 8.922; RT2(min): 16.131; Sample Solvent: EtOH-HPLC; Injection Volume: 1.3 mL. The desired fraction was combined and lyophilized to afford the products:

191

First eluting isomer: 1-(((5S,7R)-3-(5-(2-Hydroxypropan-2-yl)pyrazin-2-yl)-7-methyl-8-methylene-2-oxo-1-oxa-3-azaspiro[4.5]decan-7-yl)methyl)-1H-benzo[d]imidazole-6-carbonitrile (28.0 mg, 99.4% purity, 100% ee, 28.0% yield) as a white solid. $^1$H NMR (400 MHz, DMSO-$d_6$) δ(ppm) 9.28 (d, J=1.5 Hz, 1H), 8.64 (d, J=1.5 Hz, 1H), 8.37 (d, J=1.4 Hz, 1H), 8.21 (s, 1H), 7.80 (d, J=8.3 Hz, 1H), 7.57 (dd, J=8.3, 1.4 Hz, 1H), 5.44 (s, 1H), 5.00 (s, 1H), 4.76 (d, J=14.6 Hz, 1H), 4.49 (s, 1H), 4.44 (d, J=14.6 Hz, 1H), 4.03-3.92 (m, 2H), 2.97 (dd, J=15.2, 11.1 Hz, 1H), 2.40 (ddd, J=24.0, 14.3, 3.4 Hz, 2H), 2.28 (d, J=13.1 Hz, 1H), 1.86-1.74 (m, 2H), 1.50-1.45 (m, 6H), 0.90 (s, 3H). LCMS (ESI-MS) m/z=473 [M+H]$^+$.

Second eluting isomer: 1-(((5R,7S)-3-(5-(2-Hydroxypropan-2-yl)pyrazin-2-yl)-7-methyl-8-methylene-2-oxo-1-oxa-3-azaspiro[4.5]decan-7-yl)methyl)-1H-benzo [d]imidazole-6-carbonitrile (32.2 mg, 99.7% purity, 99.8% ee, 32.2% yield) as a white solid. $^1$H NMR (400 MHz, DMSO-$d_6$) δ(ppm) 9.28 (d, J=1.5 Hz, 1H), 8.64 (d, J=1.5 Hz, 1H), 8.37 (d, J=1.4 Hz, 1H), 8.21 (s, 1H), 7.80 (d, J=8.3 Hz, 1H), 7.57 (dd, J=8.3, 1.4 Hz, 1H), 5.44 (s, 1H), 5.00 (s, 1H), 4.76 (d, J=14.6 Hz, 1H), 4.49 (s, 1H), 4.44 (d, J=14.6 Hz, 1H), 4.03-3.92 (m, 2H), 2.97 (dd, J=15.2, 11.1 Hz, 1H), 2.40 (ddd, J=24.0, 14.3, 3.4 Hz, 2H), 2.28 (d, J=13.1 Hz, 1H), 1.86-1.74 (m, 2H), 1.50-1.45 (m, 6H), 0.90 (s, 3H). LCMS (ESI-MS) m/z=473 [M+H]$^+$.

Example 17. Preparation of: 1-(((5R,7S)-3-(5-(2-Hydroxypropan-2-yl)pyrazin-2-yl)-7,9,9-trimethyl-2-oxo-1-oxa-3-azaspiro[4.5]decan-7-yl)methyl)-1H-benzo[d]imidazole-6-carbonitrile

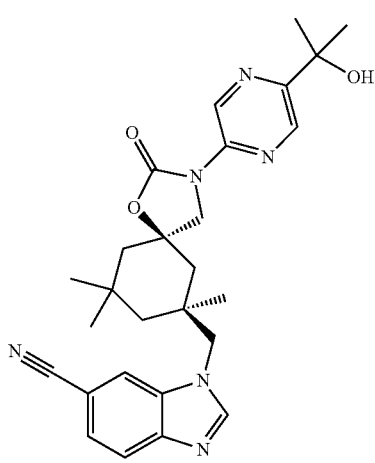 [SMILES: CC1(C)C[C@](C)(Cn2cnc3ccc(C#N)cc32)C[C@@]2(CN(c3cnc(C(C)(C)O)cn3)C(=O)O2)C1]

Detailed Procedure 3,5,5-Trimethylcyclohex-2-en-1-one

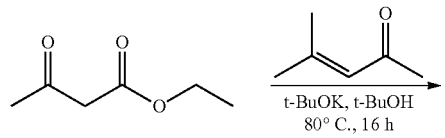

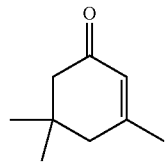

To a stirred mixture of ethyl acetoacetate (21 mL, 161.54 mmol) in tert-butanol (170 mL) was added potassium tert-butoxide (0.94 g, 8.38 mmol) and 4-methylpent-3-en-2-one (15.84 g, 161.54 mmol), the resulting mixture was stirred for 0.5 hour at room temperature. Then another batch of potassium tert-butoxide (3.63 g, 32.31 mmol) was added, the resulting mixture was heated to 80° C. and stirred for 16 hours. The reaction mixture was allowed to cool to room temperature, filtered and the filtrate was concentrated to afford the crude product. The residue was purified by silica gel column chromatography, eluted with ethyl acetate in petroleum ether from 0% to 15% to afford to afford 3,5,5-trimethylcyclohex-2-en-1-one (15 g) as colorless oil. LCMS (ESI-MS) m/z=139 [M+H]$^+$.

rac-3,3,5-Trimethyl-5-(nitromethyl)cyclohexan-1-one

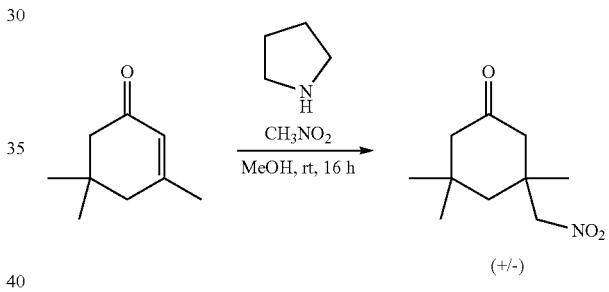

To a stirred mixture of 3,5,5-trimethylcyclohex-2-en-1-one (15 g, 108.53 mmol) in methanol (90 mL) was added nitromethane (6.62 g, 108.53 mmol) and pyrrolidine (7.72 g, 108.53 mmol). The resulting mixture was stirred for 16 hours at room temperature and concentrated under vacuum to afford the crude product. The residue was purified by silica gel column chromatography, eluted with ethyl acetate in petroleum ether from 0% to 10% to afford the desired product rac-3,3,5-trimethyl-5-(nitromethyl) cyclohexan-1-one (7 g) as yellow oil. LCMS (ESI-MS) m/z=200 [M+H]$^+$.

rac-7,7,9-Trimethyl-9-(nitromethyl)-1,4-dioxaspiro [4.5]decane

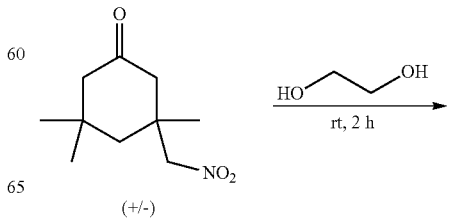

-continued

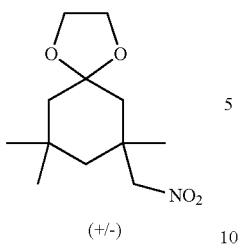

(+/-)

To a stirred mixture of rac-3,3,5-trimethyl-5-(nitromethyl)cyclohexan-1-one (7 g, 35.13 mmol) in dichloromethane (40 mL) was added ethane-1,2-diol (2.18 g, 35.13 mmol), trimethoxymethane (3.73 g, 35.13 mmol) and methanesulfonic acid (0.51 g, 5.27 mmol). The resulting mixture was stirred for 2 hours at room temperature. The reaction mixture was concentrated under vacuum to afford the crude product. The residue was purified by silica gel column chromatography, eluted with ethyl acetate in petroleum ether from 0% to 15% to afford the desired product rac-7,7,9-trimethyl-9-(nitromethyl)-1,4-dioxaspiro[4.5]decane (5 g) as yellow oil. LCMS (ESI-MS) m/z=244 [M+H]$^+$.

rac-7,9,9-Trimethyl-1,4-dioxaspiro[4.5]decan-7-yl) methanamine

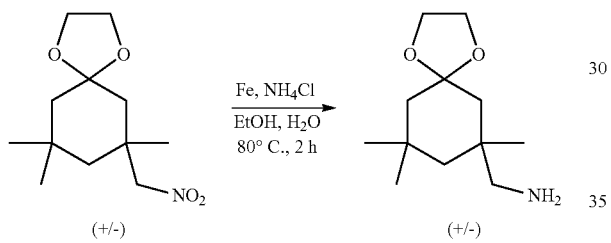

To a stirred mixture of rac-7,7,9-trimethyl-9-(nitromethyl)-1,4-dioxaspiro[4.5]decane (5 g, 20.55 mmol) in ethanol (75 mL) and water (15 mL) was added iron (5.74 g, 102.75 mmol) and ammonium chloride (3.30 g, 61.65 mmol), the resulting mixture was heated to 80° C. and stirred for 2 hours. The resulting mixture was allowed to cool to room temperature, filtered, and the filter cake was washed with ethanol (50 mL). The filtrate was diluted with water (50 mL) and extracted with dichloromethane (3×50 mL), the combined organic layers were dried over anhydrous sodium sulfate, filtered, and concentrated under vacuum to afford rac-(7,9,9-trimethyl-1,4-dioxaspiro[4.5]decan-7-yl)methanamine (3 g) as yellow oil. LCMS (ESI-MS) m/z=214 [M+H]$^+$.

rac-4-Nitro-3-(((7,9,9-trimethyl-1,4-dioxaspiro[4.5] decan-7-yl)methyl) amino) benzonitrile

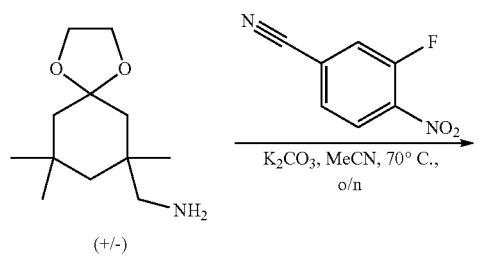

-continued

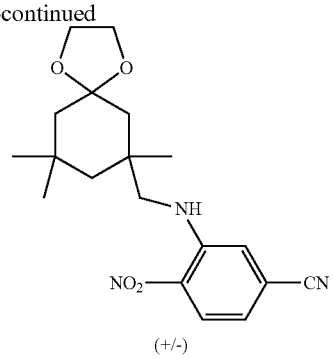

(+/-)

To a stirred mixture of rac-(7,9,9-trimethyl-1,4-dioxaspiro[4.5]decan-7-yl)methanamine (3 g, 14.06 mmol) in acetonitrile (60 mL) was added 3-fluoro-4-nitrobenzonitrile (2.34 g, 14.06 mmol) and potassium carbonate (3.89 g, 28.12 mmol). The resulting mixture was heated to 70° C. and stirred overnight. The reaction mixture was allowed to cool to room temperature, filtered, and the filtrate was concentrated under vacuum to afford the crude product. The residue was purified by silica gel column chromatography, eluted with ethyl acetate in petroleum ether from 0% to 10% to afford the desired product rac-4-nitro-3-(((7,9,9-trimethyl-1,4-dioxaspiro[4.5]decan-7-yl)methyl) amino) benzonitrile (5 g) as an orange solid. LCMS (ESI-MS) m/z=360 [M+H]$^+$.

rac-4-Amino-3-(((7,9,9-trimethyl-1,4-dioxaspiro [4.5]decan-7-yl)methyl) amino) benzonitrile

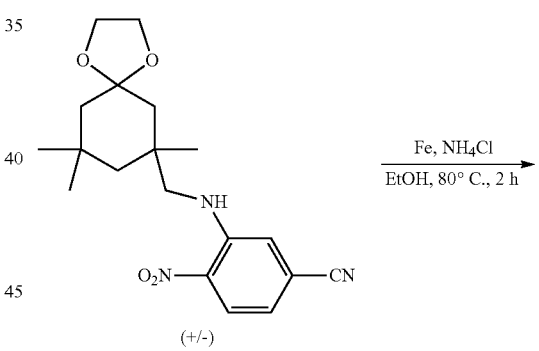

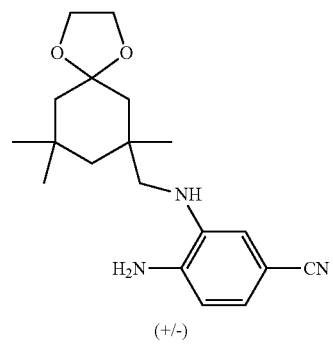

(+/-)

To a stirred mixture of rac-4-nitro-3-(((7,9,9-trimethyl-1, 4-dioxaspiro[4.5]decan-7-yl)methyl) amino) benzonitrile (3 g, 8.34 mmol) in ethanol (60 mL) and water (20 mL) was added iron (2.33 g, 41.73 mmol) and ammonium chloride (2.23 g, 41.73 mmol). The resulting mixture was heated to 80° C. and stirred for 2 hours. The mixture was allowed to cool to room temperature, filtered, and the filter cake was washed with ethanol (50 mL). The filtrate was diluted with water (50 mL) and extracted with dichloromethane (3×50 mL), the combined organic layers were dried over anhydrous sodium sulfate, filtered, and concentrated under vacuum to afford to afford the desired product rac-4-amino-3-(((7,9,9-trimethyl-1,4-dioxaspiro[4.5]decan-7-yl)methyl)amino)benzointrile (2.2 g) as a yellow solid. LCMS (ESI-MS) m/z=330 [M+H]$^+$.

rac-1-((7,9,9-Trimethyl-1,4-dioxaspiro[4.5]decan-7-yl)methyl)-1H-benzo[d]imidazole-6-carbonitrile

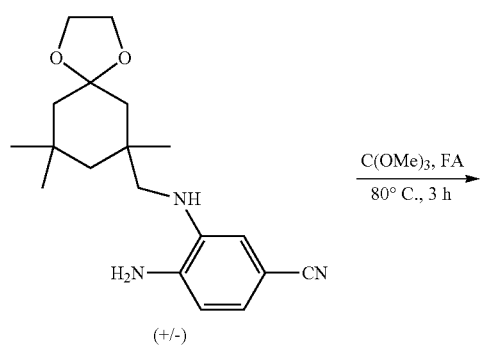

To a stirred mixture of rac-4-amino-3-(((7,9,9-trimethyl-1,4-dioxaspiro[4.5]decan-7-yl)methyl)amino)benzointrile (2.2 g, 6.67 mmol) in acetonitrile (10 mL) was added formic acid (0.25 mL, 6.67 mmol) and trimethoxymethane (0.73 mL, 6.67 mmol). The resulting mixture was heated to 80° C. and stirred for 3 hours. The reaction mixture was cooled to room temperature, diluted with water (50 ml), and extracted with dichloromethane (3×30 mL). The combined organic layers were dried over anhydrous sodium sulfate, filtered, and concentrated under vacuum to afford the crude product rac-1-((7,9,9-trimethyl-1,4-dioxaspiro[4.5]decan-7-yl)methyl)-1H-benzo[d]imidazole-6-carbonitrile (2 g) as yellow oil. LCMS (ESI-MS) m/z=340 [M+H]$^+$.

rac-1-((1,3,3-Trimethyl-5-oxocyclohexyl)methyl)-1H-benzo[d]imidazole-6-carbonitrile

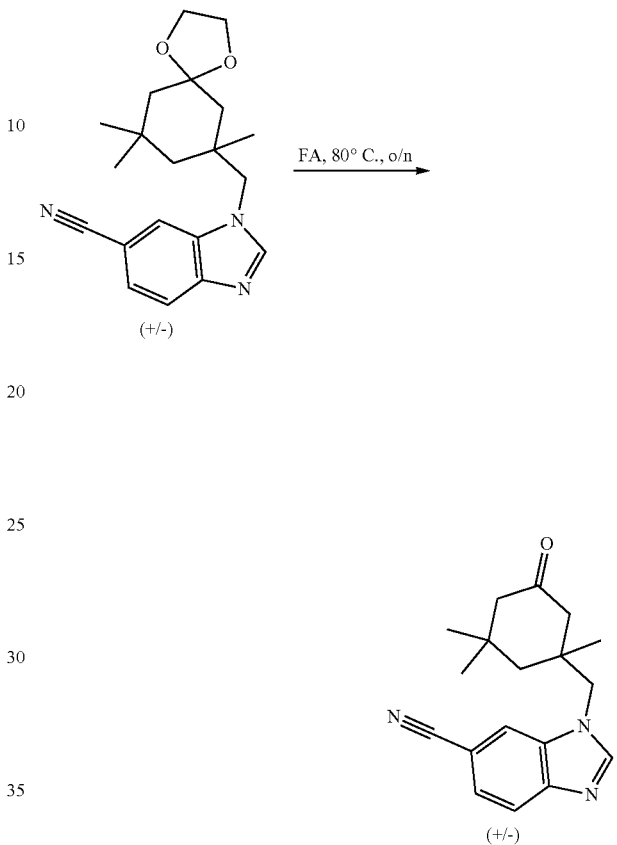

A mixture of rac-1-((7,9,9-trimethyl-1,4-dioxaspiro[4.5]decan-7-yl)methyl)-1H-benzo[d]imidazole-6-carbonitrile (2 g, 5.89 mmol) in formic acid (6 mL, 159.04 mmol) was stirred overnight at 80° C. The mixture was allowed to cool to room temperature and concentrated under vacuum to afford the crude product rac-1-((1,3,3-trimethyl-5-oxocyclohexyl)methyl)-1H-benzo[d]imidazole-6-carbonitrile (1.7 g) as yellow oil. LCMS (ESI-MS) m/z=296 [M+H]$^+$.

rac-1-(((3R,5S)-5,7,7-Trimethyl-1-oxaspiro[2.5]octan-5-yl)methyl)-1H-benzo[d]imidazole-6-carbonitrile

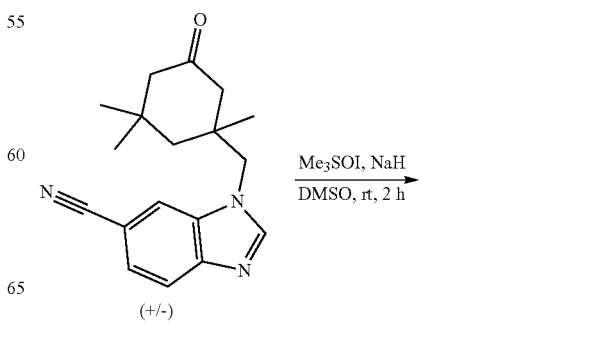

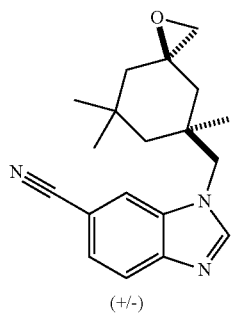

(+/-)

To a stirred mixture of rac-1-((1,3,3-trimethyl-5-oxocyclohexyl)methyl)-1H-benzo[d]imidazole-6-carbonitrile (1.7 g, 5.75 mmol) in dimethyl sulfoxide (20 mL) was added trimethylsulfoxonium iodide (1.27 g, 5.75 mmol) and potassium tert-butoxide (0.97 g, 8.63 mmol). The resulting mixture was stirred for 2 hours at room temperature. The reaction mixture was diluted with water (50 mL) and extracted with dichloromethane (3×50 mL). The combined organic layers were dried over anhydrous sodium sulfate, filtered and concentrated under vacuum to afford the crude product rac-1-(((3R,5S)-5,7,7-trimethyl-1-oxaspiro[2.5]octan-5-yl)methyl)-1H-benzo[d]imidazole-6-carbonitrile (1.5 g) as a yellow solid. LCMS (ESI-MS) m/z=310 [M+H]⁺.

rac-1-(((5R,7S)-7,9,9-trimethyl-2-oxo-1-oxa-3-azaspiro[4.5]decan-7-yl)methyl)-1H-benzo[d]imidazole-6-carbonitrile

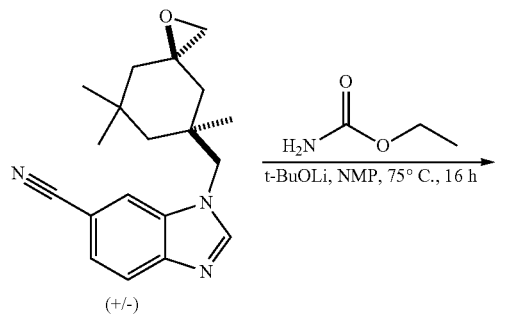

A mixture of lithium tert-butoxide (90.56 mg, 1.13 mmol) and ethyl carbamate (1007.80 mg, 11.31 mmol) in 1-methyl-2-pyrrolidinone (6 mL) was stirred for 5 min at room temperature, then rac-1-(((3R,5S)-5,7,7-trimethyl-1-oxaspiro[2.5]octan-5-yl)methyl)-1H-benzo[d]imidazole-6-carbonitrile (700 mg, 2.26 mmol) was added. The resulting mixture was heated to 75° C. and stirred for 16 hours. The reaction mixture was allowed to cool to room temperature, diluted with water (60 mL) and extracted with dichloromethane (3×60 mL). The combined organic layers were dried over anhydrous sodium sulfate, filtered, and the filtrate was concentrated under vacuum to afford the crude product rac-1-(((5R,7S)-7,9,9-trimethyl-2-oxo-1-oxa-3-azaspiro[4.5]decan-7-yl)methyl)-1H-benzo[d]imidazole-6-carbonitrile (500 mg) as a yellow solid. LCMS (ESI-MS) m/z=353 [M+H]⁺.

rac-1-(((5R,7S)-3-(5-(2-Hydroxypropan-2-yl)pyrazin-2-yl)-7,9,9-trimethyl-2-oxo-1-oxa-3-azaspiro[4.5]decan-7-yl)methyl)-1H-benzo[d]imidazole-6-carbonitrile

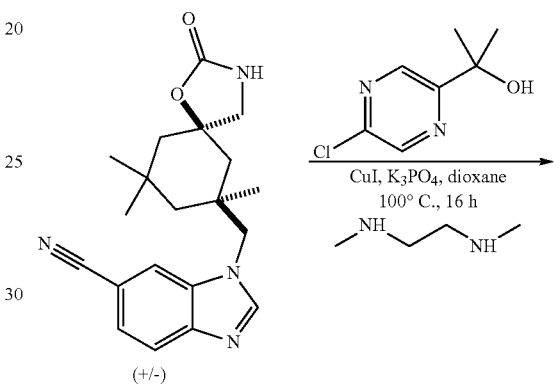

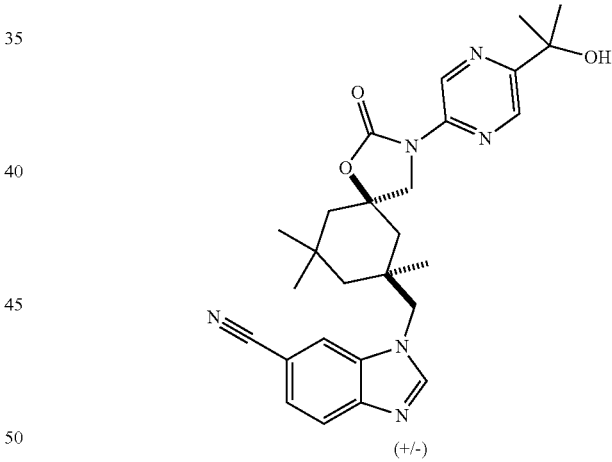

To a stirred mixture of rac-1-(((5R,7S)-7,9,9-trimethyl-2-oxo-1-oxa-3-azaspiro[4.5]decan-7-yl)methyl)-1H-benzo[d] imidazole-6-carbonitrile (500 mg, 1.42 mmol) in dioxane (12 mL) was added 2-(5-chloropyrazin-2-yl)propan-2-ol (244.88 mg, 1.42 mmol), potassium phosphate tribasic (903.41 mg, 4.25 mmol), methyl[2-(methylamino)ethyl]amine (300.15 mg, 3.41 mmol) and cuprous iodide (270.19 mg, 1.42 mmol) under nitrogen atmosphere, the resulting mixture was heated to 100° C. and stirred for 16 hours. The reaction mixture was allowed to cool to room temperature, diluted with water (60 mL) and extracted with ethyl acetate (3×60 mL). The combined organic layers were dried over anhydrous sodium sulfate, filtered, and the filtrate was concentrated under vacuum to afford the crude product. The residue was purified by silica gel column chromatography, eluted with methanol in dichloromethane from 0% to 10% to afford the desired product rac-1-(((5R,7S)-3-(5-(2-hydroxypropan-2-yl)pyrazin-2-yl)-7,9,9-trimethyl-2-oxo-1-oxa-3-azaspiro[4.5]decan-7-yl)methyl)-1H-benzo[d]imidazole-6-carbonitrile (450 mg) as a yellow solid. LCMS (ESI-MS) m/z=489 [M+H]$^+$.

1-(((5S,7R)-3-(5-(2-Hydroxypropan-2-yl)pyrazin-2-yl)-7,9,9-trimethyl-2-oxo-1-oxa-3-azaspiro[4.5]decan-7-yl)methyl)-1H-benzo[d]imidazole-6-carbonitrile and 1-(((5R,7S)-3-(5-(2-Hydroxypropan-2-yl)pyrazin-2-yl)-7,9,9-trimethyl-2-oxo-1-oxa-3-azaspiro[4.5]decan-7-yl)methyl)-1H-benzo[d]imidazole-6-carbonitrile

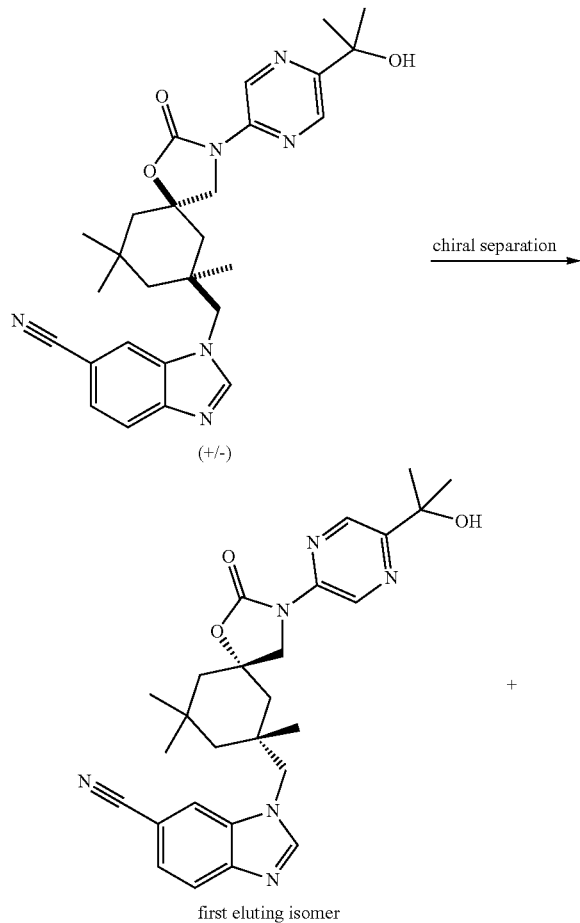

The racemate of 1-(((5R,7S)-3-(5-(2-hydroxypropan-2-yl)pyrazin-2-yl)-7,9,9-trimethyl-2-oxo-1-oxa-3-azaspiro[4.5]decan-7-yl)methyl)-1H-benzo[d]imidazole-6-carbonitrile (350 mg) was separated by Prep-Chiral HPLC with the following condition; Column: CHIRALPAK IA, 3×25 cm, 5 μm; Mobile Phase A: Hex (0.5% 2M NH$_3$-MeOH)-HPLC, Mobile Phase B: EtOH-HPLC; Flow rate: 18 mL/min; Gradient: 50% B to 50% B in 28 min; Wave Length: 220/254 nm; RT1(min): 17.68; RT2(min): 23.745; Sample Solvent: EtOH-HPLC; Injection Volume: 0.8 mL. The desired fractions were combined and lyophilized to afford the two products:

First eluting isomer: 1-(((5S,7R)-3-(5-(2-Hydroxypropan-2-yl)pyrazin-2-yl)-7,9,9-trimethyl-2-oxo-1-oxa-3-azaspiro[4.5]decan-7-yl)methyl)-1H-benzo[d]imidazole-6-carbonitrile (109.8 mg, 99.8% purity, 100.0% ee) as a white solid. LCMS (ESI-MS) m/z=489 [M+H]$^+$. $^1$H NMR (300 MHz, DMSO-d$_6$) δ (ppm) 9.30 (d, J=1.5 Hz, 1H), 8.62 (d, J=1.5 Hz, 1H), 8.52 (s, 1H), 8.45 (d, J=1.5 Hz, 1H), 7.86 (d, J=8.4 Hz, 1H), 7.62 (dd, J=8.4, 1.5 Hz, 1H), 4.72 (d, J=14.5 Hz, 1H), 4.35 (d, J=14.4 Hz, 2H), 4.05-3.91 (m, 2H), 2.17 (d, J=14.5 Hz, 1H), 1.97 (d, J=14.4 Hz, 1H), 1.79 (d, J=14.2 Hz, 1H), 1.67 (d, J=14.4 Hz, 1H), 1.56 (d, J=14.9 Hz, 1H), 1.47 (d, J=3.4 Hz, 6H), 1.35 (d, J=14.3 Hz, 1H), 1.27 (s, 3H), 1.04 (s, 3H), 0.80 (s, 3H).

Second eluting isomer: 1-(((5R,7S)-3-(5-(2-Hydroxypropan-2-yl)pyrazin-2-yl)-7,9,9-trimethyl-2-oxo-1-oxa-3-azaspiro[4.5]decan-7-yl)methyl)-1H-benzo[d]imidazole-6-carbonitrile (109.3 mg, 96.5% purity, 98.9% ee) as a white solid. LCMS (ESI-MS) m/z=489 [M+H]$^+$. $^1$H NMR (300 MHz, DMSO-d$_6$) δ (ppm) 9.30 (d, J=1.5 Hz, 1H), 8.62 (d, J=1.5 Hz, 1H), 8.55 (s, 1H), 8.46 (d, J=1.5 Hz, 1H), 7.86 (d, J=8.4 Hz, 1H), 7.63 (dd, J=8.4, 1.5 Hz, 1H), 4.73 (d, J=14.4 Hz, 1H), 4.35 (d, J=14.5 Hz, 1H), 4.03-3.95 (m, 2H), 2.17 (d, J=14.9 Hz, 1H), 1.97 (d, J=14.4 Hz, 1H), 1.79 (d, J=14.2 Hz, 1H), 1.67 (d, J=14.3 Hz, 1H), 1.56 (d, J=14.8 Hz, 1H), 1.47 (d, J=3.5 Hz, 6H), 1.35 (d, J=14.2 Hz, 1H), 1.27 (s, 3H), 1.04 (s, 3H), 0.80 (s, 3H).

Example 18. Preparation of: 5-Fluoro-1-(((5S,7S,8R)-8-fluoro-3-(5-(2-hydroxypropan-2-yl)pyrazin-2-yl)-7-methyl-2-oxo-1-oxa-3-azaspiro[4.5]decan-7-yl)methyl)-1H-benzo[d]imidazole-6-carbonitrile

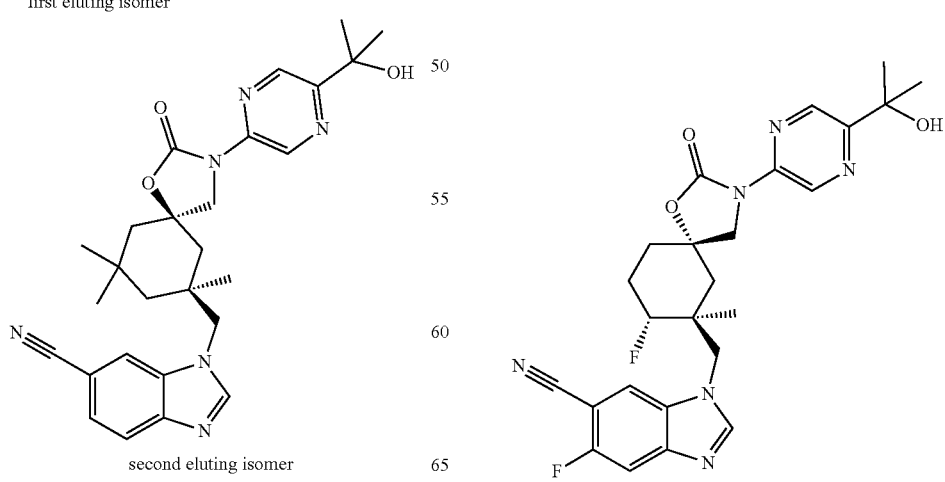

Reaction Scheme

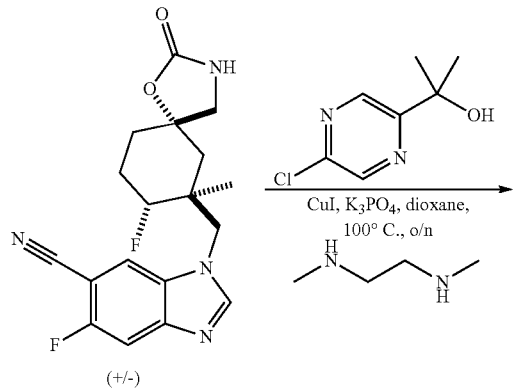

(+/-)

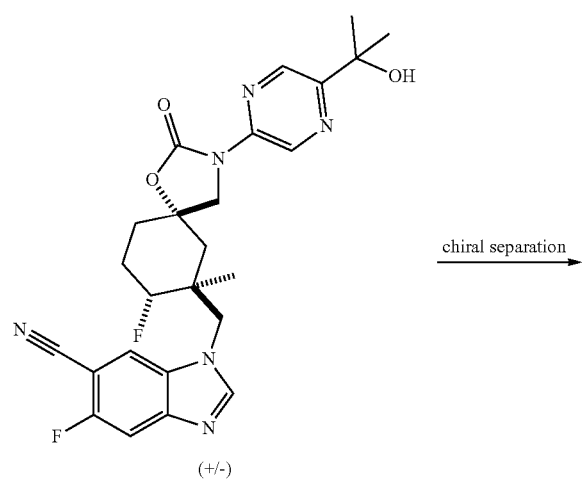

(+/-)

chiral separation

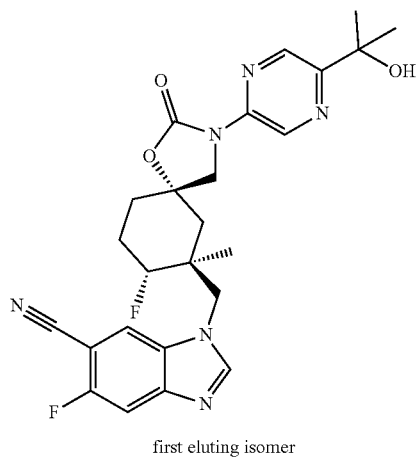

first eluting isomer

+

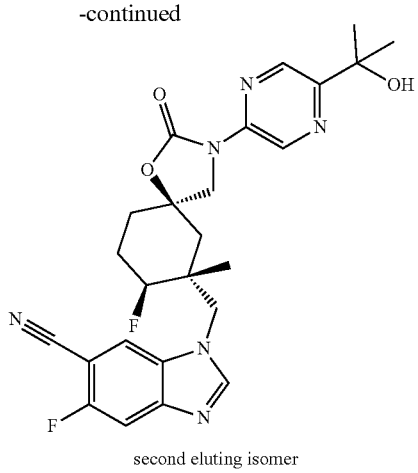

second eluting isomer

Detailed Procedure rac-5-Fluoro-1-(((5S,7S,8R)-8-fluoro-3-(5-(2-hydroxypropan-2-yl)pyrazin-2-yl)-7-methyl-2-oxo-1-oxa-3-azaspiro[4.5]decan-7-yl)methyl)-1H-benzo[d]imidazole-6-carbonitrile

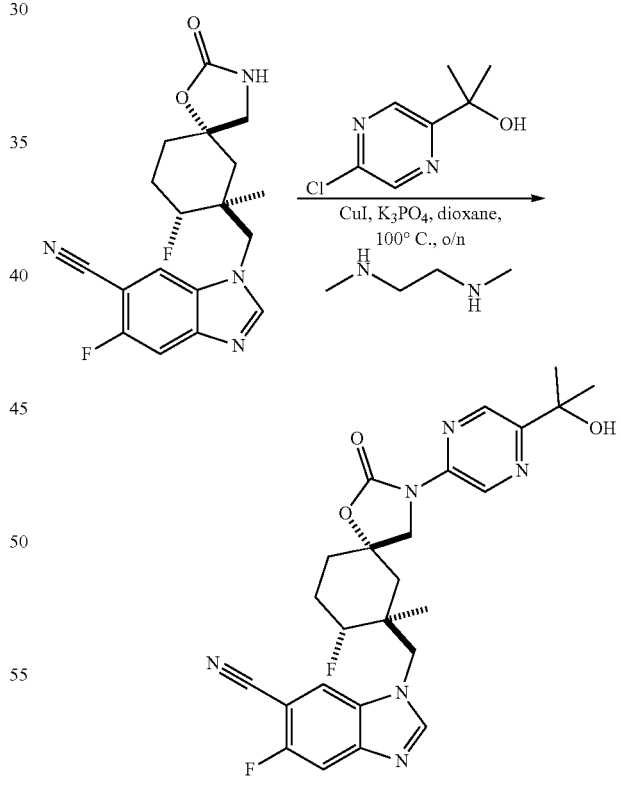

Copper(I) iodide (53.3 mg, 0.28 mmol) was added to a solution of rac-5-fluoro-1-(((5S,7S,8R)-8-fluoro-7-methyl-2-oxo-1-oxa-3-azaspiro[4.5]decan-7-yl)methyl)-1H-benzo[d]imidazole-6-carbonitrile (100 mg, 0.28 mmol), 2-(5-chloropyrazin-2-yl)propan-2-ol (48.3 mg, 0.28 mmol), $N^1,N^2$-dimethylethane-1,2-diamine (49.4 mg, 0.56 mmol) and tripotassium phosphate (119 mg, 0.56 mmol) in 1,4-dioxane (2 mL) under a nitrogen atmosphere. The resulting mixture was heated to 100° C. and stirred overnight. After cooling to room temperature, the resulting mixture was filtered, and the filtrate was concentrated under vacuum. The residue was purified by silica gel column chromatography, eluted with methanol in dichloromethane from 0% to 2%. The fractions were combined and concentrated under vacuum to afford the desired product rac-5-fluoro-1-(((5S,7S,8R)-8-fluoro-3-(5-(2-hydroxypropan-2-yl)pyrazin-2-yl)-7-methyl-2-oxo-1-oxa-3-azaspiro[4.5]decan-7-yl)methyl)-1H-benzo[d]imidazole-6-carbonitrile (100 mg) as a light yellow solid. $^1$H NMR (400 MHz, DMSO-$d_6$) δ 9.18 (d, J=1.5 Hz, 1H), 8.58 (d, J=1.5 Hz, 1H), 8.50 (s, 1H), 8.33 (d, J=5.6 Hz, 1H), 7.81 (d, J=10.1 Hz, 1H), 5.42 (s, 1H), 4.69-4.51 (m, 1H), 4.31 (d, J=2.7 Hz, 2H), 3.84 (s, 2H), 2.13-1.96 (m, 2H), 1.95-1.87 (m, 2H), 1.83-1.66 (m, 2H), 1.44 (d, J=2.0 Hz, 6H), 1.18 (s, 3H). LCMS (ESI-MS) m/z=497 [M+H]$^+$.

5-Fluoro-1-(((5S,7S,8R)-8-fluoro-3-(5-(2-hydroxypropan-2-yl)pyrazin-2-yl)-7-methyl-2-oxo-1-oxa-3-azaspiro[4.5]decan-7-yl)methyl)-1H-benzo[d]imidazole-6-carbonitrile and 5-Fluoro-1-(((5R,7R,8S)-8-fluoro-3-(5-(2-hydroxypropan-2-yl)pyrazin-2-yl)-7-methyl-2-oxo-1-oxa-3-azaspiro[4.5]decan-7-yl)methyl)-1H-benzo[d]imidazole-6-carbonitrile

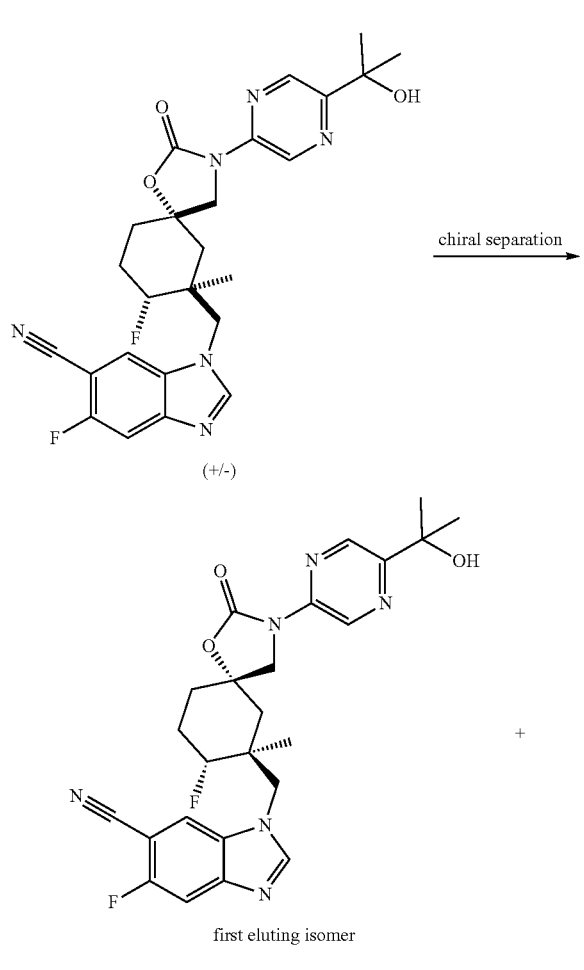

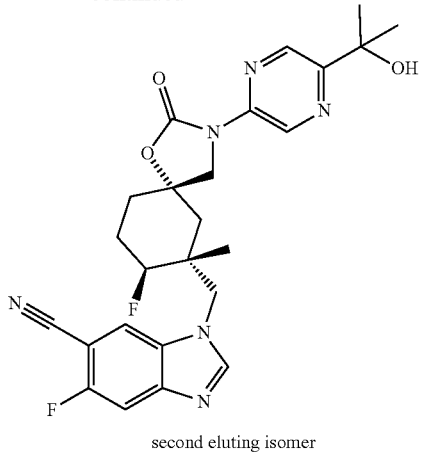

rac-5-Fluoro-1-(((5S,7S,8R)-8-fluoro-3-(5-(2-hydroxypropan-2-yl)pyrazin-2-yl)-7-methyl-2-oxo-1-oxa-3-azaspiro[4.5]decan-7-yl)methyl)-1H-benzo[d]imidazole-6-carbonitrile (100 mg, 0.20 mmol) was separated by Prep-Chiral-HPLC with the conditions: Column: CHIRALPAK IE, 2*25 cm, 5 μm; Mobile Phase A: MTBE (0.5% 2M NH$_3$-MeOH)-HPLC, Mobile Phase B: EtOH-HPLC; Flow rate: 20 ML/MIN mL/min; Gradient: isocratic 20; Wave Length: 254/220 nm nm; RT1(min): 8.262; RT2(min): 10.453; Sample Solvent: EtOH-HPLC; Injection Volume: 1.0 mL. The desired fraction was combined and lyophilized to afford the products:

First eluting isomer: 5-Fluoro-1-(((5S,7S,8R)-8-fluoro-3-(5-(2-hydroxypropan-2-yl)pyrazin-2-yl)-7-methyl-2-oxo-1-oxa-3-azaspiro[4.5]decan-7-yl)methyl)-1H-benzo[d]imidazole-6-carbonitrile (20.2 mg, 98.3% purity, 100% ee, 20.2% yield) as a white solid. $^1$H NMR (400 MHz, DMSO-$d_6$) δ 9.18 (d, J=1.5 Hz, 1H), 8.58 (d, J=1.5 Hz, 1H), 8.50 (s, 1H), 8.33 (d, J=5.6 Hz, 1H), 7.81 (d, J=10.1 Hz, 1H), 5.42 (s, 1H), 4.69-4.51 (m, 1H), 4.31 (d, J=2.7 Hz, 2H), 3.84 (s, 2H), 2.13-1.96 (m, 2H), 1.95-1.87 (m, 2H), 1.83-1.66 (m, 2H), 1.44 (d, J=2.0 Hz, 6H), 1.18 (s, 3H). LCMS (ESI-MS) m/z=497 [M+H]$^+$.

Second eluting isomer: 5-Fluoro-1-(((5R,7R,8S)-8-fluoro-3-(5-(2-hydroxypropan-2-yl)pyrazin-2-yl)-7-methyl-2-oxo-1-oxa-3-azaspiro[4.5]decan-7-yl)methyl)-1H-benzo[d]imidazole-6-carbonitrile (20.0 mg, 96.4% purity, 99.5% ee, 20.0% yield) as a white solid. $^1$H NMR (400 MHz, DMSO-$d_6$) δ 9.18 (d, J=1.5 Hz, 1H), 8.58 (d, J=1.6 Hz, 1H), 8.50 (s, 1H), 8.33 (d, J=5.6 Hz, 1H), 7.81 (d, J=10.1 Hz, 1H), 5.41 (s, 1H), 4.69-4.51 (m, 1H), 4.31 (d, J=2.7 Hz, 2H), 3.84 (s, 2H), 2.13-1.99 (m, 2H), 1.97-1.88 (m, 2H), 1.83-1.67 (m, 2H), 1.44 (d, J=2.0 Hz, 6H), 1.17 (s, 3H). LCMS (ESI-MS) m/z=497 [M+H]$^+$.

Example 19. Preparation of: 4-Chloro-1-(((5S,7S,8R)-8-fluoro-3-(5-(2-hydroxypropan-2-yl)pyrazin-2-yl)-7-methyl-2-oxo-1-oxa-3-azaspiro[4.5]decan-7-yl)methyl)-1H-benzo[d]imidazole-6-carbonitrile
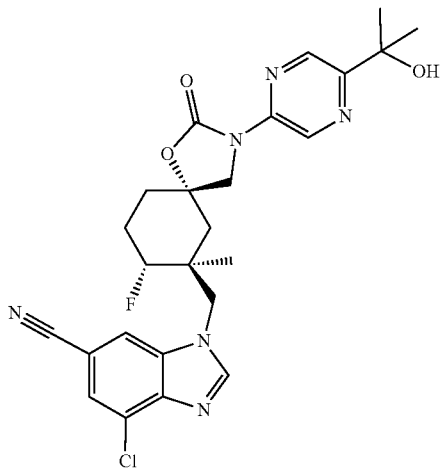 [SMILES: CC(C)(O)c1cnc(N2C[C@@]3(CC[C@@H](F)[C@](C)(Cn4cnc5c(Cl)cc(C#N)cc54)C3)OC2=O)cn1]
Reaction Scheme
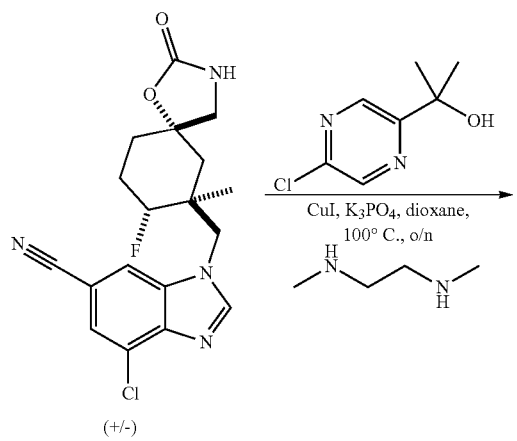
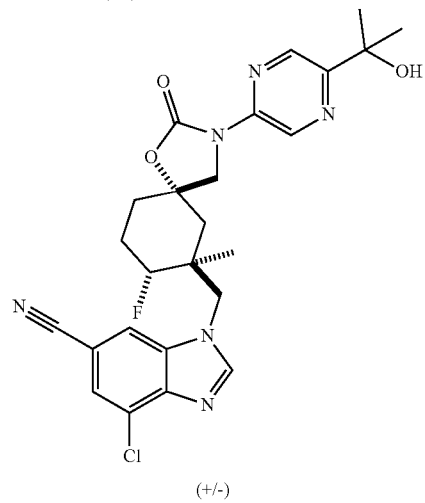
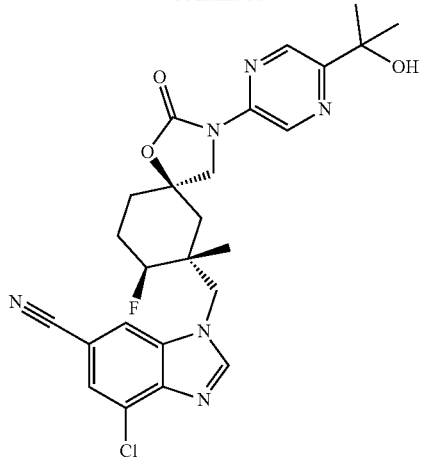
first eluting isomer
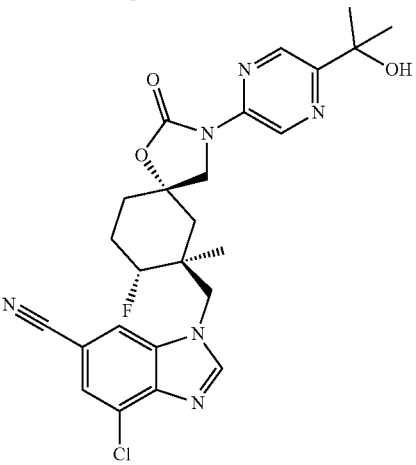
second eluting isomer
Detailed Procedure
rac-4-Chloro-1-(((5S,7S,8R)-8-fluoro-3-(5-(2-hydroxypropan-2-yl)pyrazin-2-yl)-7-methyl-2-oxo-1-oxa-3-azaspiro[4.5]decan-7-yl)methyl)-1H-benzo[d]imidazole-6-carbonitrile
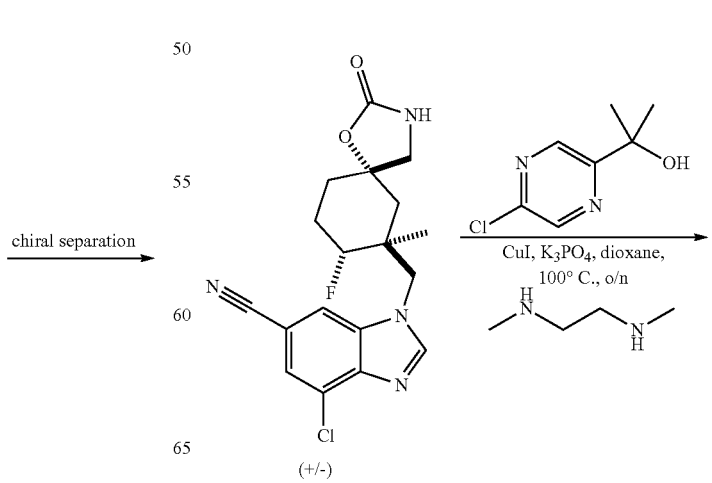

207
-continued

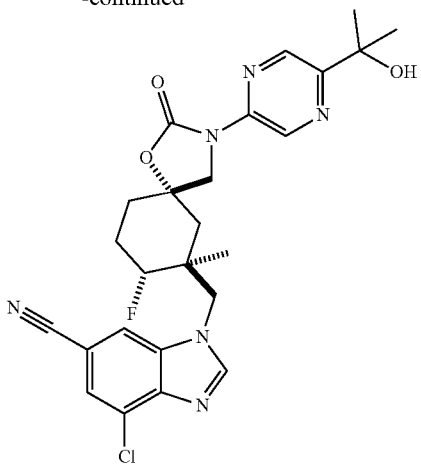

(+/-)

208
4-Chloro-1-(((5S,7S,8R)-8-fluoro-3-(5-(2-hydroxy-propan-2-yl)pyrazin-2-yl)-7-methyl-2-oxo-1-oxa-3-azaspiro[4.5]decan-7-yl)methyl)-1H-benzo[d]imidazole-6-carbonitrile and 4-chloro-1-(((5R,7R,8S)-8-fluoro-3-(5-(2-hydroxypropan-2-yl)pyrazin-2-yl)-7-methyl-2-oxo-1-oxa-3-azaspiro[4.5]decan-7-yl)methyl)-1H-benzo[d]imidazole-6-carbonitrile

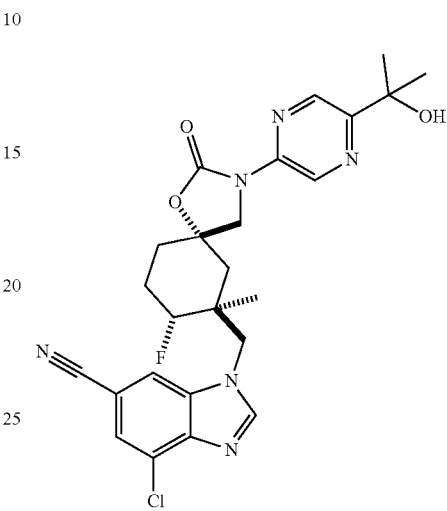

(+/-) → chiral separation

Copper(I) iodide (51.4 mg, 0.27 mmol) was added to a solution of rac-4-chloro-1-(((5S,7S,8R)-8-fluoro-7-methyl-2-oxo-1-oxa-3-azaspiro[4.5]decan-7-yl)methyl)-1H-benzo[d]imidazole-6-carbonitrile (100 mg, 0.27 mmol), 2-(5-chloropyrazin-2-yl)propan-2-ol (46.6 mg, 0.27 mmol), $N^1,N^2$-dimethylethane-1,2-diamine (47.6 mg, 0.54 mmol) and tripotassium phosphate (114.6 mg, 0.54 mmol) in 1,4-dioxane (2 mL) under a nitrogen atmosphere. The resulting mixture was heated to 100° C. and stirred overnight. After cooled to room temperature, the resulting mixture was filtered and the filtrate was concentrated under vacuum. The residue was purified by silica gel column chromatography, eluted with methanol in dichloromethane from 0% to 2%. The fractions with desired mass signal were combined and concentrated under vacuum to afford the desired product rac-4-chloro-1-(((5S,7S,8R)-8-fluoro-3-(5-(2-hydroxypropan-2-yl)pyrazin-2-yl)-7-methyl-2-oxo-1-oxa-3-azaspiro[4.5]decan-7-yl)methyl)-1H-benzo[d]imidazole-6-carbonitrile (100 mg) as a light yellow solid. $^1$H NMR (400 MHz, DMSO-$d_6$) δ 9.17 (d, J=1.5 Hz, 1H), 8.58 (d, J=1.5 Hz, 1H), 8.53 (s, 1H), 8.29 (d, J=1.3 Hz, 1H), 7.82 (d, J=1.3 Hz, 1H), 5.41 (s, 1H), 4.68-4.50 (m, 1H), 4.40-4.27 (m, 2H), 3.82 (d, J=1.4 Hz, 2H), 2.12-1.98 (m, 2H), 1.96-1.88 (m, 2H), 1.82-1.67 (m, 2H), 1.44 (d, J=2.3 Hz, 6H), 1.19 (s, 3H). LCMS (ESI-MS) m/z=513 [M+H]$^+$.

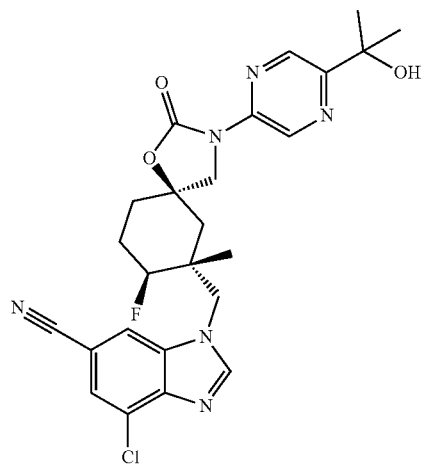

first eluting isomer

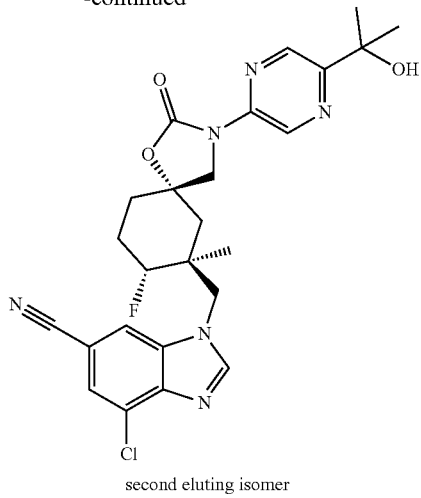

second eluting isomer rac-4-Chloro-1-(((5S,7S,8R)-8-fluoro-3-(5-(2-hydroxypropan-2-yl)pyrazin-2-yl)-7-methyl-2-oxo-1-oxa-3-azaspiro[4.5]decan-7-yl)methyl)-1H-benzo[d]imidazole-6-carbonitrile (100 mg, 0.19 mmol) was separated by Prep-Chiral-HPLC with the condition: Column: CHIRALPAK IE, 2*25 cm, 5 μm; Mobile Phase A: MtBE (0.5% 2M NH$_3$-MeOH)-HPLC, Mobile Phase B: EtOH-HPLC; Flow rate: 19 ML/MIN mL/min; Gradient: isocratic 30; Wave Length: 254/220 nm nm; RT1(min): 8.246; RT2(min): 11.53; Sample Solvent: EtOH-HPLC; Injection Volume: 0.8 mL. The desired fraction was combined and lyophilized to afford the products:

First eluting isomer: 4-Chloro-1-(((5R,7R,8S)-8-fluoro-3-(5-(2-hydroxypropan-2-yl)pyrazin-2-yl)-7-methyl-2-oxo-1-oxa-3-azaspiro[4.5]decan-7-yl)methyl)-1H-benzo[d]imidazole-6-carbonitrile (42.0 mg, 99.9% purity, 100% ee) as a white solid. $^1$H NMR (400 MHz, DMSO-d$_6$) δ 9.17 (d, J=1.5 Hz, 1H), 8.58 (d, J=1.5 Hz, 1H), 8.53 (s, 1H), 8.29 (d, J=1.3 Hz, 1H), 7.82 (d, J=1.3 Hz, 1H), 5.41 (s, 1H), 4.68-4.50 (m, 1H), 4.40-4.27 (m, 2H), 3.82 (d, J=1.4 Hz, 2H), 2.12-1.98 (m, 2H), 1.96-1.88 (m, 2H), 1.82-1.67 (m, 2H), 1.44 (d, J=2.3 Hz, 6H), 1.19 (s, 3H). LCMS (ESI-MS) m/z=513 [M+H]$^+$.

Second eluting isomer: 4-Chloro-1-(((5S,7S,8R)-8-fluoro-3-(5-(2-hydroxypropan-2-yl)pyrazin-2-yl)-7-methyl-2-oxo-1-oxa-3-azaspiro[4.5]decan-7-yl)methyl)-1H-benzo[d]imidazole-6-carbonitrile (45.3 mg, 98.8% purity, 99.7% ee) as a white solid. $^1$H NMR (400 MHz, DMSO-d$_6$) δ 9.17 (d, J=1.5 Hz, 1H), 8.58 (d, J=1.5 Hz, 1H), 8.53 (s, 1H), 8.29 (d, J=1.3 Hz, 1H), 7.82 (d, J=1.3 Hz, 1H), 5.41 (s, 1H), 4.68-4.50 (m, 1H), 4.40-4.27 (m, 2H), 3.82 (d, J=1.4 Hz, 2H), 2.12-1.98 (m, 2H), 1.96-1.88 (m, 2H), 1.82-1.67 (m, 2H), 1.44 (d, J=2.3 Hz, 6H), 1.19 (s, 3H). LCMS (ESI-MS) m/z=513 [M+H]$^+$.

Example 20. Preparation of: 1-(((5S,7S,8S)-8-Fluoro-3-(5-(2-hydroxypropan-2-yl)pyrazin-2-yl)-7-methyl-2-oxo-1-oxa-3-azaspiro[4.5]decan-7-yl)methyl)-1H-benzo[d]imidazole-6-carbonitrile

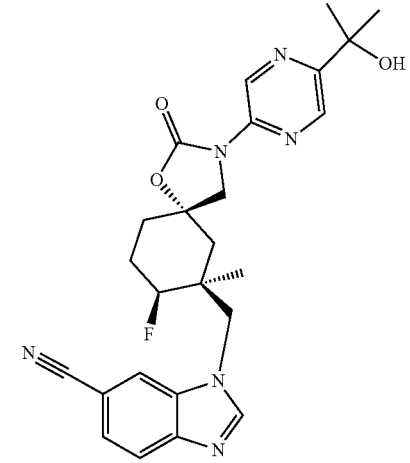 [SMILES: CC(C)(O)c1cnc(N2C[C@@]3(CC[C@H](F)[C@](C)(Cn4cnc5ccc(C#N)cc54)C3)OC2=O)cn1]

Using procedures similar to those described herein (see Scheme 7), the title compound was prepared.

Example 21. Preparation and Characterization of a Crystal Form of 1-(((5S,7S,8R)-8-Fluoro-3-(5-(2-hydroxypropan-2-yl)pyrazin-2-yl)-7-methyl-2-oxo-1-oxa-3-azaspiro[4.5]decan-7-yl)methyl)-1H-benzo[d]imidazole-6-carbonitrile

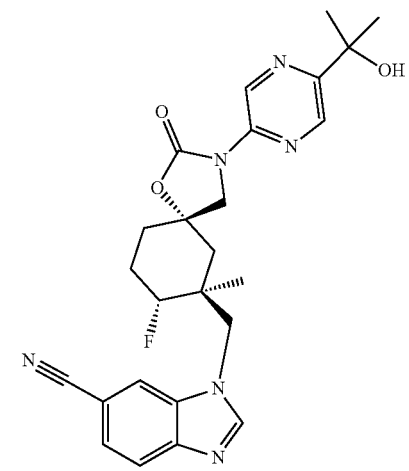 [SMILES: CC(C)(O)c1cnc(N2C[C@@]3(CC[C@@H](F)[C@](C)(Cn4cnc5ccc(C#N)cc54)C3)OC2=O)cn1]

249.15 mg of 1-(((5S,7S,8R)-8-Fluoro-3-(5-(2-hydroxypropan-2-yl)pyrazin-2-yl)-7-methyl-2-oxo-1-oxa-3-azaspiro[4.5]decan-7-yl)methyl)-1H-benzo[d]imidazole-6-carbonitrile was weighed into 40 mL glass bottle, 10 mL of anhydrous MeOH was added to bottle and the mixture was stirred (700 rpm) at 25° C. for 3 days. The suspension was dried in a vacuum oven at 30° C. for 3 hours followed by characterization by XRPD (FIG. 1).

The diffractogram was obtained at room temperature using a Bruker D8 Advance powder diffractometer using copper Kα radiation (40 kV/40 mA), a range of 3-40 degrees 0.020, a step time of 0.12 s, and detector with a 10-degree window. Selected peaks are shown in the following Table
| Selected XPRD Peaks | | | | | |
|---|---|---|---|---|---|
| 7.02 | 10.35 | 18.89 | 19.47 | 24.04 | 26.55 |
| 7.04 | 10.37 | 18.91 | 19.49 | 24.06 | 26.59 |
| 7.07 | 15.56 | 19.20 | 22.39 | 25.15 | |
| 7.09 | 15.58 | 19.22 | 22.41 | 25.21 | |
| 7.11 | 15.60 | 19.24 | 22.43 | 25.23 | |
| 10.31 | 18.85 | 19.42 | 24.00 | 26.51 | |
| 10.33 | 18.87 | 19.45 | 24.02 | 26.53 | |
Example 22. Preparation of Additional Compounds
Using known procedures and intermediates or using procedures and intermediates similar to those described in the Examples above, the following compounds can be prepared.
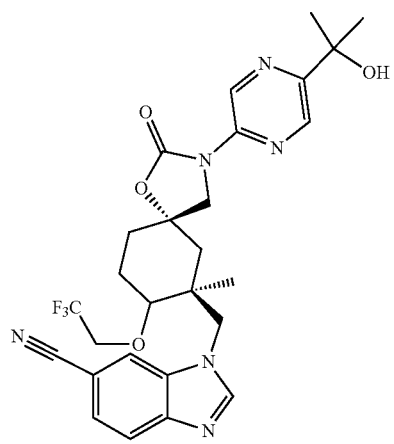
-continued
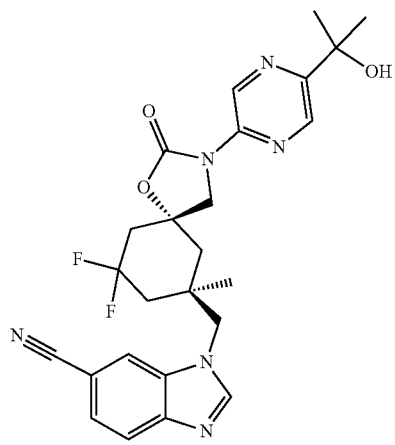
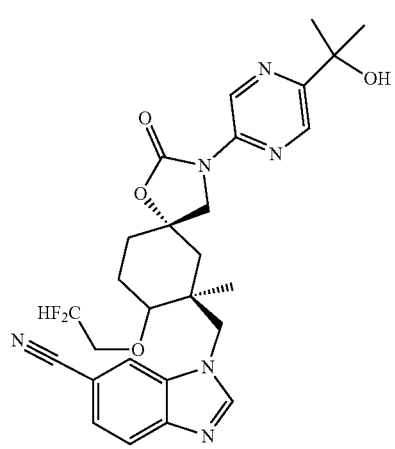
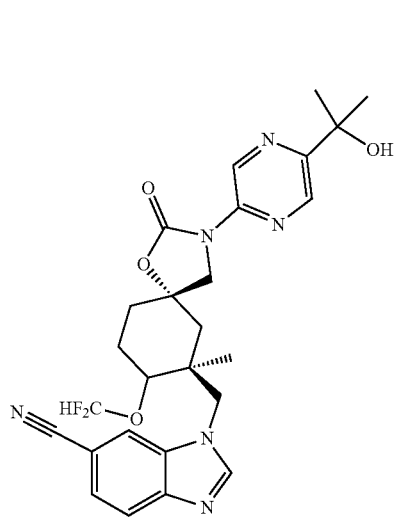
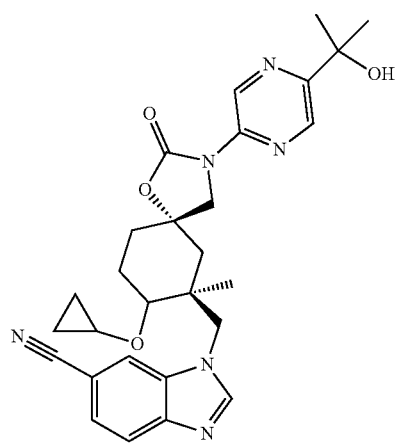

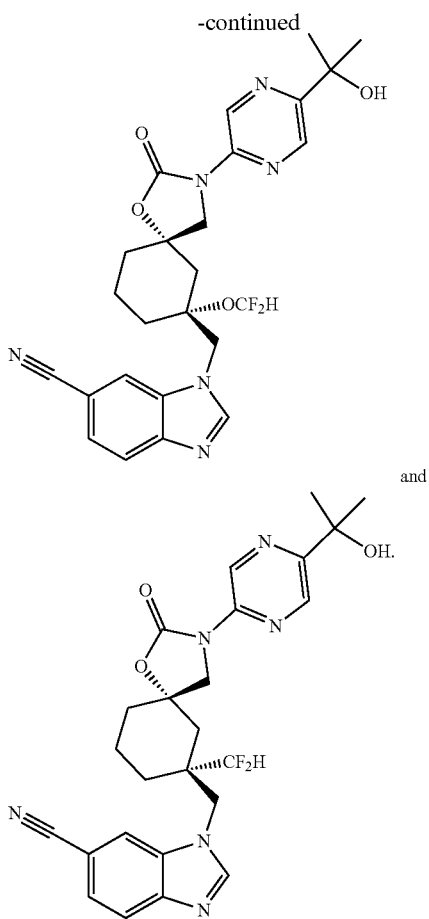

and

Example 23. TRPV4 Calcium Assay Methods

Transfection

Human embryonic kidney 293T (HEK293T/293T) cells are cultured in complete media (Dulbecco's Modified Eagle Medium (DMEM), containing 10% fetal bovine serum (FBS) and 1×penicillin-streptomycin) in a T-75 tissue culture flask. At 90% confluency, cells are detached using TrypLE™ Express cell dissociation buffer. TrypLE™ Express buffer is neutralized by adding culture media in excess. Cells are gently triturated and counted using trypan blue in a Countess 3 automated cell counter. Cells are transferred to a 50 mL conical tube and spun down at 1000 rotations per minute (RPM) for five minutes in a benchtop centrifuge. Media containing detaching enzyme is aspirated off the pellet, followed by resuspension to the desired concentration of $2 \times 10^6$ cells per mL in complete DMEM.

Transfection preparations were scaled using a combination of 6 μg of TRPV4 wild-type or mutant plasmid DNA, 36 μL of Fugene6 transfection reagent, and 1000 μL of OptiMEM media for every $2 \times 10^6$ cells needed. The transfection mix is left to incubate for 20 minutes at room temperature. Total seeding mixture (1000 μL $2 \times 10^6$ cells, 1000 μL transfection mix previously described, and 1000 μL complete DMEM) for one transfection is combined into a 15 mL conical tube. The cells and transfection plasmid are mixed thoroughly and dispensed into a reservoir. This is plated at 25pL per well in a black 384, black-well, clear-bottom, tissue-culture treated plate. This yields approximately 16,000 cells per well. Plasmid DNA constructs were designed by Actio Biosciences in conjunction with Genscript, and generated by Genscript, for all hTRPV4 wild-type and hTRPV4 P/LP (ClinVar) mutations (G78W, P82S, T891, P97R, R186Q, R232C, R232P, R237G, R237Q, R237L, R269C, R269H, R269S, G270V, R271P, F273L, K276E, E278K, G280S, Y281S, R315G, R315W, R316C, R31611, R316L, R316S, 1331F, D333G, S403T, K403T, K407E, S542P, S542Y, L543R, Y591N, R594C, R594H, R594S, G600E, Y602C, R616Q, F617L, L618P, V620I, A716S, A716T, L735R, T7401, R775K, W785R, E797D, E797K, P799A, P799R, P799S, P799L, G800D, K801E, P827H, F471del, N797del). The remaining cells are plated in the same manner, in a 384, white-well, clear-bottom, tissue-culture treated plate for expression and relative cell number determination. Plates are placed in the incubator at 37° C. overnight.

Determination of Relative Cell Number

Relative cell number were determined using the Cell-Titer Fluor (CTF) assay kit from Promega™. Reagents were prepared per manufacturer's instructions. An equal volume of CTF reagent was added to each well. The cell plate was returned to the incubator at 37° C. for 30 minutes. After 30 minutes, the plate was read on BMG CLARIOstar using EX/EM settings: 380-400 nm excitation/505 nm emission.

Determination of Expression

Nano-Glo® HiBiT Lytic reagents were prepared as per manufacturer's instructions. This assay was compatible with the CTF assay previously described. Using the same plate of cells from the CTF assay, equal volume of HiBit lytic reagent was added to each well. Reagent and cells were left at room temperature for 10 minutes before reading luminescence on the BMG CLARIOstar.

Compound Preparation

Agonist Mode

TRPV4 agonist was brought to 10 mM in DMSO. DMSO concentration was kept constant throughout the dilution of any compound. DMSO negative control and concentration-response curves were nanoliter-spotted via PICO8 automated dispenser at 6×test concentration into a 384 w clear polypropylene plate containing 1×HBSS+20 mM HEPES buffer.

Antagonist Mode

Compounds were brought to 10 mM in DMSO. DMSO concentration was kept constant throughout the dilution of any compound. DMSO negative control and concentration-response curves were nanoliter-spotted via PICO8 automated dispenser at 5×test concentration into a 384 w clear polypropylene plate containing 1×HBSS+20 mM HEPES buffer. A predetermined concentration equivalent to the $EC_{80}$ of TRPV4 agonist on hTRPV4 was prepared at 6× in 1×HBSS+20 mM HEPES and loaded into a separate 384-well v-bottom polypropylene plate.

Calcium Flux Assay

Approximately 18 hours post-transfection, the cell plates were removed from the incubator and equal volume (25 uL) Calcium 6 dye was gently added. Calcium 6 dye containing probenecid (final 5 mM) was prepared per manufacturer's instructions. Cell plate was returned to the incubator for 1 hour, at 37° C.

FLIPR Penta was programmed to add compound using the following settings

Pipettor Head=384
Read Mode 1 Excitation Wavelength=470_495
Read Mode 1 Emission Wavelength=515_575
Read Mode 1 Exposure=0.1000
Read Mode 1 Gain=6.50
Read Mode 1 Excitation Intensity=20

Volume of addition=12.5 μL
Height=40 μL
Speed=15 μL/second

Raw data was exported and analyzed for maximum signal (RFU) afer agonist addition—the average baseline (RFU) in the first 15 seconds per well. Data was plotted in GraphPad Prism to determine $EC_{50}$ or $IC_{50}$ of the molecules. Data for representative compounds is provided in the following table.

Example 24. CYP3A4 Incubation Assay

Compounds (final concentration of 1 mM) were incubated in 100 mM phosphate buffer containing 100 pmol/mL recombinant human CYP3A4 enzyme for 0, 5, 10, 15 and 25 minutes. Testosterone was used as positive control. Reaction was initiated by the addition of NADPH (final concentration of 1 mM) and carried out at 37° C. The reaction was stopped by the addition of 4 volumes of cold acetonitrile (with 100 nM alprazolam, 200 nM labetalol, 200 nM imipramine and 2 μM ketoprofen as internal standards). Samples were centrifuged at 3,220 g for 40 minutes to precipitate protein. 70 μL supernatant was transferred to the analysis plate containing 110 μL of acetonitrile for LC-MS/MS analysis.

Data for representative compounds of formula (I) from the assays of Examples 23 and 24 is provided in the following table.

| Example | Compound | Human TRPV4 $Ca^{2+}$ Assay $IC_{50}$ (nM)[1] | CYP3A4 $CI_{int}$ (μL/min/ pmol CYP450) | Hepatocytes predicted clearance (L/h/kg) in mouse/rat/dog/cyno/ human |
|---|---|---|---|---|
| GSK2798745 | | 10 | 0.18 | 2.66/1.24/0.43/1.29/<0.01 |
| 1 | | 606 | N/A | 7.11/0.65/0.69/0.24/0.27 |

-continued

| Example | Compound | Human TRPV4 Ca²⁺ Assay IC$_{50}$ (nM)[1] | CYP3A4 CI$_{int}$ (μL/min/ pmol CYP450) | Hepatocytes predicted clearance (L/h/kg) in mouse/rat/dog/cyno/ human |
|---|---|---|---|---|
| 2 | | 217 | 0.08, <0.07 | 1.86/<0.01/0.08/2.09/<0.01 |
| 3 | | 852 | N/A | 7.85/4.77/1.04/10.9/0.19 |
| 4 | | 6402 | 0.14, 0.14 | 6.41/0.07/2.46/1.33/0.07 |

-continued

| Example | Compound | Human TRPV4 Ca²⁺ Assay IC$_{50}$ (nM)[1] | CYP3A4 CI$_{int}$ (μL/min/ pmol CYP450) | Hepatocytes predicted clearance (L/h/kg) in mouse/rat/dog/cyno/ human |
|---|---|---|---|---|
| 5 | | 13 | 0.09, <0.07 | 0.77/0.46/0.66/0.06/<0.01 |
| 6 | | 8 | <0.07, <0.07 | 1.47/0.5/0.19/7.22/0.39 |
| 7 | | 11 | <0.07, <0.07 | 2.59/0.4/<0.01/0.27/0.06 |

-continued

| Example | Compound | Human TRPV4 Ca²⁺ Assay IC₅₀ (nM)[1] | CYP3A4 CI$_{int}$ (μL/min/ pmol CYP450) | Hepatocytes predicted clearance (L/h/kg) in mouse/rat/dog/cyno/ human |
|---|---|---|---|---|
| 8 | | 391^ | <0.07, <0.07 | 16.87/3.27/1.8/2.25/<0.01 |
| 9 | | 213 | 0.42, 0.33 | N/A |
| 10 | | 158 | 0.22, 0.21 | N/A |

-continued

| Example | Compound | Human TRPV4 Ca²⁺ Assay IC$_{50}$ (nM)[1] | CYP3A4 Cl$_{int}$ (μL/min/ pmol CYP450) | Hepatocytes predicted clearance (L/h/kg) in mouse/rat/dog/cyno/ human |
|---|---|---|---|---|
| 11 | | 39 | N/A | 30.91/15.07/3.8/5.43/1.04 |
| 12 | | 103 | N/A | 26.96/4.95/17.07/6.08/0.45 |
| 13 | | 496 | N/A | N/A |

-continued

| Example | Compound | Human TRPV4 Ca²⁺ Assay IC₅₀ (nM)[1] | CYP3A4 Cl$_{int}$ (μL/min/ pmol CYP450) | Hepatocytes predicted clearance (L/h/kg) in mouse/rat/dog/cyno/ human |
|---|---|---|---|---|
| 14 | | 162 | N/A | N/A |
| 15 | | 8 | 0.09, <0.07 | 1.67/0.27/0.26/1.7/0.23 |
| 16 | | 2132 | 0.20, 0.19 | 5.44/4.16/0.24/1.36/0.33 |

-continued

| Example | Compound | Human TRPV4 Ca$^{2+}$ Assay IC$_{50}$ (nM)[1] | CYP3A4 Cl$_{int}$ (μL/min/ pmol CYP450) | Hepatocytes predicted clearance (L/h/kg) in mouse/rat/dog/cyno/ human |
|---|---|---|---|---|
| 17 | | 5737 | 0.07, <0.07 | 7.13/2.36/0.08/2.62/0.09 |
| 18 | | 9 | N/A | N/A |
| 19 | | 9 | N/A | N/A |

[1] All potency values are the average of at least 3 separate experiments
*potency value only the result of one experiment

Example 25. CYP3A4 Incubation

The following table indicates the percentage remaining for the indicated examples after incubation with recombinant Human CYP3A4 after 25 minutes under the same conditions as described for Example 23.

| Example | Metabolic Stability in Recombinant Human CYP3A4 + NADPH (% remaining after 25 min) |
|---|---|
| GSK2798745 | 69.6 |
| 5 | 100 |
| 15 | 91.3 |

Example 26 TRP Selectivity for The Compound of Example 5

The compound of Example 5 was tested for selectivity against a panel of Human TRP family ion channels in a TRP Family FLIPR Assay as described below.
1. TRPC3 channels (human TRPC3 variant 1 gene, expressed in HEK293 cells).
2. TRPC4 channels (human TRPC4 gene, expressed in HEK293 cells).
3. TRPC5 channels (human TRPC5 gene, expressed in HEK293 cells).
4. TRPC6 channels (human TRPC6 gene, expressed in HEK293 cells).
5. TRPM2 channels (human TRPM2 gene, transiently expressed in HEK293 cells).
6. TRPM3 channels (human TRPM3 gene, transiently expressed in HEK293 cells).
7. TRPM4 channels (human TRPM4 gene, expressed in CHO cells).
8. TRPM5 channels (human TRPM5 gene, expressed in CHO cells).
9. TRPA1 channels (humanTRPA1 gene, expressed in CHO cells).
10. TRPV1 channels (human TRPV1 gene, expressed in HEK293 cells).
11. TRPV2 channels (human TRPV2 gene, transiently expressed in HEK293 cells).
12. TRPV3 channels (human TRPV3 gene, transiently expressed in HEK293 cells).
13. TRPV4 channels (human TRPV4 gene, expressed in CHO cells).
14. TRPV5 channels (human TRPV5 gene, transiently expressed in HEK293 cells).
15. TRPV6 channels (human,TRPV6 gene, expressed in HEK293 cells).

Data acquisition was performed via the FLIPR Control software supplied with the FLIPR System (MDS-AT) and data was analyzed using Microsoft Excel (Microsoft Corp., Redmond, WA) or GraphPad Prism. Concentration-response data was fitted to a Hill equation of the following form:

$$\text{RESPONSE} = \text{Base} + \frac{\text{Max} - \text{Base}}{1 + \left(\frac{xhalf}{x}\right)^{rate}}$$

where Base is the response at low concentrations of test article, Max is the maximum response at high concentrations, xhalf the $EC_{50}$, or $IC_{50}$, the concentration of test article producing either half-maximal activation or inhibition, and rate is the Hill coefficient. Nonlinear least squares fits were made assuming a simple binding model. If appropriate, fits were weighted by the standard deviation. No assumptions about the fit parameters was made; the fit parameters were determined by the algorithm.

Results and Summary

The effect of each test article was evaluated at eight (8) concentrations: 0.003, 0.01, 0.03, 0.1, 0.3, 1, 3 and 10 µM, n≤4 wells/concentration). The test article results are presented as % of $E_{MAX}$ (for agonists) and % of control (for antagonists) The positive control results confirmed the sensitivity of the test systems to ion channel activation and inhibition.

Agonist/Antagonist Effects of the Test Articles on TRPC3 Channels

In agonist mode, reference agonist, GSK1702934A, was used as internal control (0-30 µM). Effects of test articles were calculated as % of $E_{MAX}$ response elicited by reference agonist, GSK1702934A (30 µM).

In the antagonist mode, the channels were activated with the positive control agonist (15 µM GSK1702934A). Inhibition of the signal by test articles were calculated relatively to signal produced by agonist alone. Reference antagonist, verapamil, was used as internal control.

Agonist/Antagonist Effects of the Test Articles on TRPC4 and TRPC5 Channels

In agonist mode, reference agonist, (−)-Englerin A, was use as internal control (0-30 µM). Effects of test articles were calculated as % of $E_{MAX}$ response elicited by reference agonist, (−)-Englerin A (30 µM).

In the antagonist mode, the channels were activated with the positive control agonist (0.5 µM (−)-Englerin A). Inhibition of the signal by test articles were calculated relatively to signal produced by agonist alone. Reference antagonist, verapamil, was used as internal control.

Agonist/Antagonist Effects of the Test Articles on TRPC6 Channels

In agonist mode, reference agonist, Na-ATP, was use as internal control (0-100 µM). Effects of test articles were calculated as % of $E_{MAX}$ response elicited by reference agonist, Na-ATP (100 µM).

In the antagonist mode, the channels were activated with the positive control agonist (10 µM Na-ATP). Inhibition of the signal by test articles were calculated relatively to signal produced by agonist alone. Reference antagonist, verapamil, was used as internal control.

Agonist/Antagonist Effects of the Test Articles on TRPM2 Channels

In agonist mode, reference agonist, $H_2O_2$, was use as internal control (0-1000 µM). Effects of test articles were calculated as % of $E_{MAX}$ response elicited by reference agonist, $H_2O_2$, (333 µM).

In the antagonist mode, the channels were activated with the positive control agonist (300 µM $H_2O_2$,). Inhibition of the signal by test articles were calculated relatively to signal produced by agonist alone. Reference antagonist, flufenamic acid (0-1000 µM), was used as internal control.

Agonist/Antagonist Effects of the Test Articles on TRPM3 Channels

In agonist mode, reference agonist, pregnenolone, was use as internal control (0-100 µM). Effects of test articles were calculated as % of $E_{MAX}$ response elicited by reference agonist, pregnenolone (100 µM).

In the antagonist mode, the channels were activated with the positive control agonist (pregnenolone 30 µM). Inhibition of the signal by test articles were calculated relatively to signal produced by agonist alone. Reference antagonist, mefenamic acid (0-200 μM), was used as internal control.

Agonist/Antagonist Effects of the Test Articles on TRPM4 Channels

In agonist mode, reference agonist, A23187, was use as internal control (0-30 μM). Effects of test articles were calculated as % of $E_{MAX}$ response elicited by reference agonist, A23187 3.3 μM.

In the antagonist mode, the channels were activated with the positive control agonist (A23187 10 μM). Inhibition of the signal by test articles were calculated relatively to signal produced by agonist alone. Reference antagonist, flufenamic acid (0-200 μM), was used as internal control.

Agonist/Antagonist Effects of the Test Articles on TRPM5 Channels

In agonist mode, reference agonist, Mg-ATP, was use as internal control (0-100 μM). Effects of test articles were calculated as % of $E_{MAX}$ response elicited by reference agonist, Mg-ATP 33.3 μM.

In the antagonist mode, the channels were activated with the positive control agonist (Mg-ATP 75 μM). Inhibition of the signal by test articles were calculated relatively to signal produced by agonist alone. Reference antagonist, triphenylphosphine oxide (TPPO, 0-300 μM), was used as internal control.

Agonist/Antagonist Effects of the Test Articles on TRPA1 Channels

In agonist mode, reference agonist, mustard oil, was use as internal control (0-600 μM). Effects of test articles were calculated as % of $E_{MAX}$ response elicited by reference agonist, mustard oil 600 μM.

In the antagonist mode, the channels were activated with the positive control agonist (mustard oil 80 μM). Inhibition of the signal by test articles were calculated relatively to signal produced by agonist alone. Reference antagonist, ruthenium red (0-30 μM), was used as internal control.

Agonist/Antagonist Effects of the Test Articles on TRPV1 Channels

In agonist mode, reference agonist, capsaicin, was use as internal control (0-1 μM). Effects of test articles were calculated as % of $E_{MAX}$ response elicited by reference agonist, capsaicin 1 μM.

In the antagonist mode, the channels were activated with the positive control agonist (capsaicin 0.1 μM). Inhibition of the signal by test articles were calculated relatively to signal produced by agonist alone. Reference antagonist, ruthenium red (0-10 μM), was used as internal control.

Agonist/Antagonist Effects of the Test Articles on TRPV2 Channels

In agonist mode, reference agonist, cannabidiol, was use as internal control (0-300 μM). Effects of test articles were calculated as % of $E_{MAX}$ response elicited by reference agonist, cannabidiol 300 μM.

In the antagonist mode, the channels were activated with the positive control agonist (capsaicin 100 μM). Inhibition of the signal by test articles were calculated relatively to signal produced by agonist alone. Reference antagonist, ruthenium red (0-30 μM), was used as internal control.

Agonist/Antagonist Effects of the Test Articles on TRPV3 Channels

In agonist mode, reference agonist, 2-aminoethoxydiphenylborate (2-APB), was used as internal control (0-300 μM). Effects of test articles were calculated as % of $E_{MAX}$ response elicited by reference agonist, cannabidiol 300 μM.

In the antagonist mode, the channels were activated with the positive control agonist (2-APB 50 μM). Inhibition of the signal by test articles were calculated relatively to signal produced by agonist alone. Reference antagonist, ruthenium red (0-30 μM), was used as internal control.

Agonist/Antagonist Effects of the Test Articles on TRPV4 Channels

In agonist mode, reference agonist, GSK1016790A, was use as internal control (0-3 μM). Effects of test articles were calculated as % of $E_{MAX}$ response elicited by reference agonist, GSK1016790A 3 μM.

In the antagonist mode, the channels were activated with the positive control agonist (GSK1016790A 0.3 μM). Inhibition of the signal by test articles were calculated relatively to signal produced by agonist alone. Reference antagonist, ruthenium red (0-10 μM), was used as internal control.

Antagonist Effects of the Test Articles on TRPV5 Channels

In the antagonist mode, the channels were activated with 60 μM cadmium ion. Inhibition of the signal by test articles were calculated relative to signal produced in control. Reference antagonist, 2-APB (0-300 μM), was used as internal control.

Antagonist Effects of the Test Articles on TRPV6 Channels

In the antagonist mode, the channels were activated with 0.9 mM calcium ion. Inhibition of the signal by test articles were calculated relative to signal produced in control. Reference antagonist, 2-APB (0-300 μM), was used as internal control.

The data for the compound of Example 5 is provided in the following Table.

| Human TRP Channel | IC$_{50}$ (μM) | EC$_{50}$ (μM) |
|---|---|---|
| hTRPC3 | >10 | >10 |
| hTRPC4 | >1 | >10 |
| hTRPC5 | >10 | >10 |
| hTRPC6 | >10 | >10 |
| hTRPM2 | >10 | >10 |
| hTRPM3 | >10 | >10 |
| hTRMP4 | >10 | >10 |
| hTRPM5 | >10 | >10 |
| hTRPA1 | >10 | >10 |
| hTRPV1 | >10 | >10 |
| hTRPV2 | >10 | >10 |
| hTRPV3 | >10 | >10 |
| hTRPV4 | 0.014 | >10 |
| hTRPV5 | >10 | ND |
| hTRPV6 | >10 | ND |

Example 27. The following illustrate representative pharmaceutical dosage forms, containing a compound of formula I ('Compound X'), for therapeutic or prophylactic use in humans.

| (i) Tablet 1 | mg/tablet |
|---|---|
| Compound X= | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X= | 20.0 |
| Microcrystalline cellulose | 410.0 |

| | |
|---|---|
| Starch | 50.0 |
| Sodium starch glycolate | 15.0 |
| Magnesium stearate | 5.0 |
| | 500.0 |

| (iii) Capsule | mg/capsule |
|---|---|
| Compound X= | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
|---|---|
| Compound X= | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The disclosure has been described with reference to various specific and preferred embodiments and techniques. However, it should be understood that many variations and modifications may be made while remaining within the spirit and scope of the disclosure.

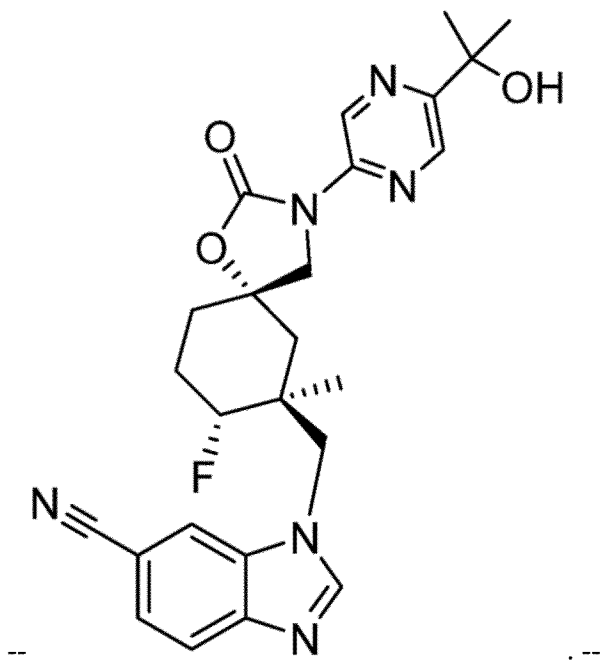

What is claimed is:

1. A compound or salt selected from the group consisting of:

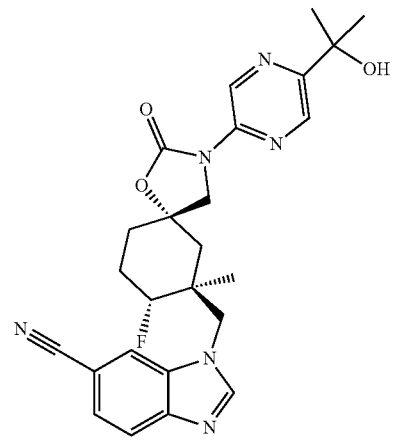

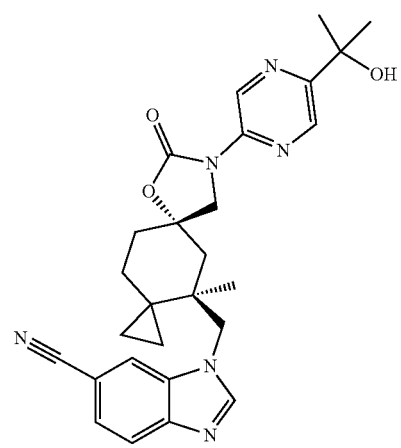

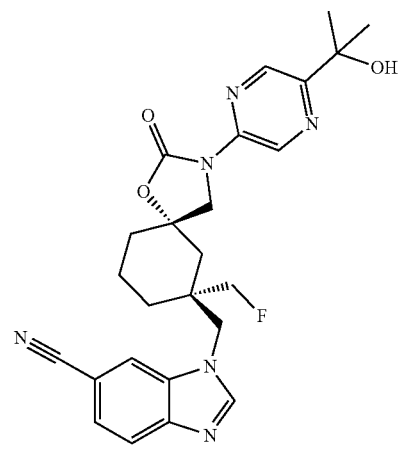

235
-continued
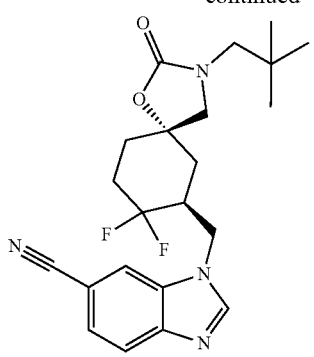
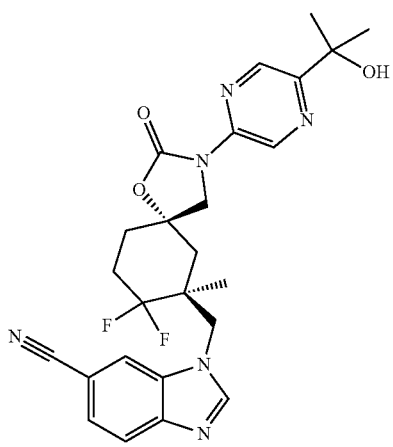
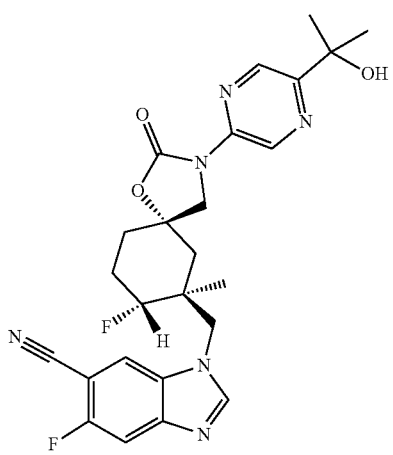
and
236
-continued
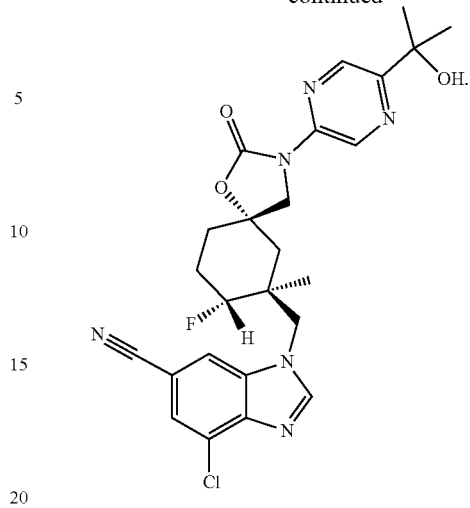
and salts thereof.
2. The compound of claim 1, which is:
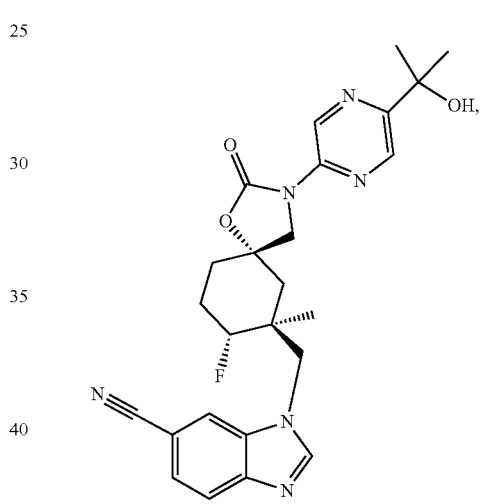
or a salt thereof.
3. The compound of claim 1, which is:
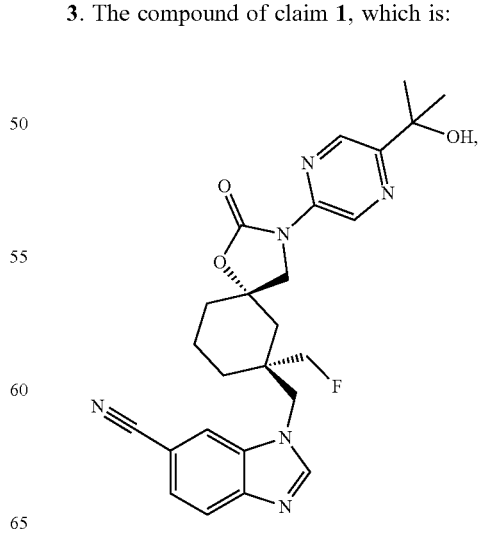
or a salt thereof.

4. The compound of claim 1, which is:

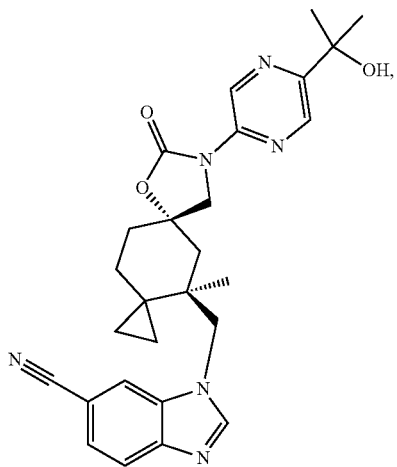 [SMILES: CC(C)(O)c1cnc(N2C[C@@]3(CCC4(CC4)[C@](C)(Cn4cnc5ccc(C#N)cc54)C3)OC2=O)cn1]

or a salt thereof.

5. The compound of claim 1, which is:

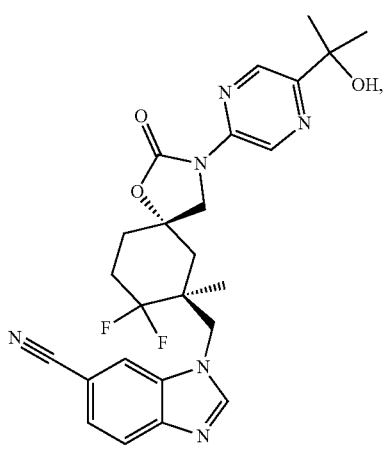 [SMILES: CC(C)(O)c1cnc(N2C[C@@]3(CCC(F)(F)[C@](C)(Cn4cnc5ccc(C#N)cc54)C3)OC2=O)cn1]

or a salt thereof.

6. The compound of claim 1, which is:

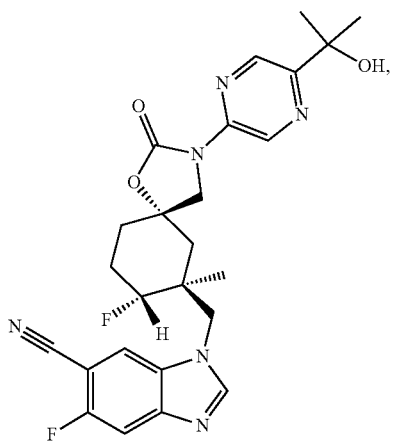 [SMILES: CC(C)(O)c1cnc(N2C[C@@]3(CC[C@@H](F)[C@](C)(Cn4cnc5cc(F)c(C#N)cc54)C3)OC2=O)cn1]

or a salt thereof.

7. The compound of claim 1, which is:

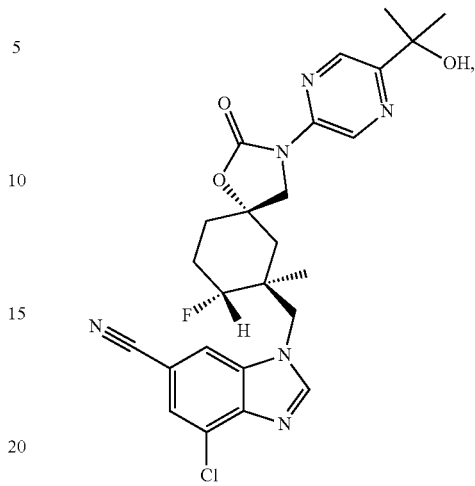

or a salt thereof.

8. A pharmaceutical composition comprising the compound of claim 1, or a salt thereof, and a pharmaceutically acceptable excipient.

9. A pharmaceutical composition comprising the compound of claim 2, or a salt thereof, and a pharmaceutically acceptable excipient.

10. A pharmaceutical composition comprising the compound of claim 3, or a salt thereof, and a pharmaceutically acceptable excipient.

11. A pharmaceutical composition comprising the compound of claim 4, or a salt thereof, and a pharmaceutically acceptable excipient.

12. A pharmaceutical composition comprising the compound of claim 5, or a salt thereof, and a pharmaceutically acceptable excipient.

13. A pharmaceutical composition comprising the compound of claim 6, or a salt thereof, and a pharmaceutically acceptable excipient.

14. A pharmaceutical composition comprising the compound of claim 7, or a salt thereof, and a pharmaceutically acceptable excipient.

15. A compound which is:

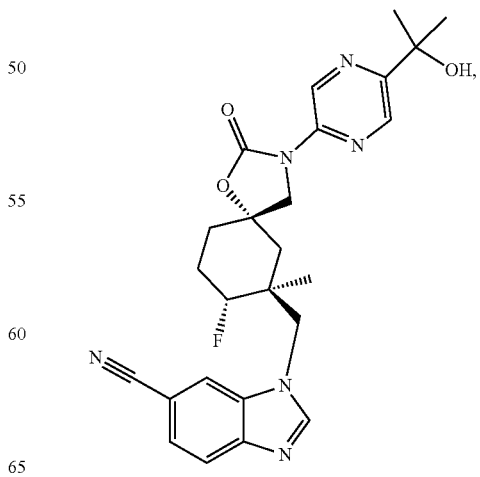

or a salt thereof.

16. A compound which is:

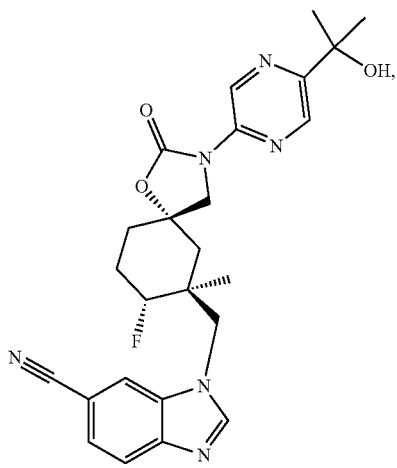 [SMILES: CC(C)(O)c1cnc(N2C[C@@]3(CC[C@@H](F)[C@](C)(Cn4cnc5ccc(C#N)cc54)C3)OC2=O)cn1]

17. A salt of a compound, wherein the compound is:

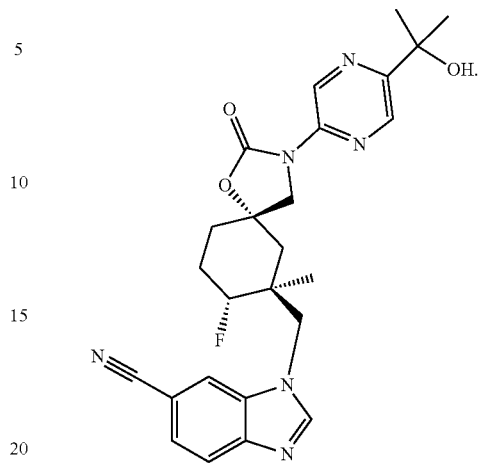

18. A pharmaceutical composition comprising the compound of claim 15, or a salt thereof, and a pharmaceutically acceptable excipient.

19. A pharmaceutical composition comprising the compound of claim 16, or a salt thereof, and a pharmaceutically acceptable excipient.

20. A pharmaceutical composition comprising the salt of claim 17 and a pharmaceutically acceptable excipient.

* * * * *

UNITED STATES PATENT AND TRADEMARK OFFICE
CERTIFICATE OF CORRECTION

PATENT NO. : 11,987,577 B2  
APPLICATION NO. : 18/363195  
DATED : May 21, 2024  
INVENTOR(S) : Ashley Katana et al.

Page 1 of 3

It is certified that error appears in the above-identified patent and that said Letters Patent is hereby corrected as shown below:

In the Claims

At Column 236, Claim number 1, Line number 5:

"  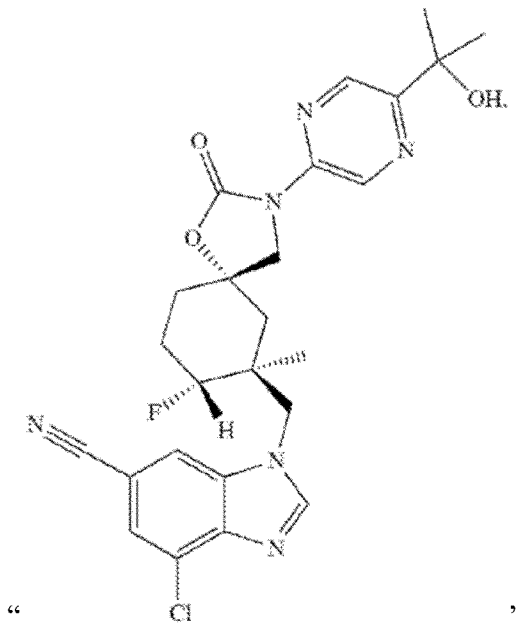  "

Signed and Sealed this  
Ninth Day of July, 2024

Katherine Kelly Vidal  
*Director of the United States Patent and Trademark Office*

CERTIFICATE OF CORRECTION (continued)
U.S. Pat. No. 11,987,577 B2

Should read:

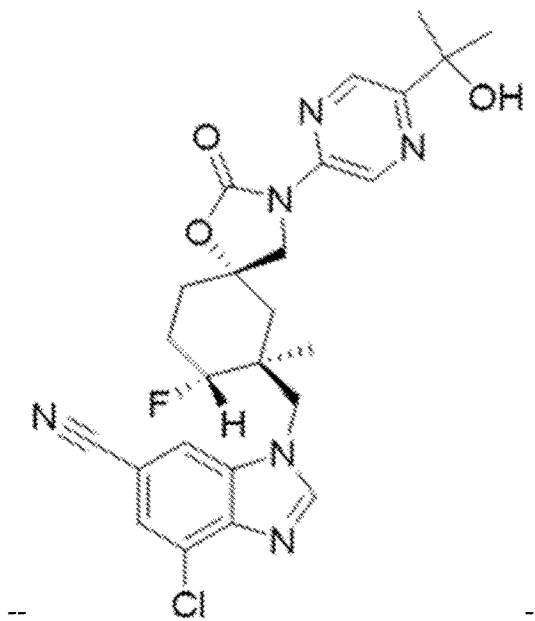

--                                    --

At Column 239, Claim 16, Line number 10:

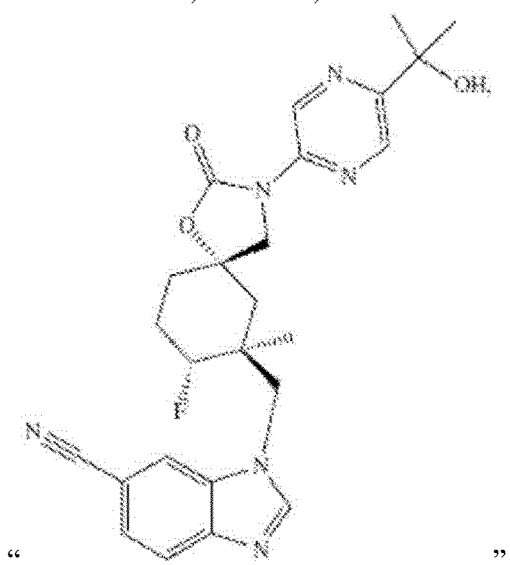

"                                    "

Should read: